US008649857B2

(12) United States Patent (10) Patent No.: US 8,649,857 B2
Stevenson et al. (45) Date of Patent: *Feb. 11, 2014

(54) TANK FILTERS PLACED IN SERIES WITH THE LEAD WIRES OR CIRCUITS OF ACTIVE MEDICAL DEVICES TO ENHANCE MRI COMPATIBILITY

(75) Inventors: Robert A. Stevenson, Canyon Country, CA (US); Warren S. Dabney, Orchard Park, NY (US); Christine A. Frysz, Orchard Park, NY (US); Richard L. Brendel, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 346 days.

This patent is subject to a terminal disclaimer.

(21) Appl. No.: 13/081,314

(22) Filed: Apr. 6, 2011

(65) Prior Publication Data

US 2011/0213233 A1 Sep. 1, 2011

Related U.S. Application Data

(60) Division of application No. 12/938,774, filed on Nov. 3, 2010, now Pat. No. 8,463,375, which is a division of application No. 11/558,349, filed on Nov. 9, 2006, now Pat. No. 7,945,322, which is a continuation-in-part of application No. 11/423,073, filed on Jun. 8, 2006, now Pat. No. 8,244,370.

(51) Int. Cl.
*A61N 1/04* (2006.01)

(52) U.S. Cl.
USPC .......................................................... 607/2

(58) Field of Classification Search
USPC .......................................................... 607/2
See application file for complete search history.

(56) References Cited

U.S. PATENT DOCUMENTS 3,871,382 A 3/1975 Mann
3,968,802 A 7/1976 Ballis
(Continued)

FOREIGN PATENT DOCUMENTS

EP 0243573 11/1987
EP 0145430 5/1991
(Continued)

OTHER PUBLICATIONS

Ariel Roguin et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

*Primary Examiner* — George Manuel
(74) *Attorney, Agent, or Firm* — Michael F. Scalise

(57) ABSTRACT

A TANK filter is provided for a lead wire of an active medical device (AMD). The TANK filter includes a capacitor in parallel with an inductor. The parallel capacitor and inductor are placed in series with the lead wire of the AMD, wherein values of capacitance and inductance are selected such that the TANK filter is resonant at a selected frequency. The Q of the inductor may be relatively maximized and the Q of the capacitor may be relatively minimized to reduce the overall Q of the TANK filter to attenuate current flow through the lead wire along a range of selected frequencies. In a preferred form, the TANK filter is integrated into a TIP and/or RING electrode for an active implantable medical device.

14 Claims, 76 Drawing Sheets

(56) References Cited

U.S. PATENT DOCUMENTS

| | | | |
|---|---|---|---|
| 4,633,181 A | 12/1986 | Murphy-Boesch et al. |
| 4,654,880 A | 3/1987 | Sontag |
| 4,689,621 A | 8/1987 | Kleinberg |
| 4,799,499 A | 1/1989 | Bisping |
| 4,858,623 A | 8/1989 | Bradshaw et al. |
| 5,209,233 A | 5/1993 | Holland et al. |
| 5,217,010 A | 6/1993 | Tsitlik et al. |
| 5,246,438 A | 9/1993 | Langberg |
| 5,300,108 A | 4/1994 | Rebell et al. |
| 5,333,095 A | 7/1994 | Stevenson et al. |
| 5,363,845 A | 11/1994 | Chowdhury et al. |
| 5,398,683 A | 3/1995 | Edwards et al. |
| 5,514,173 A | 5/1996 | Rebell et al. |
| 5,545,201 A | 8/1996 | Helland et al. |
| 5,629,622 A | 5/1997 | Scampini |
| 5,697,958 A | 12/1997 | Paul et al. |
| 5,716,390 A | 2/1998 | Li |
| 5,722,998 A | 3/1998 | Prutchi et al. |
| 5,741,321 A | 4/1998 | Brennen |
| 5,751,539 A | 5/1998 | Stevenson et al. |
| 5,759,202 A | 6/1998 | Schroeppel |
| 5,905,627 A | 5/1999 | Brendel et al. |
| 5,959,829 A | 9/1999 | Stevenson et al. |
| 5,964,705 A | 10/1999 | Truwit et al. |
| 5,973,906 A | 10/1999 | Stevenson et al. |
| 5,978,204 A | 11/1999 | Stevenson |
| 6,008,980 A | 12/1999 | Stevenson et al. |
| 6,055,457 A | 4/2000 | Bonner |
| 6,101,417 A | 8/2000 | Vogel et al. |
| 6,141,594 A | 10/2000 | Flynn et al. |
| 6,159,560 A | 12/2000 | Stevenson et al. |
| 6,236,205 B1 | 5/2001 | Ludeke et al. |
| 6,275,369 B1 | 8/2001 | Stevenson et al. |
| 6,280,385 B1 | 8/2001 | Melzer et al. |
| 6,424,234 B1 | 7/2002 | Stevenson |
| 6,456,481 B1 | 9/2002 | Stevenson |
| 6,473,291 B1 | 10/2002 | Stevenson |
| 6,493,591 B1 | 12/2002 | Stokes |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,606,513 B2 | 8/2003 | Lardo et al. |
| 6,643,903 B2 | 11/2003 | Stevenson et al. |
| 6,675,033 B1 | 1/2004 | Lardo et al. |
| 6,675,779 B2 | 1/2004 | King et al. |
| 6,675,780 B1 | 1/2004 | Wendels et al. |
| 6,687,550 B1 | 2/2004 | Doan |
| 6,701,176 B1 | 3/2004 | Halperin et al. |
| 6,847,837 B1 | 1/2005 | Melzer et al. |
| 6,868,288 B2 | 3/2005 | Thompson |
| 6,871,091 B2 * | 3/2005 | Wilkinson et al. ............ 607/2 |
| 6,876,885 B2 | 4/2005 | Swoyer et al. |
| 6,882,248 B2 | 4/2005 | Stevenson et al. |
| 6,898,454 B2 | 5/2005 | Atalar et al. |
| 6,925,328 B2 | 8/2005 | Foster et al. |
| 6,931,286 B2 | 8/2005 | Sigg et al. |
| 6,949,929 B2 | 9/2005 | Gray et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,999,818 B2 | 2/2006 | Stevenson et al. |
| 7,013,180 B2 | 3/2006 | Villaseca et al. |
| 7,092,766 B1 | 8/2006 | Salys et al. |
| 7,113,387 B2 | 9/2006 | Stevenson et al. |
| 7,123,013 B2 | 10/2006 | Gray |
| 7,155,271 B2 | 12/2006 | Halperin |
| 7,388,378 B2 * | 6/2008 | Gray et al. ............ 324/318 |
| 2003/0028094 A1 | 2/2003 | Kumar et al. |
| 2003/0050557 A1 | 3/2003 | Susil et al. |
| 2004/0167392 A1 | 8/2004 | Halperin et al. |
| 2004/0263173 A1 | 12/2004 | Gray |
| 2004/0263174 A1 | 12/2004 | Gray et al. |
| 2005/0077984 A1 | 4/2005 | Villaseca et al. |
| 2005/0197677 A1 | 9/2005 | Stevenson |
| 2006/0009819 A1 | 1/2006 | Przybyszewski |
| 2006/0100506 A1 | 5/2006 | Halperin et al. |

FOREIGN PATENT DOCUMENTS

| | | |
|---|---|---|
| EP | 0498996 | 3/1997 |
| EP | 0930509 | 12/1998 |
| EP | 1021730 | 4/1999 |
| JP | 60141034 | 7/1985 |
| JP | 61181925 | 8/1985 |
| JP | 62233905 | 10/1987 |
| JP | 4071536 | 3/1992 |
| JP | 6054823 | 3/1994 |
| JP | 11239572 | 9/1999 |
| JP | 2005-117606 | 4/2005 |
| WO | 99/19739 | 4/1999 |
| WO | 02/083016 | 10/2002 |

* cited by examiner

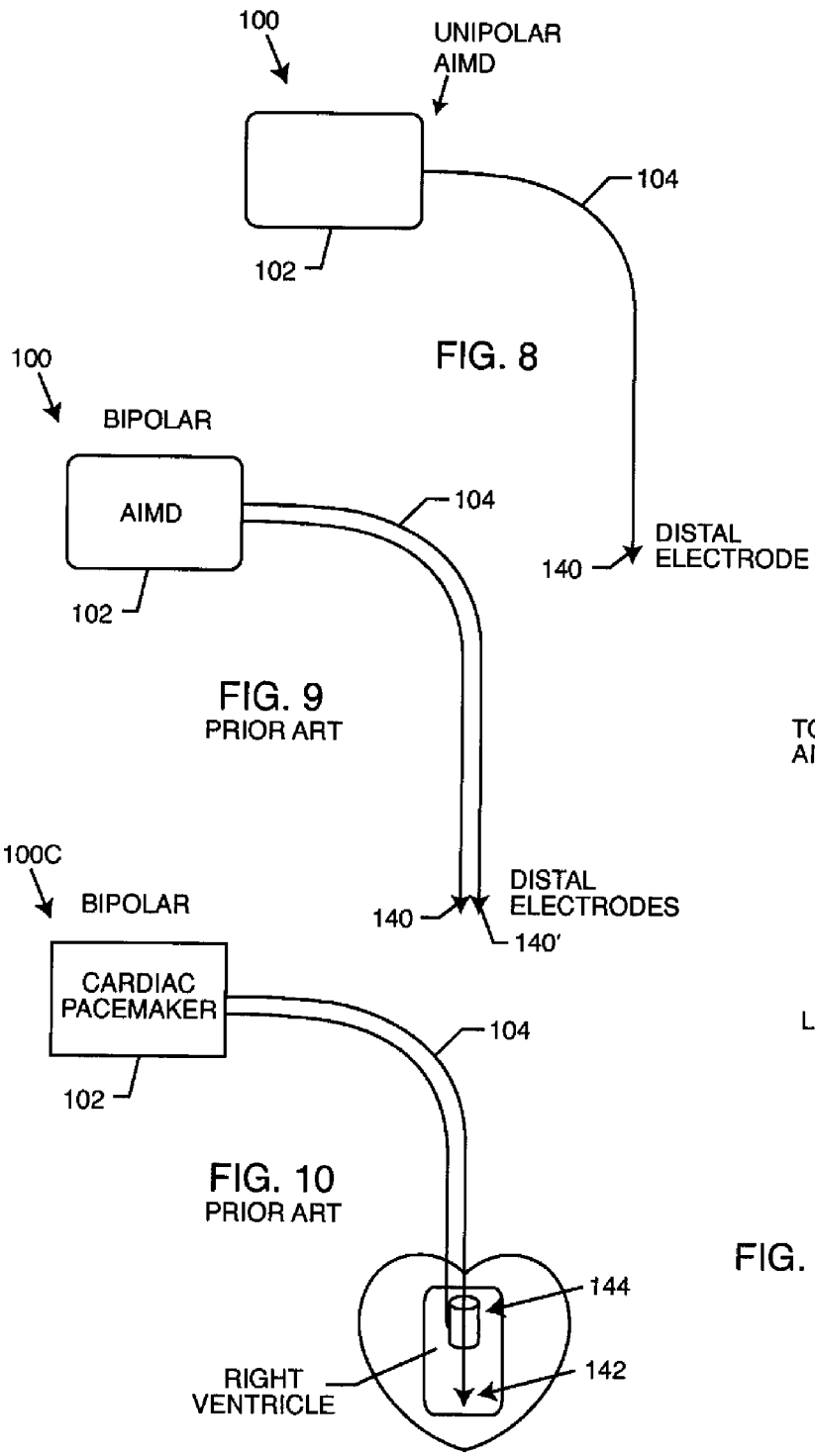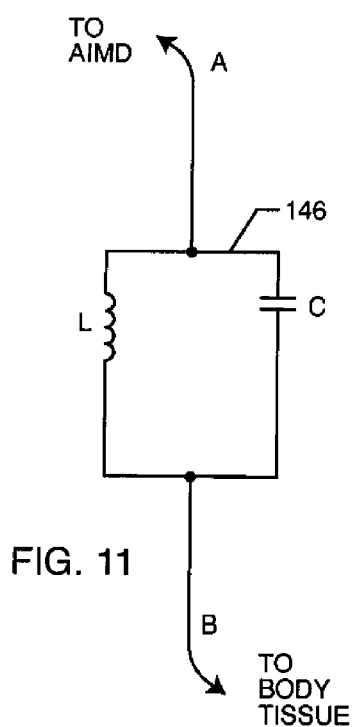

$$f_r = \frac{1}{2\pi\sqrt{LC}}$$

Where: $f_r$ = resonant frequency
$L$ = inductance in henries
$C$ = capacitance in farads Solving for C:  Solving for L:

$$C = \frac{1}{(f_r)^2 (2\pi)^2 L} \qquad L = \frac{1}{(f_r)^2 (2\pi)^2 C}$$

→ assume a 1.5 Tesla MRI System,
then the RF pulsed frequency = 64 MHz

→ assume that $L$ = 150 nanohenry (150 x $10^{-9}$ H)

then; solving for C:

FIG. 14  $z_{ab} = \dfrac{(j\omega L)(-j/\omega C)}{(j\omega L - j/\omega C)}$

FIG. 15  $X_L = +j(2\pi fL) = +j\omega L$
$X_C = -j\left(\dfrac{1}{2\pi fC}\right) = \dfrac{-j}{\omega C}$ $C_L = C_1 + C_2 + C_3 \ldots\ldots C_n$

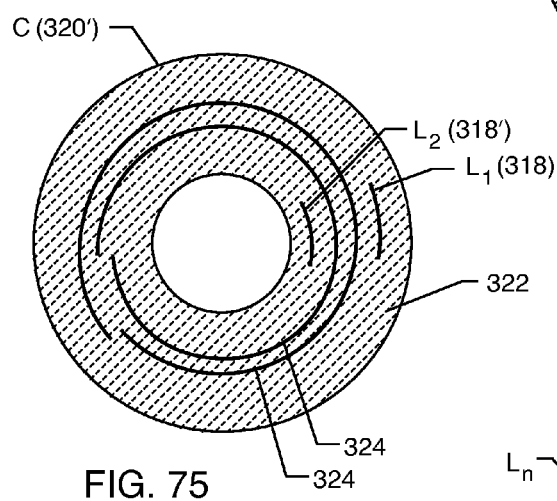
FIG. 74
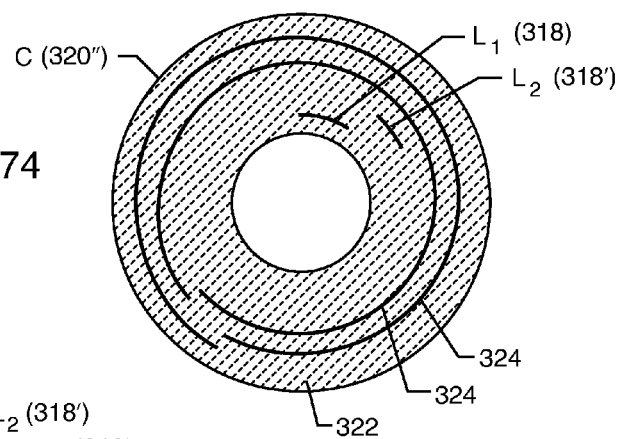
FIG. 75
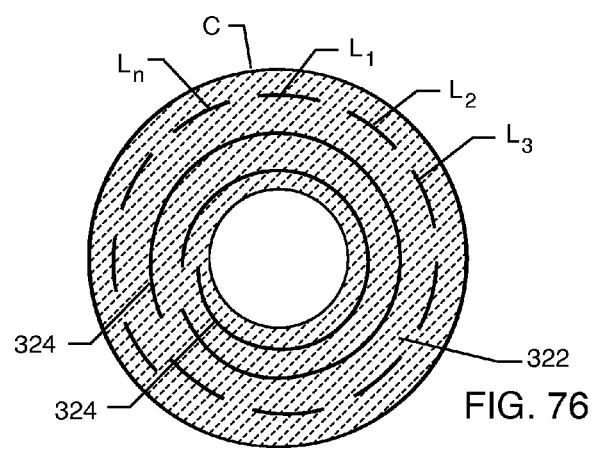
FIG. 76
$$L_{TOTAL} = \frac{1}{\frac{1}{L_1} + \frac{1}{L_2} + \frac{1}{L_3} + \ldots \frac{1}{L_n}}$$
FIG. 77

$$L_{TOTAL} = \frac{1}{\frac{1}{L_1} + \frac{1}{L_2} + \frac{1}{L_3}}$$
FIG. 84
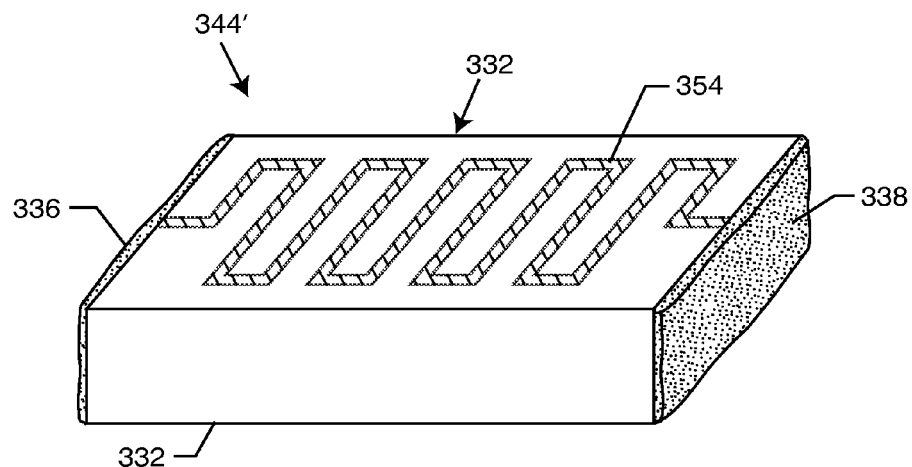
FIG. 85
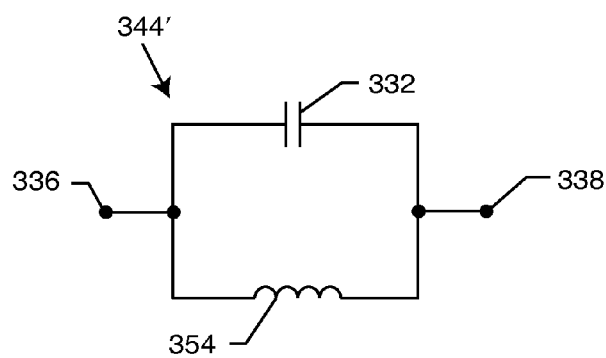
FIG. 86

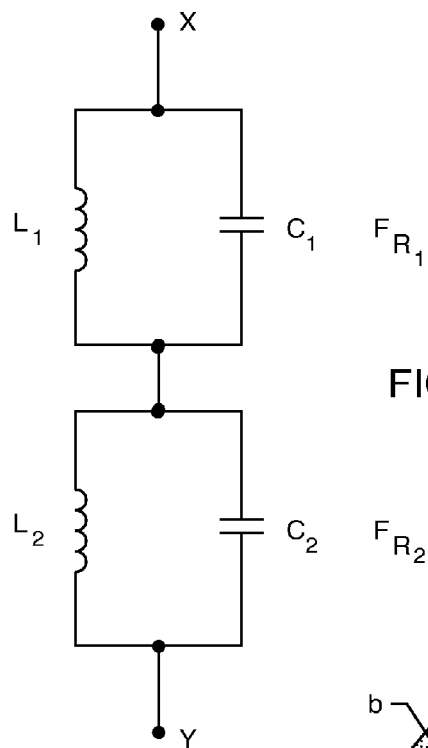
FIG. 110
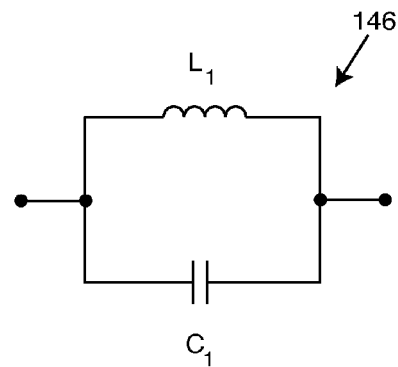
FIG. 114
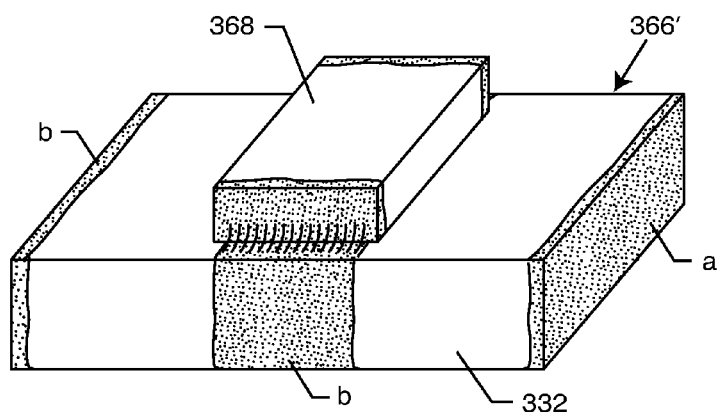
FIG. 111
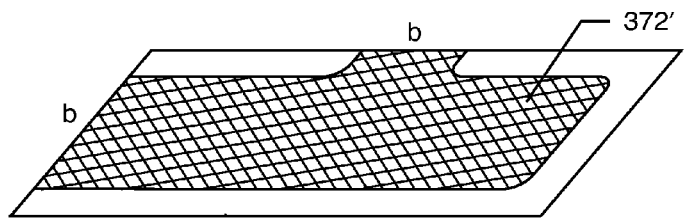
FIG. 112
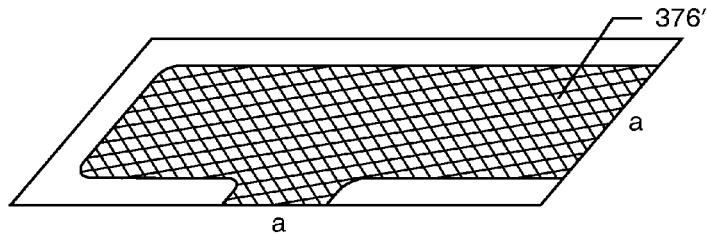
FIG. 113

| FABRICATION METHOD | TYPICAL INDUCTOR MATERIALS |
|---|---|
| LTCC | Ag,Au |
| HTCC | Al,Cu,Al/Cu |
| MMIC | GaAs,InP' |
| MCM-D | Tr,Cu,Aol |
FIG. 135
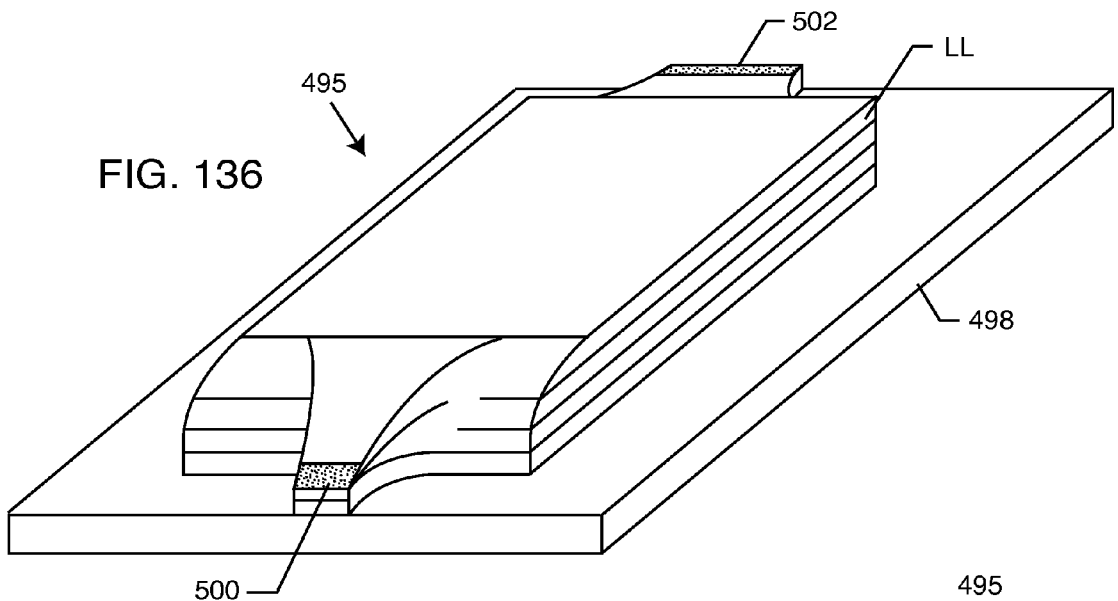
FIG. 136
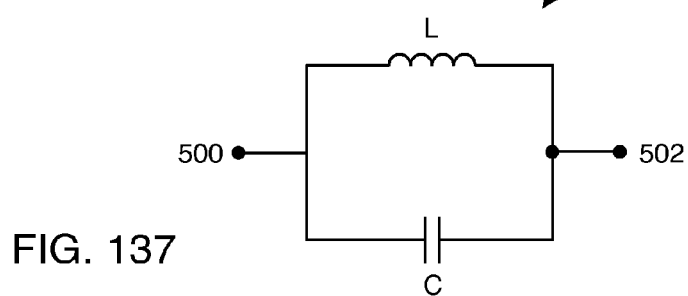
FIG. 137

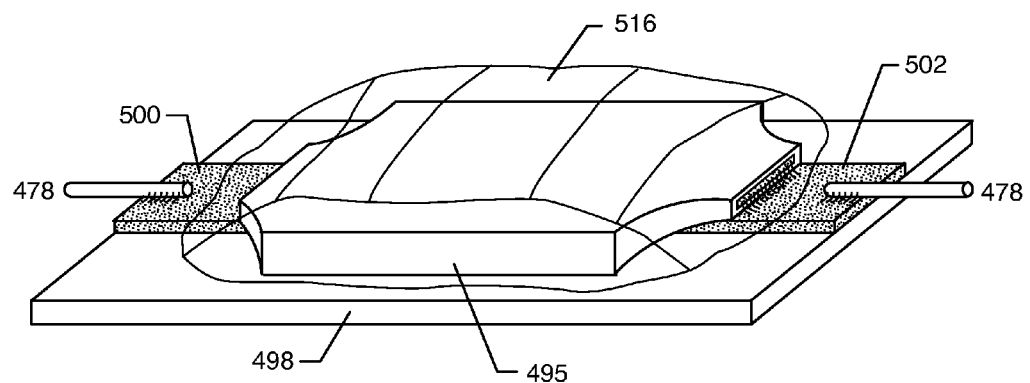
FIG. 139
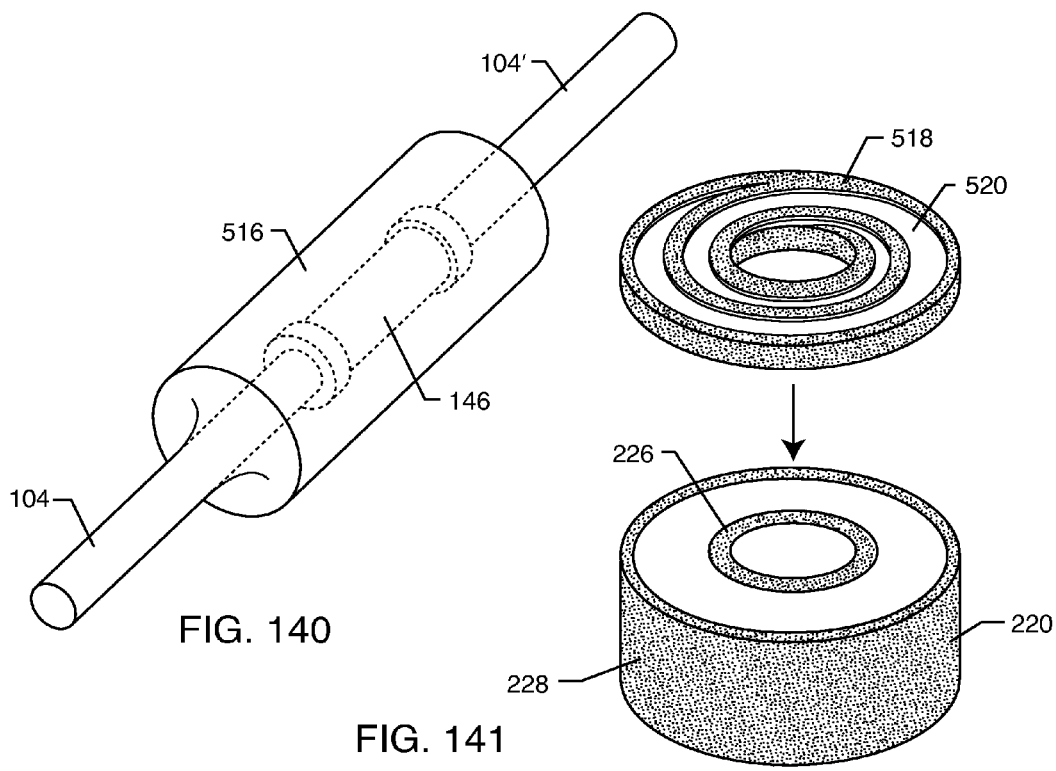
FIG. 140
FIG. 141

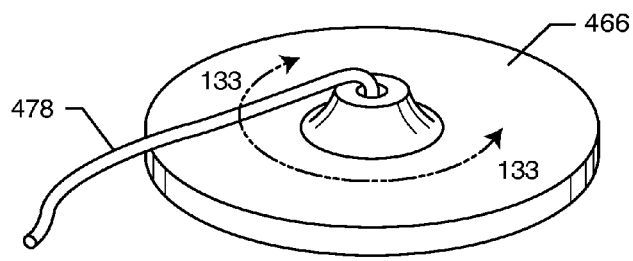
FIG. 167
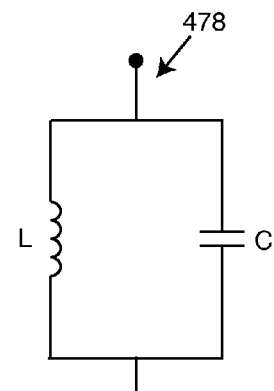
FIG. 168
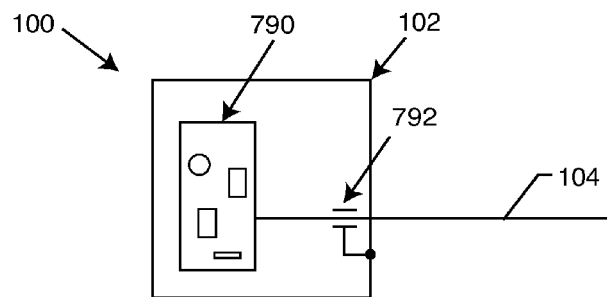
FIG. 169
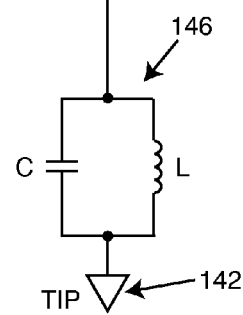

TANK FILTERS PLACED IN SERIES WITH THE LEAD WIRES OR CIRCUITS OF ACTIVE MEDICAL DEVICES TO ENHANCE MRI COMPATIBILITY

BACKGROUND OF THE INVENTION

This invention relates generally to electromagnetic interference (EMI) TANK filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals. The invention is also applicable to a wide variety of commercial, telecommunications, military and space applications. The present invention is also applicable to a wide range of external medical devices, including externally worn drug pumps, EKG/ECG electrodes, neurostimulators, ventricular assist devices and the like. The present invention is also applicable to a wide range of probes, catheters, monitoring lead wires and the like that may be temporarily inserted into or onto a patient or that a patient may be wearing or connected to during medical diagnostic procedures such as MRI.

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific CRM (formerly Guidant), one will see that the use of MRI is generally contra-indicated with pacemakers and implantable defibrillators. A similar contra-indication is found in the manuals of MRI equipment manufacturers such as Siemens, GE, and Phillips. See also "Safety Aspects of Cardiac Pacemakers in Magnetic Resonance Imaging", a dissertation submitted to the Swiss Federal Institute of Technology Zurich presented by Roger Christoph Lüchinger. "Dielectric Properties of Biological Tissues: I. Literature Survey", by C. Gabriel, S. Gabriel and E. Cortout; "Dielectric Properties of Biological Tissues: II. Measurements and the Frequency Range 0 Hz to 20 GHz", by S. Gabriel, R. W. Lau and C. Gabriel; "Dielectric Properties of Biological Tissues: III. Parametric Models for the Dielectric Spectrum of Tissues", by S. Gabriel, R. W. Lau and C. Gabriel; and "Advanced Engineering Electromagnetics, C. A. Balanis, Wiley, 1989, all of which are incorporated herein by reference.

However, an extensive review of the literature indicates that MRI is indeed often used with pacemaker patients, in spite of the contra indications. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). Other papers go up to 1.5 T for non-pacemaker dependent patients under highly controlled conditions. MRI is one of medicine's most valuable diagnostic tools. MRI is, of course, extensively used for imaging, but is also increasingly used for real-time procedures such as interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. However, because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the applied power of the MRI in terms of the specific absorption rate—SAR programming the pacemaker to fixed or asynchronous pacing mode, having emergency personnel and resuscitation equipment standing by (known as "Level II" protocol), and careful reprogramming and evaluation of the pacemaker and patient after the procedure is complete. There have been reports of latent problems with cardiac pacemakers after an MRI procedure occurring many days later (such as increase in or loss of pacing pulse capture).

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 6 Tesla. At the recent International Society for Magnetic Resonance in Medicine (ISMRM), which was held on 5 and 6 Nov. 2005, it was reported that certain research systems are going up as high as 11.7 Tesla and will be ready sometime in 2007. A 1.5 T MRI system is over 100,000 times the magnetic field strength of the earth. A static magnetic field of this magnitude can induce powerful magnetomechanical forces on any magnetic materials implanted within the patient, including certain components within the cardiac pacemaker and/or lead wire systems themselves. It is unlikely that the static MRI magnetic field can induce currents (dB/dt) into the pacemaker lead wire system and hence into the pacemaker itself. It is a basic principle of physics that a magnetic field must either be time-varying as it cuts across the conductor (dB/dt), or the conductor itself must move within the magnetic field for currents to be induced (dB/dx).

The second type of field produced by magnetic resonance imaging equipment is the pulsed RF field which is generated by the body coil or head coil, also referred to as $B_1$. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulsed varies with the field strength of the main static field, as expressed in the Lamour Equation:: RF PULSED FREQUENCY (in MHz)= (42.56) (STATIC FIELD STRENGTH (T); where 42.56 MHz per Tesla is the Lamour constant for $H^+$ protons.

The third type of electromagnetic field is the time-varying magnetic gradient field designated $G_{x,y,z}$ which is used for spatial localization. The gradient field changes its strength along different orientations and operating frequencies on the order of 1 to 2.2 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. There have been some reports of gradient field induced ventricular arrhythmias which could be life threatening. However, in contrast, the gradient field is not considered by some researchers to create any significant adverse effects.

As previously stated, the third type of electromagnetic field is the time-varying magnetic gradient fields, designated as $G_x$, $G_y$, and $G_z$. The $G_z$ gradient is used to distort the $B_0$ field in the z direction, thereby creating body 'slices' of specific thickness. The $G_x$ and $G_y$ fields are used to introduce phase and frequency 'markers' to specific protons, allowing for an x-y image to be generated.

The fields operate at roughly 1 to 2.2 kHz, and are generated by three distinct, orthogonally oriented coils. These fields are only active during image generation protocols, and have been shown to have adverse effects on human physiology. These effects are largely due to the induced voltages that are generated by the application of a moving magnetic field on a large area. Following is Faraday's Law of Induction, $$V = A\frac{dB}{dt},$$

Where A is the area of the loop, and dB/dt is change in magnetic flux with respect to time, it has been shown that the induced voltages generated by the gradient fields, if high enough, can induce peripheral nerve stimulation (PNS). This has been reported in literature as a sensation of pain or other discomfort while running relatively high MRI gradients. In more extreme animal testing, cardiac stimulation has been detected, although this has taken roughly 80 times more energy to achieve than that of PNS. To prevent PNS or cardiac stimulation from occurring, industry standards have limited dB/dt to roughly 20 T/sec.

Of interest is the effect of the gradient fields on AIMDs, which typically have implanted lead systems. In the case of AIMDs with unipolar lead systems, a circuit loop is formed between the AIMD can, the lead system, the distal TIP, and body tissue (as the return path). An average area created by such a loop is around 225 cm² with the higher limit about 350 cm². When considering this with the 20 T/sec maximum, it can be seen that the maximum induced voltage in the loop is 0.700V. When one looks at the induced voltage at the pacing tip, it is typically an order of magnitude lower than the induced voltage in the loop (due to relatively high lead system and device impedances). This is much lower than the typical pacing threshold required for an AIMD to stimulate heart tissue.

It is instructive to note how voltages and EMI are induced into an implanted or external lead wire system. At very low frequency (VLF), voltages are induced at the input to the cardiac pacemaker as currents circulate throughout the patient's body and create differential voltage drops. In a unipolar system, because of the vector displacement between the pacemaker housing and, for example, the TIP electrode, voltage drop across body tissues may be sensed due to Ohms Law and the circulating RF signal. At higher frequencies, the implanted lead wire systems actually act as antennas where currents are induced along their length. These antennas are not very efficient due to the damping effects of body tissue; however, this can often be offset by extremely high power fields and/or body resonances. At very high frequencies (such as cellular telephone frequencies), EMI signals are induced only into the first area of the lead wire system (for example, at the header block of a cardiac pacemaker). This has to do with the wavelength of the signals involved and where they couple efficiently into the system.

Magnetic field coupling into an implanted lead wire system is based on loop areas. For example, in a cardiac pacemaker, there is a loop formed by the lead wire as it comes from the cardiac pacemaker housing to its distal TIP located in the right ventricle. The return path is through body fluid and tissue generally straight from the TIP electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (greater than 450 square centimeters).

Relating now to the specific case of MRI, the magnetic gradient fields would be induced through enclosed loop areas. However, the pulsed RF fields, which are generated by the body coil, would be primarily induced into the lead wire system by antenna action.

There are a number of potential problems with MRI, including:

(1) Closure of the pacemaker reed switch. A pacemaker reed switch, which can also be a Hall Effect device, is designed to detect a permanent magnet held close to the patient's chest. This magnet placement allows a physician or even the patient to put the implantable medical device into what is known as the "magnet mode response." The "magnet mode response" varies from one manufacturer to another, however, in general, this puts the pacemaker into a fixed rate or asynchronous pacing mode. This is normally done for short times and is very useful for diagnostic purposes. However, when a pacemaker is brought close to the MRI scanner, the MRI static field can make the pacemaker's internal reed switch close, which puts the pacemaker into a fixed rate or asynchronous pacing mode. Worse yet, the reed switch may bounce or oscillate. Asynchronous pacing may compete with the patient's underlying cardiac rhythm. This is one reason why pacemaker/ICD patients have generally been advised not to undergo MRI. Fixed rate or asynchronous pacing for most patients is not an issue. However, in patients with unstable conditions, such as myocardial ischemia, there is a substantial risk for life threatening ventricular fibrillation during asynchronous pacing. In most modern pacemakers the magnetic reed switch (or Hall Effect device) function is programmable. If the magnetic reed switch response is switched off, then synchronous pacing is still possible even in strong magnetic fields. The possibility to open and re-close the reed switch in the main magnetic field by the gradient field cannot be excluded. However, it is generally felt that the reed switch will remain closed due to the powerful static magnetic field. It is theoretically possible for certain reed switch orientations at the gradient field to be capable of repeatedly closing and re-opening the reed switch.

(2) Reed switch damage. Direct damage to the reed switch is theoretically possible, but has not been reported in any of the known literature. In an article written by Roger Christoph Lüchinger of Zurich, he reports on testing in which reed switches were exposed to the static magnetic field of MRI equipment. After extended exposure to these static magnetic fields, the reed switches functioned normally at close to the same field strength as before the test.

(3) Pacemaker displacement. Some parts of pacemakers, such as the batteries and reed switch, contain ferrous magnetic materials and are thus subject to mechanical forces during MRI (testing is done to ASTM Standards). Pacemaker displacement may occur in response to magnetic force or magnetic torque (newer pacemakers and ICDs have less ferrous materials and are less susceptible to this).

(4) Radio frequency field. At the pulsed RF frequencies of interest in MRI, RF energy can be absorbed and converted to heat. The power deposited by RF pulses during MRI is complex and is dependent upon the power. duration and shape of the RF pulse, the relative long term time averages of the pulses, the transmitted frequency, the number of RF pulses applied per unit time, and the type of configuration of the RF transmitter coil used. Specific absorption rate (SAR) is a measure of how much energy is induced into body tissues. The amount of heating also depends upon the volume of the various tissue (i.e. muscle, fat, etc.) imaged, the electrical resistivity of tissue and the configuration of the anatomical region imaged. There are also a number of other variables that depend on the placement in the human body of the AIMD and its associated lead wire(s). For example, it will make a difference how much current is induced into a pacemaker lead wire system as to whether it is a left or right pectoral implant. In addition, the routing of the lead and the lead length are also very critical as to the amount of induced current and heating that would occur. Also, distal TIP design is very important as the distal TIP itself can act as its own antenna. Location within the MRI bore is also important since the electric fields required to generate the RF increase exponentially as the patient is moved away from MRI bore center-line (ISO center). The cause of heating in an MRI environment is two fold: (a) RF field coupling to the lead can occur which induces significant local heating; and (b) currents induced during the RF transmission can flow into body tissue and cause local Ohm's Law heating next to the distal TIP electrode of the implanted lead. The RF field in an MRI scanner can produce enough energy to induce lead wire currents sufficient to destroy some of the adjacent myocardial tissue. Tissue ablation has also been observed. The effects of this heating are not readily detectable by monitoring during the MRI. Indications that heating has occurred would include an increase in pacing threshold, venous ablation, Larynx ablation, myocardial perforation and lead penetration, or even arrhythmias caused by scar tissue. Such long term heating effects of MRI have not been well studied yet.

(5) Alterations of pacing rate due to the applied radio frequency field. It has been observed that the RF field may induce undesirable fast cardiac pacing (QRS complex) rates. There are various mechanisms which have been proposed to explain rapid pacing: direct tissue stimulation, interference with pacemaker electronics or pacemaker reprogramming (or reset). In all of these cases, it would be desirable to raise the lead system impedance (to reduce RF current), make the feedthrough capacitor more effective and provide a very high degree of protection to AIMD electronics. This will make alterations in pacemaker pacing rate and/or pacemaker reprogramming much more unlikely.

(6) Time-varying magnetic gradient fields. The contribution of the time-varying gradient to the total strength of the MRI magnetic field is negligible, however, pacemaker systems could be affected because these fields are rapidly applied and removed. The time rate of change of the magnetic field is directly related to how much electromagnetic force (EMF) and hence current can be induced into a lead wire system. Lüchinger reports that even using today's gradient systems with a time-varying field up to 60 Tesla per second, the induced currents are likely to stay below the biological thresholds for cardiac fibrillation. A theoretical upper limit for the induced voltage by the time-varying magnetic gradient field is 20 volts. Such a voltage during more than 0.1 milliseconds could be enough energy to directly pace the heart.

(7) Heating. Currents induced by time-varying magnetic gradient fields may lead to local heating. Researchers feel that the calculated heating effect of the gradient field is much less as compared to that caused by the RF field and therefore may be neglected.

There are additional problems possible with implantable cardioverter defibrillators (ICDs). ICDs use different and larger batteries which could cause higher magnetic forces. The programmable sensitivity in ICDs is normally much higher than it is for pacemakers, therefore, ICDs may falsely detect a ventricular tacchyarrhythmia and inappropriately deliver therapy. In this case, therapy might include anti-tachycardia pacing, cardio version or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern. There have also been reports of older model ICDs being severely effected by the MRI pulsed RF field. In these cases, there have been multiple microprocessor resets and even cases of permanent damage where the ICD failed to function after the MRI procedure. In addition, ICDs have exhibited a different type of problem when exposed to MRI fields. That is, during an MRI exposure, the ICD might inappropriately sense the MRI RF-field or gradient fields as a dangerous ventricular arrhythmia. In this case, the ICD will attempt to charge its high energy storage capacitor and deliver a high voltage shock to the heart. However, within this charging circuit, there is a transformer that is necessary to function in order to fully charge up the high energy storage capacitor. In the presence of the main static field ($B_0$) field, the ferrite core of this transformer tends to saturate thereby reducing its efficiency. This means the high energy storage capacitor cannot fully charge. Reports of repeated low voltage shocks are in the literature. These repeated shocks and this inefficient attempt to charge the battery can cause premature battery depletion of the ICD. Shortening of battery life is of course, a highly undesirable condition.

In summary, there are a number of studies that have shown that MRI patients with active implantable medical devices, such as cardiac pacemakers, can be at risk for potential hazardous effects. However, there are a number of anecdotal reports that MRI can be safe for extremity imaging of pacemaker patients (i.e. the AIMD is outside the bore). These anecdotal reports are of interest; however, they are certainly not scientifically convincing that all MRI can be safe. As previously mentioned, just variations in the pacemaker lead wire length can significantly effect how much heat is generated. From the layman's point of view, this can be easily explained by observing the typical length of the antenna on a cellular telephone compared to the vertical rod antenna more common on older automobiles. The relatively short antenna on the cell phone is designed to efficiently couple with the very high frequency wavelengths (approximately 950 MHz) of cellular telephone signals. In a typical AM and FM radio in an automobile, these wavelength signals would not efficiently couple to the relatively short antenna of a cell phone. This is why the antenna on the automobile is relatively longer. An analogous situation exists on the MRI system. If one assumes, for example, a 3.0 Tesla MRI system, which would have an RF pulsed frequency of 128 MHz, there are certain exact implanted lead lengths that would couple efficiently as fractions of the 128 MHz wavelength. Ignoring the effects of body tissue, as an example, the basic wavelength equation in meters is 300 divided by the frequency in MHz. Accordingly, for a 3.0 Tesla MRI system, the wavelength is 2.34 meters or 234 centimeters. An exact ¼ wavelength antenna then would be ¼ of this which is 58.59 centimeters. This falls right into the range for the length of certain pacemaker lead wire implants. It is typical that a hospital will maintain an inventory of various leads and that the implanting physician will make a selection depending on the size of the patient, implant location and other factors. Accordingly, the implanted or effective lead wire length can vary considerably. Another variable has to do with excess lead wire. It is typical that the physician, after doing a pacemaker lead wire insertion, will wrap up any excess lead wire in the pectoral pocket. This can form one, two or even three turns of excess lead. This forms a loop in that specific area, however, the resulting longer length of wire that goes down into the right ventricle, is what would then couple efficiently with the MRI RF pulsed frequency. As one can see, the amount of unwound up lead length is considerably variable depending upon patient geometry. There are certain implanted lead wire lengths that just do not couple efficiently with the MRI frequency and there are others that would couple very efficiently and thereby produce the worst case for heating. The actual situation for an implanted lead wire is far more complex due to the varying permittivity and dielectric properties of body tissues and the accompanying shifts in wavelengths.

The effect of an MRI system on the function of pacemakers, ICDs and neurostimulators depends on various factors, including the strength of the static magnetic field, the pulse sequence (gradient and RF field used), the anatomic region being imaged, and many other factors. Further complicating this is the fact that each manufacturer's pacemaker and ICD designs behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. RF ablation treatment of such a tumor may require stereotactic imaging only made possible through real time fine focus MRI. With the patient's life literally at risk, and with informed patient consent, the physician may make the decision to perform MRI in spite of all of the previously described attendant risks to the pacemaker system.

Insulin drug pump systems do not seem to be of a major current concern due to the fact that they have no significant antenna components (such as implanted lead wires). However, implantable pumps presently work on magneto-peristaltic systems, and must be deactivated prior to MRI. There are newer (unreleased) systems that would be based on solenoid systems which will have similar problems.

It is clear that MRI will continue to be used in patients with an active implantable medical device. There are a number of other hospital procedures, including electrocautery surgery, lithotripsy, etc., to which a pacemaker patient may also be exposed. Accordingly, there is a need for circuit protection devices which will improve the immunity of active implantable medical device systems to diagnostic procedures such as MRI.

As one can see, many of the undesirable effects in an implanted lead wire system from MRI and other medical diagnostic procedures are related to undesirable induced currents in the lead wire system. This can lead to overheating either in the lead wire or at the tissue interface at the distal TIP. At the 2006 SMIT Conference, the FDA reported on a neurostimulator patient whose implanted leads were sufficiently heated that severe burns occurred resulting in the need for multiple amputations. In pacemaker patients, these currents can also directly stimulate the heart into sometimes dangerous arrhythmias. The above descriptions of problems that a pacemaker, ICD or neurostimulator patients may encounter during MRI or similar medical diagnostic procedures are only examples of a general need. A patient wearing external devices, such as an external drug pump, an external neurostimulator, EKG leads, (skin patches) or ventricular assist devices, may also encounter problems during an MRI procedure. All of the above descriptions regarding overheating of lead wires, overheating of distal tips or electromagnetic interference are all concerns. The novel resonant TANK filter of the present invention is equally applicable to all of these other devices. It is also applicable to probes and catheters that are used during certain real time medical imaging procedures such as MRI. The present invention is applicable to a wide range of both implanted and external medical device systems. In general, the present invention is a circuit protection device that protects a patient undergoing high RF power medical diagnostic procedures.

Accordingly, there is a need for a novel resonant EMI TANK filter assembly which can be placed at various locations along the medical device lead wire system, which also prevents current from circulating at selected frequencies of the medical therapeutic device. Preferably, such novel TANK filters would be designed to resonate at or near 64 MHz for use in an MRI system operating at 1.5 Tesla (or 128 MHz for a 3 Tesla system), and have broad application to other fields, including telecommunications, military, space and the like. The present invention fulfills these needs and provides other related advantages.

SUMMARY OF THE INVENTION

The present invention consists of novel resonant TANK filters to be placed at the distal TIP and/or at various locations along the medical device lead wires or circuits. These TANK filters inhibit or prevent current from circulating at selected frequencies of the medical therapeutic device. For example, for an MRI system operating at 1.5 Tesla, the pulse RF frequency is 64 MHz, as described by the Lamour Equation. The novel TANK filter of the present invention can be designed to resonate at or near 64 MHz and thus create a high impedance (ideally an open circuit) in the lead wire system at that selected frequency. For example, the novel TANK filter of the present invention, when placed at the distal TIP of a pacemaker lead wire, will significantly reduce RF currents from flowing through the distal TIP and into body tissue. The novel TANK filter also reduces EMI from flowing in the lead wires of a pacemaker, for example, thereby providing added protection to sensitive electronic circuits. It will be obvious to those skilled in the art that all of the embodiments described herein are equally applicable to a wide range of other implantable and external medical devices, including deep brain stimulators, spinal cord stimulators, drug pumps, probes, catheters and the like. The present invention fulfills all of the needs regarding reduction or elimination of undesirable currents and associated heating in medical devices and/or their associated lead wire systems. The novel TANK filter structures as described herein also have a broad application to other disciplines, including telecommunications, military, space and the like.

Electrically engineering a capacitor in parallel with an inductor is known as a TANK filter. It is also well known that when a near-ideal TANK filter is at its resonant frequency, it will present a very high impedance. Since MRI equipment produces very large RF pulsed fields operating at discrete frequencies, this is an ideal situation for a specific resonant TANK filter. TANK filters are more efficient for eliminating one single frequency than broadband filters. Because the TANK filter is targeted at this one frequency, it can be much smaller and volumetrically efficient. In addition, the way MRI couples with lead wire systems, various loops and associated currents are generated. For example, at the distal TIP of a cardiac pacemaker, direct electromagnetic forces (EMFs) can be produced which result in current loops through the distal TIP and into the associated myocardial tissue. This current system is largely decoupled from the currents that are induced near the active implantable medical device, for example, near the cardiac pacemaker. There the MRI may set up a separate loop with its associated currents. Accordingly, one or more TANK filters may be required to completely control all of the various induced EMI and associated currents in a lead wire system.

A major challenge for designing a TANK filter for human implant is that it must be very small in size, biocompatible, and highly reliable. Coaxial geometry is preferred. The reason that coaxial is preferred is that lead wires are placed at locations in the human body primarily by one of two main methods. These include guide wire lead insertion. For example, in a cardiac pacemaker application, a pectoral pocket is created. Then, the physician makes a small incision between the ribs and accesses the subclavian vein. The pacemaker lead wires are stylus guided/routed down through this venous system through the aortic arch, through the right atrium, through the tricuspid valve and into, for example, the right ventricle. Another primary method of installing lead wires (particularly for neurostimulators) in the human body is by tunneling. In tunneling, a surgeon uses special tools to tunnel under the skin and through the muscle, for example, up through the neck to access the Vagus nerve or the deep brain. In both techniques, it is very important that the lead wires and their associated electrodes at the distal TIPs be very small. The present invention solves these issues by using very novel miniature coaxial or rectilinear capacitors that have been adapted with an inductance element to provide a parallel TANK circuit. Prior art capacitors are well known and consist of ceramic discoidal feedthrough capacitors and also single layer and multilayer tubular capacitors and multilayer rectangular capacitors, and thick-film deposited capacitors. The present invention shows design methodologies to adapt all of these previous tubular, feedthrough or rectangular technologies to incorporate a parallel inductor in novel ways. It will be obvious to those skilled in the art that a number of other capacitor technologies can be adapted to the present invention. This includes film capacitors, glass capacitors, tantalum capacitors, electrolytic capacitors, stacked film capacitors and the like.

As previously mentioned, the value of the capacitance and the associated parallel inductor can be adjusted to achieve a specific resonant frequency (SRF). The novel TANK filters described herein can be adapted to a number of locations within the overall implantable medical device system. That is, the novel TANK filter can be incorporated at or near any part of the medical device lead wire system or the distal TIP. In addition, the novel TANK filter can be placed anywhere along the lead wire system. In another embodiment, the TANK filter can actually be placed inside the active implantable medical device.

The present invention which resides in novel coaxial or rectilinear TANK filters is also designed to work in concert with the EMI filter which is typically used at the point of lead wire ingress and egress of the active implantable medical device. For example, see U.S. Pat. No. 6,999,818 filed Apr. 15, 2004, entitled INDUCTOR CAPACITOR EMI FILTER FOR HUMAN IMPLANT APPLICATIONS; U.S. patent application Ser. No. 11/097,999 filed Mar. 31, 2005, entitled APPARATUS AND PROCESS FOR REDUCING THE SUSCEPTIBILITY OF ACTIVE IMPLANTABLE MEDICAL DEVICES TO MEDICAL PROCEDURES SUCH AS MAGNETIC RESONANCE IMAGING; U.S. patent application Ser. No. 11/163,915 filed Nov. 3, 2005, entitled PROCESS FOR TUNING AN EMI FILTER TO REDUCE THE AMOUNT OF HEAT GENERATED IN IMPLANTED LEAD WIRES DURING MEDICAL PROCEDURES SUCH AS MAGNETIC RESONANCE IMAGING; and U.S. Patent Application No. 60/767,484 filed Apr. 3, 2006, entitled LOW LOSS BAND PASS FILTER FOR RF DISTANCE TELEMETRY PIN ANTENNAS OF ACTIVE IMPANTABLE MEDICAL DEVICES; the contents of all being incorporated herein by reference. All four of these documents describe novel inductor capacitor combinations for low pass EMI filter circuits. It is of particular interest that by increasing the number of circuit elements of the passive low pass filter at the AIMD hermetic feedthrough, one can reduce the overall capacitance value of said filter which primarily defines the input impedance of the AIMD. It is important to reduce the capacitance value to raise the input impedance of the AIMD. Increasing the input impedance of the AIMD will reduce the amount of current that would flow in lead wire systems at high frequencies such as those associated with the RF pulsed frequencies of MRI equipment. Accordingly, it is a feature of the present invention that the novel TANK filters are designed to be used in concert with prior art low pass filters.

The present invention is also applicable to probes and catheters. For example, ablation probes are used to selectively cauterize or burn tissue on the outside or inside of the heart to control erratic pulses from the sinus node or the outside of the A-V node. These procedures are best performed during real time MRI imaging. However, a major concern is the overheating of the distal TIP at inappropriate times because of the induced currents from the MRI system. It will be obvious to one skilled in the art that the novel TANK filters of the present invention can be adapted to any probe, TIP or catheter that is used in or on the human body.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 8 is a diagram of a unipolar active implantable medical device;

FIG. 9 is a diagram similar to FIG. 8, illustrating a bipolar AIMD system;

FIG. 10 is a diagram similar to FIGS. 8 and 9, illustrating a bipolar lead wire system with a distal TIP and RING, typically used in a cardiac pacemaker;

FIG. 11 is a schematic diagram showing a parallel combination of an inductor L and a capacitor C forming the TANK filter of the present invention placed in the lead wire systems of FIGS. 8-10;

FIG. 12 is a chart illustrating calculation of frequency of resonance for the parallel TANK of FIG. 11;

FIG. 14 is an equation for the impedance $Z_{ab}$ of an inductor in parallel with a capacitor;

FIG. 15 is a chart illustrating impedance equations for the inductive reactance ($X_L$) and the capacitive reactance ($X_C$) of the parallel TANK circuit in FIG. 11;

FIG. 74 is a sectional view taken generally along the line 74-74 of FIG. 73;

FIG. 75 is a sectional view taken generally along the line 75-75 of FIG. 72;

FIG. 76 is a sectional view similar to FIGS. 74 and 75, illustrating another possible arrangement of a number of parallel inductor spirals within the tubular capacitor;

FIG. 77 is an equation for inductors in parallel;

FIG. 84 is a chart showing the total inductance equation for three parallel inductors;

FIG. 85 is a perspective view of the prior art MLCC of FIG. 78 showing an exemplary inductor circuit trace applied to an upper surface thereof;

FIG. 86 is a schematic diagram of the MLCC-T of FIG. 85;

FIG. 110 is an electrical schematic diagram for the MLCC-T structure of FIG. 107;

FIG. 111 is a perspective view of an alternative embodiment MLCC-T wherein a single inductor chip is placed across a specially formed MLCC chip capacitor;

FIG. 112 is a perspective view of a first set of electrode plates forming the capacitor of the structure in FIG. 111;

FIG. 113 is a perspective view of a second set of electrode plates incorporated into the capacitor of the MLCC-T structure shown in FIG. 111;

FIG. 114 is an electrical schematic diagram for the MLCC-T structure of FIG. 111;

FIG. 119 illustrates a method of using an abrasive microblaster or laser trimmer to erode electrode plates in order to tune the resonant frequency of the tank;

FIG. 120 illustrates eroding away a portion of one of the electrode sets from the capacitor of FIG. 119 taken generally along the line of 120-120;

FIG. 121 illustrates eroding one of the opposite electrode plate sets taken from FIG. 119 taken generally along the line of 121-121;

FIG. 122 is a methodology of trimming any of the inductors of the tank of the present invention, by adding an electrical conductive material to short adjacent turns;

FIG. 123 is an alternate methodology of actually tuning the inductor by increasing its inductor value, by removing short circuits across turns by laser trimming and the like;

FIG. 124 is a close up view taken generally from the area 124-124 from FIG. 123, illustrating laser ablation to open up turns of the inductor;

FIG. 125 is a sectional view of a novel hermetically sealed unipolar feedthrough capacitor-inductor TANK filter embodying the present invention;

FIG. 126 is a sectional view similar to FIG. 125, illustrating an alternative embodiment for a hermetically sealed TANK filter assembly;

FIG. 127 is an electrical schematic illustration for the TANK filter of FIGS. 125 and 126;

FIG. 128 is a sectional and partially exploded view of yet another hermetically sealed package containing the novel inductor-capacitor MLCC-T embodying the present invention;

FIG. 129 is a perspective view of a distal electrode pad applicable to a wide variety of neurostimulator applications;

FIG. 130 is a sectional view taken generally along the line 130-130 of FIG. 129;

Figure 2:
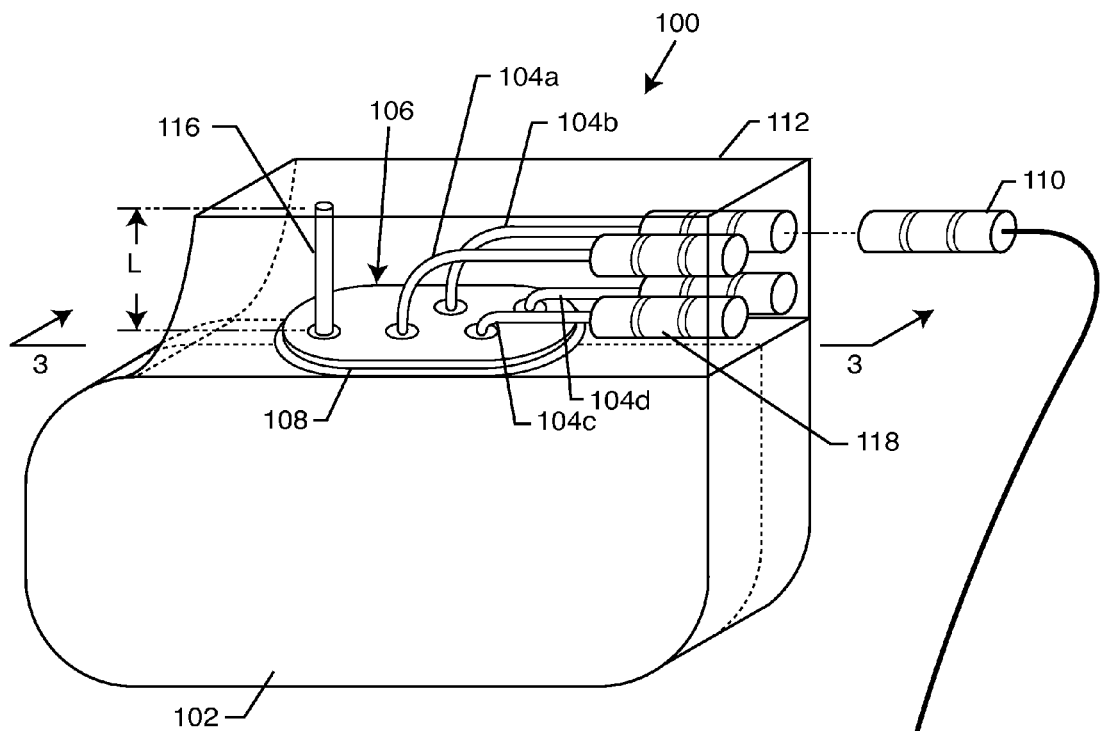
FIG. 2 is a perspective and somewhat schematic view of a prior art active implantable medical device (AIMD) including a lead wire directed to the heart of a patient.
Figure 3:
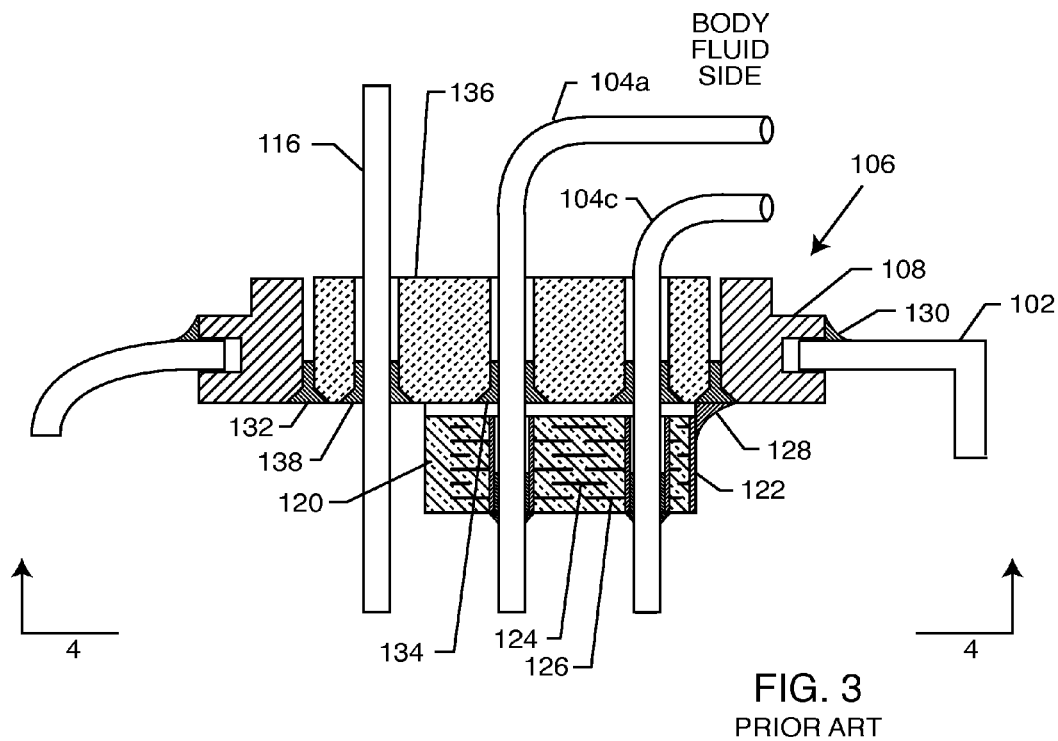
FIG. 3 is an enlarged sectional view taken generally along the line 3-3 of FIG. 2.
Figure 129:
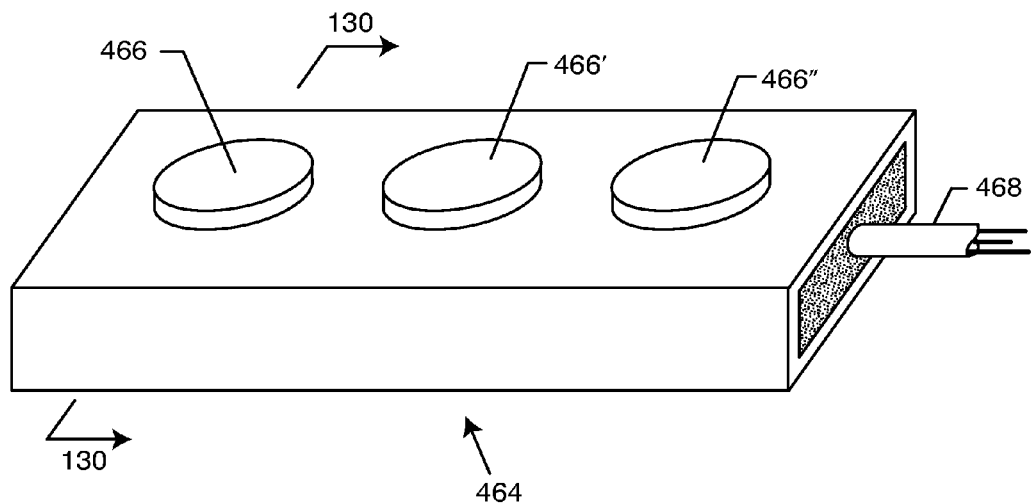
Figure 130:
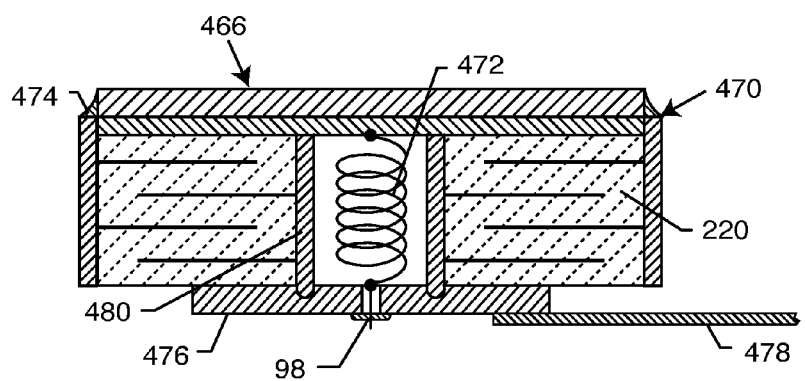
Figure 131:
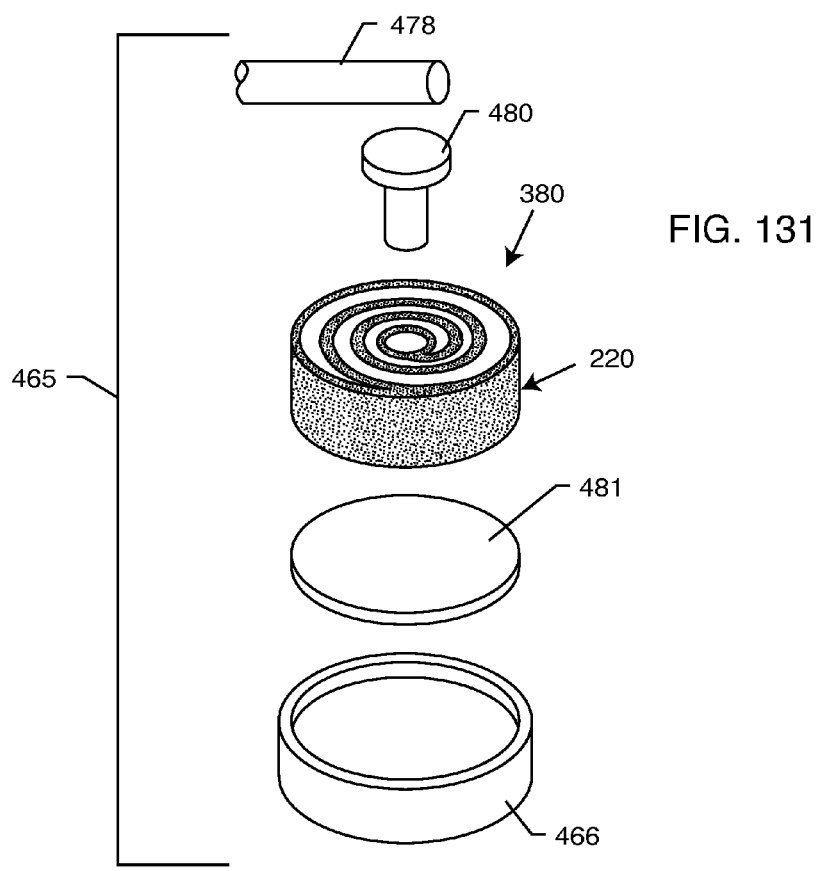
Figure 132:
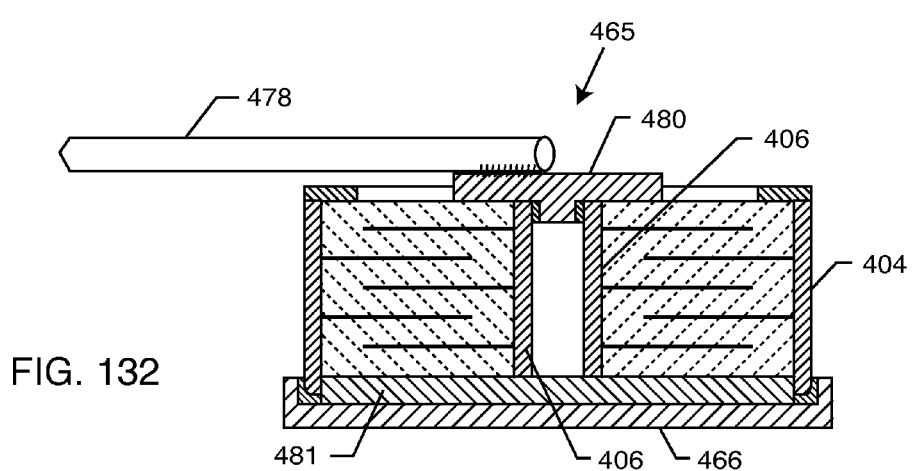
Figure 133:
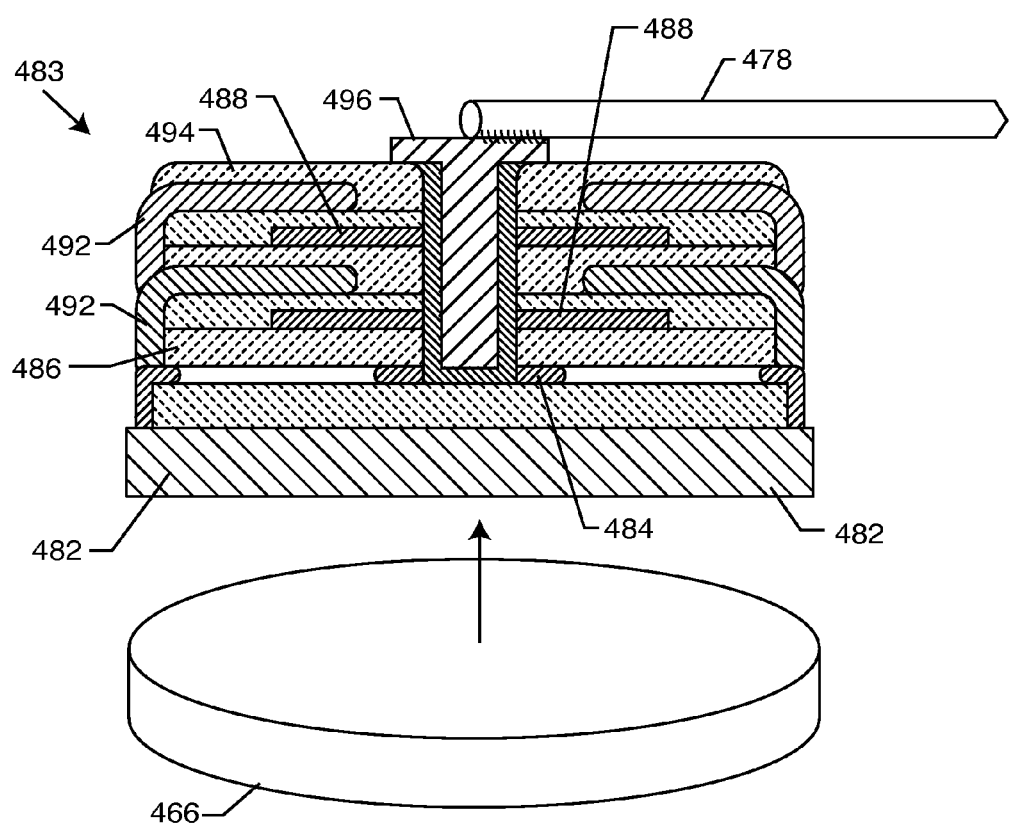
Figure 134:
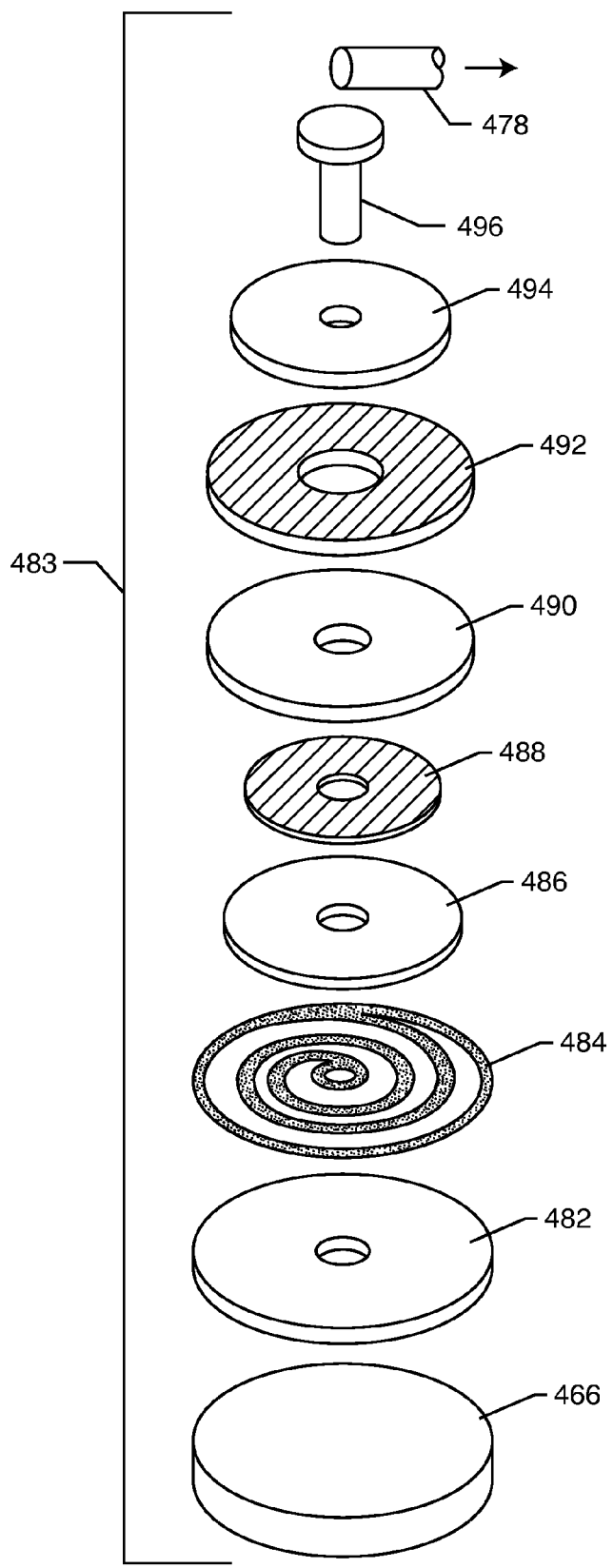
Figure 138:
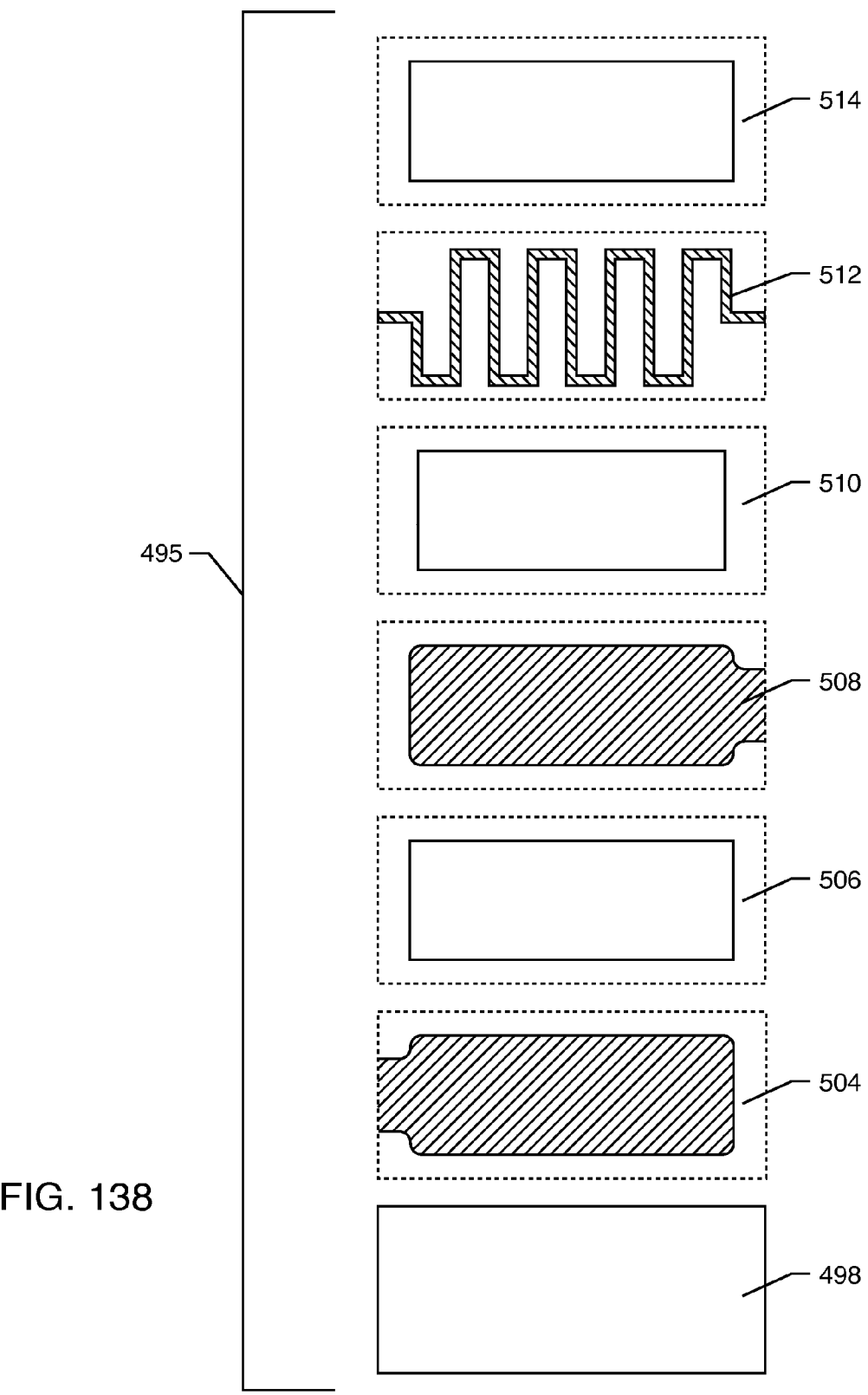
Figures 142, 143, 144:
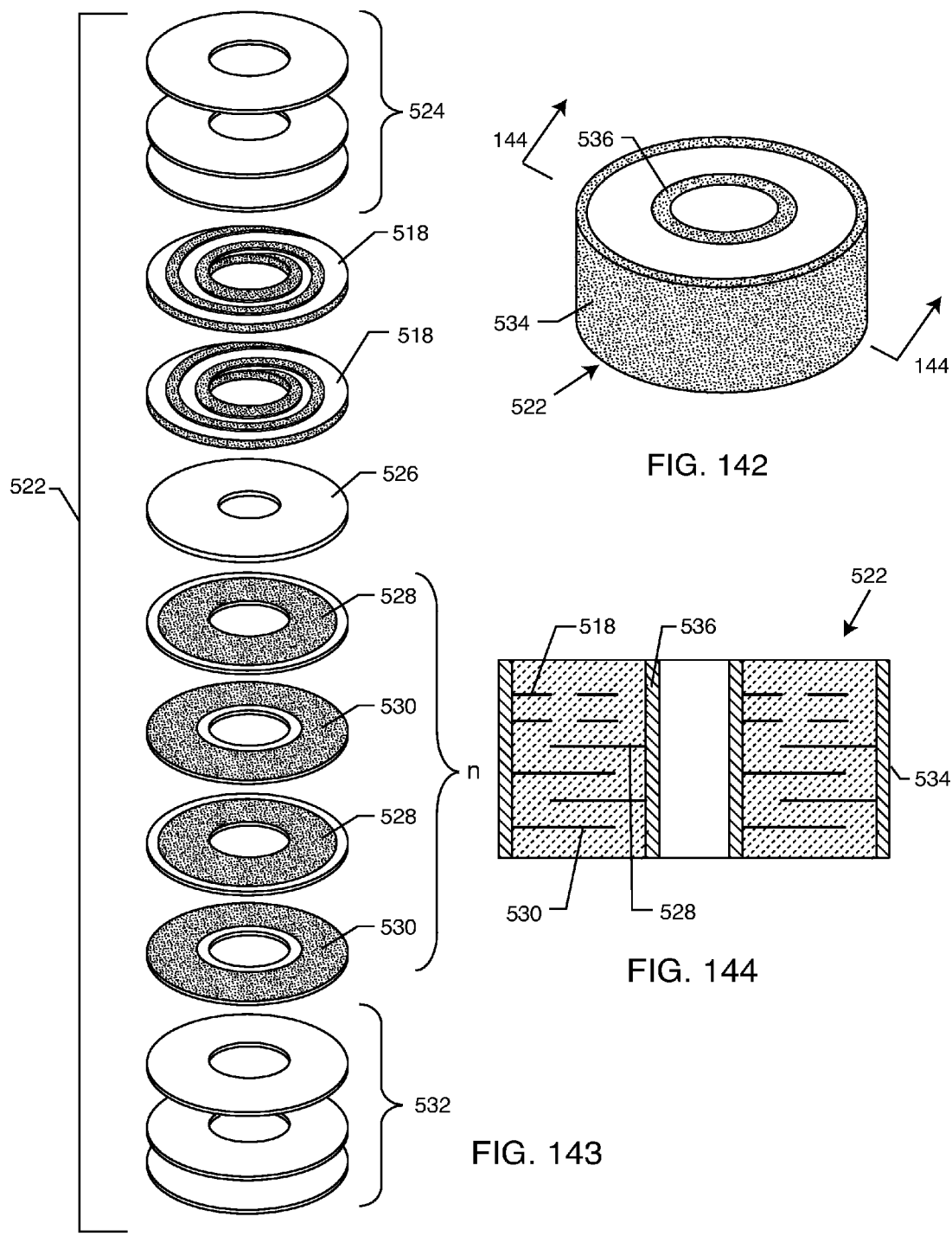
Figure 145:
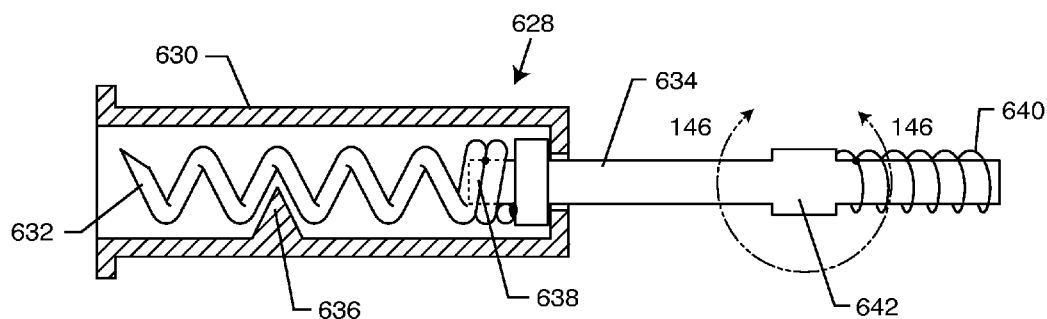
Figure 146:
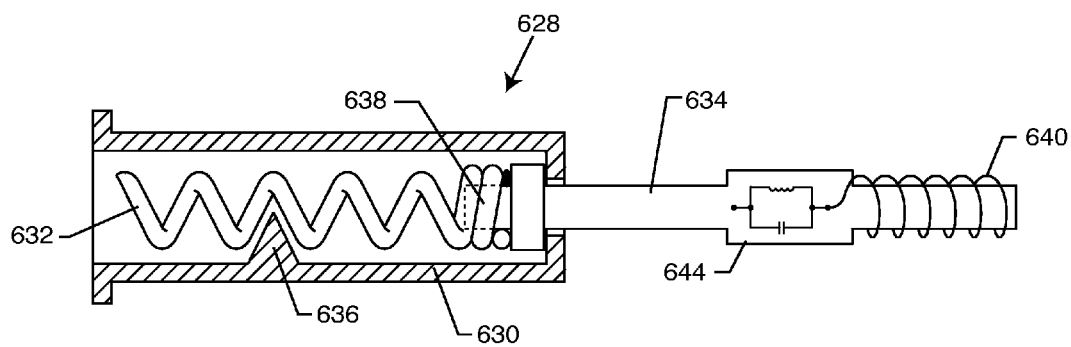
Figure 147:
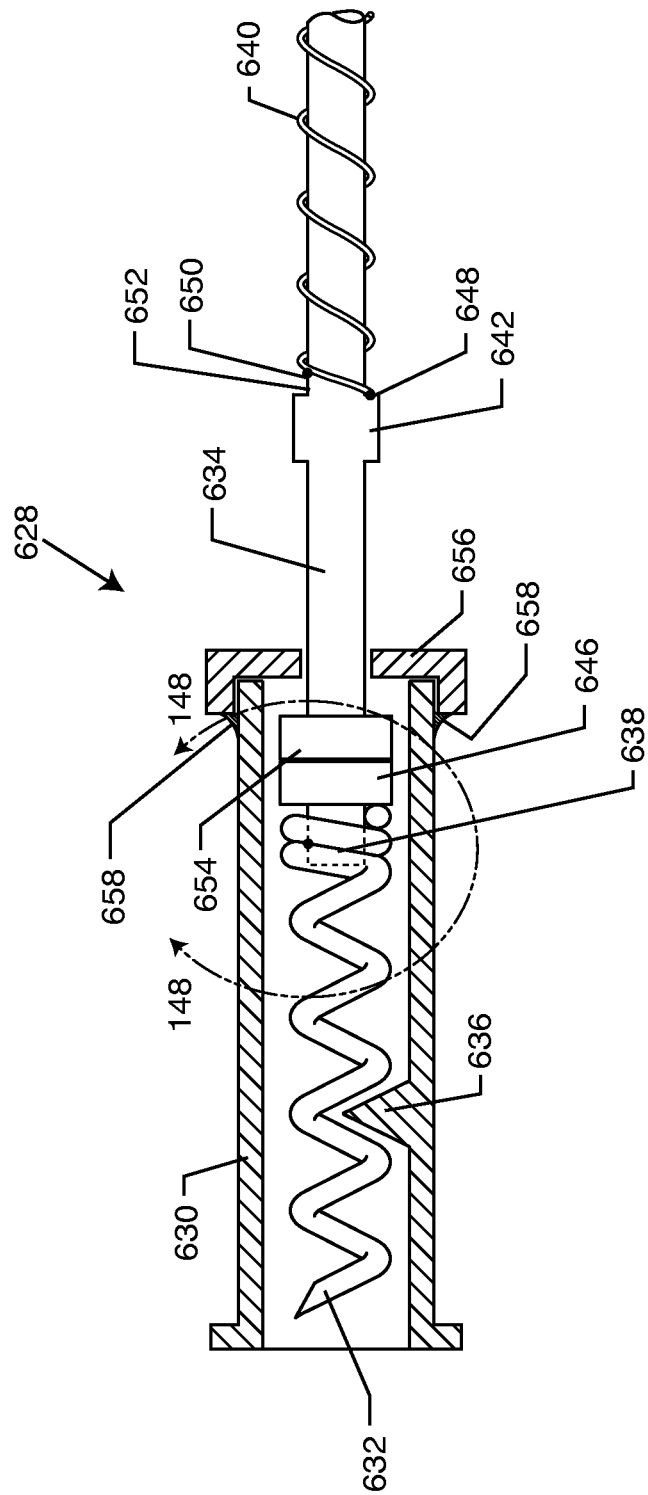
Figure 148:
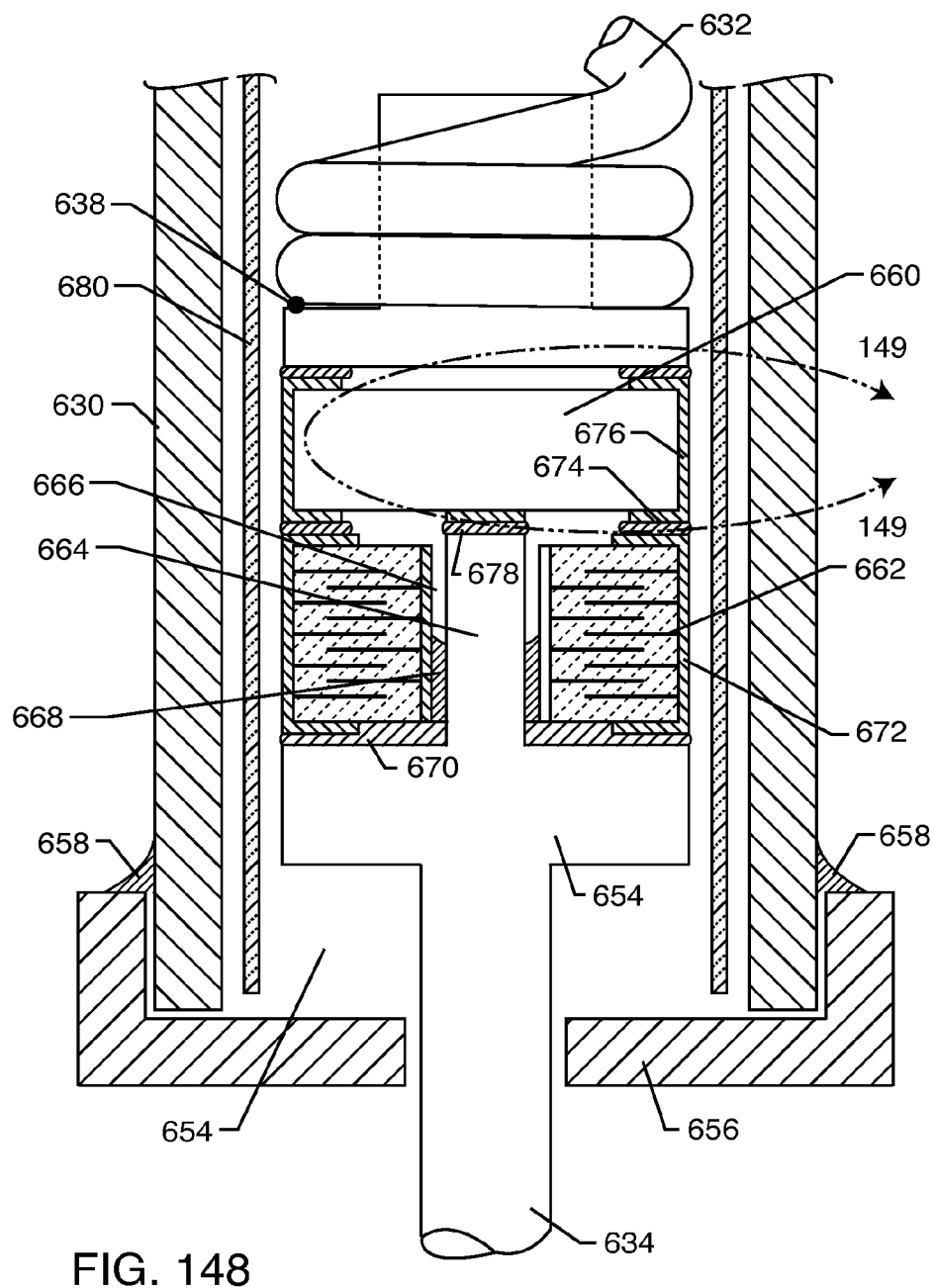
Figure 149:
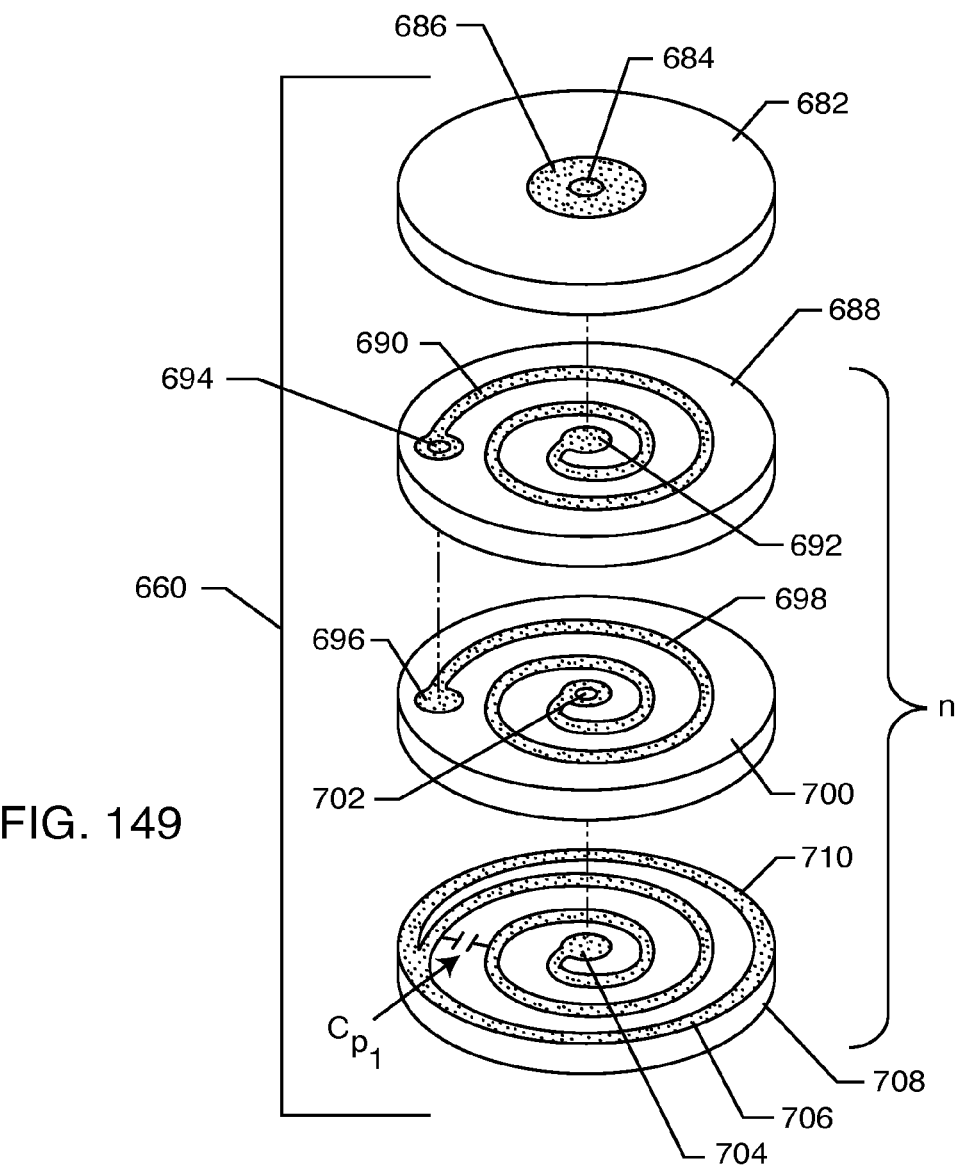
Figure 149A:
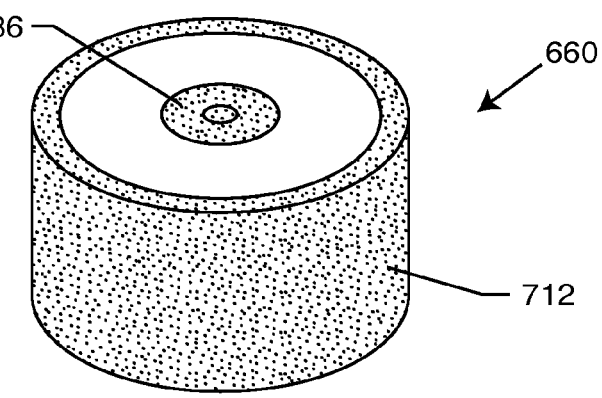
Figure 150:
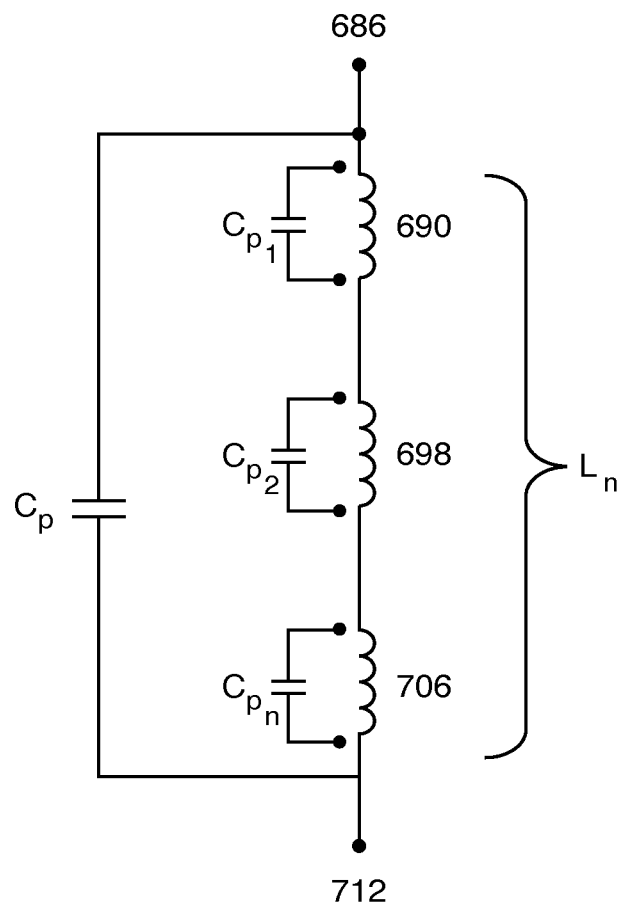
Figure 151:
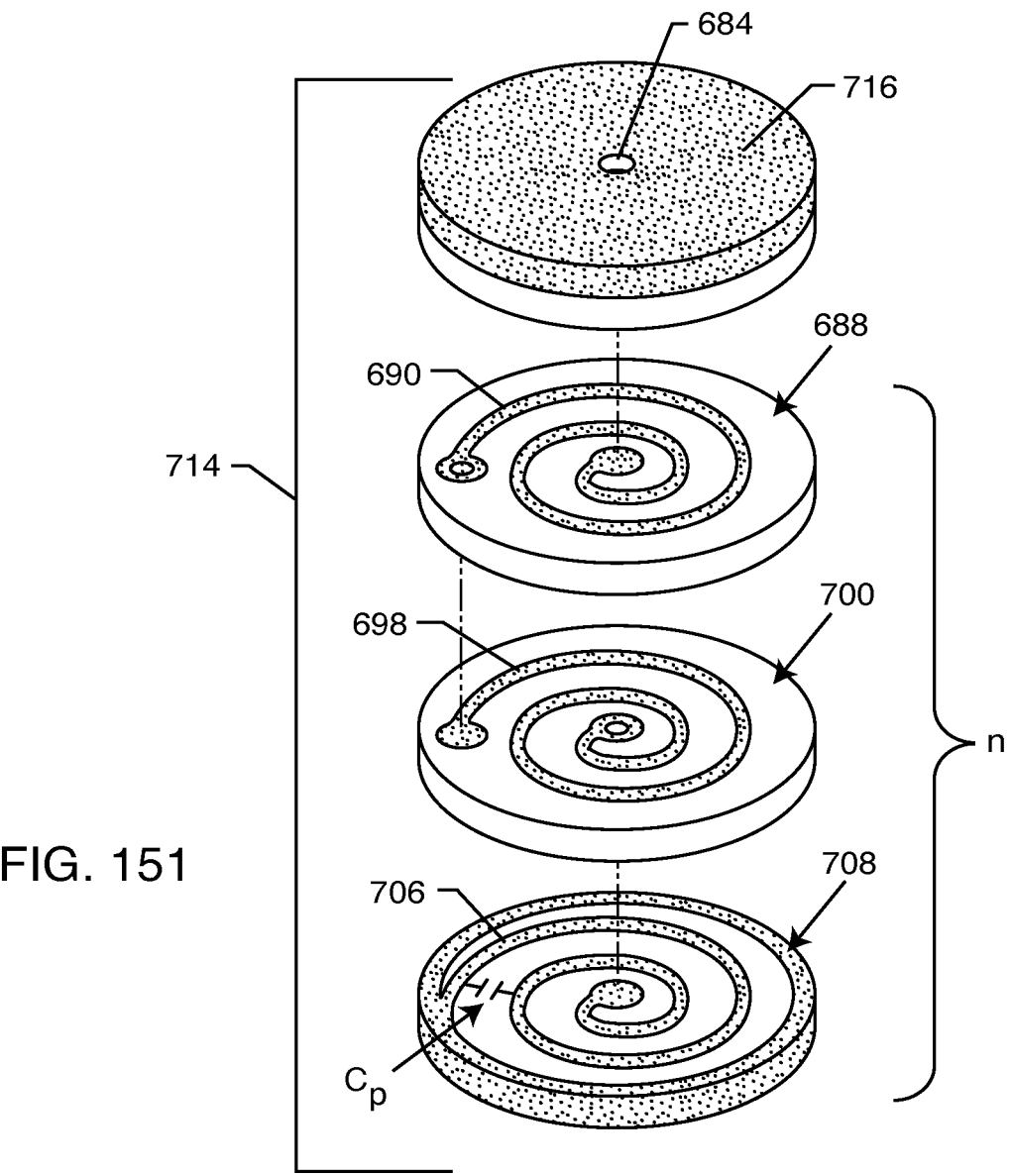
Figure 151A:
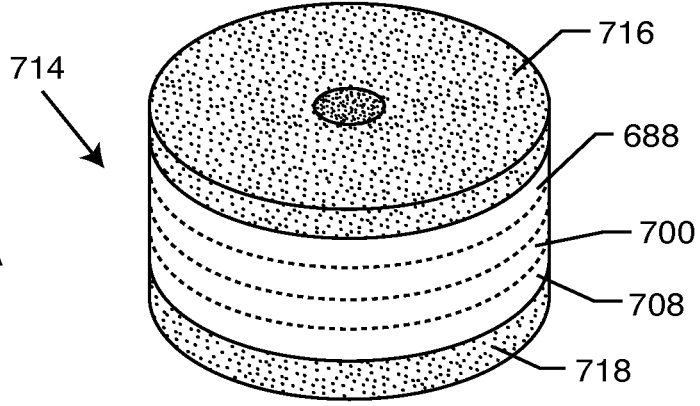
Figure 152:
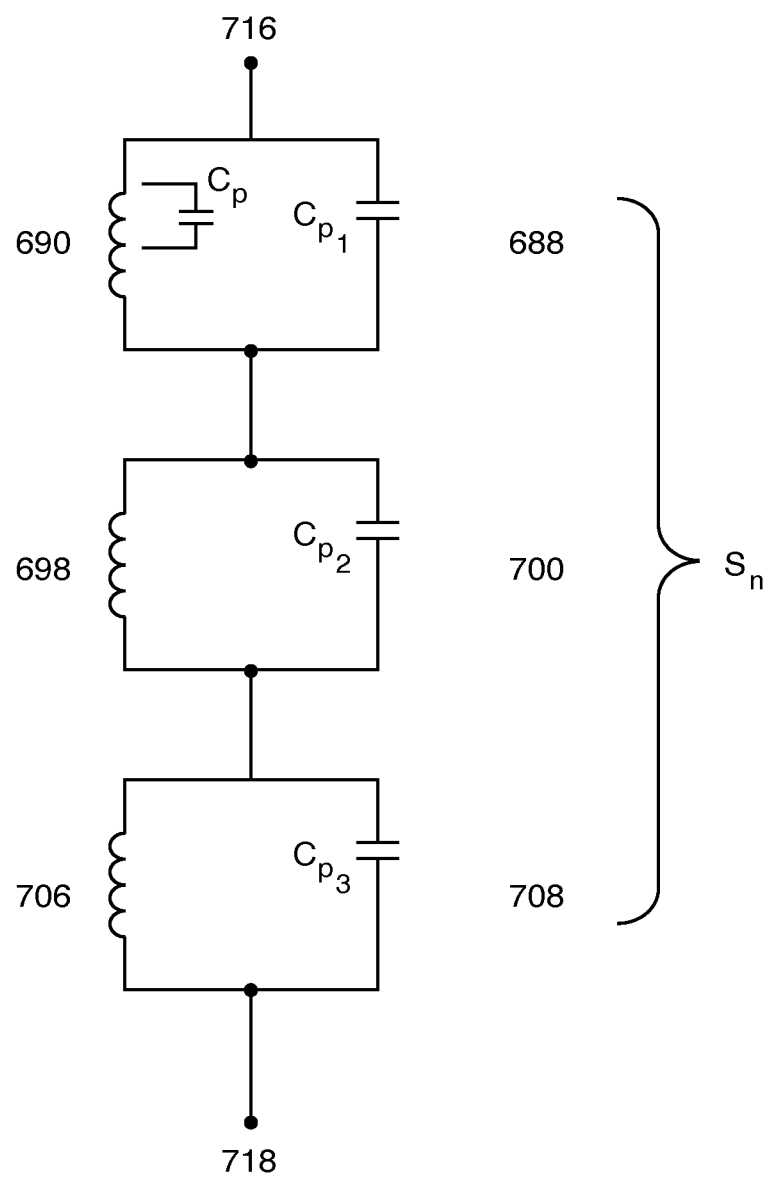
Figure 153:
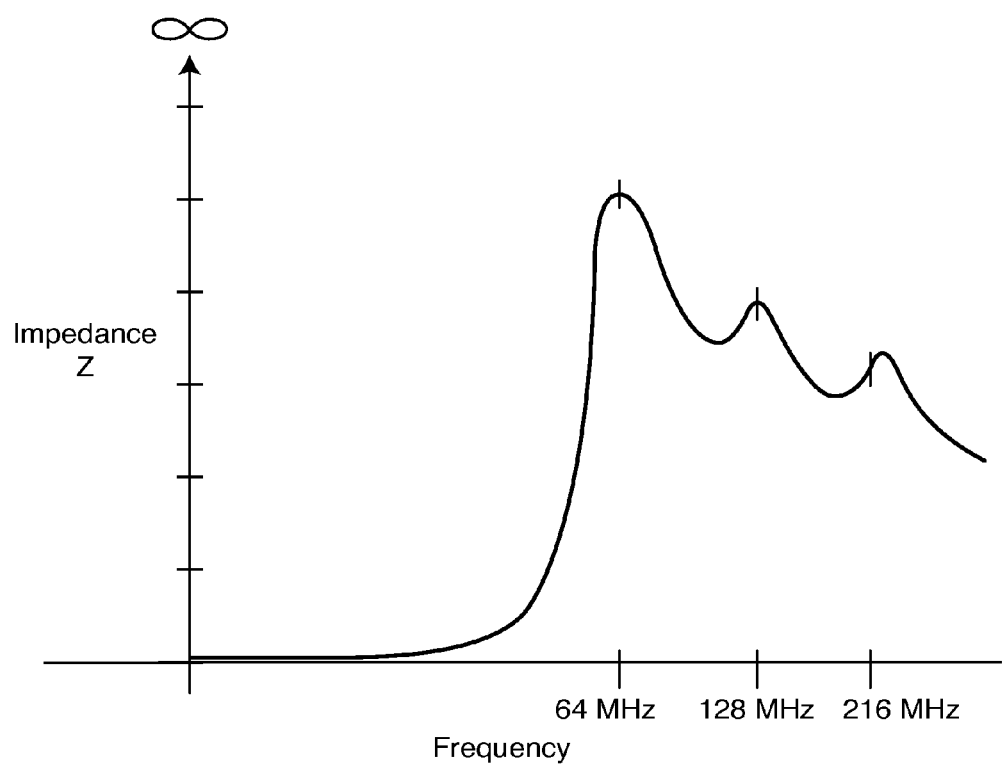
Figure 154:
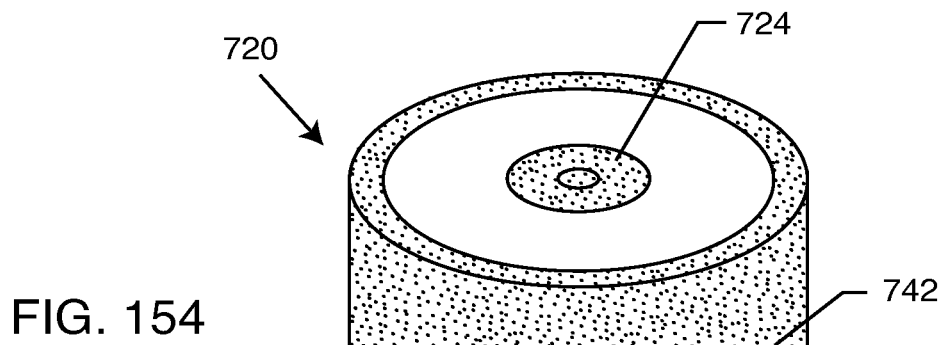
Figure 155:
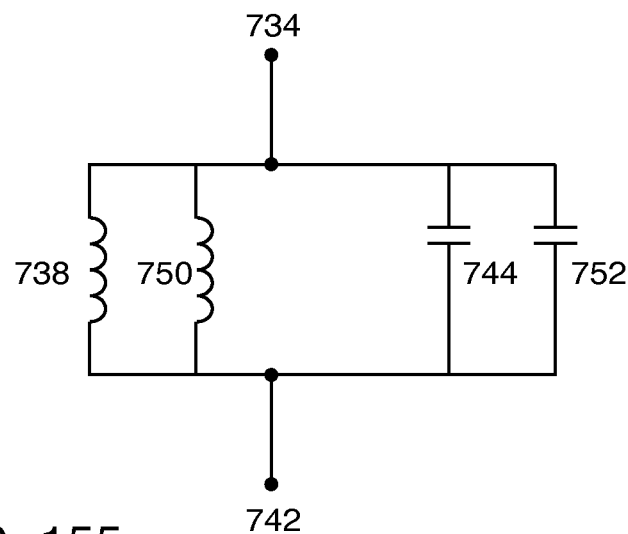
Figure 156:
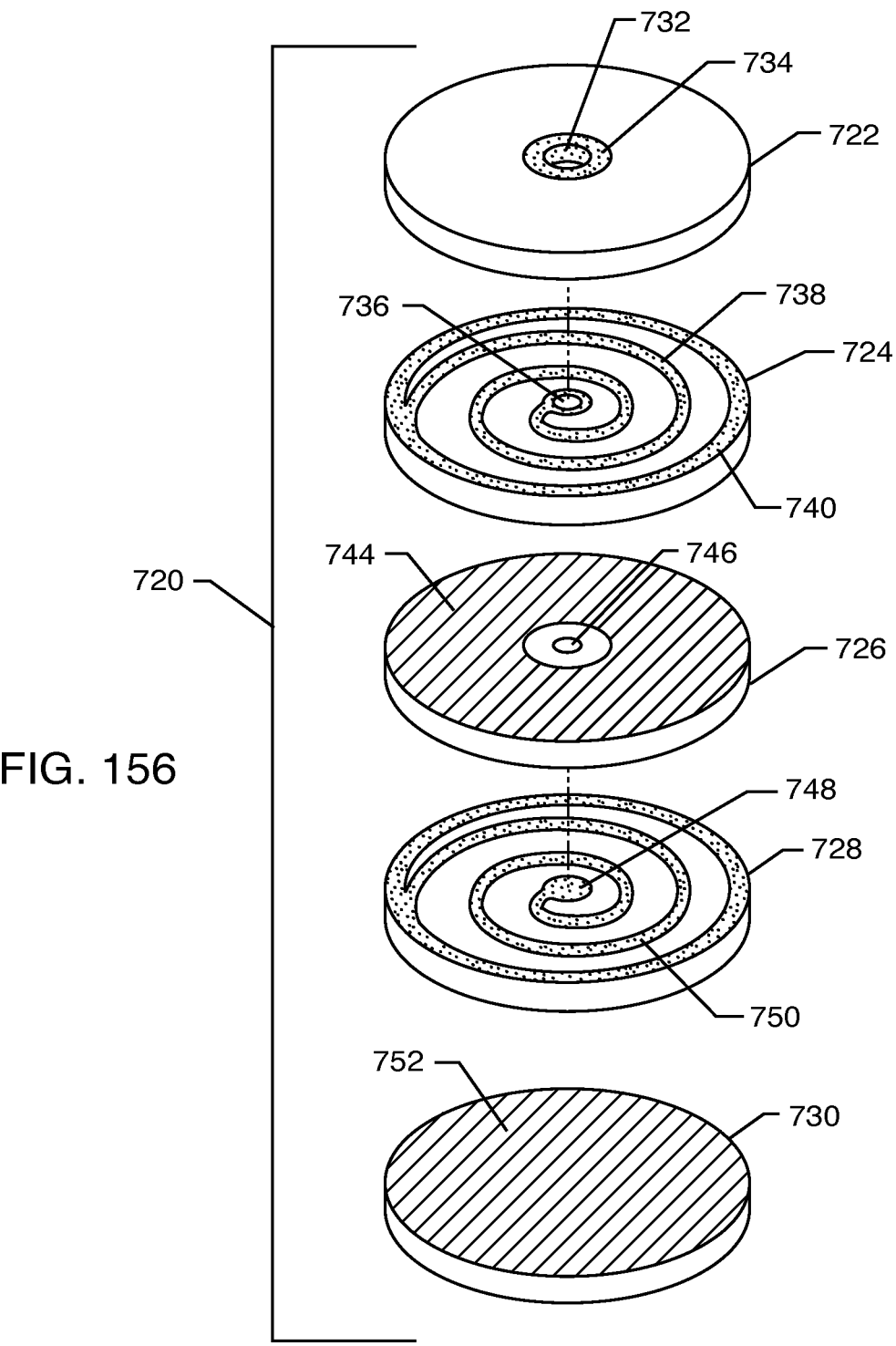
Figures 157, 157A:
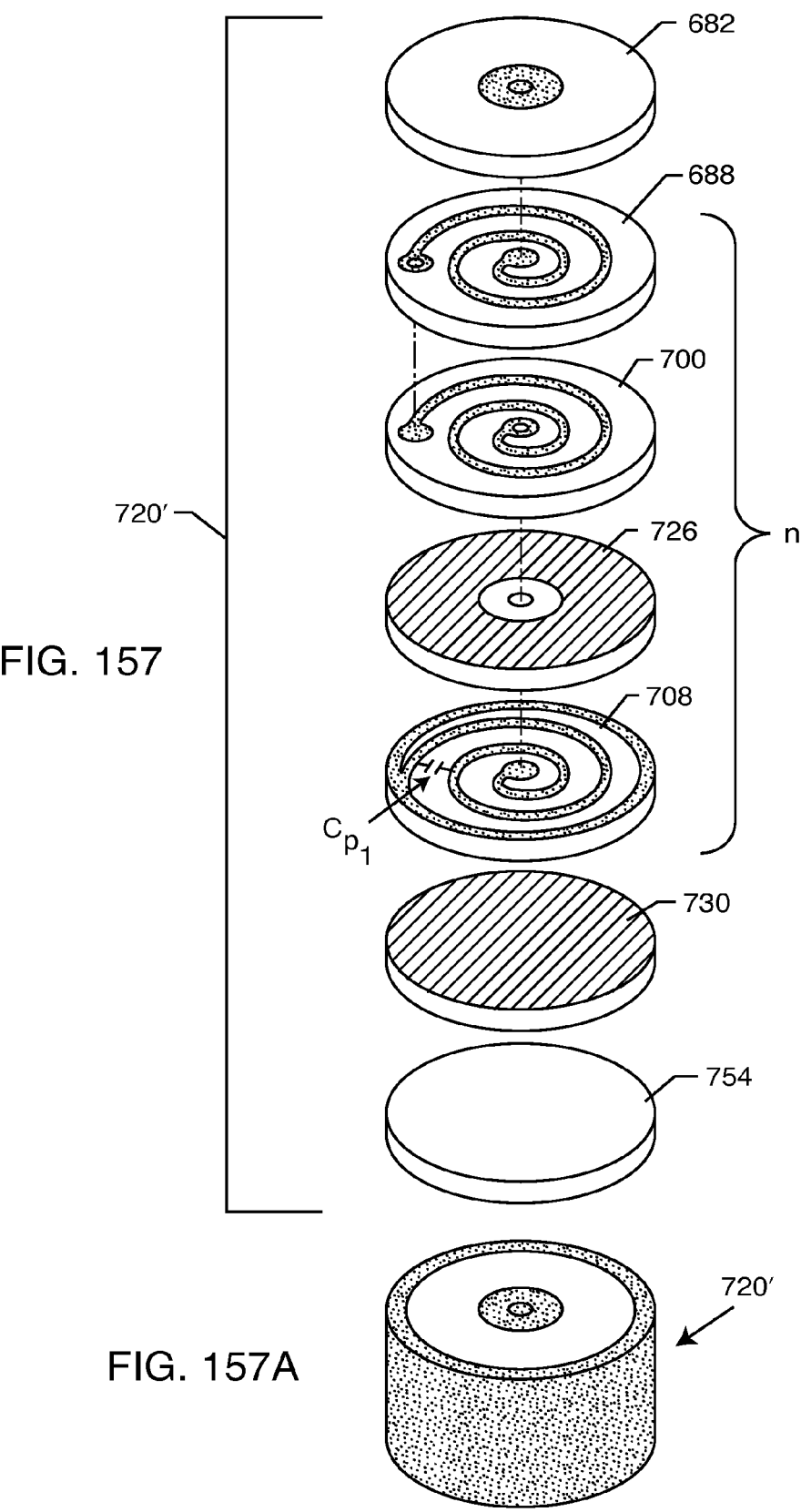
Figure 158:
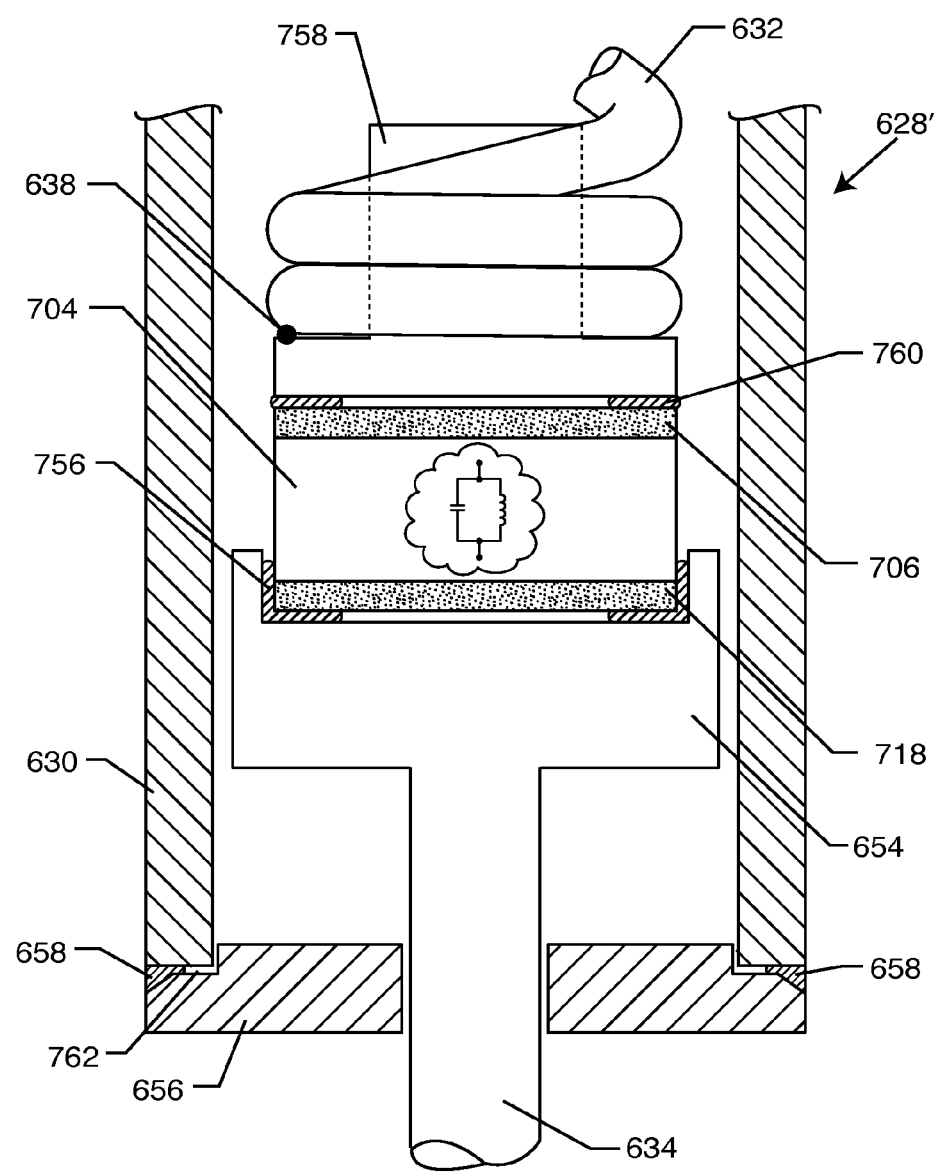
Figure 159:
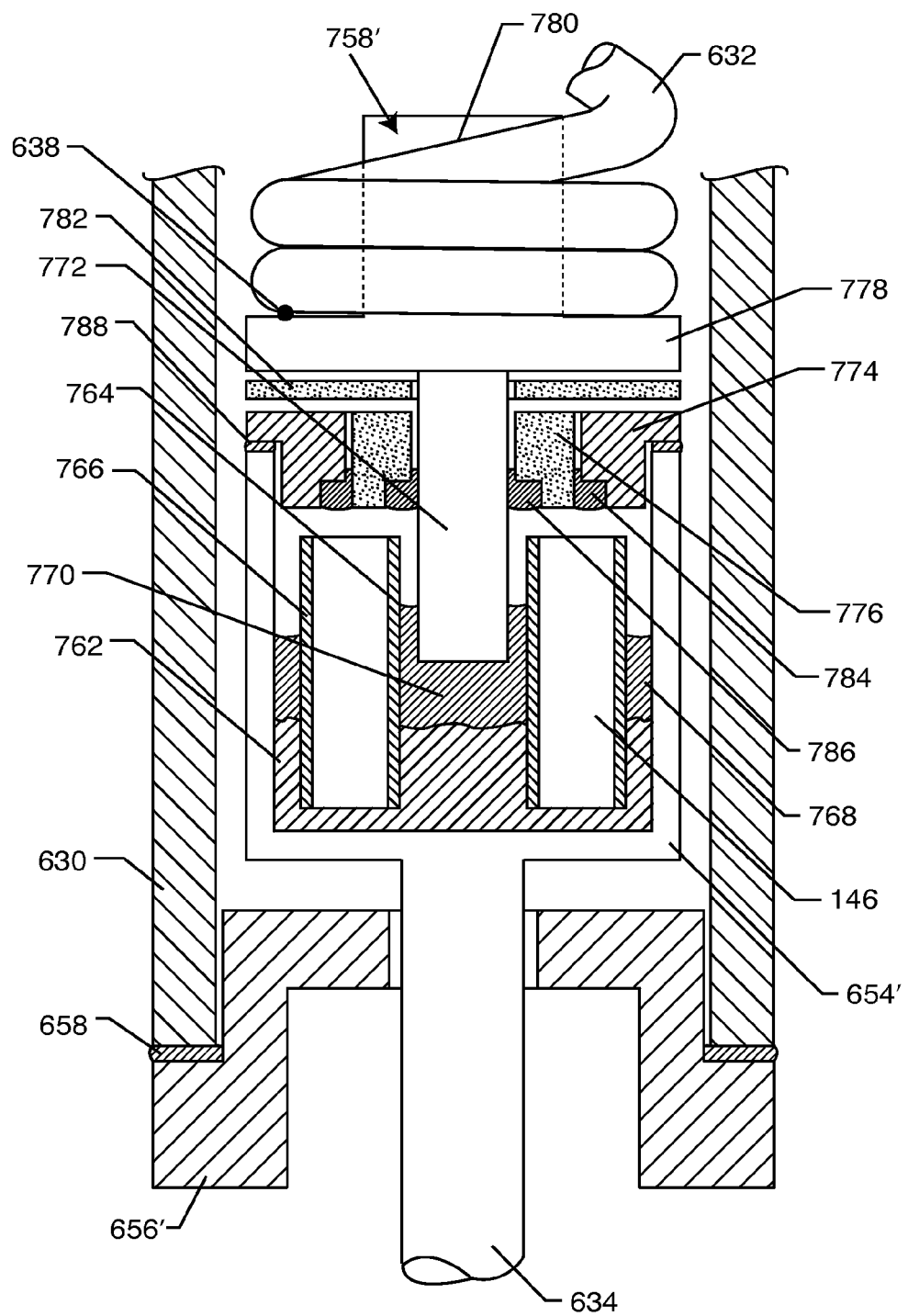
Figure 160:
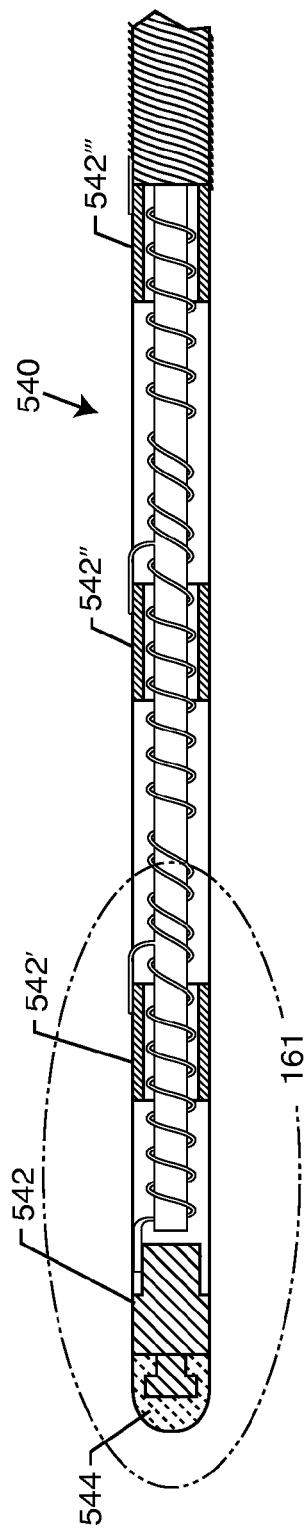
Figure 161:
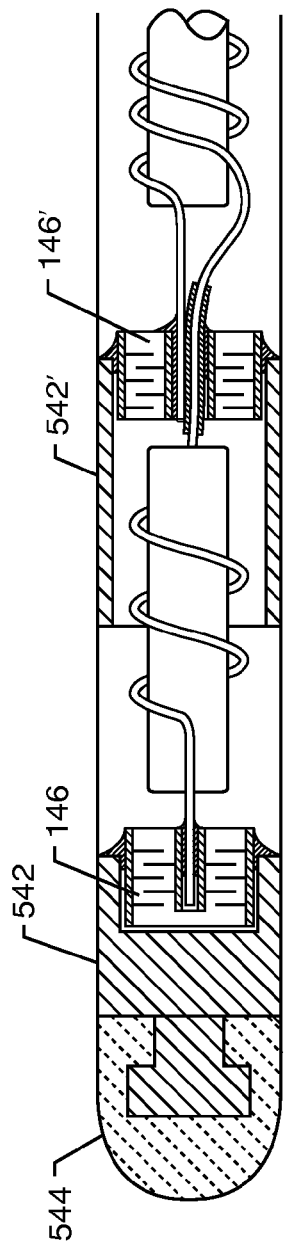
Figure 162:
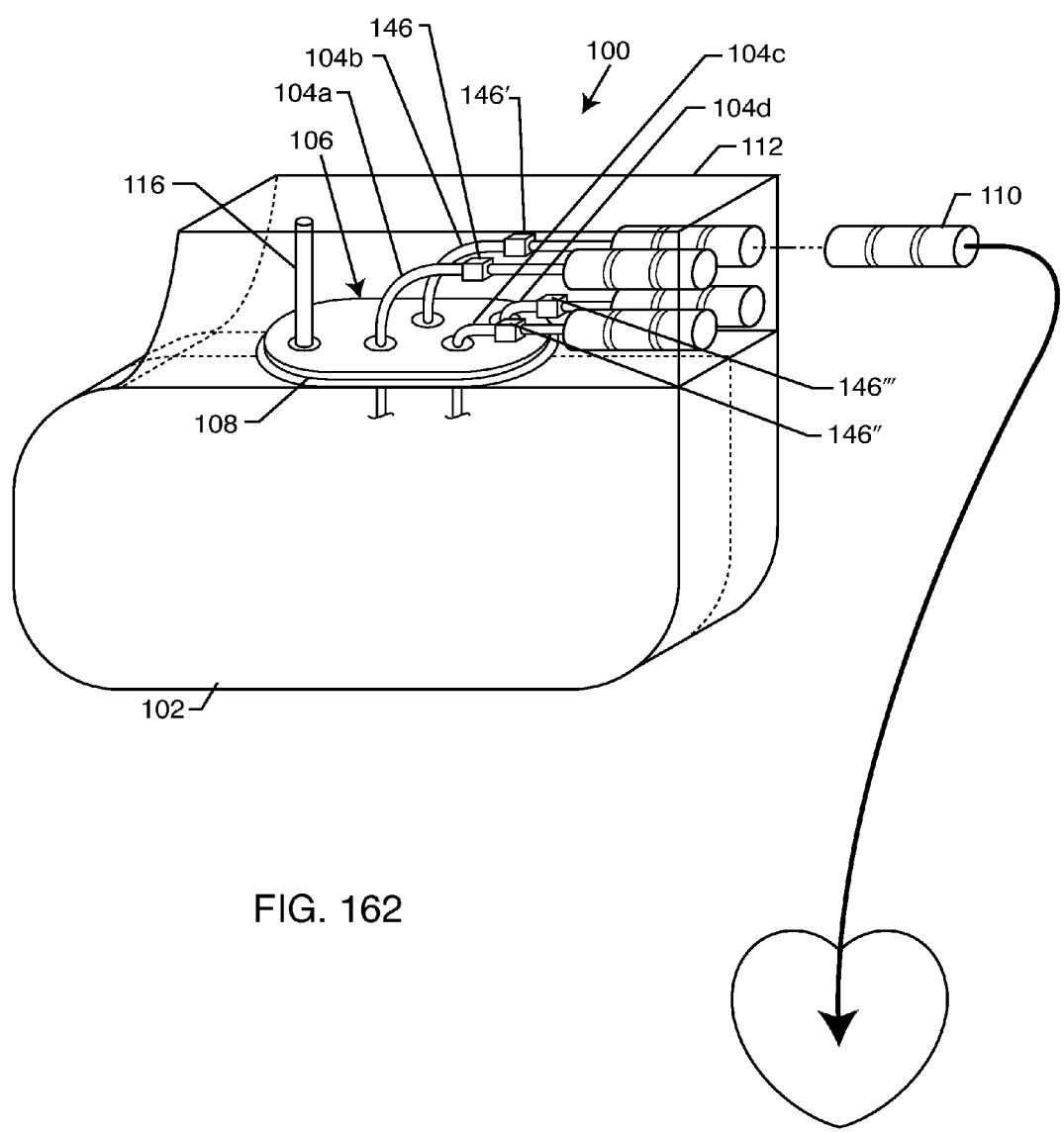
Figure 163:
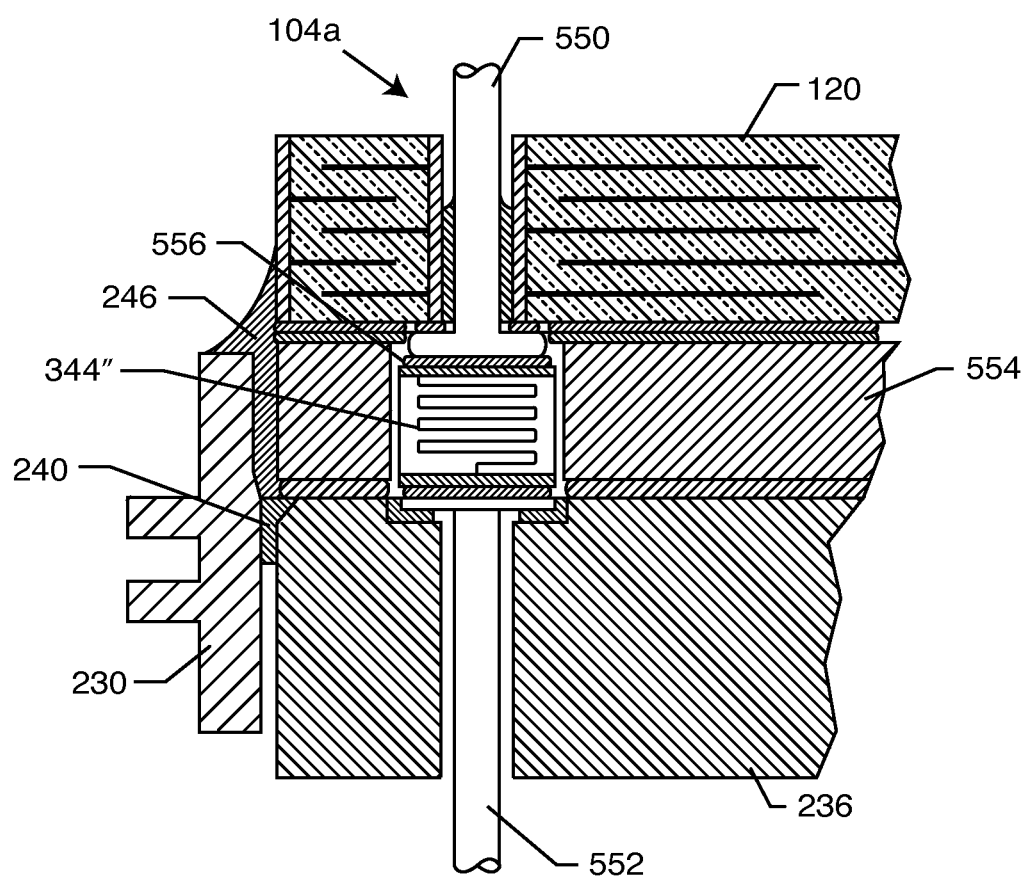
Figure 164:
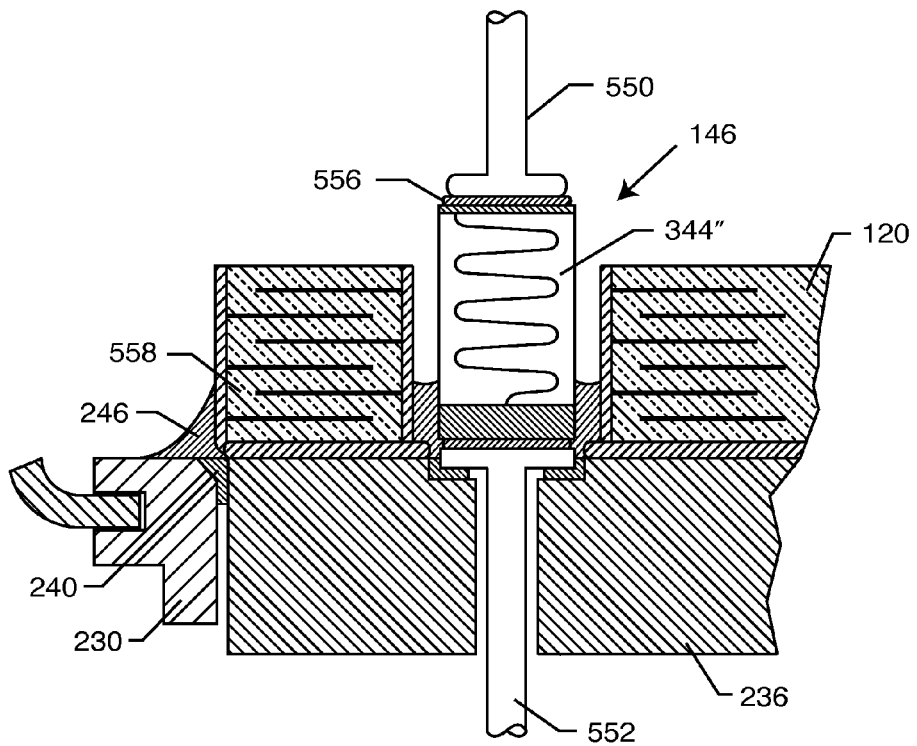
Figure 165:
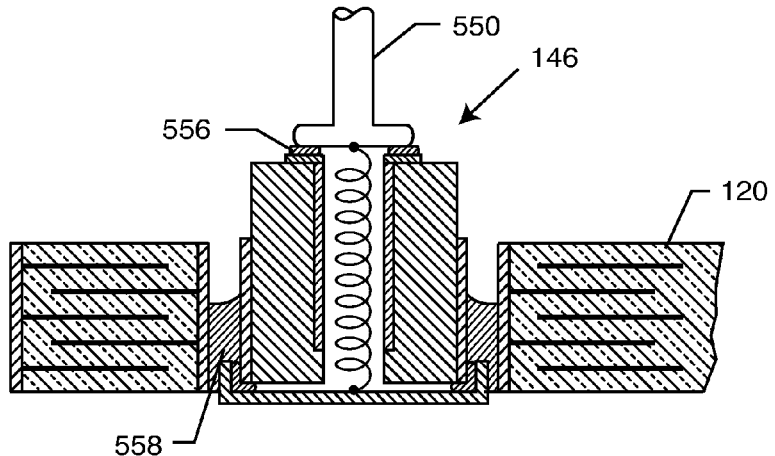
Figure 166:
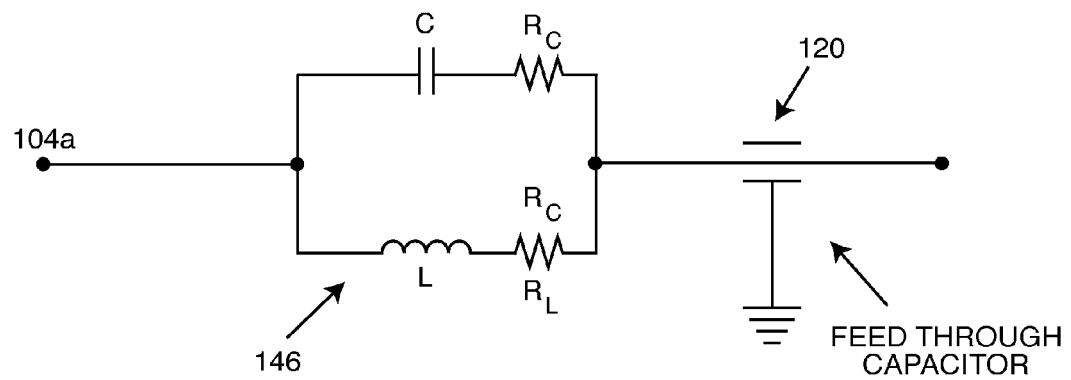

FIG. 131 is an exploded perspective view of an alternative structure accomplishing the same filtering result as the structure shown in FIGS. 129 and 130;

FIG. 132 is a vertical sectional view of the components illustrated in FIG. 131, in their assembled configuration;

FIG. 133 is a sectional view similar to FIG. 132, illustrating another alternative for building up the novel parallel inductor TANK filter for neurostimulator applications;

FIG. 134 is an exploded perspective view of the components of the structure shown in FIG. 133;

FIG. 135 is a table illustrating various fabrication methods for manufacturing a thick film TANK circuit;

FIG. 136 is a perspective view of an alternative rectilinear construction for a thick film deposited TANK filter embodying the present invention;

FIG. 137 is an electrical schematic diagram of a neurostimulator electrodes shown in FIGS. 130, 132, 133 and 136;

FIG. 138 is an exploded view of the neurostimulator electrode of FIG. 136, showing how the various layers of the novel distal TIP TANK circuit are laid down;

FIG. 139 is a perspective view of the novel inductor TANK filter shown in FIG. 136, which has been hermetically sealed by a glass seal or biocompatible polymer overlay;

FIG. 140 is a perspective representation illustrating how a glass seal or biocompatible polymer similar to that shown in FIG. 139 may be used to hermetically seal other types of TANK filters of the present invention;

FIG. 141 is an exploded perspective view of a prior art feedthrough capacitor and a co-bonded inductor spiral substrate which is adhered to the capacitor;

FIG. 142 is a perspective view of a composite unipolar MLCC-T feedthrough in accordance with the present invention;

FIG. 143 is an exploded perspective view of the various layers comprising the MLCC-T of FIG. 142;

FIG. 144 is a sectional view taken generally along the line 144-144 of FIG. 142;

FIG. 145 is a sectional view of a prior art active fixation distal TIP;

FIG. 146 is taken along the line 146-146 from FIG. 145 incorporating the tank circuit of the present invention;

FIG. 147 is a cross-section of an active fixation TIP similar to FIG. 145 except that a tank filter of the present invention has been added inside;

FIG. 148 is a cross-section taken generally from line 148-148 from FIG. 147 illustrating the tank filter of the present invention inside an active fixation distal TIP;

FIG. 149 is taken generally from section 149-149 from FIG. 148 and illustrates a novel series inductor which is highly volumetrically efficient;

FIG. 149A is an isometric view of the complete structure shown in FIG. 149;

FIG. 150 is the schematic diagram for the inductor of FIGS. 149 and 149A;

FIG. 151 is an exploded assembly view illustrating an alternative embodiment of the inductor capacitor tank previously illustrated in FIG. 148;

FIG. 151A is an isometric view of the completed structure shown in FIG. 151;

FIG. 152 is the schematic diagram of the novel tank filter chip previously illustrated in FIGS. 151 and 151A;

FIG. 153 illustrates the impedance vs. frequency curves for the novel tank filter previously illustrated in FIGS. 151 and 151A;

FIG. 154 is an isometric view of a novel composite tank filter of the present invention which could also be placed into the active fixation TIP previously illustrated in FIGS. 147 and 148;

FIG. 155 is the schematic diagram of the novel tank filter previously illustrated in FIG. 154;

FIG. 156 is an exploded view of the internal layers of the novel tank shown in FIG. 154;

FIG. 157 is an exploded view of an alternative embodiment of the novel MLCC tank previously illustrated in FIGS. 154 and 156;

FIG. 157A is an isometric view showing the completed tank filter from FIG. 157;

FIG. 158 is a sectional view of an active fixation distal TIP embodying the novel tank filters previously illustrated in FIGS. 154 and 157A;

FIG. 159 is a sectional view of an active fixation TIP employing tubular capacitor tank filters of the present invention;

FIG. 160 is a fragmented sectional view of a prior art neurostimulation electrode probe;

FIG. 161 is an enlarged sectional view of the area 161 in FIG. 160, illustrating modifications to the prior art structure to incorporate the novel MLCC-T TANK filter of the present invention;

FIG. 162 is a view similar to FIG. 2, but illustrating how the TANK filters of the present invention may be incorporated at the point of lead wire ingress and at other strategic locations inside the circuitry of the active implantable medical device;

FIG. 163 is a fragmented sectional view of the prior art broadband low pass feedthrough capacitor of FIG. 3, illustrating how an MLCC-T in accordance with the present invention is incorporated therein;

FIG. 164 is a sectional view illustrating an alternative method for installing MLCC-T TANK filters in series with a prior art broadband feedthrough capacitor;

FIG. 165 illustrates how tank filters that have been previously described in FIGS. 35, 37, 42, and 68-76 could all be used in combination with a prior art feedthrough capacitor;

FIG. 166 is an electrical schematic illustration for the MLCC-T TANK filters shown in FIGS. 163, 164 and 165;

FIG. 167 is an isometric view of a typical electrocardiogram (EKG/ECG) skin patch and lead wire that can be placed on a patient's chest, legs or other parts of the body to enable cardiac monitoring, or alternatively an EEG lead wire and patch that would be placed on the head.

FIG. 168 illustrates the schematic of TANK filter of the present invention placed either at or near the skin electrode patch of FIG. 167; and FIG. 169 illustrates the overall system of an implantable medical device such as a cardiac pacemaker illustrating the role of the prior art feedthrough capacitor technology in conjunction with the TANK shown at a distal TIP.

DETAILED DESCRIPTION OF THE PREFERRED EMBODIMENTS

As shown in the drawings, for purposes of illustration, the present invention resides in the placement of TANK filters in series with lead wires or circuits of active medical devices to protect the patient and/or medical device from undesirable electromagnetic interference signals, such as those generated during MRI and other medical procedures. The present invention also resides in the design, manufacturing, and tuning of such TANK filters to be used in the lead wires or active medical devices. As will be explained more fully herein, the invention is applicable to a wide range of external medical devices, probes, catheters, monitoring lead wires and the like that may be temporarily inserted onto a patient or that a patient may be wearing or connected to during medical diagnostic procedures, such as MRI.

In the following description, functionally equivalent elements shown in various embodiments will often be referred to utilizing the same reference number.

Figure 1:
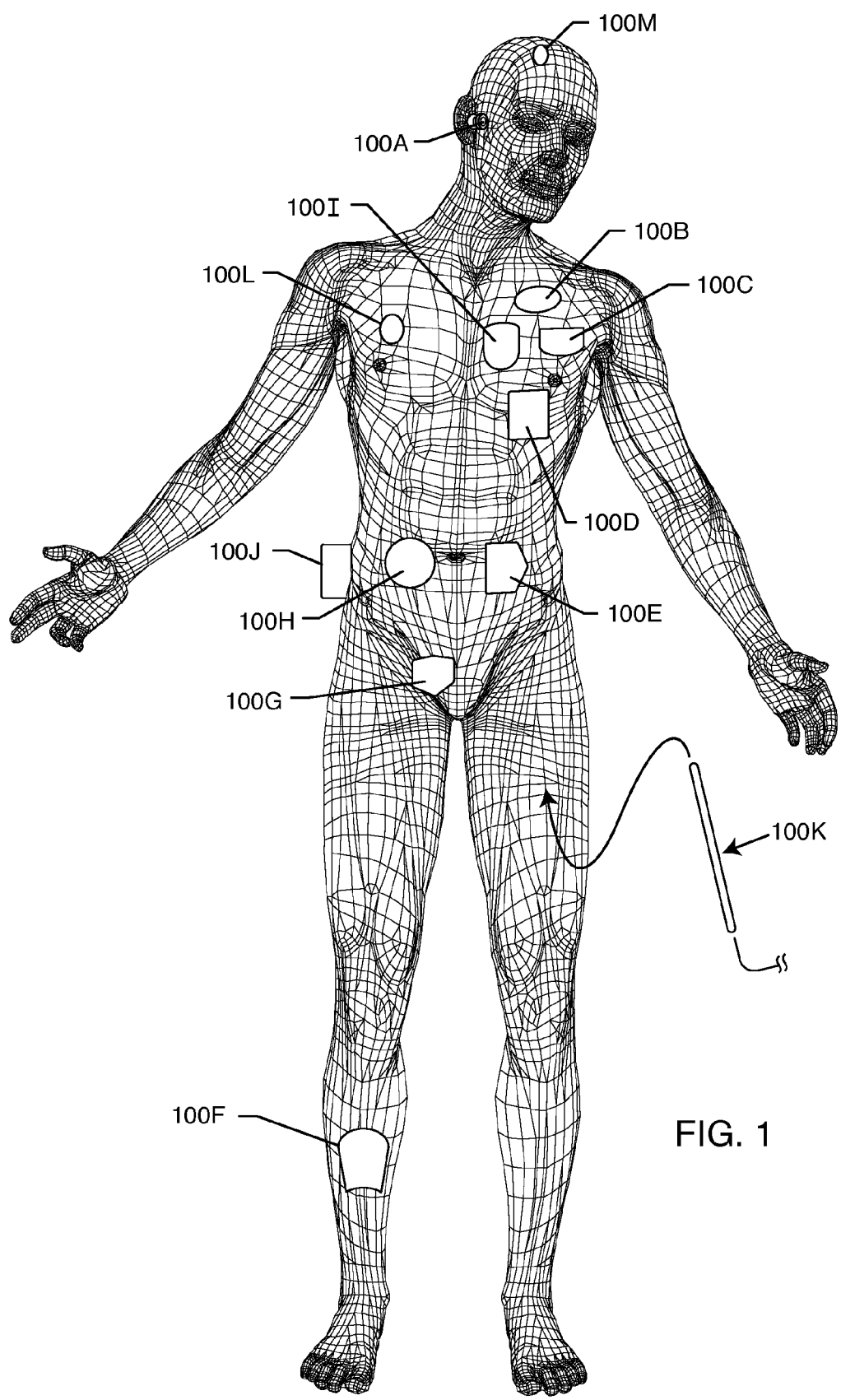
FIG. 1 is a wire-formed diagram of a generic human body showing a number of active medical devices (AMDs) and associated internal and external lead wires.

FIG. 1 illustrates various types of active implantable and external medical devices 100 that are currently in use. FIG. 1 is a wire formed diagram of a generic human body showing a number of implanted medical devices. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. The lead wires associated with a deep brain stimulator are often placed using real time MRI imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body. 100L illustrates one of various types of EKG/ECG external skin electrodes which can be placed at various locations. 100M are external EEG electrodes placed on the head.

Referring now to FIG. 2, a prior art active implantable medical device (AIMD) 100 is illustrated. In general, the AIMD 100 could, for example, be a cardiac pacemaker 100C which is enclosed by a titanium housing 102 as indicated. The titanium housing is hermetically sealed, however there is a point where lead wires 104 must ingress and egress the hermetic seal. This is accomplished by providing a hermetic terminal assembly 106. Hermetic terminal assemblies are well known and generally consist of a ferrule 108 which is laser welded to the titanium housing 102 of the AIMD 100. The hermetic terminal assembly 106 with its associated EMI filter is better shown in FIG. 3. Referring once again to FIG. 2, four lead wires are shown consisting of lead wire pair 104a and 104b and lead wire pair 104c and 104d. This is typical of what's known as a dual chamber bipolar cardiac pacemaker.

The IS1 connectors 110 that are designed to plug into the header block 112 are low voltage (pacemaker) connectors covered by an ANSI/AAMI standard IS-1. Higher voltage devices, such as implantable cardioverter defibrillators (ICDs), are covered by a standard known as the ANSI/AAMI DF-1. There is a new standard under development which will integrate both high voltage and low voltage connectors into a new miniature connector series known as the IS-4 series. These connectors are typically routed in a pacemaker application down into the right ventricle and right atrium of the heart 114. There are also new generation devices that have been introduced to the market that couple lead wires to the outside of the left ventricle. These are known as biventricular devices and are very effective in cardiac resynchronization and treating congestive heart failure (CHF).

Referring once again to FIG. 2, one can see, for example, the bipolar lead wires 104a and 104b that could be routed, for example, into the right ventricle. The bipolar lead wires 104c and 104d could be routed to the right atrium. There is also an RF telemetry pin antenna 116 which is not connected to the IS-1 or DS-1 connector block. This acts as a short stub antenna for picking up telemetry (programming) signals that are transmitted from the outside of the device 100.

It should also be obvious to those skilled in the art that all of the descriptions herein are equally applicable to other types of AIMDs. These include implantable cardioverter defibrillators (using the aforementioned DF-1 connectors), neurostimulators (including deep brain stimulators, spinal cord stimulators, cochlear implants, incontinence stimulators and the like), and drug pumps. The present invention is also applicable to a wide variety of minimally invasive AIMDs. For example, in certain hospital catheter lab procedures, one can insert an AIMD for temporary use such as an ICD. Ventricular assist devices also can fall into this type of category. This list is not meant to be limiting, but is only example of the applications of the novel technology currently described herein.

FIG. 3 is an enlarged, fragmented cross-sectional view taken generally along line 3-3 of FIG. 2. Here one can see in cross-section the RF telemetry pin 116 and the bipolar lead wires 104a and 104c which would be routed to the cardiac chambers by connecting these lead wires to the internal connectors 118 of the IS-1 header block 112 (FIG. 2). These connectors are designed to receive the plug 110 which allows the physicians to thread lead wires through the venous system down into the appropriate chambers of the heart 114. It will be obvious to those skilled in the art that tunneling of deep brain electrodes or neurostimulator leads are equivalent.

Referring back to FIG. 3, one can see a prior art feedthrough capacitor 120 which has been bonded to the hermetic terminal assembly 106. These feedthrough capacitors are well known in the art and are described and illustrated in U.S. Pat. Nos. 5,333,095, 5,751,539, 5,905,627, 5,959,829, 5,973,906, 5,978,204, 6,008,980, 6,159,560, 6,275,369, 6,424,234, 6,456,481, 6,473,291, 6,529,103, 6,566,978, 6,567,259, 6,643,903, 6,675,779, 6,765,780 and 6,882,248, all of which are incorporated herein by reference. In this case, a rectangular quadpolar feedthrough capacitor 120 is illustrated which has an external metallized termination surface 122 and includes embedded electrode plate sets 124 and 126. Electrode plate set 124 is known as the ground electrode plate set and is terminated at the outside of the capacitor 120 at the termination surface 122. These ground electrode plates 124 are electrically and mechanically connected to the ferrule 108 of the hermetic terminal assembly 106 using a thermosetting conductive polyimide or equivalent material 128 (equivalent materials will include solders, brazes, conductive epoxies and the like). In turn, the hermetic seal terminal assembly 106 is designed to have its titanium ferrule 108 laser welded 130 to the overall housing 102 of the AIMD 100. This forms a continuous hermetic seal thereby preventing body fluids from penetrating into and causing damage to the electronics of the AIMD.

It is also essential that the lead wires 104 and insulator 136 be hermetically sealed, such as by the gold brazes 132, 134 and 138. The gold braze 132 wets from the titanium ferrule 108 to the alumina ceramic insulator 136. In turn, the ceramic alumina insulator 136 is also gold brazed at 134 to each of the lead wires 104. The RF telemetry pin 116 is also gold brazed at 138 to the alumina ceramic insulator 136. It will be obvious to those skilled in the art that there are a variety of other ways of making such a hermetic terminal. This would include glass sealing the leads into the ferrule directly without the need for the gold brazes.

As shown in FIG. 3, the RF telemetry pin 116 has not been included in the area of the feedthrough capacitor 120. The reason for this is the feedthrough capacitor 120 is a very broadband single element low pass EMI filter which would eliminate the desirable telemetry frequency, typically above 400 MHz.

Figure 4:
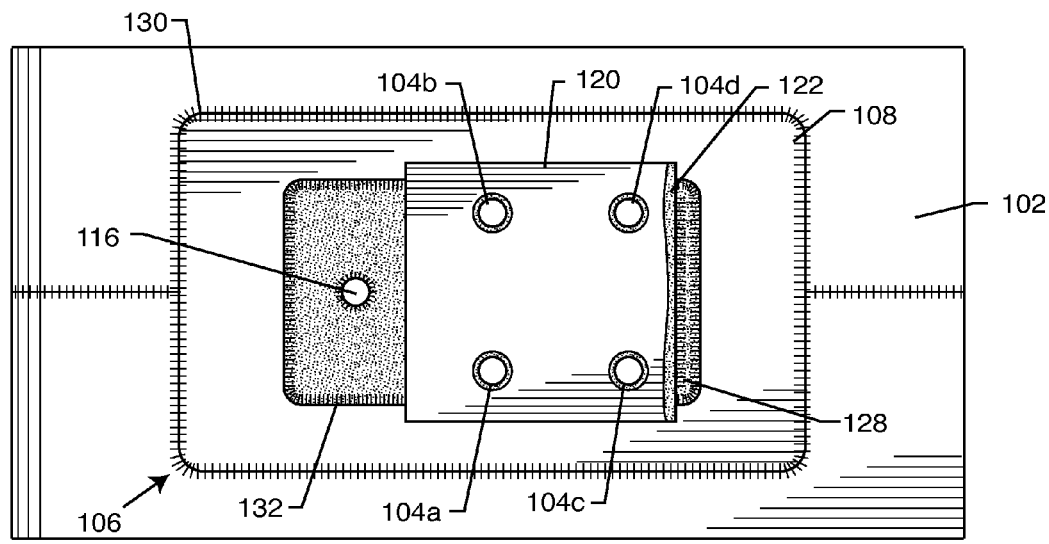
FIG. 4 is a view taken generally along the line 4-4 of FIG. 3.

FIG. 4 is a bottom view taken generally along line 4-4 in FIG. 3. One can see the gold braze 132 which completely seals the hermetic terminal insulator 136 into the overall titanium ferrule 108. One can also see the overlap of the capacitor attachment materials, shown as a thermosetting conductive adhesive 128, which makes contact to the gold braze 132 that forms the hermetic terminal 106.

Figure 5:
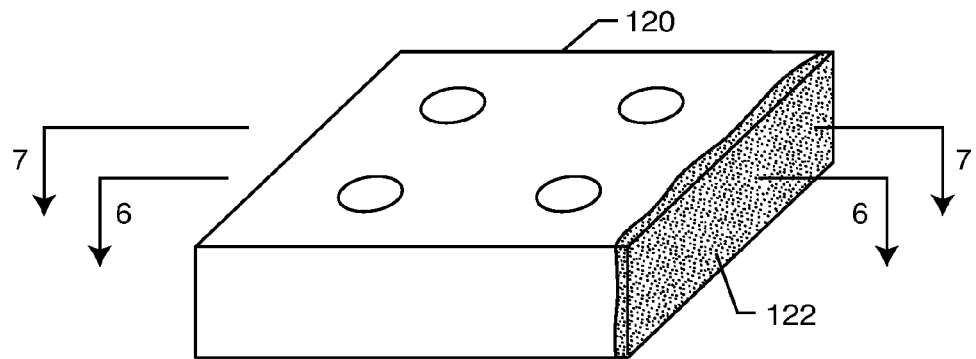
FIG. 5 is a perspective/isometric view of a prior art rectangular quadpolar feedthrough capacitor of the type shown in FIGS. 3 and 4.
Figure 6:
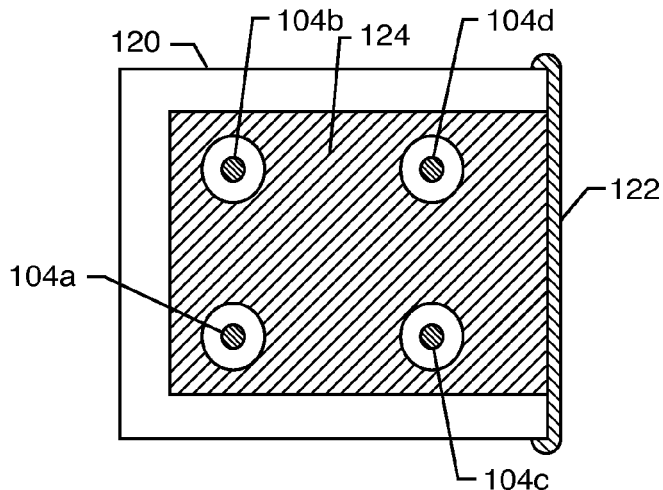
FIG. 6 is a sectional view taken generally along the line 6-6 of FIG. 5.
Figure 7:
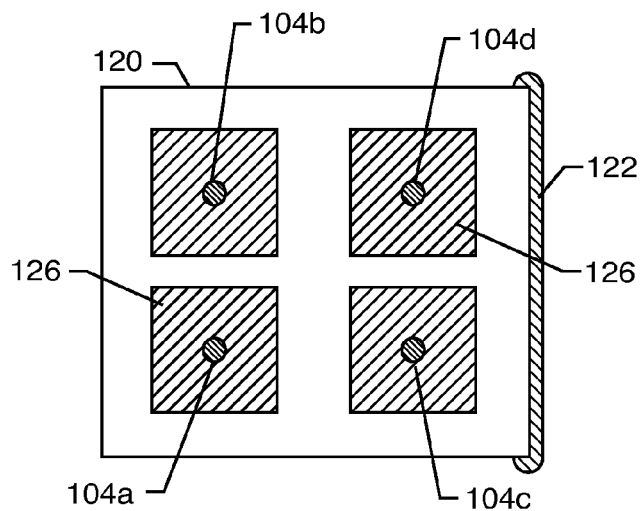
FIG. 7 is a sectional view taken generally along the line 7-7 of FIG. 5.

FIG. 5 is an isometric view of the feedthrough capacitor 120. As one can see, the termination surface 122 connects to the capacitor's internal ground plate set 124. This is best seen in FIG. 6 where ground plate set 124, which is typically screen printed onto ceramic layers, is brought out and exposed to the termination surface 122. The capacitor's active electrode plate set 126 is illustrated in FIG. 7. In FIG. 6 one can see that the lead wires 104 are in non-electrical communication with the ground electrode plate set 124. However, in FIG. 7 one can see that each one of the lead wires 104 is in electrical contact with the active electrode plate sets 126. The amount of capacitance is determined, in part, by the overlap of the active electrode plate area 126 over the ground electrode plate area. One can increase the amount of capacitance by increasing the area of the active electrode plate set 126. One can also increase the capacitance by adding additional layers. In this particular application, we are only showing six electrode layers: three ground plates 124 and three active electrode plate sets 126 (FIG. 3). However, 10, 60 or even more than 100 such sets can be placed in parallel thereby greatly increasing the capacitance value. The capacitance value is also related to the dielectric thickness or spacing between the ground electrode set 124 and the active electrode set 126. Reducing the dielectric thickness increases the capacitance significantly while at the same time reducing its voltage rating. These relationships are expressed ideally by the following equation:

$$C = \frac{n\kappa A}{t},$$

where n is the number of plate sets, κ is the dielectric constant of the material, A is the effective capacitive area, and t is the thickness between opposing plates. This gives the designer many degrees of freedom in selecting the capacitance value.

FIG. 8 is a general diagram of a unipolar active implantable medical device system 100. The housing 102 of the active implantable medical device 100 is typically titanium, stainless steel or the like, and acts as one conductive electrode. Inside of the device housing are the AIMD electronics. Usually AIMDs include a battery, but that is not always the case. For example, a Bion may receive its energy from an external pulsing magnetic field. A lead wire 104 is routed in insulative relationship with the AIMD housing to a point 140 where it is embedded in body tissue. In the case of a spinal cord stimulator 100H, the distal TIP 140 could be in the spinal cord. In the case of a deep brain stimulator 100S, the distal electrode 140 would be placed deep into the brain tissue, etc. In the case of a cardiac pacemaker 100C, the unipolar distal electrode 140 would typically be placed in the cardiac right ventricle.

FIG. 9 is very similar to FIG. 8 except that it is a bipolar system. In this case, the return path is between the two distal electrodes 140 and 140'. In the case of a cardiac pacemaker 100C, this would be known as a bipolar lead wire system with one of the electrodes known as the distal TIP 142 and the other electrode which would float in the blood pool known as the RING 144 (see FIG. 10). In contrast, the return path in FIG. 8 is between the distal electrode 140 through body tissue to the conductive housing 102 of the implantable medical device 100.

FIG. 10 further illustrates a bipolar lead wire system with a distal TIP 142 and RING 144 typically as used in a cardiac pacemaker 100C In all of these applications, the patient could be exposed to the fields of an MRI scanner or other powerful emitter used during a medical diagnostic procedure. RF currents that are directly induced in the lead wire system 104 can cause heating by Ohmic ($I^2R$) losses in the lead wire system or by heating caused by current flowing in body tissue. If these currents become excessive, the associated heating can cause damage or even destructive ablation to body tissue.

The distal TIP 142 is designed to be implanted adjacent to or affixed into the actual myocardial tissue of the heart. The RING 144 is designed to float in the blood pool. In a pacemaker cardiac chamber, the blood is flowing (i.e. perfusion) and is thermally conductive, therefore RING 144 structure is substantially cooled. However, the distal TIP 142 is thermally insulated by surrounding body tissue and can readily heat up due to the RF pulse currents of an MRI field. Accordingly, for a cardiac pacemaker application, the novel TANK concepts of the present invention will be more directed to the distal TIP 142 as opposed to the RING 144 electrode (although the concepts of the present invention can be applied to both). For poorly perfused areas, such as is typical in neurostimulator electrodes, then both TIP and RING electrodes must have a tank circuit of the present invention.

FIG. 11 is a schematic diagram showing an ideal parallel combination of an inductor L and a capacitor C to be placed in the lead wire systems 104 previously described. This combination forms an ideal parallel TANK circuit filter 146 which will resonate at a particular frequency ($f_r$). (Ideal means that resistive losses have been omitted from the model for simplicity).

FIG. 12 gives the frequency of resonance $f_r$ for the parallel L-C TANK circuit 146 of FIG. 11: where $f_r$ is the frequency of resonance in Hertz, L is the inductance in Henries and C is the capacitance in Farads. Clinical MRI systems vary in static field strength from 0.5 Tesla all the way up to 3 Tesla with newer research machines going as high as 11.4 T. The frequency of the pulsed RF field associated with the static field is given by the Lamour Equation, $f=\gamma_H T$, where T is the field strength in Teslas, and $\gamma$ is gyromagnetic ratio for hydrogen, which is 42.58 MHz/T. Accordingly, a 3 Tesla MRI system has a pulsed RF field of approximately 128 MHz.

By referring to FIG. 12, one can see that the resonant frequency fr of an ideal TANK filter can be predicted by using the equation:

$$f_r = \frac{1}{2\pi\sqrt{LC}},$$

Where $f_r$ is the resonant frequency, L is the inductance, in Henries, of the inductor component, and C is the capacitance, in Farads, of the capacitor component. In this equation, there are three variables: $f_r$, L, and C. The resonant frequency, $f_r$, is a function of the MRI system of interest. As previously discussed, a 1.5 T MRI system utilizes an RF system operating at approximately 64 MHz, a 3.0 T system utilizes a 128 MHz RF, and so on. By determining the MRI system of interest, only L and C remain. By artificially setting one of these parameters, a filter designer needs only to solve for the remaining variable. This is illustrated in FIG. 12.

This equation, however, only deals with ideal inductor and capacitor elements. Real inductor and capacitor components exhibit series resistive elements, which are represented by the circuit diagram in FIG. 16. These resistive components are due to material and design considerations, and are not necessarily independent of the respective inductive and capacitive values of the components.

Figure 16:
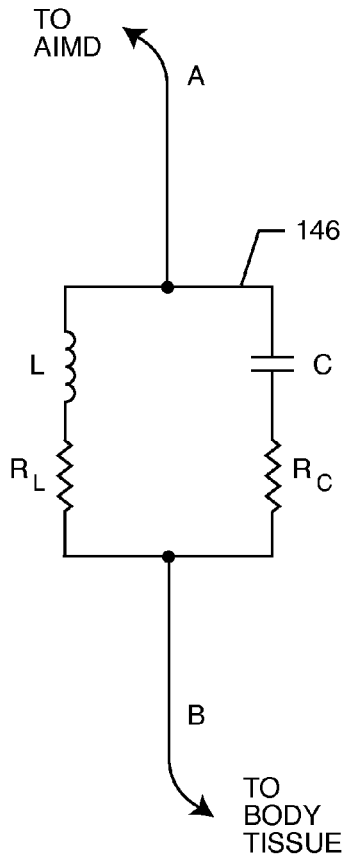
FIG. 16 is a schematic diagram illustrating the parallel TANK circuit of FIG. 11, except in this case the inductor and the capacitor have parasitic or deliberate resistive losses and are not ideal.

By modeling the resistive elements with the reactive elements in a circuit modeling program such as P-Spice, one can see that the $R_L$ and $R_C$, as shown in FIG. 16, provide a significant contribution. As the total real resistance in the circuit increases, the 3 dB bandwidth of the TANK filter widens. This is a desired effect in this invention, since the widened 3 dB bandwidth corresponds to a broader range of filtered frequencies. For example, an 'ideal' TANK filter would resonate at only 64 MHz (for a 1.5 T MRI), and have no attenuation effect on a 3.0 T MRI (128 MHz). However, a TANK filter with a real resistive contribution would display a significant increase in the 3 dB bandwidth, and if a designer chose appropriate components, the TANK filter could provide filtering at both 64 MHz and 128 MHz.

This increase in filtering does not come without performance drawbacks. Since the energy dissipated by the TANK is finite, broadening the bandwidth of the TANK also has the effect of depressing the maximum attenuation of the circuit at resonance. If the attenuation drops too low, filtering performance at MRI RF pulse frequency can be negatively affected.

Additionally, the series resistance of the inductor component is of concern. Since the inductor component is acting as the current path at lower frequencies, the series resistance should be as low as possible, so as to not filter out desirable low frequency biological signal sensing or therapy delivery signals. Because of this, it is preferred to choose the inductive component first, then calculate the required capacitive component. In this case, the left side of FIG. 12 should be followed (resonance equation solved for C), to determine the needed capacitor for the circuit.

In the preferred methodology, a relatively high inductance should be chosen (>100 nH). The selectivity of the TANK filter is determined by the ratio of L/C. Accordingly, too low of an inductance value will not provide the proper amount of attenuation or the proper 3 dB bandwidth at the selected MRI pulsed frequency. Using the equation in FIG. 12, one can see that the required capacitance to meet a 64 MHz system is 41 pF. However, it becomes obvious to one skilled in the art that a relatively low series resistance is required of the inductor to guarantee low attenuation at lower frequencies. Since the series resistance in an inductor is a function of the material properties and the design geometry, careful component selection becomes critical.

Referring once again to FIG. 12, one can see that if the values of the inductor and the capacitor are selected properly, one could obtain a parallel TANK resonant frequency of 21.3 MHz (0.05 T), 64 MHz (1.5 T), 128 MHz (3.0 T), and so on. Referring to FIG. 12, one can see the calculations first assuming that the inductor value L is equal to 150 nanohenries. The 150 nanohenries comes from the fact that given the small geometries involved inside of the human body, a very large inductor is not practical. This is in addition to the fact that the use of ferrite materials or iron cores for such an inductor are undesirable for two reasons: 1) the static magnetic field from the MRI scanner would align the magnetic dipoles in such a ferrite and therefore make the inductor ineffective; and 2) the presence of ferrite materials will cause MRI image artifacts. This means that if one were imaging the right ventricle of the heart, for example, a fairly large area of the image would be blacked out due to the presence of these ferrite materials and the way it interacts with the MRI field. It is also important that the inductor not vary while in the presence of the main static field.

It should be also noted that below resonance, particularly at very low biologic frequencies, the current in the lead wire system passes through the inductor element. Accordingly, it is important that the series resistance of the inductor element be quite low. Conversely, at very low frequencies, no current passes through the capacitor element. However, at high frequencies, the reactance of the capacitor element drops to a much lower value, but there is no case (except for telemetry pins of an AIMD) where it is actually desirable to have high frequencies pass through the TANK filter. Accordingly, for almost all applications, the resistive loss of the capacitor is not particularly important. This is also known as the capacitor's equivalent series resistance (ESR). A component of capacitor ESR is the dissipation factor of the capacitor (a low frequency phenomena). At frequencies well above resonance, it is not particularly important how high the capacitor's dissipation factor or overall ESR is when used as a component of a parallel TANK circuit 146 as described herein.

Referring once again to FIG. 12, one can see the calculations for capacitance by solving the resonant frequency $f_r$ equation shown for C. Assuming an inductance value of 150 nanohenries, one can see that 41.3 picofarads of capacitance would be required. Appropriate ceramic dielectrics that provide a high dielectric constant are well known in the art and are very volumetrically efficient. They can also be made of biocompatible materials making them an ideal choice for use in the present invention.

Figure 13:
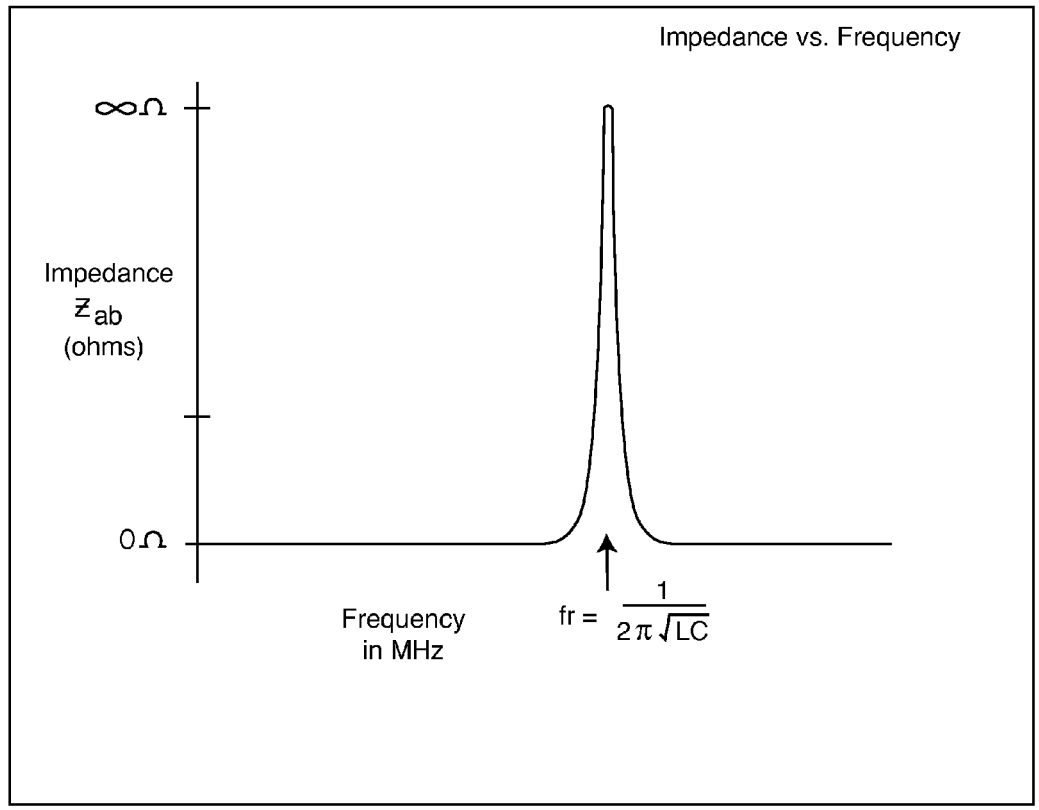
FIG. 13 is a graph showing impedance versus frequency for the ideal parallel TANK circuit of FIG. 11.

FIG. 13 is a graph showing impedance versus frequency for the ideal parallel TANK circuit 146 of FIG. 11. As one can see, using ideal (zero resistance) circuit components, the impedance measured between points A and B for the parallel TANK circuit 146 shown in FIG. 11 is zero until one approaches the resonant frequency $f_r$. At the frequency of resonance, these ideal components combine together to approach an infinite impedance. This comes from the equation $Z_{ab}$ for the impedance for the inductor in parallel with the capacitor shown as FIG. 14. When the inductive reactance is equal to the capacitive reactance, the two imaginary vectors cancel each other and sum to zero. Referring to the equations in FIGS. 14 and 15, one can see in the impedance equation for $Z_{ab}$, that a zero will appear in the denominator when $X_L=X_C$. This has the effect of making the impedance approach infinity as the denominator approaches zero. This means that at one unique frequency, the impedance between points A and B in FIG. 11 will appear very high (analogous to opening a switch). Accordingly, it would be possible, for example, in the case of a cardiac pacemaker, to design the cardiac pacemaker for compatibility with one single popular MRI system. For example, in the patient literature, the device manual and perhaps contained in the digitally stored information on an implanted RFID chip, it could be noted that the pacemaker lead wire system has been designed to be compatible with 3 Tesla MRI systems. Accordingly, with this particular device, a distal TIP TANK filter 146 would be incorporated where the L and the C values have been carefully selected to be resonant at 128 MHz, presenting a high or almost infinite impedance at the MRI pulse frequency.

FIG. 16 is a schematic drawing of the parallel TANK circuit 146 of FIG. 11, except in this case the inductor L and the capacitor C are not ideal. That is, the capacitor C has its own internal resistance $R_C$, which is otherwise known in the industry as dissipation factor or equivalent series resistance (ESR). The inductor L also has a resistance $R_L$. For those that are experienced in passive components, one would realize that the inductor L would also have some parallel capacitance ($C_P$). This parasitic capacitance comes from the capacitance associated with adjacent turns. However, the inductance value contemplated is so low that one can assume that at MRI RF pulse frequencies, the inductor's parallel capacitance is negligible. One could also state that the capacitor C also has some internal inductance which would appear in series. However, the novel capacitors described herein are very small or coaxial and have negligible series inductance. Accordingly, the circuit shown in FIG. 16 is a very good approximation model for the novel parallel TANK circuits 146 as described herein.

This is best understood by looking at the FIG. 16 TANK circuit 146 at the frequency extremes. At very low frequency, the inductive reactance equation is $X_L=2\pi fL$. When the frequency f is close to zero (DC), this means that the inductor looks like a short circuit. It is generally the case that biologic signals are low frequency, typically between 10 Hz and 1000 Hz. For example, in a cardiac pacemaker 100C, all of the biologic frequencies of interest appear between 10 Hz and 1000 Hz. At these low frequencies, the inductive reactance $X_L$ will be close to zero ohms. Over this range, on the other hand, the capacitive reactance $X_C$ which has the equation $X_C=1/(2\pi fc)$ will look like an infinite or open circuit. As such, at low frequencies, the impedance between points A and B in FIG. 16 will be substantially equal to $R_L$. Accordingly, the resistance of the inductor ($R_L$) should be kept as small as possible to minimize attenuation of biologic signals or attenuation of electrical stimulation pulses to body tissues. This will allow biologic signals and pacing pulses to pass through the TANK filter 146 freely. It also indicates that the amount of capacitive loss $R_C$ is not particularly important. As a matter of fact, it would be desirable if that loss were fairly high so as to not freely pass very high frequency signals (such as undesirable EMI from cellular phones). It is also desirable to have the Q of the circuit shown in FIG. 16 carefully balanced so that the TANK frequency bandwidth can be a little wider. In other words, in a preferred embodiment, it would be possible to have a TANK wide enough to block both 64 MHz and 128 MHz thereby making the medical device compatible for use in both 1.5 Tesla and 3 Tesla MRI systems.

Figure 17:
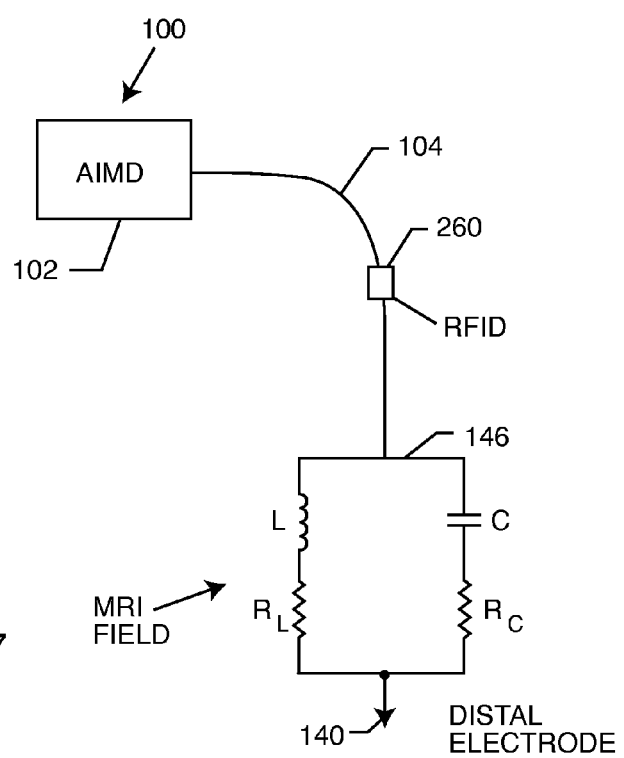
FIG. 17 is a diagram similar to FIG. 8, illustrating the TANK filter circuit added near a distal electrode of an AIMD.

FIG. 17 is a drawing of the unipolar AIMD lead wire system, previously shown in FIG. 8, with the TANK filter 146 of the present invention added near the distal electrode 140. As previously described, the presence of the TANK circuit 146 will present a very high impedance at one or more specific MRI RF pulse frequencies. This will prevent currents from circulating through the distal electrode 140 into body tissue at this selected frequency(s). This will provide a very high degree of important protection to the patient so that distal TIP heating does not cause tissue damage.

Referring once again to FIG. 17, one can see that an optional RFID tag 260 has been placed at the lead wire near the active implantable medical device. U.S. patent application Ser. No. 11/307,145, filed Jan. 25, 2006, the contents of which are incorporated herein, describes how to place RFID tags and hermetically seal them in the header block of a cardiac pacemaker or the like. It is common in the art that "mix and match" goes on between the implantable medical device and the lead wire systems. This is particularly true for cardiac pacemakers. For example, it is very common that a St. Jude pacemaker could be used with Medtronic lead wires and vice versa. It is also common that lead wires will stay implanted in the human body much longer than the actual active implantable medical device. For example, a pacemaker patient may have lead wires implanted for forty years or longer where the pacemaker itself is replaced in the pectoral pocket and plugged in every five to seven years. The TANK filter of the present invention is designed to work with any model pacemaker to prevent overheating during MRI procedures of the lead wires and its associated distal TIP. Accordingly, it is very important over time that a hospital or MRI lab be able to identify which patients have MRI compatible lead wire systems and which do not. It is a feature of the present invention that an RFID tag 260 can be affixed to or placed adjacent to an implantable device or in the electrode wire system so it can be appropriately identified. The RFID tag 260 could also include important information such as the resonant frequency that the distal TIP TANK was designed for. For example, the RFID tag 260 could emit a pulse indicating that it is RFID compatible at 1.5 T (64 MHz). It is important that the active implantable medical device also incorporate robust EMI filters such that the RFID emitter (reader or scanner) not interfere with the electronics of the AIMD itself. An ideal RFID frequency for the present invention would be 13.56 MHz which would readily penetrate body tissue and be detected by the RFID tag 260 that is attached to the lead wire. There are a variety of fixation methods that can be used to attach the RFID tag 260 to the lead wire, including bonding within the encapsulation material of the lead wire itself or by using a tie or suture attachment. It is not even necessary that the RFID tag 260 be directly attached to the lead wires themselves. For example, it is also known in the art that RFID tags can be injected anywhere in the human body, for example, near the wrist. In this case, the RFID tag 260 would include important information about the presence and MRI compatibility of the lead wire system and/or the AIMD itself. A company called Verichip already has implantable RFID tags for both animal and human identification. A problem with Verichip and other prior art RFID tags is that they are not truly hermetic. Novel hermetically sealed canisters to hold RFID chips is disclosed in U.S. application Ser. No. 11/307,145, filed Jan. 25, 2006, the contents of which are incorporated herein by reference. Because of the potential length of implant AIMD lead wire systems (for example, cochlear or pacemaker lead wires that could be implanted for 40 years or even longer), it is very important that the implanted RFID tag be reliable over a long period of time. This means that it has to be truly hermetic to a leak rate that at least exceeds $1 \times 10^{-7}$ cc per second. Accordingly, the hermetic assemblies as described in the U.S. application Ser. No. 11/307,145 are the preferred embodiment.

Figure 18:
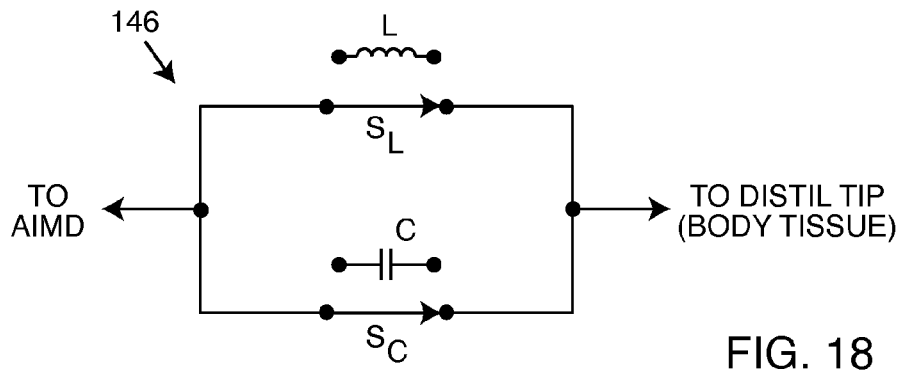
FIG. 18 is a schematic representation of the ideal TANK filter of the present invention, using switches to illustrate its function.

FIG. 18 is an ideal representation of the novel TANK filter 146 using switches to illustrate its function. Inductor L has been replaced with a switch $S_L$. When the impedance of the inductor is quite low, the switch $S_L$ will be closed. When the impedance or inductive reactance of the inductor is high, the switch $S_L$ will be shown open. There is a corresponding analogy for the capacitor element C. When the capacitive reactance looks like a very low impedance, the capacitor switch $S_C$ will be shown closed. When the capacitive reactance is shown as a very high impedance, the switch $S_C$ will be shown open. This analogy is best understood by referring to FIGS. 19, 20 and 21.

Figure 19:
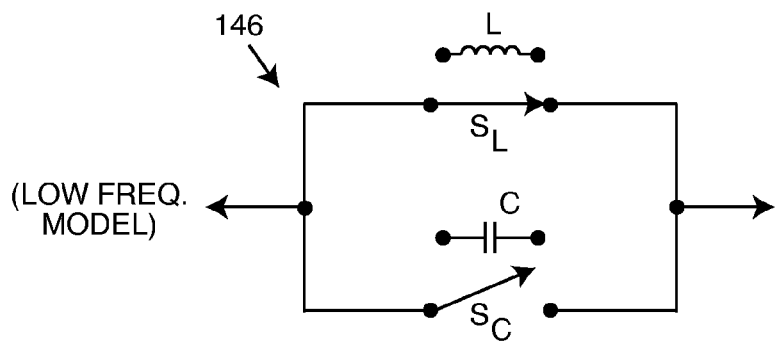
FIG. 19 is a schematic diagram similar to FIG. 18, illustrating the low frequency model of the TANK filter.

FIG. 19 is the low frequency model of the TANK filter 146. At low frequencies, capacitors tend to look like open circuits and inductors tend to look like short circuits. Accordingly, switch $S_L$ is closed and switch $S_C$ is open. This is an indication that at frequencies below the resonant frequency of the TANK filter 146 currents will flow through the inductor element. This is an important consideration for the present invention that low frequency biological signals not be attenuated. For example, in a cardiac pacemaker, frequencies of interest generally fall between 10 Hz and 1000 Hz. Pacemaker pacing pulses fall within this general frequency range. In addition, the implantable medical device is also sensing biological frequencies in the same frequency range. Accordingly, such signals must be able to flow readily through the TANK filter's inductor element. A great deal of attention should be paid to the inductor design so that it has a very high quality factor (Q) and a low parasitic series resistance.

Figure 20:
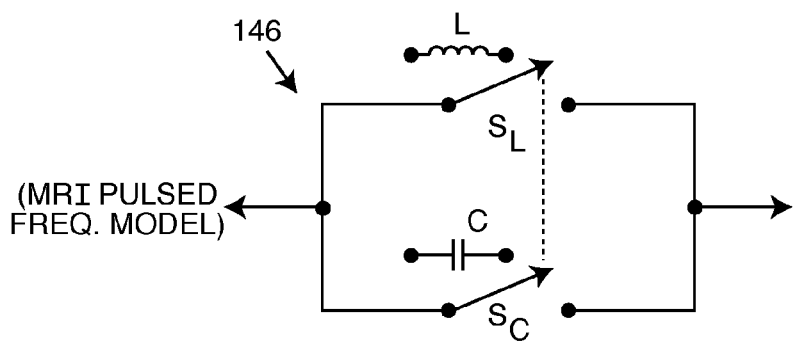
FIG. 20 is a schematic diagram similar to FIGS. 18 and 19, illustrating the model of an ideal TANK filter of the present invention at its resonant frequency.

FIG. 20 is a model of the novel TANK filter 146 at its resonant frequency. By definition, when a parallel TANK circuit is at resonance, it presents a very high impedance to the overall circuit. Accordingly, both switches $S_L$ and $S_C$ are shown open. For example, this is how the TANK filter 146 prevents the flow of MRI currents through pacemaker lead wires and/or into body tissue at a selected MRI RF pulsed frequency.

Figure 21:
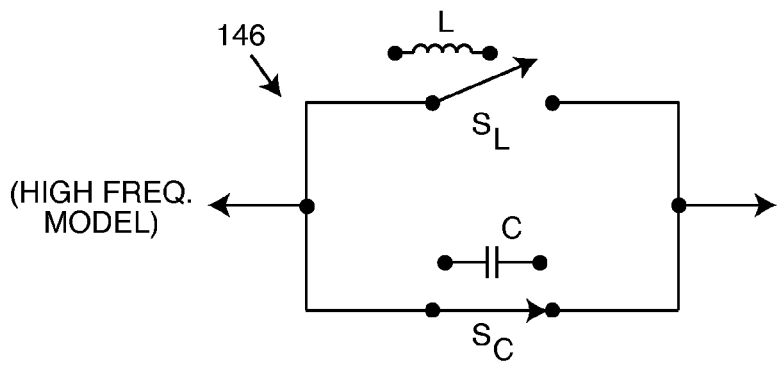
FIG. 21 is a schematic diagram similar to FIGS. 18-20, illustrating a model of the TANK filter at high frequencies (well above resonance)

FIG. 21 is a model of the TANK filter 146 at high frequency. At high frequencies, inductors tend to look like open circuits. Accordingly, switch $S_L$ is shown open. At high frequencies, ideal capacitors tend to look like short circuits, hence switch $S_C$ is closed. It should be noted that real capacitors are not ideal and tend to degrade in performance at high frequency. This is due to the capacitor's equivalent series inductance and equivalent series resistance. Fortunately, for the present invention, it is not important how lossy the capacitor element C becomes at high frequency. This will only serve to attenuate unwanted electromagnetic interference, for example, from cell phones, from flowing in the lead wire system. Accordingly, the quality factor of the capacitor element C is not nearly as important as the quality factor of the inductor element L. The equation for inductive reactance ($X_L$) is given in FIG. 15. The capacitor reactance equation ($X_C$) is also given in FIG. 15. As one can see, when one inserts zero for the frequency, one derives the fact that at very low frequencies inductors tend to look like short circuits and capacitors tend to look like open circuits. By inserting a very high frequency into the same equations, one can see that at very high frequency ideal inductors look like an infinite or open impedance and ideal capacitors look like a very low or short circuit impedance.

Figure 22:
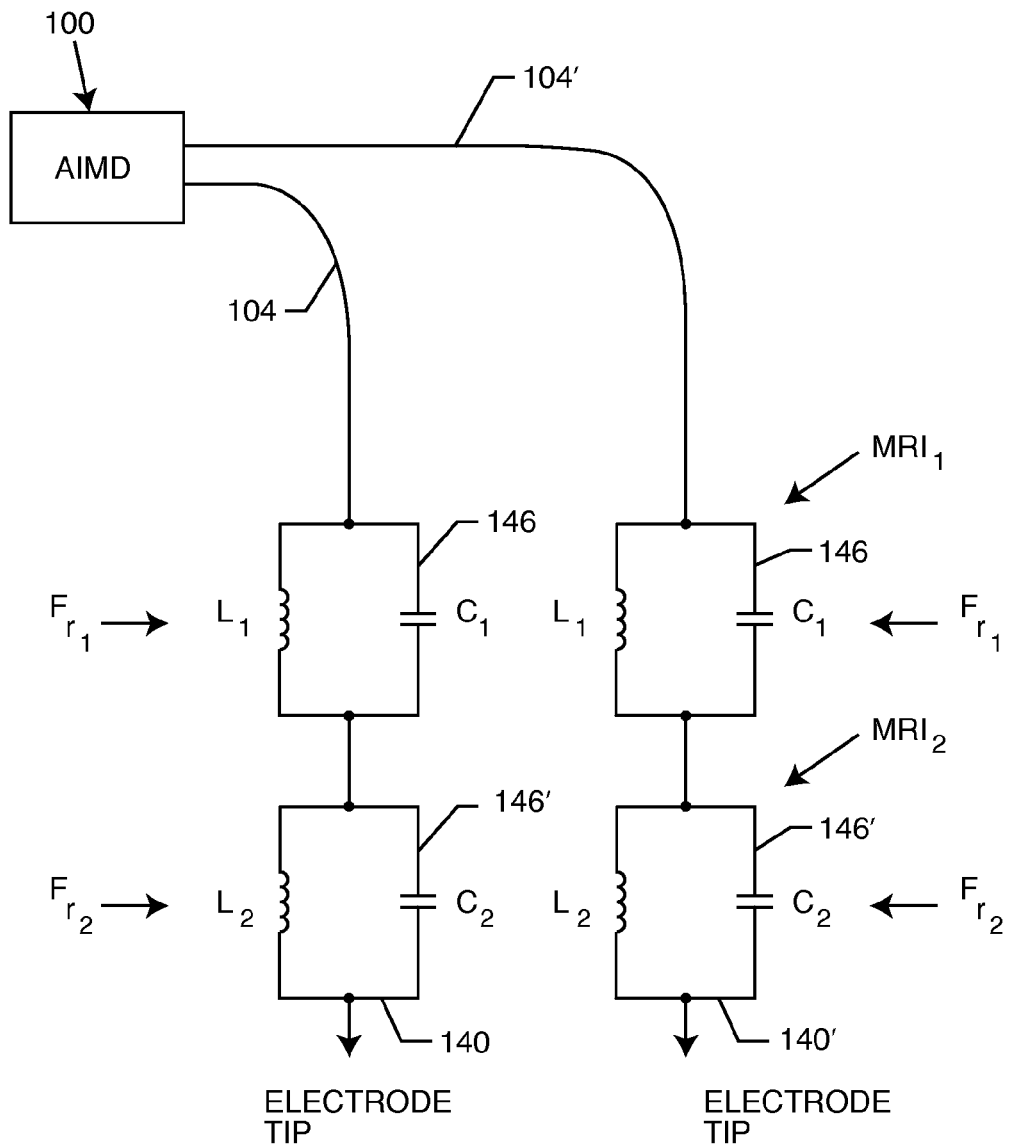
FIG. 22 is a diagram similar to FIG. 9, redrawn to show multiple TANK filters in multiple electrodes.

FIG. 22 is the bipolar system of FIG. 9 redrawn to show two novel TANK filters 146 in each lead wire 104, 104'. In this case, there is a TANK circuit $F_{r1}$ consisting of $L_1$ and $C_1$ in both of the bipolar lead wires 104, 104', which is designed to resonate at one selected frequency. For a 1.5 Tesla MRI system, this would be 64 MHz. These are then placed in series with a second set of TANK filters 146' which are designed to resonate at $F_{r2}$. These consist of $L_2$, $C_2$ parallel inductor capacitor combinations. These could be designed for operation in a 3 Tesla MRI system and would therefore be designed to resonate at 128 MHz. In this way, currents would be blocked from both types of MRI systems. The trade off in this example is that the distal electrodes 140, 140' would be physically elongated due to the additional components necessary. An RFID chip, such as that described in relation to FIG. 17, could be associated with each 104, 104' lead wire so as to identify each electrode or lead wire 104, 104' as incorporating a TANK filter 146, in accordance with the present invention.

Alternatively, a single RFID chip could be associated with either lead wire 104, 104' or anywhere in the patient, so as to identify both of the lead wires 104 and 104' as incorporating TANK filters 146.

Figure 23:
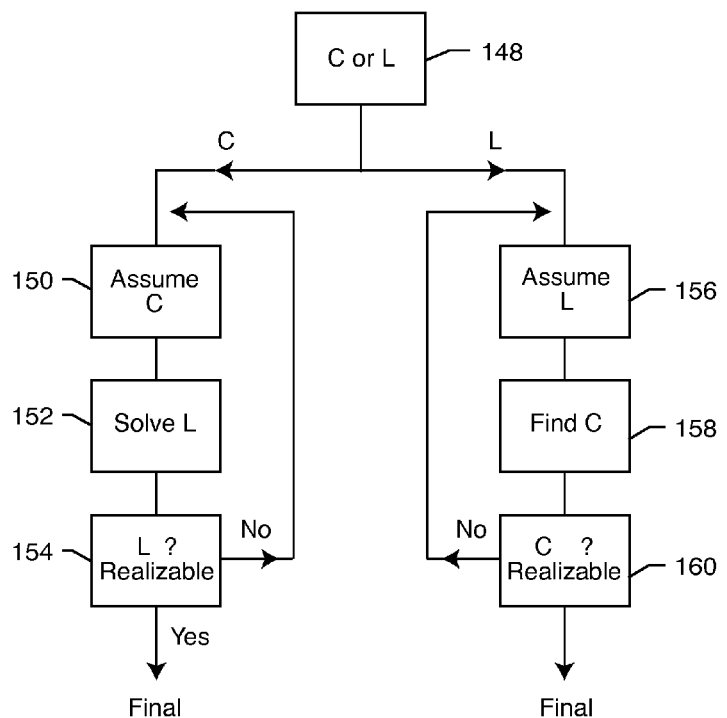
FIG. 23 is a decision tree block diagram illustrating a process for designing the TANK filters of the present invention.

FIG. 23 is a decision tree block diagram that better illustrates the design process herein. Block 148 is an initial decision step the designer must make. For illustrative purposes, we will start with a value of capacitance that is convenient. This value of capacitance is generally going to relate to the amount of space available in the AIMD lead wire system and other factors. These values for practical purposes generally range in capacitance value from a few tens of picofarads up to about 10,000 picofarads. This puts practical boundaries on the amount of capacitance that can be effectively packaged within the scope of the present invention. However, that is not intended to limit the general principles of the present invention, but just describe a preferred embodiment. Accordingly, in the preferred embodiment, one will select capacitance values generally ranging from 10 picofarads up to about 4000 picofarads and then solve for a corresponding inductance value required to be self-resonant at the selected telemetry frequency. Referring back to FIG. 23, one makes the decision whether the design was C first or L first. If one makes a decision to assume a capacitance value C first then one is directed to the left to block 150. In block 150, one does an assessment of the overall packaging requirements of a distal TIP 142 TANK filter 146 and then assumes a realizable capacitance value. So, in decision block 150, we assume a capacitor value. We then solve the resonant TANK equation $f_r$ from FIG. 12 at block 152 for the required value of inductance (L). We then look at a number of inductor designs to see if the inductance value is realizable within the space and other constraints of the design. If the inductance value is realizable, then we go on to block 154 and finalize the design. If the inductance value is not realizable within the physical and practical constraints, then we need to go back to block 150 and assume a new value of capacitance. One may go around this loop a number of times until one finally comes up with a compatible capacitor and an inductor design. In some cases, one will not be able to achieve a final design using this alone. In other words, one may have to use a custom capacitor value or design in order to achieve a result that meets all of the design criteria. That is, a capacitor design with high enough internal losses $R_C$ and an inductor design with low internal loss $R_L$ such that the TANK filter 146 has the required quality factor (Q), has sufficient band width (but not too much), that it be small enough in size, that it have sufficient current and high voltage handling capabilities and the like. In other words, one has to consider all of the design criteria in going through this decision tree.

In the case where one has gone through the left hand decision tree consisting of blocks 150, 152 and 154 a number of times and keeps coming up with a "no," then one has to assume a realizable value of inductance and go to the right hand decision tree starting at block 156. One then assumes a realizable value of inductance (L) with a low enough equivalent series resistance for the inductor $R_L$ such that it will work and fit into the design space and guidelines. After one assumes that value of inductance, one then goes to decision block 158 and solves the equation C in FIG. 12 for the required amount of capacitance. After one finds the desired amount of capacitance C, one then determines whether that custom value of capacitance will fit into the design parameters. If the capacitance value that is determined in step 160 is realizable, then one goes on and finalizes the design. However, if it is not realizable, then one can go back up to step 156, assume a different value of L and go through the decision tree again. This is done over and over until one finds combinations of L and C that are practical for the overall design. For purposes of the present invention, it is possible to use series discrete inductors or parallel discrete capacitors to achieve the same overall result. For example, in the case of the inductor element L, it would be possible to use two, three or even more (n) individual inductor elements in series. The same is true for the capacitor element that appears in the parallel TANK filter 146. By adding or subtracting capacitors in parallel, we are also able to adjust the total capacitance that ends up resonating in parallel with the inductance.

It is also possible to use a single inductive component that has significant parasitic capacitance between its adjacent turns. A careful designer using multiple turns could create enough parasitic capacitance such that the coil becomes self-resonant at a predetermined frequency. In this case, the predetermined frequency would be the MRI pulsed frequency.

Figure 24:
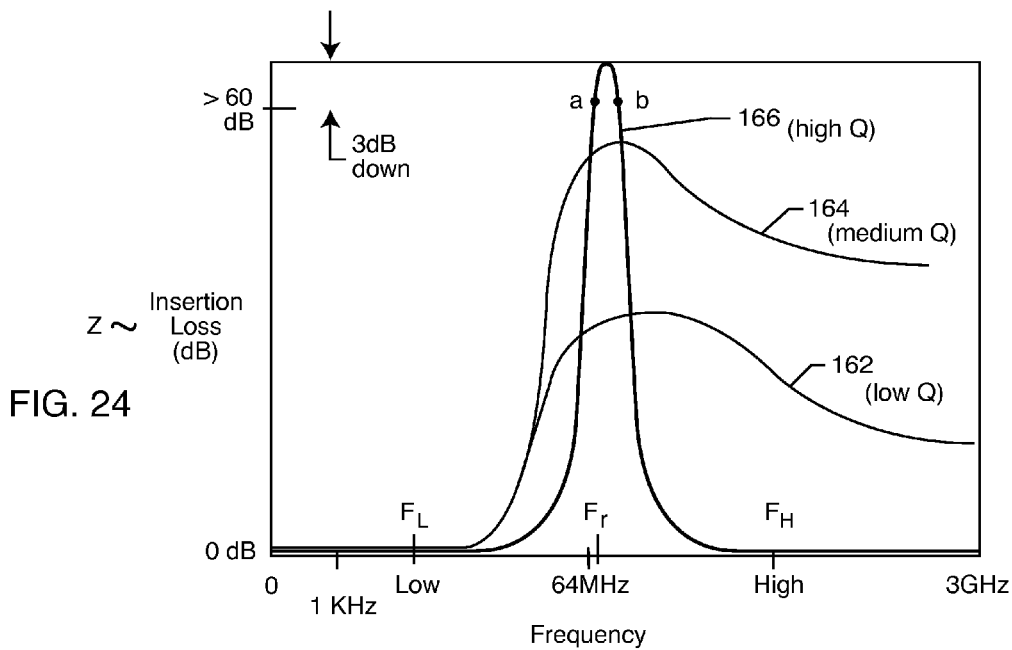
FIG. 24 is a graph of insertion loss verses frequency for TANK filters having differing quality "Q" factors.

Efficiency of the overall TANK circuit 146 is also measured in terms of a quality factor, Q, although this factor is defined differently than the one previously mentioned for discrete capacitors and inductors. The circuit Q is typically expressed using the following equation:

$$Q = \frac{f_r}{\Delta f_{3\,\text{dB}}}$$

Where $f_r$ is the resonance frequency, and $\Delta f_{3dB}$ shown as points a and b in FIG. 24, is the bandwidth of the TANK filter 146. Bandwidth is typically taken as the difference between the two measured frequencies, $f_1$ and $f_2$, at the 3 dB loss points as measured on an insertion loss chart, and the resonance frequency is the average between $f_1$ and $f_2$. As can be seen in this relationship, higher Q values result in a narrower 3 dB bandwidth.

Material and application parameters must be taken into consideration when designing TANK filters. Most capacitor dielectric materials age 1%-5% in capacitance values per decade of time elapsed, which can result in a shift of the resonance frequency of upwards of 2.5%. In a high-Q filter, this could result in a significant and detrimental drop in TANK performance. A low-Q filter would minimize the effects of resonance shift and would allow a wider frequency band through the filter. However, low Q filters also display lower than desirable attenuation behavior at the desired TANK frequency (see FIG. 24, curve 162). For this reason, the optimum Q for the TANK filter of the present invention will embody a high Q inductor L and a relatively low Q capacitor C which will result in a medium Q TANK filter as shown in curve 164 of FIG. 24.

Accordingly, the "Q" or quality factor of the TANK circuit is very important. As mentioned, it is desirable to have a very low loss circuit at low frequencies such that the biological signals not be undesirably attenuated. The quality factor not only determines the loss of the filter, but also affects its 3 dB bandwidth. If one does a plot of the filter response curve (Bode plot), the 3 dB bandwidth determines how sharply the filter will rise and fall. With reference to curve 166 of FIG. 24, for a TANK that is resonate at 128 MHz, an ideal response would be one that had infinite attenuation at 128 MHz, but had zero attenuation at low frequencies below 1 KHz. Obviously, this is not possible given the space limitations and the realities of the parasitic losses within components. In other words, it is not possible (other than at cryogenic temperatures) to build an inductor that has zero internal resistance. On the other hand, it is not possible to build a perfect (ideal) capacitor either.

Capacitors have internal resistance known as equivalent series resistance and also have small amounts of inductance. Accordingly, the practical realization of a circuit, to accomplish the purposes of the present invention, is a challenging one. This is particularly true when one also considers that the tank circuit must also be miniature, highly reliable, and completely biocompatible.

The performance of the circuit is directly related to the efficiency of both the inductor and the capacitor; the less efficient each component is, the more heat loss that results, and this can be expressed by the addition of resistor elements to the ideal circuit diagram. The effect of lower Q in the TANK circuit is to broaden the resonance peak about the resonance frequency. By deliberately using a low Q capacitor, one can broaden the resonance such that relatively high impedance (high attenuation) is presented at multiple MRI RF frequencies, for example 64 MHz and 128 MHz.

Referring again to FIG. 24, one can see curve 164 wherein a high Q inductor has been used in combination with a low Q capacitor. This has a very desirable effect in that at very low frequencies, the impedance of the TANK circuit 146 is essentially zero (below 1 ohm) ohms (or zero dB loss). This means that biologic frequencies are not undesirably attenuated. However, one can see that the 3 db bandwidth is much larger. This is desirable as it will block multiple RF frequencies. As one goes even higher in frequency, curve 164 will desirably attenuate other high frequency EMI signals, such as those from cellular telephones, microwave ovens and the like. Accordingly, it is often desirable that very low loss inductors be used in combination with relatively high loss capacitors to achieve a medium or lower Q TANK filter. Again referring to FIG. 24, one can see that if the Q of the overall circuit or of the individual components becomes too low, then we have a serious degradation in the overall attenuation of the TANK filter. Accordingly, a careful balance between component design and TANK circuit Q must be achieved.

Figure 25:
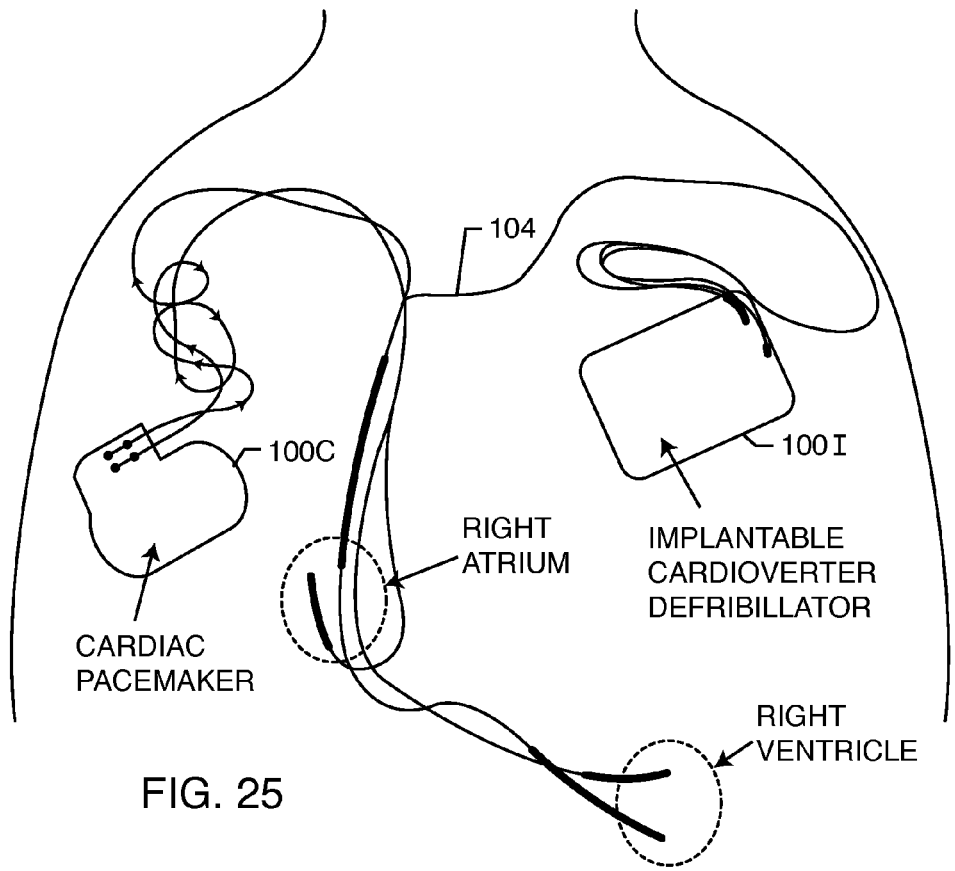
FIG. 25 is a tracing of an exemplary patient x-ray showing an implanted cardiac pacemaker and cardioverter defibrillator and corresponding wire system.

FIG. 25 is a tracing of an actual patient X-ray from the Association for the Advancement of Medical Instrumentation (AAMI) PC69 Pacemaker EMC Task Force. This particular patient required both a cardiac pacemaker 100C and an implantable cardioverter defibrillator 100I. The corresponding lead wire system 104, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

Referring again to FIG. 25, one can see that from the pacemaker 100C, there are electrodes in both the right atrium and in the right ventricle. Both these involve a TIP and RING electrode. In the industry, this is known as a dual chamber bipolar lead wire system. Accordingly, at a minimum the TANK filters 146 of the present invention should be placed at the distal TIP in the right atrium and the distal TIP in the right ventricle from the cardiac pacemaker. One can also see that the implantable cardioverter defibrillator (ICD) 100I is implanted directly into the right ventricle. Its shocking TIP and sense electrodes would also require a TANK filter so that MRI exposure cannot induce excessive currents in that lead wire system. Modern implantable cardioverter defibrillators (ICDs) incorporate both pacing and cardioverting (shock) features. Accordingly, it is becoming quite rare for a patient to have two discrete AIMD systems, as shown in FIG. 25. However, the number of electrodes remain the same. There are also newer combined pacemaker/ICD systems which include biventricular pacemaking (pacing of the left ventricle). These systems can have as many as nine to even twelve lead wires.

Figure 26:
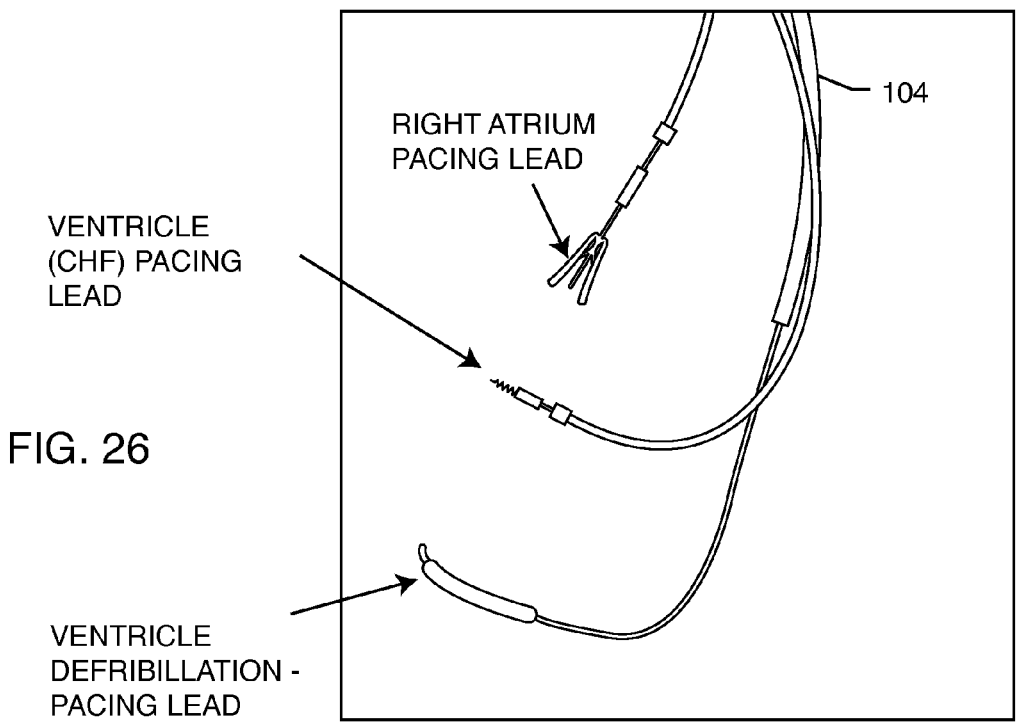
FIG. 26 is a line drawing of an exemplary patient cardiac x-ray of a bi-ventricular lead wire system.

FIG. 26 is a line drawing of an actual patient cardiac X-ray of one of the newer bi-ventricular lead wire systems. The new bi-ventricular systems are being used to treat congestive heart failure, and make it possible to implant leads outside of the left ventricle. This makes for a very efficient pacing system; however, the lead wire system 104 is quite complex. When a lead wire system 104, such as those described in FIGS. 8, 9, 10 and 11, are exposed to RF fields, electric currents can be induced into such lead wire systems. For the bi-ventricular system, TANK filters 146 would be required at each of the three distal TIPs.

Figure 27:
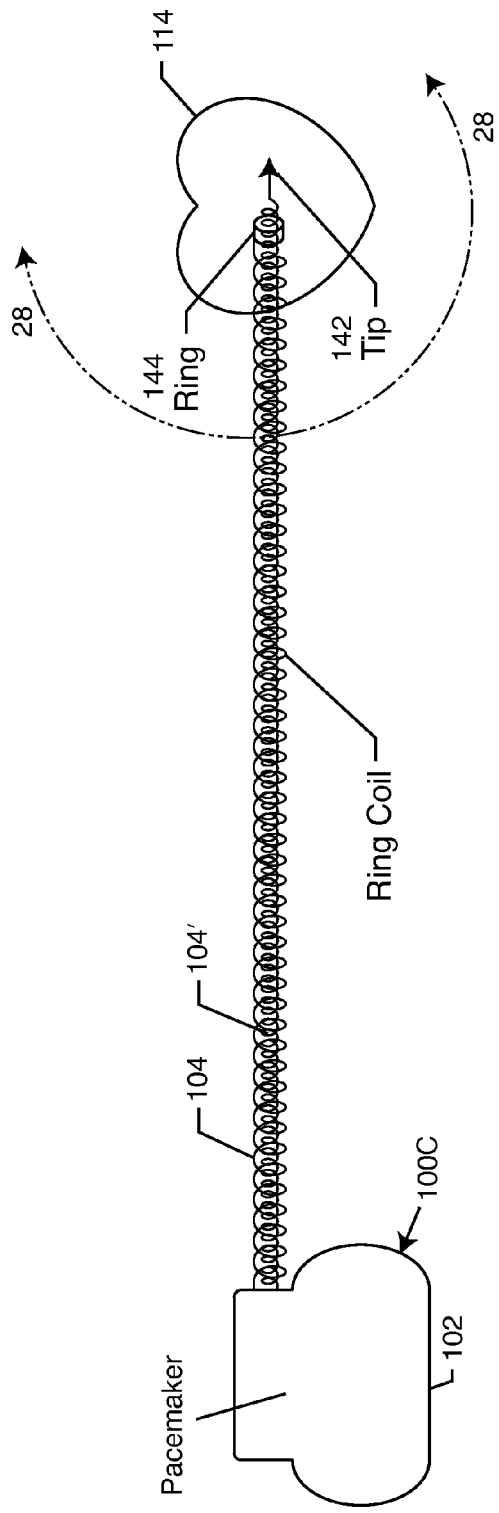
FIG. 27 illustrates a bipolar cardiac pacemaker lead wire showing the distal TIP and the distal RING electrodes.

FIG. 27 illustrates a single chamber bipolar cardiac pacemaker lead wire showing the distal TIP 142 and the distal RING 144 electrodes. This is a spiral wound (coaxial) system where the RING coil 104 is wrapped around the TIP coil 104'. There are other types of pacemaker lead wire systems in which these two leads lay parallel to one another (known as a bifilar lead system).

Figure 28:
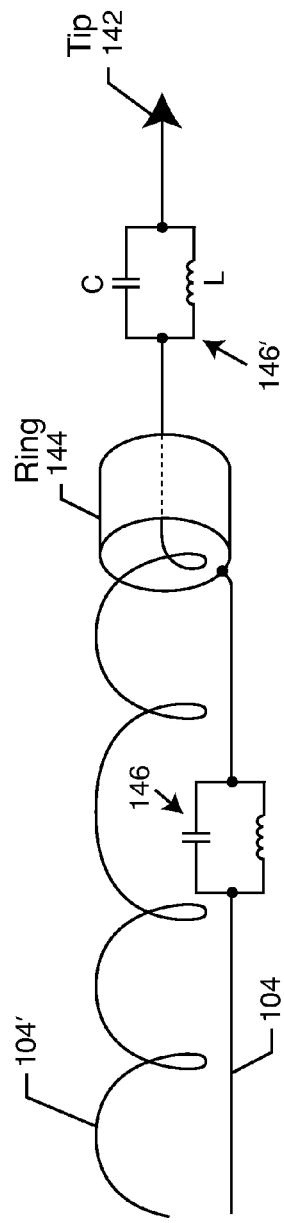
FIG. 28 is an enlarged, fragmented schematic illustration of the area illustrated by the line 28-28 in FIG. 27 with the L-C TANK of the present invention shown in series with both the distal TIP and the RING electrodes.

FIG. 28 is a schematic illustration of the area 28-28 in FIG. 27. In the area of the distal TIP 142 and RING 144 electrodes, TANK filters 146 and 146' have been placed in series with each of the respective RING and TIP circuits. The RING circuit wire 104 has been drawn straight instead of coiled for simplicity. Accordingly, at an MRI pulsed RF frequency, a high impedance will be presented thereby reducing or stopping the flow of undesirable MRI induced RF current.

The TIP 142 is designed to be inserted into intimate contact with myocardial tissue. Over time it becomes encapsulated and fully embedded or buried within such tissue. However, the RING 144 is designed to float within the blood pool, for example, in the ventricle or atrium. With the constant blood perfusion, the RING 144 is somewhat cooled during medical diagnostic procedures, such as MRI. However, the TIP 142 which is embedded in the myocardial tissue, is thermally insulated in comparison. It can't always be assumed that a RING electrode that is floating in the blood pool will be adequately cooled by the flow of blood. There are certain types of patients that have illnesses that lead to very low blood flow rates and perfusion issues. Accordingly, in a preferred embodiment both the distal TIP and the RING would both be filtered with the TANK of the present invention. Accordingly, the operation of the novel TANK filter 146 is more important in the TIP 142 than it is in the RING 144 in order to prevent distal TIP heating and associated tissue damage. In most cardiac applications, only a TIP TANK filter is required for MRI compatibility.

Figure 29:
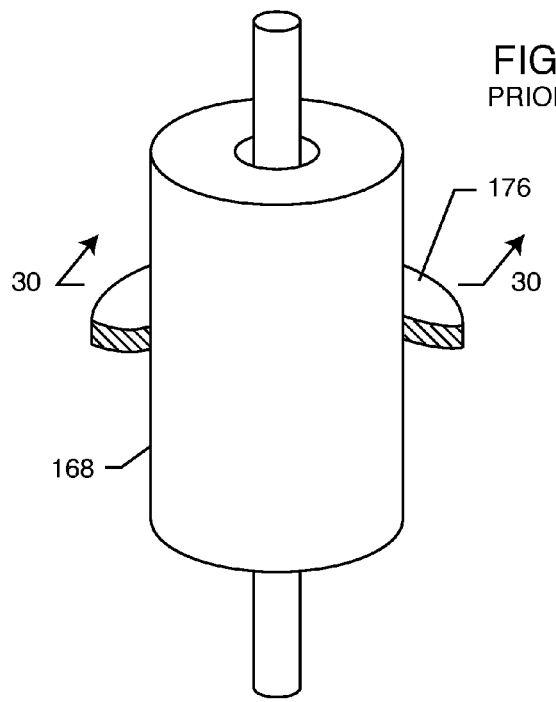
FIG. 29 is a perspective view of a prior art tubular feedthrough capacitor.
Figure 30:
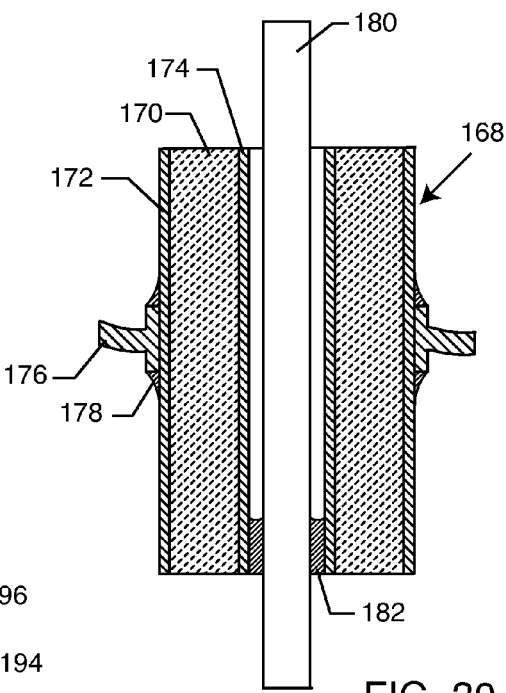
FIG. 30 is a sectional view taken along the line 30-30 of FIG. 29.

FIGS. 29 and 30 illustrate a prior art tubular feedthrough capacitor 168. In the art, this is known as a single wall or extruded tubular capacitor, and is very commonly used in commercial electronic applications. Such capacitors 168 are fabricated in a drawing-extrusion process. The tubes are cut off at a desired length and are fired (sintered). The material in this case is a high K ceramic dielectric 170. The tube 170 is then metallized on the outside 172 and also metallized on the inside diameter 174 as illustrated. The capacitance is formed between the inner and outer diameter metallizations 172, 174 (two concentric cylinders separated by the high K dielectric). A flange 176 is typically associated with capacitor 168 by high temperature solder attachment 178 for convenient mounting into a bulkhead. There is also a lead wire 180 which passes continuously through the feedthrough capacitor 168 and is attached to the inside diameter metallization 174 using a high temperature solder 182. This continuous lead wire distinguishes all prior art feedthrough capacitors from the present TANK invention which always features a novel discontinuous lead. These prior art feedthrough capacitors are very efficient low inductance capacitors and, as mentioned, are used in a wide variety of prior art electronic low pass EMI filter applications.

Figure 31:
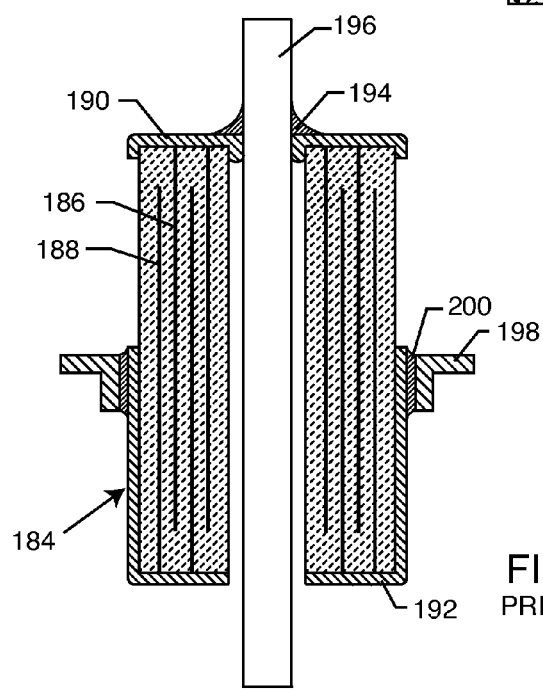
FIG. 31 is a sectional view similar to that shown in FIG. 30, illustrating a prior art multilayer tubular capacitor.

FIG. 31 is a cross-section of a prior art multilayer tubular capacitor 184. This is very similar to the capacitor 168 shown in FIG. 30 except that it is not formed by tube extrusion processes. This capacitor 184 is rolled, has embedded electrode plates 186, 188, and has a cylindrical shape. It is then fired and metallization is placed on its top end 190 and bottom end 192 as shown. An electrical connection 194 is made to lead wire 196. Metallization 192 is attached to the electrode set 188 at the bottom of the cross-section. An optional flange 198 is added for convenient mounting into a bulkhead. This flange is attached using high temperature solder, braze, or the like 200.

Figure 32:
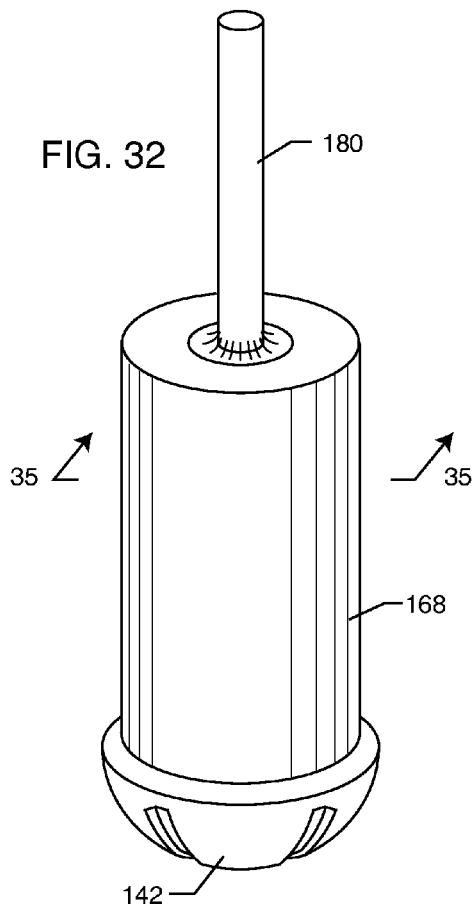
FIG. 32 is a perspective view similar to FIG. 29, illustrating a modification including the distal TIP electrode in accordance with the present invention of the tubular feedthrough capacitor of the tank filter.

FIG. 32 is a modification of the prior art single wall tubular capacitor 168 illustrated in FIGS. 29 and 30 showing the features of the present invention. In FIG. 32, one can see that there is a lead wire 180 which is a lead wire coming from an active implantable medical device 100 (not shown). The distal TIP 142 makes contact with body tissue. In this case, this could be the distal TIP 142 in the ventricle of a cardiac pacemaker.

Figure 33:
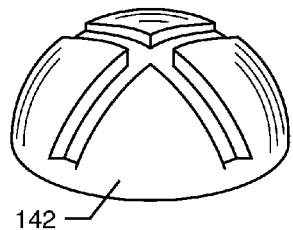
FIG. 33 is an inverted perspective view of a high surface area distal TIP illustrated in FIG. 32.

FIG. 33 is an inverted view of the high surface area distal TIP 142 shown in FIG. 32 (passive fixation wings not shown). There are a number of distal TIPs that are common in the art. Generally, these are of very high surface area to optimize electrical performance with body tissue. These are known as low polarization TIPs. Some of these TIP designs are even designed to elute certain drugs to minimize tissue inflammation, necrosis, etc.

Figure 34:
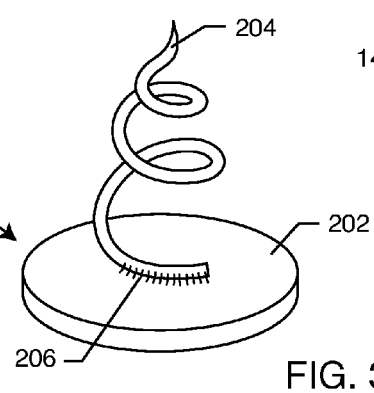
FIG. 34 illustrates an active fixation helix TIP alternative to the inverted distal TIP shown in FIG. 33.

FIG. 34 illustrates an alternative to the inverted distal TIP previously illustrated in FIG. 33. FIG. 34 is known in the art as an active fixation helix TIP 142' whose sharp point 204 and helix coil are generally designed to be threaded into body tissue. The TIP 142' includes a base plate 202 generally consisting of a biocompatible material, such as platinum, titanium or the like, and a helix lead wire 204 generally attached to the base plate by laser welding 206.

Figure 35:
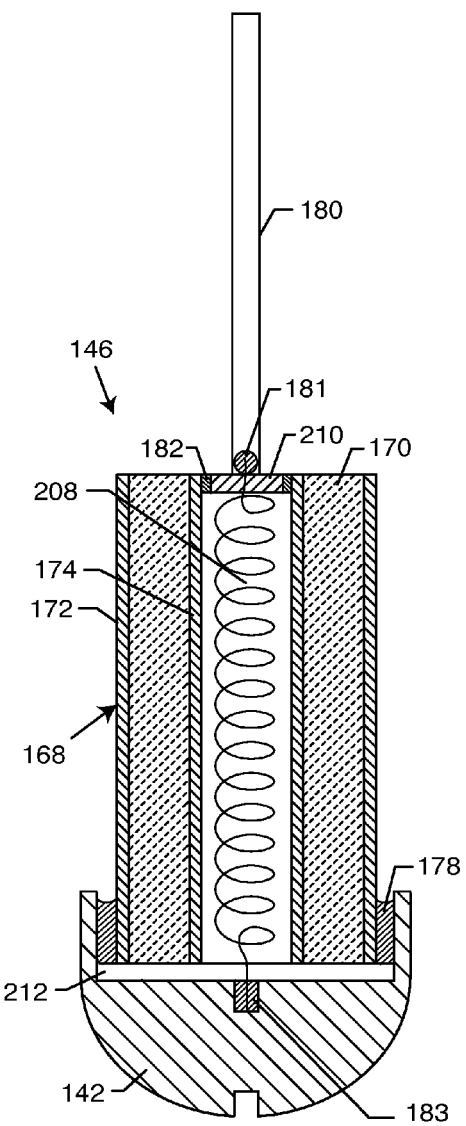
FIG. 35 is a sectional view taken along the line 35-35 of FIG. 32.

The novel structure illustrated in FIG. 32 is better understood by looking at the cross-section in FIG. 35 taken generally along the lines 35-35 from FIG. 32. Referring to FIG. 35 and comparing it with FIG. 30, one can see that there is a significant difference between the two. First of all, the novel lead wire 180 is discontinuous in that it does not pass all the way through the center of the feedthrough capacitor 168. Instead, it has been replaced by the inductive structure 208. It is desirable, but not required, that structure 208 be an air wound or equivalent non-ferrous inductor. In this case, the air wound coil is inside of the tubular capacitor element and is thereby protected by direct exposure to body fluids. As previously described, embedding inductor coils in body fluid is problematic because of the varying dielectric constant of the body fluid and also its electrical conductivity properties. However, the present application also has broad application to a variety of non-medical implant applications, including military, space and various other commercial applications. Accordingly, the inductor 208 could also include the group of a toroidal inductor, a solenoid inductor wound around a ferrite or iron or other ferro-magnetic core, a ferrite chip inductor involving various ferro-magnetic materials, and the like. As previously mentioned, the use of these ferro-magnetic materials in the presence of an MRI system is not ideal. The reason for this is that ferromagnetic materials exhibit hysteretic behavior, which results in changing electrical performance in high magnetic fields. In addition, substantial MRI image artifact would also be induced. However, for a non-medical application, there is no reason why the inductor L could not be made from a variety of materials. One can also see that the device has been integrated with coaxial TIP 142 such that it is ready for implantation into a ventricle or atrium of a cardiac patient.

Figure 36:
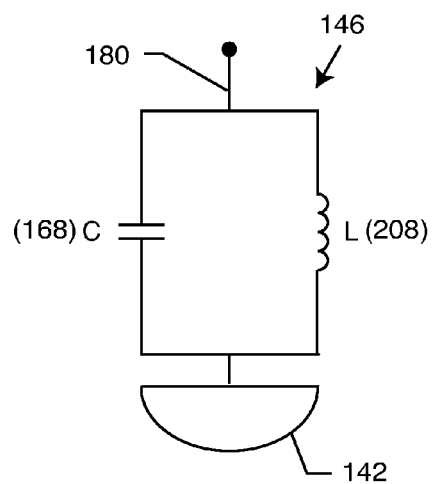
FIG. 36 is an electrical schematic diagram for the ideal TANK filter of FIGS. 32 and 35.

The ideal schematic diagram for the novel TANK filter 146 of FIGS. 32 and 35 is shown in FIG. 36. As previously mentioned, the values of C (168) and L (208) are carefully selected to be resonant such that a high impedance L-C TANK filter is achieved at a selected MRI pulse frequency or band of frequencies.

Referring once again to FIG. 35, one can see that an electrical connection is required between lead wire 180 and a conductive end cap 210 which is shown electrically attached to the capacitor inside diameter metallization 174 at point 182. There is also an electrical connection required between the distal TIP 142 and the capacitor outside diameter metallization 172 at point 178. There is also an electrical connection 183 required between the inductor spiral 208 and the conductive distal TIP 142. This electrical connection places the inductor element 208 in parallel with the capacitor element 170 thereby forming the novel tank of the present invention. Again, lead wire 180 is discontinuous to the distal TIP 142 with said discontinuity replaced by the inductor spiral 208. It is very important that all of the electrical connections be of suitable biocompatible materials. For example, electrical connection 181 could be of a suitable laser weld. Electrical connection 182 and 183 could be of biocompatible thermosetting conductive adhesives such as gold or platinum flake loaded silicones, polyimides or the like. The gap 212 shown between the distal TIP 142 and the inside diameter metallization 174 can be air, but it is preferably an insulator such as a biocompatible plastic thermo-setting polymer, or the like.

Figure 37:
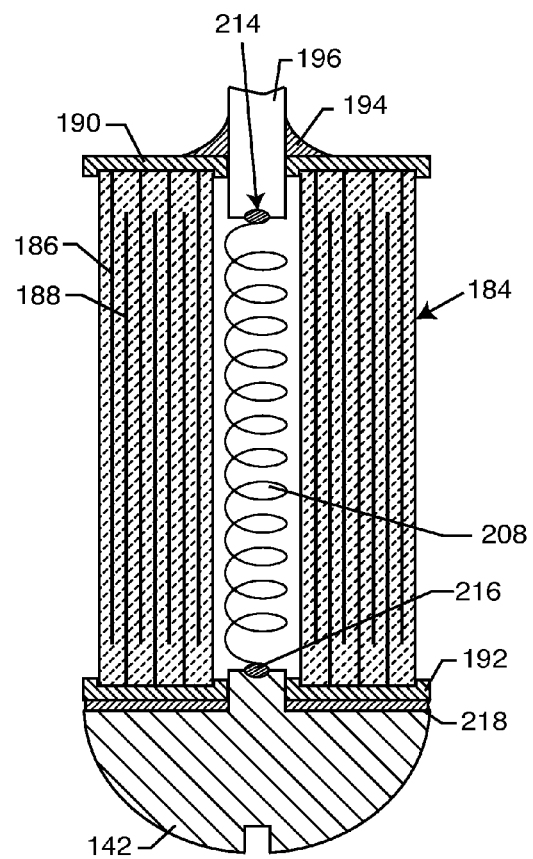
FIG. 37 is a cross-sectional diagram similar to FIG. 35, illustrating the present invention applied to the multilayer capacitor shown in FIG. 31.
Figure 38:
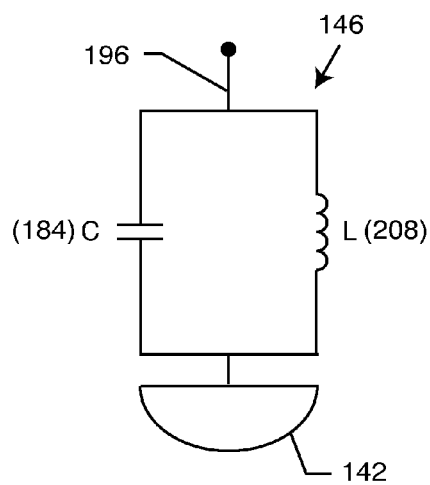
FIG. 38 is an electrical schematic similar to FIG. 36.

FIG. 37 is a cross-sectional drawing incorporating the prior art multilayer capacitor 184 previously described in FIG. 31. Referring to FIG. 37, one can see that the lead wire 196 is discontinuous. In fact, the lead wire 196 is terminated at point 214 where it attaches to the internal inductor 208, which can be an air wound spiral type inductor as illustrated in other applications, or a ferrite chip inductor or the like. The inductor could also be wound around the outside around the capacitor 184. As previously discussed, winding the inductor around the outside of the capacitor would have directly exposed its turns to body fluid, which would be undesirable. Body fluid is relatively conductive and would cause currents to flow from turn to turn. In addition, the dielectric constant of the body fluid would change the parasitic capacitance between turns and thereby affect the resonant frequency of the parallel tank. There is an electrical and mechanical attachment 194 between lead wire 196 and the capacitor top metallization layer 190. This metallization contacts electrode plate set 186. At the opposite end of the multilayer tubular capacitor structure 184, there is a distal TIP electrode 142. This is electrically attached to the inductor 208 at point 216. There is also an electrical attachment to the opposite electrode plate set 188 through capacitor termination layer 192. This has the effect of taking the capacitance formed by the multilayer capacitor 184 and putting it in parallel with the inductance. This is best understood by referring to the schematic diagram in FIG. 38. For a specific dielectric constant material, the capacitance value is adjusted by the relative overlapping area of the electrode plate sets 186 and 188 and the dielectric spacing thickness between them. In other words, one can design this to have any capacitance value desired, so that it will self-resonate with the inductor at specific frequencies. An optional insulative washer 218 is disposed between the metallization 192 and the distal TIP 142.

Figure 39:
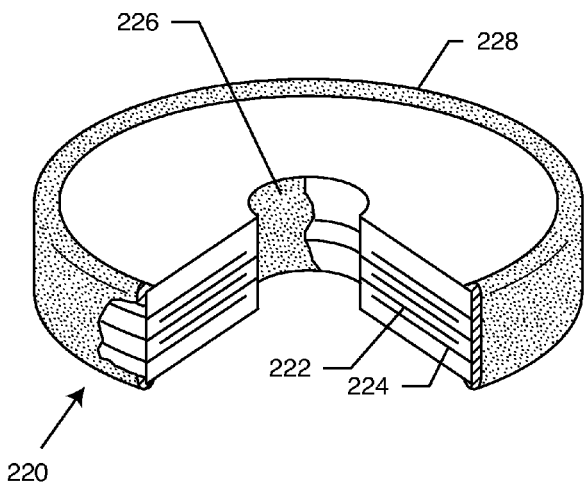
FIG. 39 is a partially fragmented perspective view of a prior art unipolar discoidal feedthrough capacitor.

FIG. 39 illustrates a prior art unipolar discoidal feedthrough capacitor 220. This is a multilayer coaxial capacitor which is well known in the prior art. One of its advantages is that it operates at very high frequency. This is because of its coaxial transmission line nature and the fact that it has very low internal inductance. The capacitor 220 includes overlapping circular electrode plate sets 222 and 224. Electrode plate set 222 is known as the active electrode plate set and is electrically connected to the capacitor inside diameter metallization 226 as shown. The ground electrode plate set 224 is attached to the outside diameter metallization 228. Such prior art feedthrough capacitors are often used in conjunction with EMI filters for active implantable medical devices. These are generally shown and described in U.S. Pat. Nos. 4,424,551; 5,905,627; 6,008,980; 6,643,903; 6,765,779 and many others.

Figure 40:
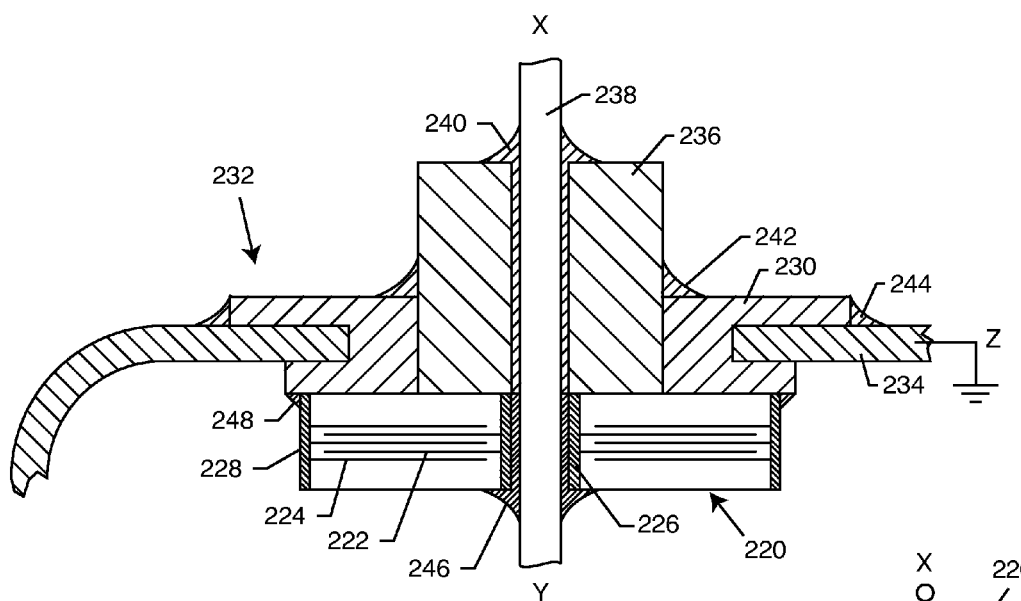
FIG. 40 is a fragmented sectional view of the feedthrough capacitor of FIG. 39 mounted to a ferrule and hermetic terminal of an AIMD.

FIG. 40 shows the prior art feedthrough capacitor 220 of FIG. 39 mounted to a ferrule 230 of hermetic terminal 232 of an active implantable medical device housing 234. In all prior art devices, lead wire 238 is continuous. The hermetic terminal 232 is attached to, typically, a titanium housing 234, for example, of a cardiac pacemaker. An insulator 236, like alumina ceramic or glass, is disposed within the ferrule 230 and forms a hermetic seal against body fluids. A terminal pin or lead wire 238 extends through the hermetic terminal 232, passing through aligned passageways through the insulator 236 and the capacitor 220. A gold braze 240 forms a hermetic seal joint between the terminal pin 238 and the insulator 236. Another gold braze 242 forms a hermetic seal joint between the alumina insulator 236 and the titanium ferrule 230. A laser weld 244 provides a hermetic seal joint between the ferrule 230 and the housing 234. The feedthrough capacitor 220 is shown surface mounted in accordance with U.S. Pat. No. 5,333,095, and has an electrical connection 246 between its inside diameter metallization 226 and hence the active electrode plate set 222 and lead wire 238. There is also an outside diameter electrical connection 248 which connects the capacitor's outside diameter metallization 228 and hence the ground electrodes 224 to the ferrule 230. Feedthrough capacitors are very efficient high frequency devices that have minimal series inductance. This allows them to operate as EMI low-pass filters over very broad frequency ranges.

Figure 41:
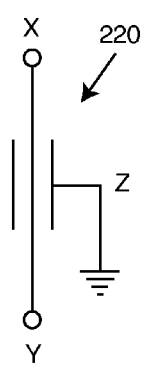
FIG. 41 is an electrical schematic diagram of the feedthrough capacitor of FIGS. 39 and 40.

FIG. 41 is the schematic diagram of the prior art feedthrough capacitor 220 illustrated in FIGS. 39 and 40.

Figure 42:
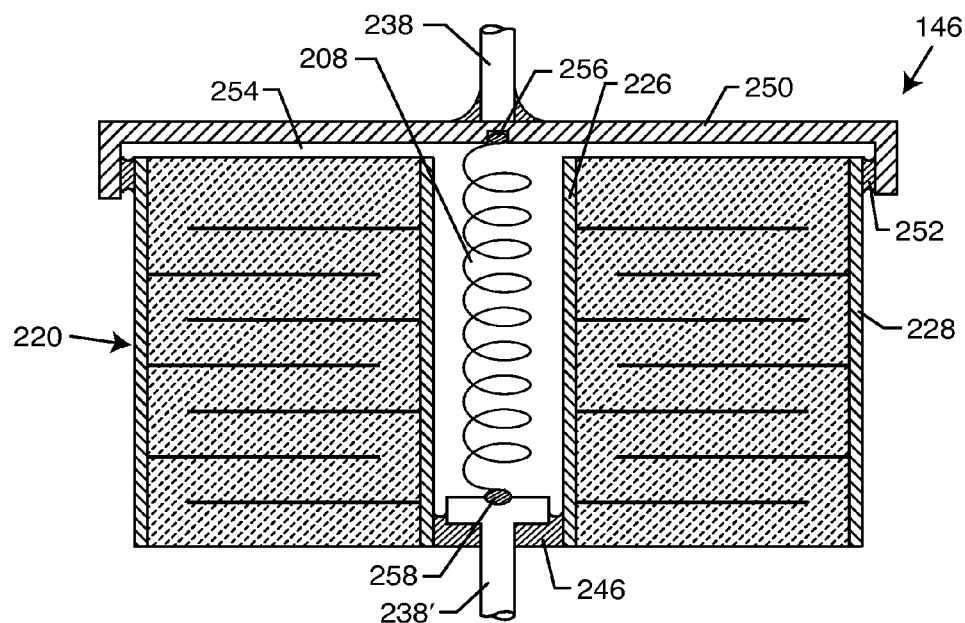
FIG. 42 is a sectional and diagrammatic view of a novel adaptation of the prior art feedthrough capacitor shown in FIGS. 39 and 40, adapted in accordance with the present invention.
Figure 43:
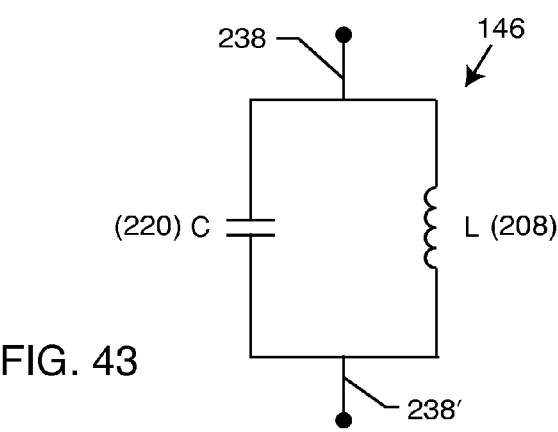
FIG. 43 is an electrical schematic diagram illustrating the electrical characteristics of the structure shown in FIG. 42.

FIG. 42 is a novel adaptation of the prior art feedthrough capacitor of FIGS. 39 and 40 in accordance with the present invention. An end cap 250 is seated over the top of the feedthrough capacitor 220 such that it makes electrical contact at point 252 with the capacitor outside diameter metallization 228. There is a space or air gap 254 which separates the end cap 250 from the capacitor inside diameter metallization 226 so that a short circuit does not occur. In a preferred embodiment the gap 254 would be filled with an insulative material such as a non-conductive epoxy or thermal setting polymer or a spacer disk such as a silicone disk or other biocompatible material. Referring once again to FIG. 42, one can see that there is a novel inductor 208 contained within the capacitor 220 inside diameter. As will be more fully discussed herein, the inductor 208 can be an air wound spiral, chip inductors and the like. The lead wire system 238 and 238' in this case, is discontinuous. That is, unlike other prior art feedthrough capacitors, the lead wire 238 does not pass all the way through the center of the capacitor 220. The inductor 208 is connected to the end plate 250 at location 256. The inductor 208 is also connected to the other lead wire segment 238' at the opposite end at point 258. Biocompatible electrical and mechanical attachments at points 256 and 258 can be accomplished by laser welding, brazing, mechanical attachments and the like. In general, the use of solders is undesirable in that they are generally not considered biocompatible. An exception to this would be to surround the entire structure shown in FIG. 42 with a glass encapsulant or sapphire to hermetically seal the entire assembly and thereby prevent body fluids from reaching this TANK filter structure (see FIG. 140 for example). Referring once again to the bottom of the novel feedthrough capacitor 220 of FIG. 42, one can see that lead wire 238' has been terminated with a convenient nail head shape so that electrical connection 246 can be made from the lead wire 238' to the capacitor's inside diameter metallization 226. This forms the novel filter TANK circuit 146 consisting of the parallel inductor 208 and capacitor 220 as shown in the schematic in FIG. 43. A particular advantage of the structure shown in FIG. 42 is that high volume manufacturing techniques that are presently employed for ceramic feedthrough capacitors can be used. With the exception of the discontinuous lead, there is nothing structurally different about the feedthrough capacitor itself as compared with the prior art capacitor 220 of FIG. 39. In other words, this is a novel adaptation of feedthrough capacitors for convenient use in a TANK filter configuration, for example, in the distal TIP 142 of implantable medical devices. The miniature coaxial structure of such capacitors is ideal for insertion, for example, through veins or tunneling through body tissue.

Referring once again to FIG. 42, one can see that the capacitor 220 and the inductor 208 and the end cap 250 are all exposed to body fluids. This is also true of all of the various electrical connections. It is very important that all of these materials be long term biocompatible, as disclosed in U.S. Pat. No. 7,113,387 which is incorporated by reference herein. Referring once again to FIG. 42, one can see that the capacitor 220 would be composed of biocompatible materials as described in U.S. Pat. No. 7,113,387. In a preferred embodiment, the capacitor electrodes would be of either high-fired pure platinum or a ternary system consisting of gold, platinum and palladium. The capacitor's terminations 228 would be of pure gold or platinum plating or a loaded glass frit. The same would be true of the inside diameter capacitor termination 226. The end plate 250 would be of platinum, platinum iridium, titanium or other suitable biocompatible material. The discontinuous lead wires 238 and 238' would be comprised of MP-35N or equivalent. The electrical connections 256 would generally consist of laser welding and not introduce foreign materials at all. Electrical connection material 252 and 246 would be of a suitable thermally conductive biocompatible material. Examples of this would be gold or platinum flake loaded ISO qualified silicones, polyimides, thermal setting polymers and the like.

Figure 44:
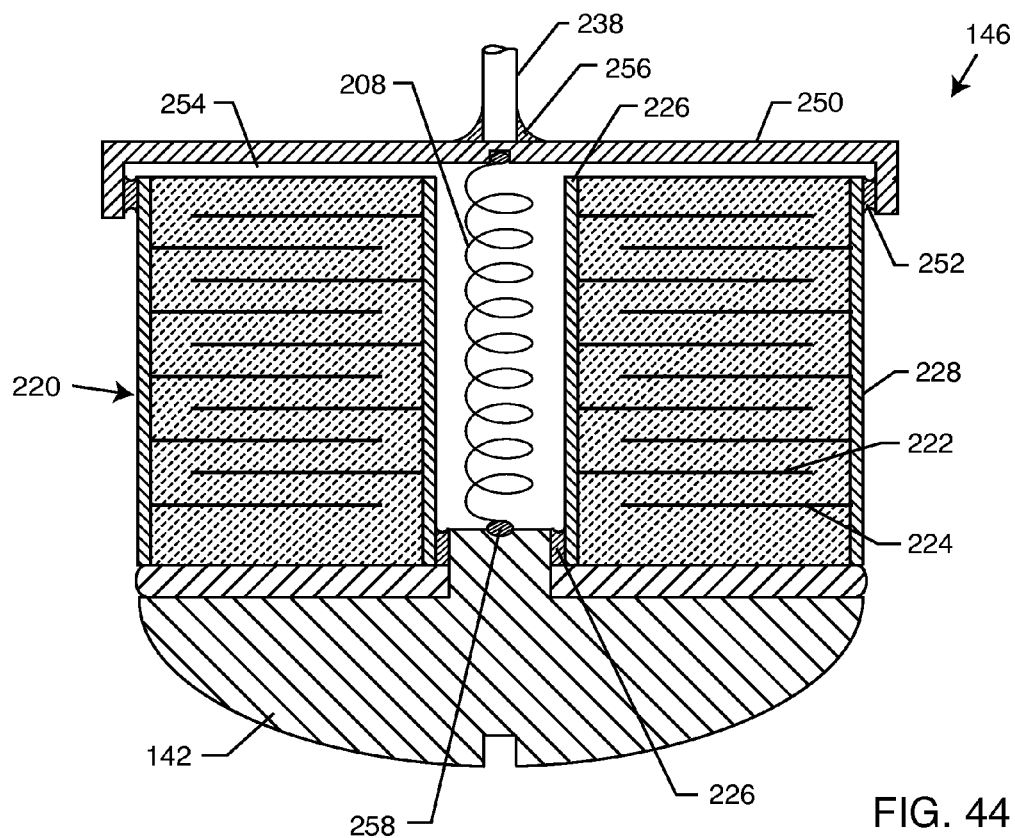
FIG. 44 is a sectional view similar to FIG. 42 illustrating the novel structure placed at the terminus of a distal TIP.

FIG. 44 is very similar to FIG. 42 except that instead of being placed in the midpoint or other location of a lead wire system, the novel L-C TANK now terminates in distal TIP 142. The distal TIP 142 is designed for direct contact with, in the case of a cardiac pacemaker, myocardial tissue. All of the other features of the TANK filter 146 of FIG. 44 are very similar to the structure of the TANK filter 146 of FIG. 42.

Figure 45:
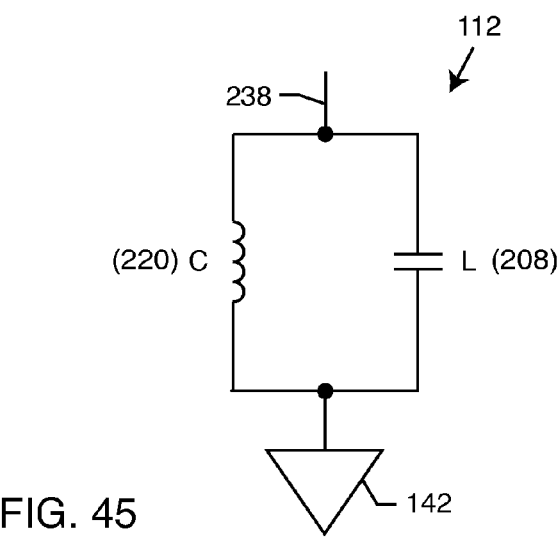
FIG. 45 is an electrical schematic diagram of the structure shown in FIG. 44.

FIG. 45 is the schematic diagram of the distal TIP TANK circuit 146 of the substrate shown in FIG. 44.

Figure 46:
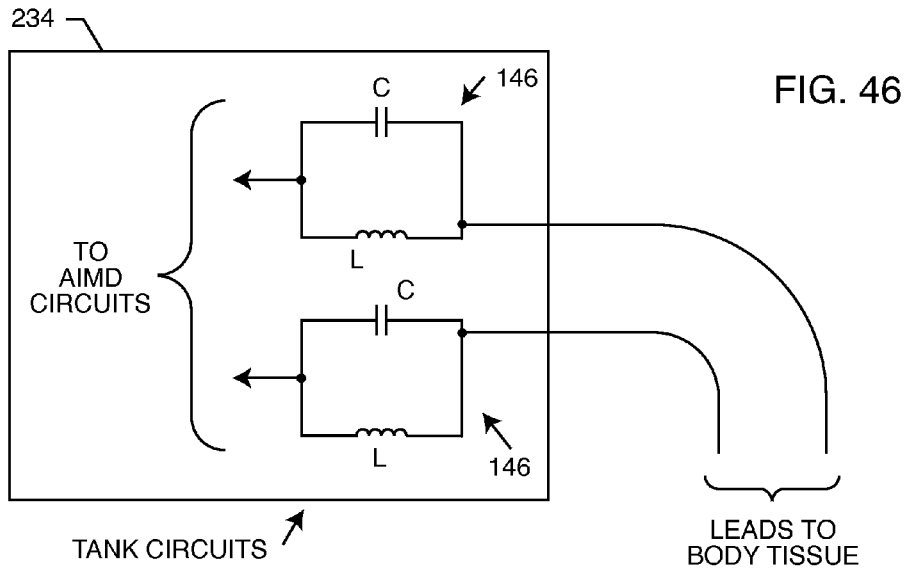
FIG. 46 is a diagram showing another arrangement wherein the novel TANK circuits described herein can be placed inside the hermetically sealed housing of an AIMD.

FIG. 46 shows yet another novel arrangement wherein any of the novel TANK circuits 146 as previously described herein can also be placed inside the housing 234 of the active implantable medical device. An advantage to this is that the TANK inductor and capacitor components are completely protected from body fluid. For example, the novel feedthrough capacitor arrangement as previously described in FIG. 42, could be placed inside the active implantable medical device. These particular LC TANK filters 146 could be placed at the distal TIP and/or anywhere along the lead wire system as well as inside the active implantable medical device itself. This is also true for the TANK filters 146 shown in FIG. 32, 35 or 37. In other words, any of the TANK L-C filters of the present invention can be conveniently located inside the active implantable medical device 100. In actual practice, it may be required to have distal electrode TIP TANK filters 146 in addition to TANK filters 146 installed inside the AIMD. In another embodiment, it would be possible to have a distal TIP tank filter placed inside the AIMD, one or more distal TIP tanks placed along the associated lead wire, and a tank placed at the distal electrode TIP. The reason for this has to do with the unique way that MRI couples into an implanted lead wire system. Because of the distributed inductances in a typical implanted lead wire system, the distal TIP is largely decoupled at MRI RF pulsed frequencies from the active implantable medical device itself. In other words, the pulsed RF field from MRI can induce localized loop currents at the distal TIP while at the same time inducing currents at other locations in the lead wire system. It is also desirable to prevent high frequency electromagnetic interference that is due to the RF pulsed field of MRI from entering into the sensitive AIMD circuits. For example, in a cardiac pacemaker application, this could cause the pacemaker to malfunction during the MRI procedure thereby placing the patient's life in danger. Accordingly, it is a feature of the present invention that any of the TANK filters 146 as described herein can be placed anywhere in the lead wire system, in conjunction with a distal tissue electrode, and/or inside the AIMD itself.

Figure 47:
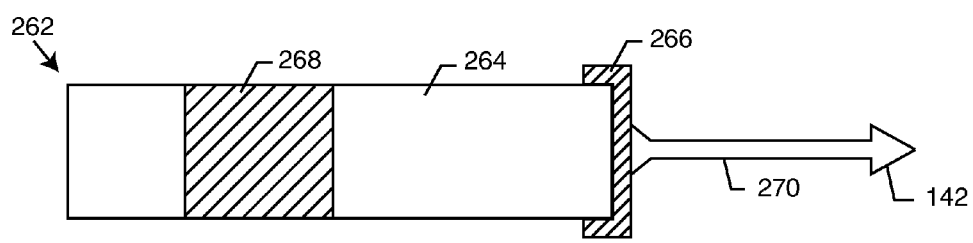
FIG. 47 is an external view of a novel active implantable medical device that may or may not have lead wires, known as a Bion.

FIG. 47 illustrates a prior art active implantable medical device that may or may not incorporate implanted lead wires. This is known in the industry as a Bion 262. Bions 262 generally come in two different categories. That is, certain Bions have an internal battery and are a stand-alone stimulation device used for urinary incontinence and other applications. These are generally large needle injectable systems. The Bion 262 generally is encased in a ceramic tube 264 that has an end cap electrode 266. The end cap electrode 266, for example, could be titanium or platinum and is generally welded or brazed to the ceramic tube 264 to make a hermetic seal thereby protecting the sensitive electronics that are inside of the ceramic tube 264 from damage due to body fluid. There is also an opposite polarity RING electrode 268 as shown. This particular device stimulates body tissue between the cap electrode 266 and the RING electrode 268.

Other types of Bions have no battery, but instead have a resonant coil. The device picks up its energy from an externally worn or externally placed pulsing magnetic field pack. A patient can wear some sort of a device around his or her waist or shoulder, for example, with a large battery and circuit coil that produces this field. The Bion would get its energy by coupling with this field. No matter whether the Bion 262 is passive or has an internal battery, it is still important to protect the internal circuits of the Bion from temporary or permanent malfunction due to the RF pulse frequency of MRI systems. There are also cases where the diameter of the Bion 262 is too large for it to effectively make contact with a precise location within a nerve or muscle. In this case, the Bion 262 may have an associated lead wire 270 with a distal TIP 142. In this case, the end cap 266 and the lead wire would be insulative wherein the electrical connection to body tissue would occur at distal TIP 142. A small diameter of lead wire 270 and distal TIP 142 allows the surgeon to tunnel the lead wire 270 into a precise location and have the Bion TIP 142 placed at a location within muscle, nerve or other body tissue where its location can be precise. However, lead wire 270 can act very much like pacemaker lead wires, in that it could act as an antenna and pick up undesirable RF fields from MRI. Accordingly, overheating of lead wire 270, in conjunction with the distal TIP 142, and/or coupling of electromagnetic interference into the circuits of the Bion 262 are a concern. Accordingly, it is a feature of the present invention that novel TANK filters 146 could be placed in series with lead wire 270 and/or could be placed internal to the Bion 262 as shown in FIG. 48.

Figure 48:
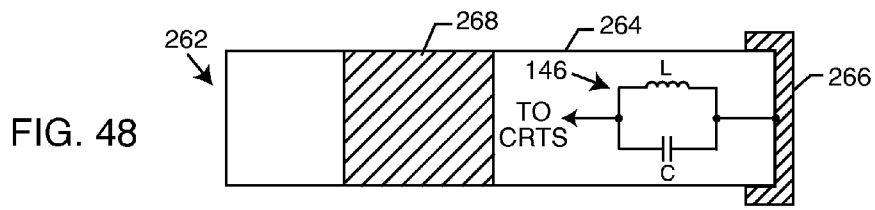
FIG. 48 is a sectional view similar to FIG. 47, wherein a TANK filter of the present invention is placed inside at the cap electrode.

Referring to FIG. 48, one can see an application of the present invention where inside of the Bion device 262 the parallel TANK circuit 146 can be placed at the end cap electrode 266. This would prevent selected pulse RF frequencies, for example, those from a 3 Tesla MRI system from entering into and disrupting or damaging the sensitive electronics of the Bion 262. This placement is the preferred embodiment for the tank filter because not only will it protect the internal circuits, but it will also prevent MRI pulsed currents from flowing into the associated body tissues, or in the case of an external lead wire 270, it would prevent RF currents from flowing in that lead wire as well. Alternatively, the novel TANK circuit 146 of the present invention could also be placed at the ground electrode 268. One could also place resonant parallel TANK circuits at both the cap 266 and the ground 268 electrodes. In a preferred embodiment, these could be of different resonant frequencies. For example, this would make the Bion 262 resistant to both 1.5 Tesla and 3 Tesla MRI system which have pulsed RF frequencies of 64 MHz and 128 MHz respectively. The Bion 262 is just one example of an AIMD that may or may not have implanted lead wires. Other examples include drug pumps and the like. Accordingly, the present invention is very useful to protect the electronic circuits of active medical devices that do not have associated lead wires, from the high fields involved with certain hospital and other medical diagnostic procedures such as MRI.

Figure 49:
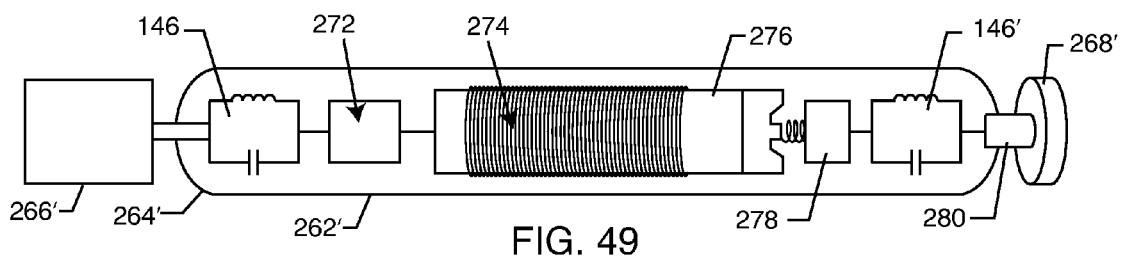
FIG. 49 is a sectional view similar to FIGS. 47 and 48, illustrating an alternative inline Bion, wherein a TANK filter of the present invention is disposed at each end.

FIG. 49 is a perspective view of an inline Bion 262'. A sintered tantalum electrode 266' has a tantalum stem that penetrates an overall glass seal bead 264'. The glass seal bead 264' protects all of the electronic components from body fluid intrusion. The Bion 262' includes a circuit board 272 containing a Schottky diode, wire bond pads and other components for convenient attachment to the embedded copper coils 274 and ferrite 276 that are used to couple with the external pulsing magnetic field. As previously mentioned, the pulsing external magnetic field is how the Bion 262' is energized. A moisture getter 278 solves the problem that body fluid will slowly penetrate through the glass 264'. An iridium electrode 268' is coupled through the glass with a tantalum tube 280. The Bion 262' of FIG. 49 has been modified in accordance with the features of the present invention to show novel TANK circuits 146 and 146'. If one wanted the Bion 262' to be compatible with only one type of MRI system, then only one novel TANK circuit 146 would be required. For example, the TANK circuit 146 could be designed to be resonant at a 3 Tesla MRI pulsed frequency of 128 MHz. This would prevent MRI currents from flowing from the left hand electrode 266' and through the electronics to the right hand electrode 268' by creating an open circuit. On the other hand, if one wanted the Bion 262' to be compatible with two types of MRI fields, then one could include the two TANK circuits 146 and 146' as shown in FIG. 49. In this case, the TANK circuit 146' would be designed to resonate at a selected MRI frequency different than that of the TANK circuit 146.

Figure 50:
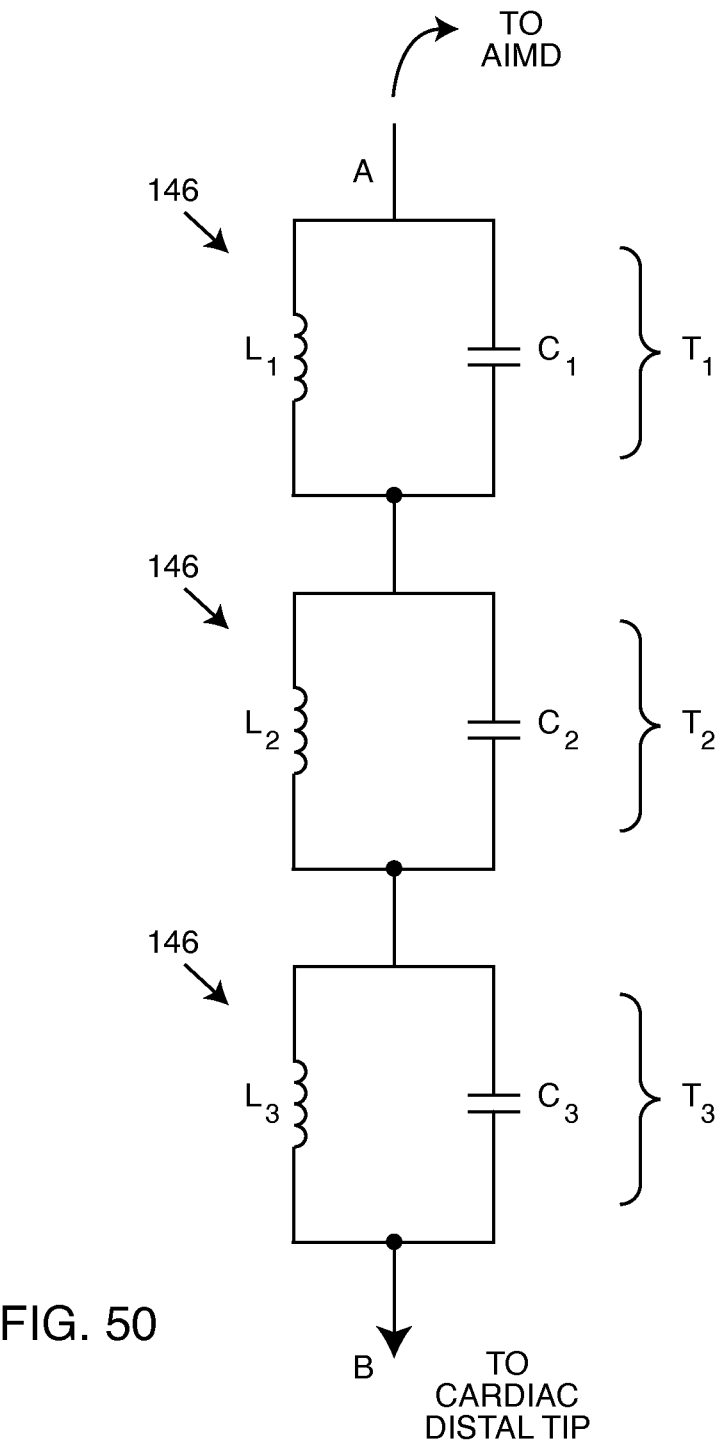
FIG. 50 is an electrical schematic diagram illustrating utilization of the TANK filter circuits of the present invention in a multiple resonant frequency series configuration.

FIG. 50 illustrates utilizing the present invention in a multiple TANK series configuration. One can see that there are three TANK circuits $T_1$, $T_2$ and $T_3$. TANK circuit $T_1$ consists of a parallel combination of an $L_1$ and a $C_1$, TANK $T_2$ consists of a parallel combination of an $L_2$ and a $C_2$ and TANK $T_3$ consists of a parallel combination of an $L_3$ and a $C_3$. It would be desirable to be able to have a patient capable of exposure to not just one type of MRI system. For example, in a 0.5 Tesla MRI system, the pulsed RF frequency is 21 MHz. One could then desirably design $L_1$ and $C_1$ to be self-resonant at 21 MHz. 1.5 Tesla MRI systems have a pulse RF frequency of 64 MHz. Accordingly, TANK circuit $T_2$ could have a parallel inductor and capacitor arrangement consisting of $L_2$ and $C_2$ that would self-resonate at 64 MHz. The now popular 3 Tesla MRI systems have a pulse RF frequency of 128 MHz. Accordingly, the parallel combination of $L_3$ and $C_3$ could be designed to self-resonate at 128 MHz. This would mean that the impedance of the system of FIG. 50, as measured between points A and B, would be very high at all three of these selected MRI RF pulse frequencies, allowing a patient to be subjected to MRI in any of these types of MRI systems without fear of overheating the lead wires or distal TIP electrode. Another adaptation of the schematic shown in FIG. 50 would be, for example, to have one or two of these parallel TANK filters 146 designed for MRI and perhaps the third TANK filter 146 designed to protect the patient against electrocartery surgery. For example, Bovi knife surgery operates primarily at one particular frequency. Thus, it would be possible to design an active implantable medical device that would be immune to certain types of electrocartery surgery and also selected MRI frequencies. It will be obvious to those skilled in the art that any number of series TANK filters 146 can be configured using the novel designs as described herein.

Figure 51:
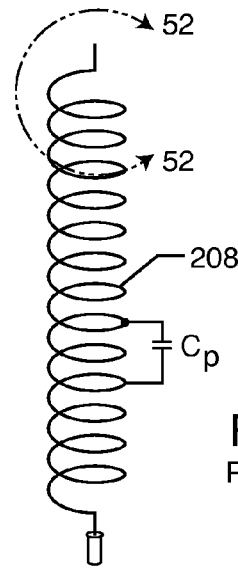
FIG. 51 is an isometric view of a prior art air-wound inductor.

FIG. 51 is an isometric view of the prior art air wound inductor 208 shown and described previously. The air wound inductor 208 has multiple turns and is first wound around a mandrel (not shown). The mandrel is then removed. The structure holds its shape by selecting materials that take a permanent set as shown.

Figure 52:
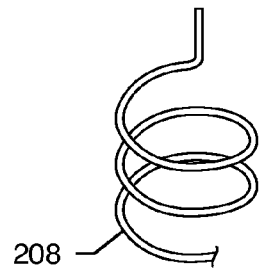
FIG. 52 is an enlarged fragmented perspective view taken along the area 52-52 in FIG. 51.

FIG. 52 is a blow up taken generally from the sectional view 52-52 from FIG. 51. The blow up view shows a section of the air wound inductor 208. Using a non-ferrous inductor is an advantage in the presence of MRI signals because the main static field of MRI can cause a ferromagnetic core to saturate. This is not the case for an air wound inductor as illustrated in FIG. 51. The inductor of FIG. 51 will be impervious to the effect of the static field of MRI because there are no ferromagnetic materials. In addition, air wound inductors produce very little MRI image artifact. However, it is important that air wound inductors, such as those illustrated in FIG. 51, be protected from body fluid. When immersed in body fluid, they will become subject to stray electrical leakage currents from turn to turn. Worse yet, the turn-to-turn parasitic capacitance will change due to the dielectric properties of the body fluid itself. Insulating the lead wire 208 will help to reduce or prevent circulating electrical current. However, such insulation will do little or nothing to reduce the amount of turn-to-turn capacitance. One could postulate that by balancing the turn-to-turn capacitance with the inductor structure as shown in FIG. 51, one could create the tank circuit of the present invention. However, there are a number of practical reductions to practice problems associated with this. One is, that any change in turn-to-turn spacing (i.e. mechanical manipulation), would effect the capacitance and hence the resonant frequency. Also, it would be very difficult to test this device in a production situation. Testing such a device in air would not work because the permittivity or dielectric constant of air is 1. Depending on where the inductor would be placed into body fluid (blood, tissue, spinal fluid and the like), will affect the dielectric constant and hence the amount of distributed capacitance. As stated, if the distributive capacitance varies, the resonant frequency of the tank filter will also vary. One could overcome part of this difficulty by performing production testing in a saline or gel tank whose dielectric and electrical conductivity properties closely match that of the body fluids into which the device is later to be implanted. This would improve the situation, however, not all patients are alike. For example, a cardiac patient undergoing difficulties could have wide variances in their electrolytes and hence body fluid dielectric properties.

Figure 53:
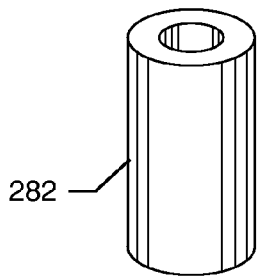
FIG. 53 is a perspective view of a prior art hollow ferrite core which has high permeability.
Figure 54:
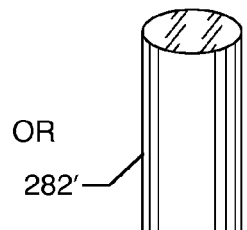
FIG. 54 is a view similar to FIG. 53, illustrating an optional prior art solid ferrite or powdered iron core.

FIG. 53 shows a prior art hollow ferrite core 282 which has a high permeability. This core contains magnetic dipoles. An optional prior art solid ferrite or powdered iron core 282' is shown in FIG. 54. The hollow core 282 is preferred as it has a larger mean magnetic pathway for the amount of weight and volume of material.

Figure 55:
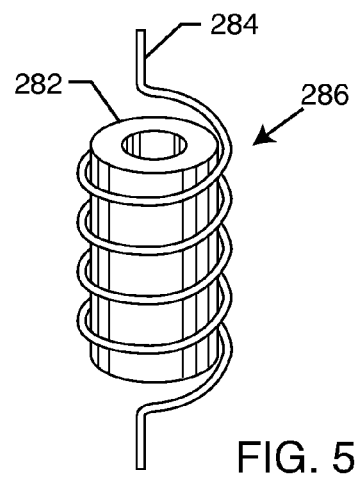
FIG. 55 is a perspective view illustrating a prior art wire wound around the high permeability ferrite core shown in FIG. 53.

FIG. 55 shows a wire 284 wound around the high permeability ferrite core 282. The resulting wound inductor 286 is suitable for insertion within any of the novel capacitor elements as previously described herein. However, the presence of the ferrite or iron core material can be a problem in the presence of MRI. The reason for this is that magnetic dipoles will align within the static fields of the MRI scanner and saturate.

Figure 56:
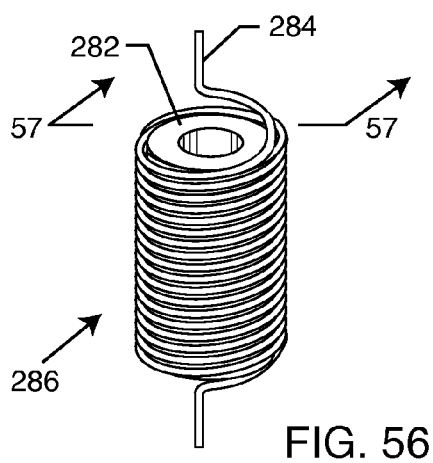
FIG. 56 is a perspective view of the ferrite core of FIG. 53 with multiple turns of wire placed thereon.

FIG. 56 illustrates the ferrite core 282 with additional turns of wire 284 in comparison with the wound inductor 286 of FIG. 55.

Figure 57:
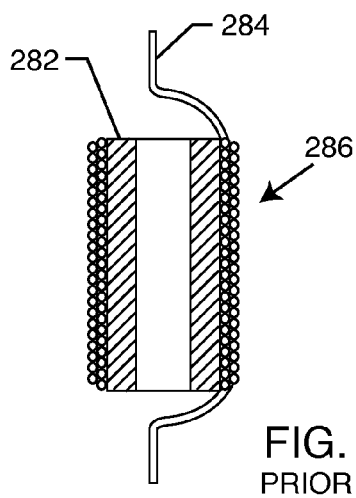
FIG. 57 is a cross-sectional view taken generally along the line 57-57 of FIG. 56.

FIG. 57 is a cross-sectional view taken generally along section 57-57 from FIG. 56. As mentioned, using a ferrite core 282 in MRI fields can cause core saturation and image artifacts. However, one could use a non-magnetizing core such as a plastic or phenolic core. Even a ceramic material could be used. In this case, while the amount of available inductance would be significantly lower, no core saturation or image artifacts would be realized in the presence of main static field. It will be apparent that any of the wound, air wound or core wound inductors, as shown, could also be wound around the outside diameter of any of the cylindrical capacitor structures as illustrated herein. This could be understood by referring back to FIGS. 35 and 37. The wound inductor 208 could be wound around the outside of the capacitor element 168, 184 and then connected to the distal TIP 142. This is less volumetrically efficient, but it will increase the length of the inductor and thereby the overall inductance.

Figure 58:
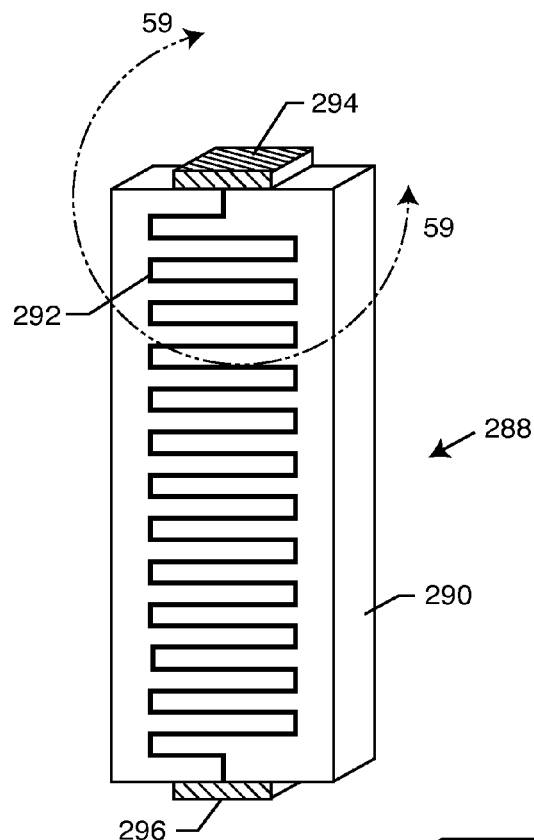
FIG. 58 is a perspective view of a novel non-ferrite chip inductor that may be utilized to build a TANK in place of the spiral wound inductors shown above.
Figure 59:
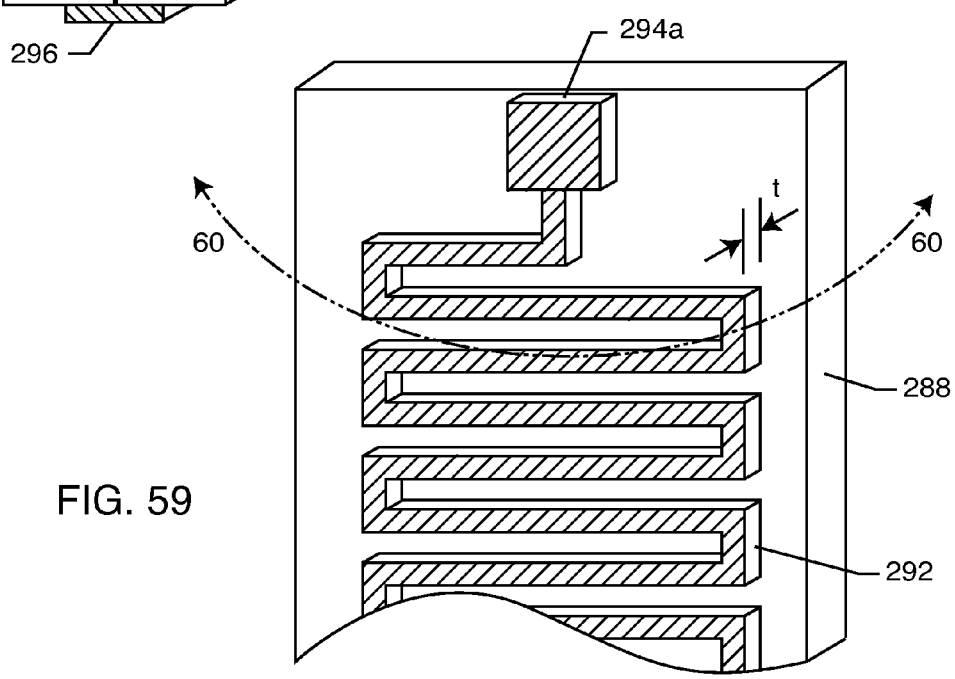
FIG. 59 is an enlarged fragmented view taken generally of the area designated by 59-59 in FIG. 58, and showing an alternative configuration.

FIG. 58 is an isometric drawing of a chip inductor 288 which could be used in place of any of the spiral wound inductors discussed previously. The chip inductor 288 includes a thin substrate 290 which can be ceramic, circuit board material or the like. The inductor circuit trace 292 includes convenient wire bond pads 294 and 296. This is better understood by looking at the enlarged fragmented view illustrated in FIG. 59. There, an optional wire bond pad 294a is shown which has been surface mounted. This provides another way to attach a lead wire, for example, by gold wire bonding. Also, evident from FIG. 59 is the thickness t of the inductor circuit trace 292. By depositing a relatively thick circuit trace 292, one can minimize the inductor ohmic losses (series resistance Rs). By minimizing Rs, there is less attenuation to the desired low frequency biologic signals. For example, in the case of a cardiac pacemaker, biological signals of interest are in the 10 Hz to 1000 Hz frequency range. At these frequencies, the inductive reactance is negligible (approaches zero). However, the series resistance $R_s$ of the inductor is still present and if too high could attenuate desired biologic signals. Additionally, the cardiac pacemaker output pulse could be attenuated by too much inductor resistive loss thereby presenting an inefficient use of AIMD energy and a potential problem for electrical capture (pacing) of the heart. Referring back to the inductor 286 shown in FIGS. 56 and 57, a major problem with winding multiple turns of small diameter wire is the relatively high value of direct current (DC) resistance that would result. This high resistance would be undesirable at low frequency in that it could potentially attenuate pacing or stimulation pulses and also degrade sensing of biologic signals. An additional problem associated with inductors made from many turns of fine wire is that they can become their own heating element in the presence of MRI. This is also true if the patient were exposed to an MRI system that was not at the resonant frequency of the TANK circuit. Accordingly, placing a lot of small diameter wire with a high series resistance in the implantable device lead wire system is generally not a good idea. An aspect of the present invention is that relatively small values of inductance are to be used in the TANK circuits 146. The structure of FIGS. 58 and 59 overcomes such disadvantages by providing a volumetrically efficient inductor while at the same time minimizing the DC resistance.

Figure 60:
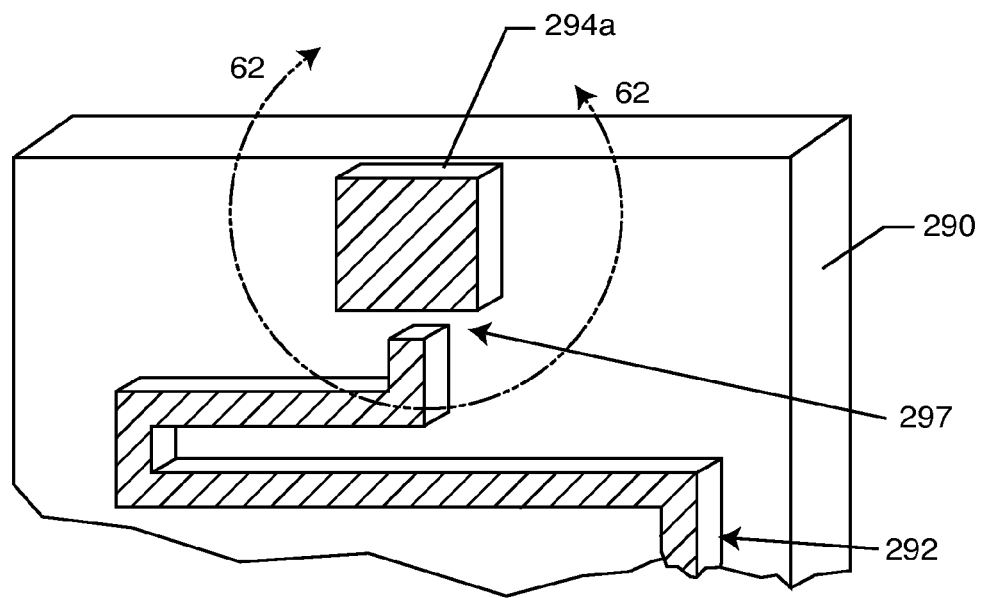
FIG. 60 is the inductor meander substrate of FIG. 59 with a small gap added to facilitate electrical testing of the capacitor element of the tank by itself.
Figure 61:
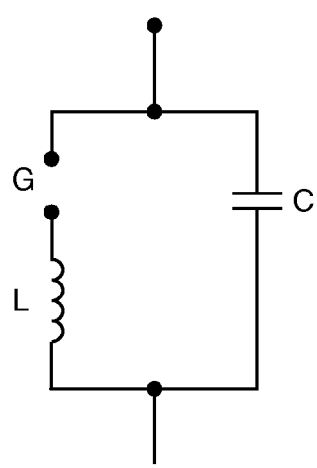
FIG. 61 is the schematic diagram taken from FIG. 60.

FIG. 60 is an exploded isometric view taken from area 60-60 in FIG. 59. The only difference is that a small gap 297 has been left between the inductor circuit trace and the termination pad 294A. When this is co-bonded to a ceramic capacitor, this will essentially leave the parallel inductor element mechanically attached but electrically disconnected from the capacitor element. This is better illustrated in FIG. 61 which shows the capacitor in parallel with the inductor with the inductor electricity disconnected by gap G. For high reliability testing and screening of the TANK circuit, it is very important to be able to electrically disconnect the capacitor in order to perform high reliability electrical testing and screening of the tank circuit. High reliability capacitor testing and screening generally consists of thermal shock, high voltage burn in, and many electrical measurements of the capacitor, including capacitance value, insulation resistance, dissipation factor and equivalent series resistance. None of these measurements can be effectively accomplished with the capacitor connected in parallel with the inductor. Capacitor measurements are usually made at low frequency. If the inductor was placed in parallel, this would tend to short the capacitor out at these frequencies. Therefore, by separating the inductor from the capacitor, it is then possible to perform all of these critical high reliability screening measurements. This is important to eliminate infant mortality from the capacitor lot population. Another advantage of disconnecting the inductor from the capacitor is that it is now also possible to perform electrical tests on the inductor element. As will be seen later, it is important that the inductor and capacitor values be selected so that they are resonant at the proper frequency. By having them disconnected, it is also possible that their values be selected and adjusted such that they will be resonant at precisely the correct frequency. It is also very important that high reliability testing be performed at the highest level of assembly possible. That is, one would not want subsequent assembly operations to introduce either immediate or latent defects into the component population. For example, the ceramic capacitors are quite sensitive to thermal shock, wherein cracks or delaminations can be introduced. It takes extensive electrical screening, including thermal shock and burn in, to detect such defects.

Figure 62:
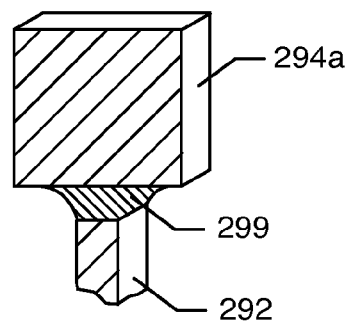
FIG. 62 illustrates electrically closing the gap of FIG. 60 with a small amount of conductive material.

Accordingly, a very small (innocuous) electrical attachment is made to fill the gap to join the capacitor and inductor back into parallel to form the TANK of the present invention. It is very important that this electrical connection be done in such a way that it does not thermally or mechanically stress the capacitor, inductor or electrical connection elements of the TANK assembly in any way. This is best seen by referring to FIG. 62 which is generally taken from the area 62-62 of FIG. 60. FIG. 62 shows a small area of electrical connection material 299. As previously stated, it is critical that the application of electrical material 299 be done is such a way that is simple, and not damaging to the overall component in any way. Accordingly, an ideal connection material to fill the gap 299 would consist of the group of a low temperature thermal setting conductive polymer, a low energy laser weld, a low temperature braze, a low temperature solder (for non-biocompatible applications) or even conductive inks. Any of these can be applied by automated processes, including robotic dispensing, by screen-printing, stencil or the like. The group of thermal setting conductive adhesives could include biocompatible adhesives, such as polyimide, silicones, or a number of epoxies and the like.

Referring once again to FIG. 62, the electrical filler material 299 not need in all cases to be a solid metallurgical bond material. A piece of conductive rubber, a conductive spring, a metal clip, or conductive fuzz material could be temporarily inserted into the gap 297 so that the resonant frequency of the TANK could be measured (and the TANK tuned). This material could then be easily removed in order to perform the aforementioned high reliability screening test of the capacitor and the inductor element by themselves. This will be more thoroughly described in the descriptions of how to tune the TANK filter after it is built which will follow in the descriptions of FIG. 119 through 123. After the aforementioned tuning of the TANK is accomplished, then the temporary electrical connection clip could be removed and the capacitor high reliability screening could be accomplished. At the very end, after all the high reliability testing is done, then the permanent (innocuous) electrical connection 299 could be placed as shown in FIG. 62.

Figures 63, 64:
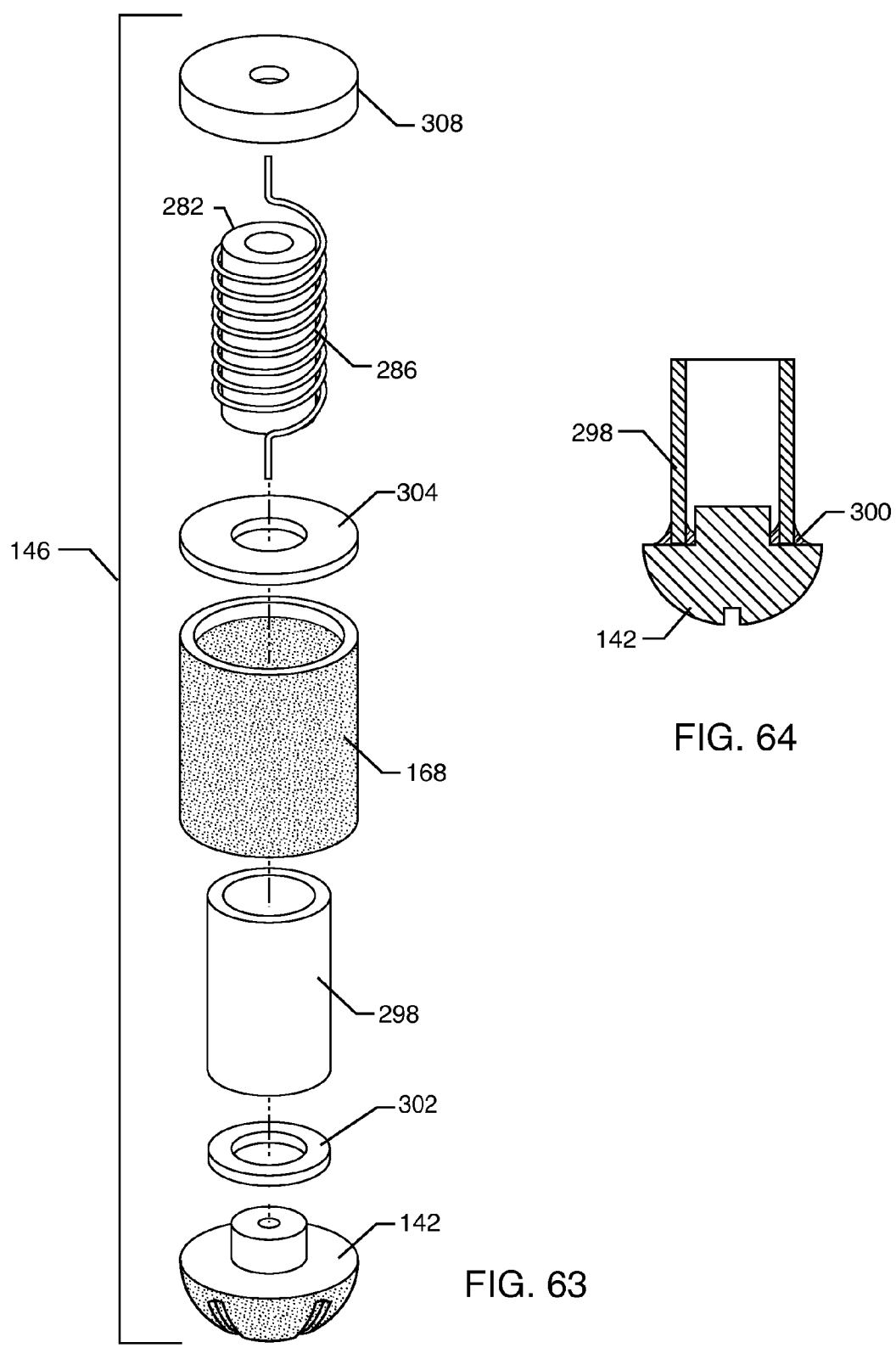
FIG. 63 is an exploded perspective view illustrating an hermetically sealed assembly of the novel distal TIP TANK filter of the present invention.
FIG. 64 is a sectional view illustrating the assembly of the bottom three components illustrated in FIG. 63.

FIG. 63 is an exploded view illustrating a methodology of assembling the novel distal TIP TANK filter 146 of the present invention, which is adaptable to a number of the TANK filter designs described previously, including the single layer tubular capacitor, the multilayer tubular capacitor and the feedthrough capacitors of FIGS. 35, 37 and 42.

Referring once again to FIG. 63, one can see that there is a wound inductor 286 having a ferrite core 282. This allows the use of relatively few turns of large wire due to the high permeability core. As mentioned, however, it is a problem in an MRI field in that the core may saturate. The inductor 286 is inserted into a nickel sleeve 298 which provides shielding against the main static field of the MRI thus preventing inductor core saturation. A negative to this approach is that a very large MRI image artifact would result. In terms of manufacturing, it is desired to pre-assemble the novel nickel sleeve 298 to the distal TIP 142. As shown in FIG. 64, the nickel sleeve 298 is laser welded 300 to the distal TIP 142. All of this pre-assembly is inserted in an optional insulation washer 302 which consists of a medical grade plastic material which is biocompatible. A single wall extruded tubular capacitor 168 is then slipped onto this assembly. A second insulative plastic washer 304 is then placed onto the tubular capacitor 168. The capacitor 168 is placed over the pre-assembly of the nickel sleeve 298 and distal TIP 142. The inductor 286 is then inserted inside of the nickel sleeve 298. All of this is best illustrated in the cross-sectional view shown in FIG. 65.

Figures 65, 66:
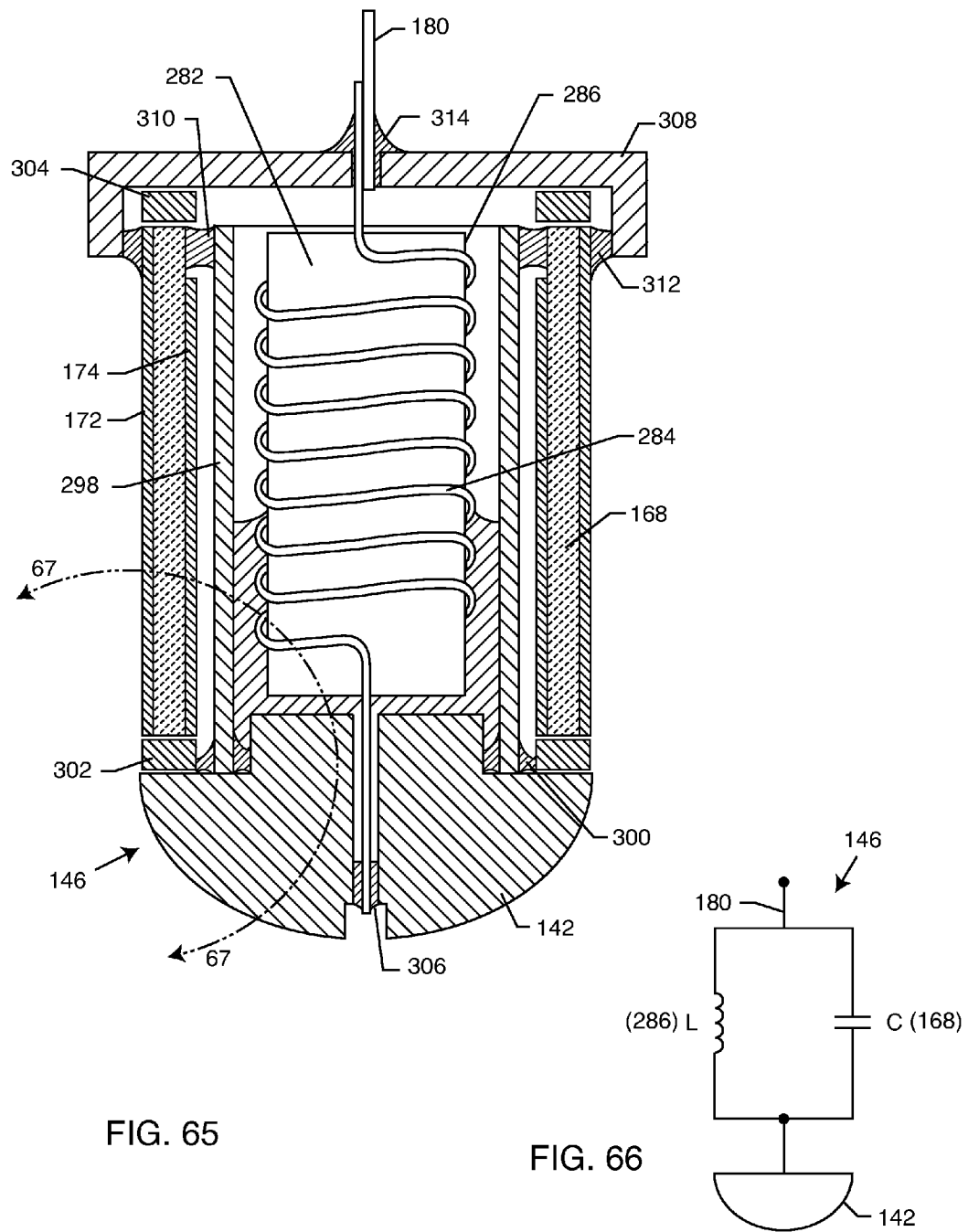
FIG. 65 is a sectional view illustrating assembly of all of the components of FIG. 63.
FIG. 66 is an electrical schematic diagram relating to the assembly of FIG. 65.

Referring to FIG. 65, there is a hole through the distal TIP 142 which allows for a laser weld 306 which connects the end of the inductor wire 284 to the distal TIP 142. The inductor structure 286 is housed within the optional novel nickel sleeve 298 to prevent it from saturating in the presence of the MRI main static field. To provide additional shielding against the main static field, the end cap 308 could be a gold plated nickel and nickel could even be incorporated as a part of the distal TIP 142. This provides complete shielding of the ferrite core 282 of the inductor 286. Accordingly, the inductor core 282 is prevented from saturating in the presence of the MRI static field. As previously mentioned, a trade off is that there would be relatively large MRI image artifact from the presence of the nickel and high permeability core material (accordingly, this is not a preferred embodiment). An electrical connection 310 is made between the nickel sleeve 298 and the inside diameter metallization 174 of the capacitor 168. At the distal TIP 142, one can see a cross-section of the laser weld 300 that was previously accomplished in the pre-assembly shown in FIG. 64.

Referring once again to FIG. 65, the end cap 308 has been gold brazed or otherwise electrically attached 312 to the outside diameter metallization 172 of the tubular feedthrough capacitor 168. To avoid a short circuit, insulative washer 304 is required to space the conductive cap 308 away from the nickel sleeve 298. Referring once again to the end cap 308, one can see that the inductor lead wire 284 has been routed through the end cap in position to abut lead wire 180 that comes from the active implantable medical device. For example, the lead wire 180 could be part of the bipolar lead wire from a cardiac pacemaker. In this case, this would be the lead wire to connect to the TIP 142 (fixation clips not shown) which will contact myocardial tissue. Laser weld or gold braze 314 is used to make an electrical connection to the lead wire 180, the inductive wire 284 and the end cap 308 simultaneously. Referring now to the other end of the parallel TANK structure, one can see the high surface area TIP 142 which is used to stimulate myocardial tissue. Such distal TIPs are well known in the art and can have a variety of shapes and coatings. Distal TIPs that are capable of eluting drugs are used to prevent tissue inflammation are also available to the present invention. Optional insulative washer 302 is shown to prevent the distal TIP 142 from shorting to the capacitor outside diameter metallization 172. It should be noted that for AIMD applications, it is required that all of the materials be biocompatible. With specific reference to the nickel sleeve 298, it is noted that nickel in and of itself is not considered a biocompatible material. Accordingly, a gold plating or equivalent biocompatible coating material is required for AIMD applications. Certain plated iron-containing material or high permeability nano-materials could be substituted.

A schematic diagram for the novel TANK filter 146 of FIGS. 63-65 is shown in FIG. 66. As previously described, the values of L (286) and C (168) are carefully selected in accordance with the FIG. 12 equation so that the resonant frequency of the filter 146 that occurs at a selected RF pulse frequency of an MRI or other electronic system that produces high power fields at a specific frequency.

Figure 67:
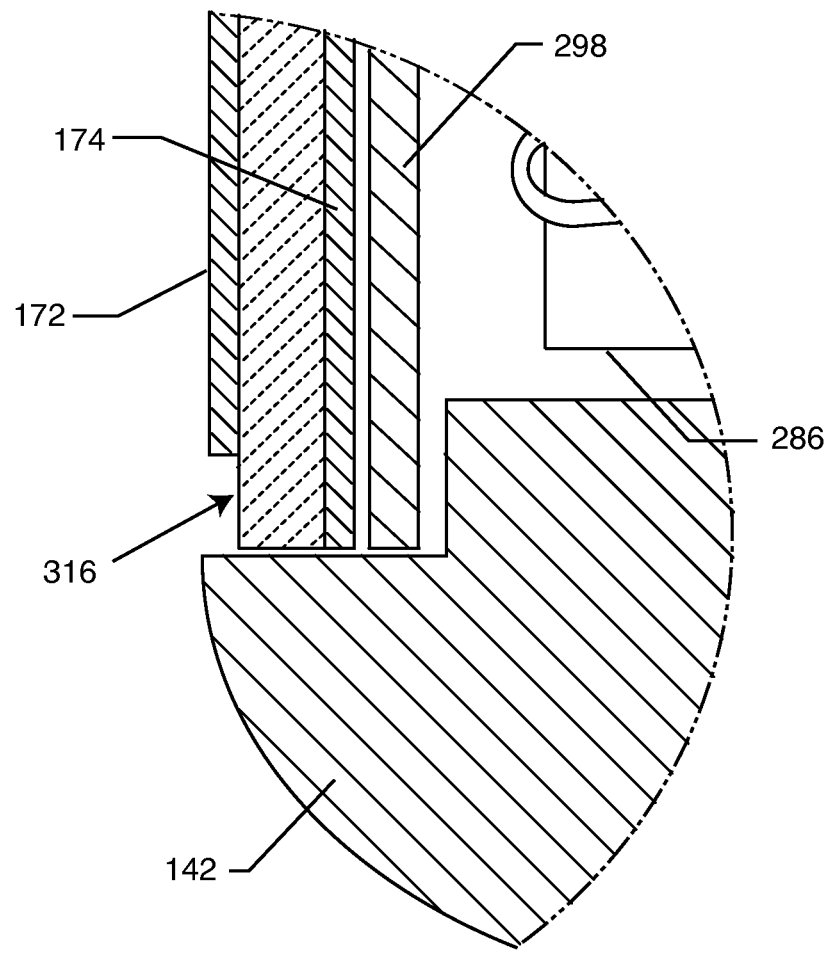
FIG. 67 is an enlarged fragmented sectional view taken of the area indicated by the line 67-67 in FIG. 65.

FIG. 67 is an enlarged fragmented sectional view taken generally of area 67-67 from FIG. 65. One can see that the optional insulative washer 302 has been removed. This is made possible because the external diameter metallization 172 of the tubular capacitor 168 has been held back as shown in area 316. In other words, this unmetallized portion prevents the distal TIP 142 from shorting to the capacitor outside diameter metallization 172. So, as one can see, there are two ways to accomplish this: by the insulating washer 302 as shown in FIG. 65, or by selective metallization as shown in FIG. 67.

While FIGS. 63, 64, 65 and 67 show an optional nickel shield 298 that would prevent a high permeability core 282 of the inductor 286 from saturating, there is another way of accomplishing this more efficiently. Referring to FIG. 37, there is illustrated a multilayer tubular capacitor 184. It is known in the art that nickel electrodes may be used. This is also known as a base metal electrode. Nickel electrodes have become quite common in commercial applications due to relatively low cost. Conventional monolithic ceramic capacitors had electrodes made from silver, palladium silver, platinum and the like. By constructing the multilayer tubular capacitor 184 of the present invention as described in FIG. 37 with nickel electrodes, the electrodes themselves would then shield the inductor 208 from the main static field of an MRI system. It is a feature of the present invention that nickel capacitor electrodes can be used in combination with any of the embodiments herein to provide degrees of shielding to the embedded inductor. It will be obvious to those skilled in the art that gold plated nickel end caps or their equivalent could also be added to the novel multilayer tubular capacitor 184 shown in FIG. 37 to add additional shielding against the main static field from MRI. As previously mentioned, too much high permeability material can distort the MRI signals and create serious problems with image artifacts. Accordingly, in the preferred embodiment, the electrodes will not be nickel and the inductor will be an air wound inductor. This will make the distal TIP impervious to MRI induced heating and also will eliminate any image artifact issues.

Figure 68:
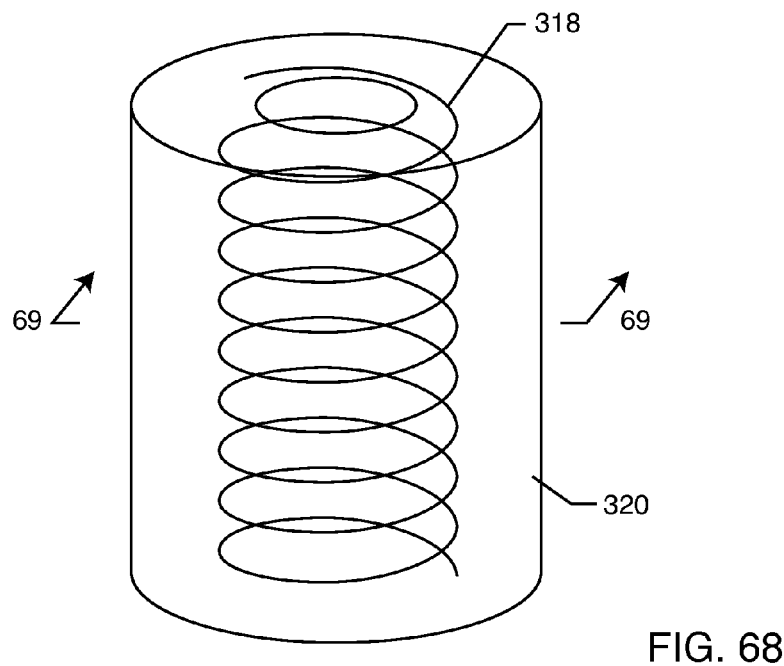
FIG. 68 is a perspective and somewhat schematic illustration of an inductive element which is completely imbedded within a novel tubular ceramic capacitor structure.

The present invention also embraces an inductive element 318 which is completely embedded within a novel tubular ceramic capacitor structure 320. FIG. 68 is a perspective schematic view of such structure, which is particularly adaptable to prior art multilayer tubular capacitor 184 manufacturing techniques as previously described in FIG. 31. Such capacitors are generally made by screen printing electrodes while the green dielectric is laid flat. After electrode laydown, the capacitor is then rolled up into the desired tubular shape. The novel tubular capacitor 320 will include the inductor element spiral 318 as an embedded component. Before the capacitor is rolled up, the inductor trace is laid down on the unfired ceramic wafer by screen printing a diagonal line at a selected layer such that when its rolled up it forms the spiral as illustrated in FIG. 68.

Figure 69:
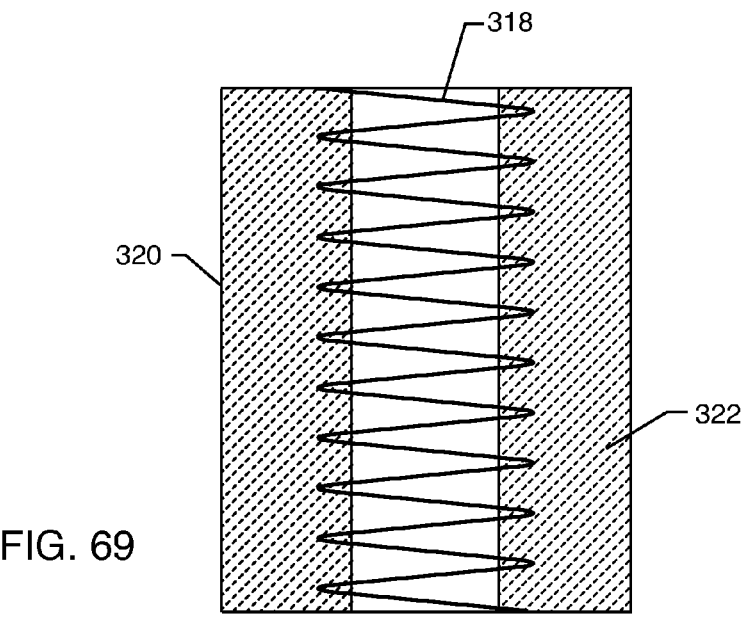
FIG. 69 is a schematic cross-sectional view taken generally along the line 69-69 of FIG. 68, illustrating the manner in which the inductor is imbedded within the capacitor dielectric material.

FIG. 69 is a schematic cross-sectional view generally taken along line 69-69 from FIG. 68. This clearly illustrates that the inductor element 318 has been embedded within the capacitor dielectric material 322.

Figure 70:
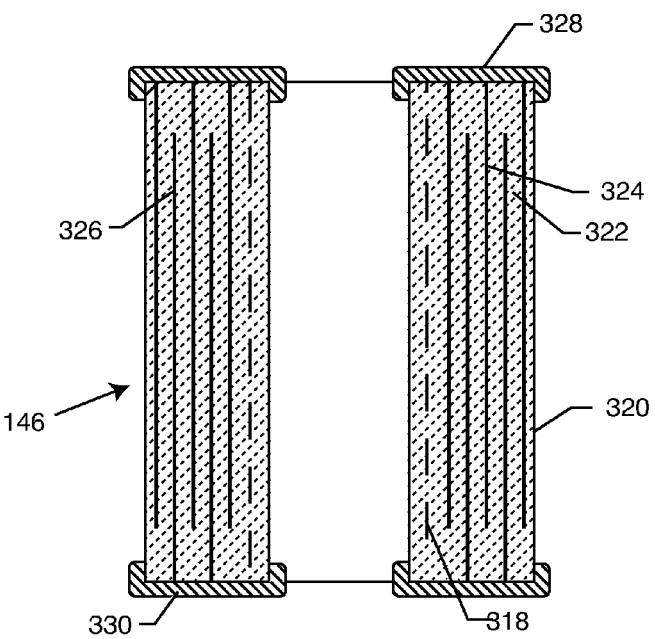
FIG. 70 is an enlarged sectional view taken generally along the line 69-69 of FIG. 68, of a multilayer tubular capacitor with an embedded inductor element.
Figure 71:
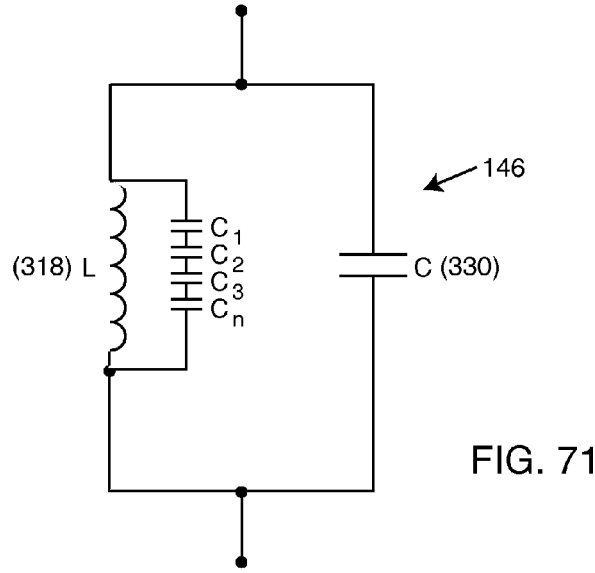
FIG. 71 is an electrical schematic diagram illustrating the TANK filter of FIGS. 68-70.

FIG. 70 is a more detailed cross-section of the hybrid capacitor 320 with an embedded inductor element 318 generally described in connection with FIGS. 68 and 69. The hybrid capacitor 320 includes internal electrode plates 324 and 326 which are typical of multilayer tubular capacitors such as those shown in FIGS. 31 and 37. Also shown are the top and bottom metallization layers 328 and 330. The embedded inductor element 318 spiral winds from top to bottom of the capacitor 320. Because the inductive element 318 is screen printed and fired within the high dielectric constant material 322, this will increase the turn-to-turn parasitic capacitance. This capacitance is actually desirable as it will add to the amount of capacitance available in the parallel TANK circuit 146. This is better understood by referring to FIG. 71 where it is seen that the inductor element L (318) has a number of parasitic capacitive elements $C_1$ through $C_n$ shown in parallel with it. The total parasitic capacitance of the inductor is designated $C_L$. This capacitance $C_L$ ends up in parallel with the main TANK circuit capacitor C (320) and tends to increase its capacitance value. $C_{TOTAL} = C + C_L$.

Accordingly, this aids in the overall volumetric efficiency of the parallel TANK circuit 146.

Figure 72:
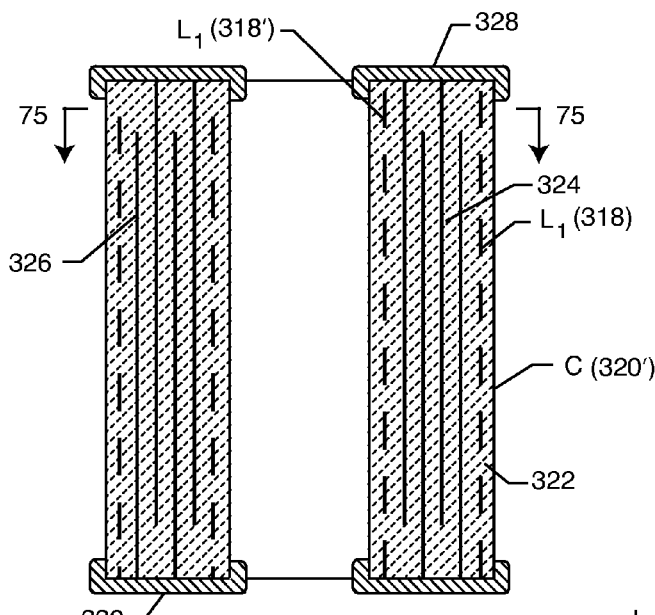
FIG. 72 is a sectional view similar to FIG. 70, illustrating an alternative arrangement of capacitive and inductive elements.

FIG. 72 illustrates an alternative hybrid capacitor 320' which is very similar to FIG. 70. One can see that there are parallel embedded spiral wound inductors $L_1$ (318) and $L_2$ (318'). $L_1$ (318) is near the outside diameter of the tubular capacitor C (320') and $L_2$ (318') is near the inside diameter of the capacitor. The reason this embodiment is shown is that in order that the capacitor not delaminate, the inductor traces $L_1$ and $L_2$ must be deposited relatively thin in a manner similar to the capacitor electrodes 324 and 326. During firing, this allows good grain growth of the ceramic and makes for a rugged monolithic structure. However, a negative of using very thin traces for the inductor pattern L is that this will tend to increase the DC resistance. A way to overcome this is to use parallel traces $L_1$ and $L_2$ (or even n traces) as illustrated in FIG. 72. Of course, using parallel structures puts the inductance from inductor spiral $L_1$ and $L_2$ in parallel. This reduces that overall inductance by the parallel inductance formula. However, this does have the added advantage of placing the resistances of the two inductors in parallel thereby significantly reducing the overall DC resistance of the novel structure.

Figure 73:
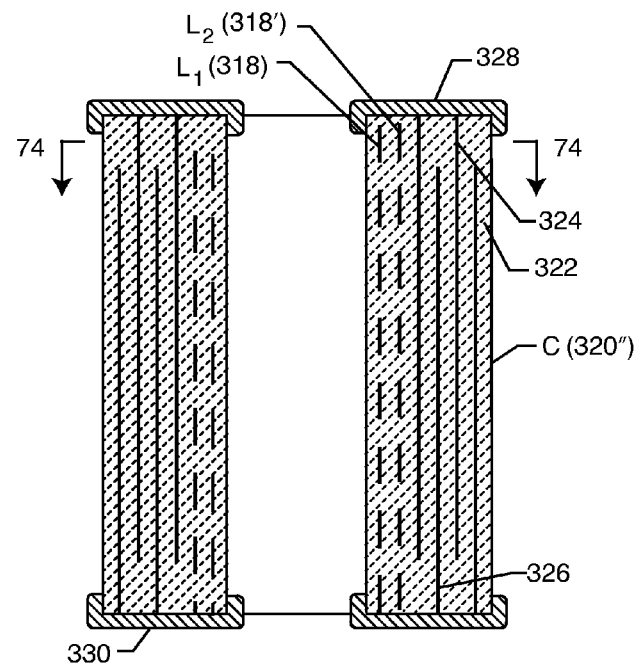
FIG. 73 is another sectional view similar to FIGS. 70 and 72 illustrating yet another alternative construction of the TANK filter of the present invention.

FIG. 73 illustrates yet another hybrid capacitor 320" which is again very similar to FIG. 70. In this case, novel embedded inductor spirals $L_1$ (318) and $L_2$ (318') have both been placed near the inside diameter. It will be obvious to those skilled in the art that such novel inductor spiral structures could be placed literally anywhere within the capacitor C (320"). It would be generally undesirable to place the inductor spirals between the electrode plates 324 and 326 because this would interfere with the electrostatic field and effective capacitance area (ECA) that develops between such plates.

FIG. 74 is a cross-section taken along line 74-74 in FIG. 73, where the end view of the two inductor spirals $L_1$ (318) and $L_2$ (318') is shown. Also shown is the top view of the electrode plate set 324. As one can see, as the capacitor C (320") is rolled up, the electrode 324 would appears as a spiral.

FIG. 75 is a cross-section taken along line 75-75 in FIG. 72. One can see the top penetration of inductor spirals $L_1$ (318) and $L_2$ (318'). One can also see the top view of the electrode plate set 324 which appears as a spiral.

FIG. 76 is a sectional view similar to FIGS. 74 and 75 except that a number of parallel inductor spirals $L_1$ through $L_n$ are illustrated. These are electrically isolated from each other until they are connected at the respective end metallization areas and related caps. The overall inductance is given by the equation for $L_{total}$ as shown in FIG. 77. It will be obvious to those skilled in the art that multiple parallel inductor traces could be placed near the capacitor OD or the ID or both.

For non-implant applications, conventional capacitor materials can be used for any of the novel TANK circuit embodiments as described herein. For example, referring to FIGS. 35, 37, 42, 44, 68 and the like, for industrial, commercial, military and space applications, conventional capacitor materials can be used. This is best understood by referring specifically to FIG. 37. For non-medical implant applications the capacitor electrode plates 186 and 188 could be of palladium silver, nickel or other low cost commercial electrode materials. In addition, termination surfaces 190 and 192 which make attachment to the capacitor electrode plates could also be of conventional silver, palladium silver or even commercial plated terminations. In addition, electrical connections 194 and 216 could be of solder or other non-biocompatible materials. Lead wire material 196, for example, could be of conventional copper and the inductor 308 could also be of copper or any other conductive material. However, for active implantable medical device applications, it is important that all of the materials used in the construction of the novel TANK filters 146 be of biocompatible materials. Referring once again to FIG. 37, in the preferred embodiment for AIMD applications, the electrode plates 186 and 188 would be of pure platinum or equivalent noble metal. Metallization layers 190 and 192, for example, could be pure gold or pure platinum. Lead wire 196 could be platinum, platinum-iridium alloy, tantalum or niobium. The inductor wire material 308 could be from MP35, platinum, NITINOL or any of the materials that were previously mentioned for lead wire 196. The electrical connection points 194, 214 and 216 would all be either done by precious metal brazing or by laser welding.

Reference is made to U.S. Pat. No. 6,985,347, entitled EMI FILTER CAPACITORS DESIGNED FOR DIRECT BODY FLUID EXPOSURE, the contents of which are incorporated herein. This patent goes into much greater detail for the need for all materials to be biocompatible when the capacitor itself is to be exposed to body fluids. An alternative to this would be to construct the novel TANK circuits herein of non-biocompatible materials and enclose them in a completely hermetically sealed structure. This could be accomplished by glass sealing the entire structure as, for example, illustrated in FIG. 37. It will also be obvious to those skilled in the art that the entire structure shown in FIG. 37 could be placed in an alumina ceramic housing with gold brazed end caps thereby hermetically sealing the entire structure.

Figure 78:
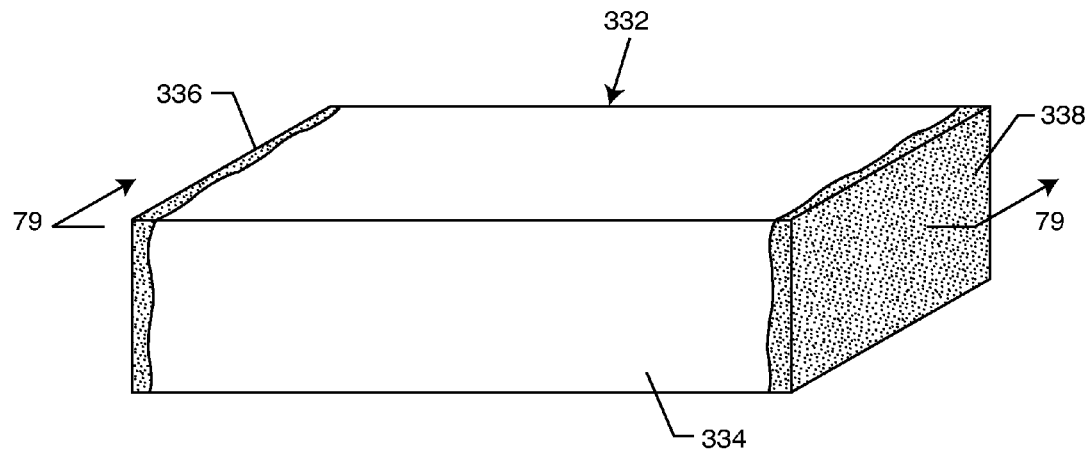
FIG. 78 is a perspective view of a prior art rectangular monolithic ceramic capacitor (MLCC)
Figure 79:
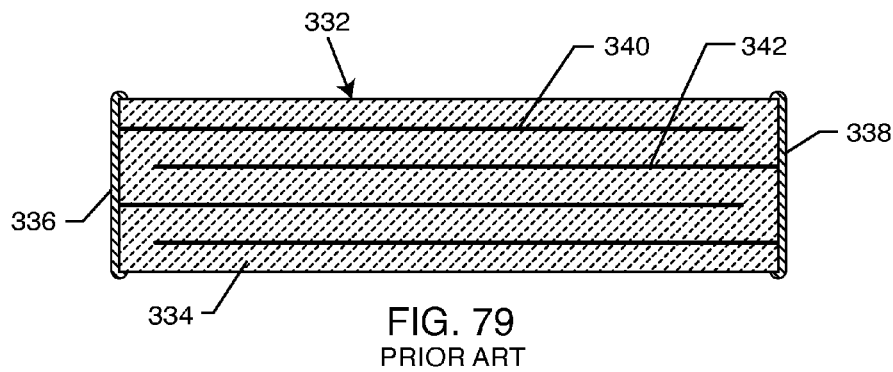
FIG. 79 is a sectional view taken generally along the line 79-79 of FIG. 78.

FIG. 78 is an isometric view of a prior art rectangular monolithic ceramic capacitor (MLCC) 332. It comprises a main ceramic body 334 and it has termination surfaces 336 and 338 for convenient mounting to a circuit board, lead wires or the like. FIG. 79 is a cross-section of the capacitor 332 taken generally along line 79-79 in FIG. 78. One can see in the cross-section that there are two overlapping electrode plate sets 340 and 342. The overlapping of these electrode plate sets forms the active area of the capacitor 332. Such capacitors are well known in the art and are literally produced in the hundreds of millions for many commercial, military and space applications.

Figure 80:
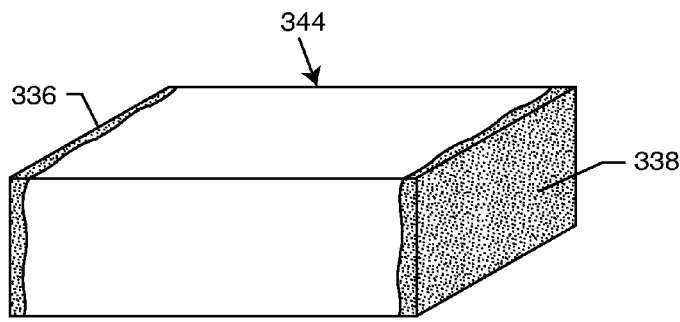
FIG. 80 is a perspective/isometric view of a novel composite monolithic ceramic capacitor-parallel resonant TANK (MLCC-T) which forms a TANK filter in accordance with the present invention.

FIG. 80 is an isometric view of a novel composite monolithic ceramic capacitor-parallel resonant TANK (MLCC-T) 344 which forms a TANK filter 146 in accordance with the present invention. Viewed externally, one can see no difference between the MLCC-T 344 of the present invention and prior art MLCC capacitor 332 as shown in FIG. 78. However, the novel MLCC-T 344 has an embedded inductor 346 which is connected in parallel across the capacitor between its opposite termination surfaces 336 and 338.

Figure 81:
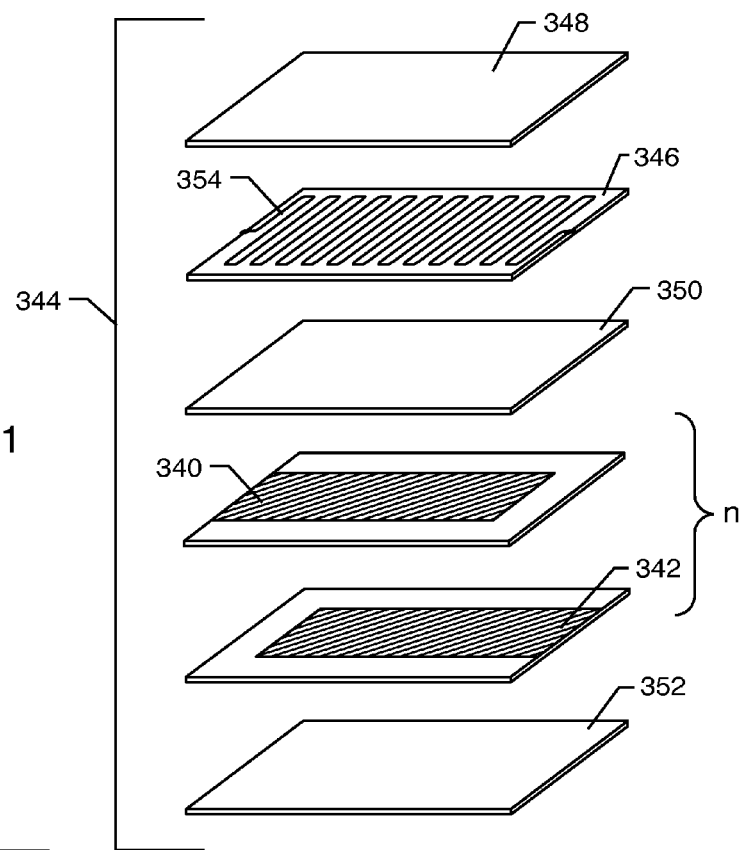
FIG. 81 is an exploded view of the various layers of the MLCC-T TANK filter of FIG. 80.

FIG. 81 illustrates an exploded view of the various layers of the novel MLCC-T TANK filter 344 shown in FIG. 80. The novel MLCC TANK (MLCC-T) 344 of the present invention includes an embedded inductor 346. At low frequencies, the embedded inductor 346 shorts out the capacitor from one end to the other. However, at high frequency, this forms a parallel TANK circuit 146 which is better understood by referring to the schematic diagram in FIG. 82. Referring once again to FIG. 81, one can see that as the capacitor stacks up from the top, we have an area of blank cover sheets 348 followed by one or more embedded inductor layers 346. These inductor meander shapes can have a variety of shapes as further illustrated in FIG. 83. The meander shapes illustrated in FIG. 83 are illustrative examples and are not meant to be entirely inclusive. It will be obvious to those skilled in the art that there are a variety of optional shapes that could also be used. Then there are a number of other blank interleafs 350 before one gets to the capacitor electrode plate sets, 340 and 342. One can see the capacitor electrode plate set 340 which connects to the left hand termination 336 and one can also see the capacitor electrode plate set 342 which connects to the right hand termination 338. In FIG. 81, only single electrodes are shown as 340, 342. However, it will be obvious to those skilled in the art that any number of plates n could be stacked up to form the capacitance value that is desired. Then bottom blank cover sheets 352 are added to provide insulative and mechanical strength to the overall TANK filter MLCC-T 344. The meander inductor trace 354 is deposited or silk screened onto another layer of the monolithic ceramic TANK. This can be one layer or many layers as desired. As previously noted, when many inductor layers 346 are put in parallel, this tends to reduce the overall inductance, but also desirably reduces the DC resistance of the inductor traces. The embedded inductor layer 346 is known as a meander because it tends to meander back and forth as it goes through the MLCC-T 344.

FIG. 83 shows a number of alternate meander shapes 354 that are available for the inductor 346. After the inductor layer 346 is added to the stack as shown in FIG. 81, then one or more blank ceramic cover sheets 348 are added. The blank cover sheets provide mechanical strength, rigidity and electrical insulation protection to the embedded inductor and ceramic capacitor electrode layers 340 and 342. In a typical monolithic ceramic capacitor manufacturing operation, the aforementioned stack up, as illustrated in FIG. 81, could be done both by wet-stack processing wherein each ceramic layer is sprayed down as a liquid or in a waterfall process, then pre-dried, and then the electrical layers (other capacitor electrodes or inductor traces) are laid down and dried. In a typical ceramic capacitor thick film process, these layers are laid down in ceramic tape and then stacked and pressed. In either case, a monolithic structure is formed which is then stacked and pressed. The methodology that is illustrated in FIGS. 80 through 83 inclusive is also applicable to a wide range of other types of capacitor technologies including tantalum, electrolytic and film. For example, film capacitors can be stacked like an MLCC or rolled encompassing any of the embedded inductor traces as illustrated herein. Referring back to FIG. 68 through 77 inclusive, one can also see that wound film capacitors could also be constructed with an embedded inductor in a similar fashion. Accordingly, the concepts of the present invention are applicable to a wide variety of equivalent capacitor technologies. At this point, there is a binder burn-out process which raises the green (unfired) capacitor from relatively low temperature to an elevated temperature. This process is to allow volatiles and solvents that were included in the ceramic slurry or tape to volatilize and slowly evolve and dissipate out of the monolithic structure. Eliminating these volatiles prior to high temperature firing or sintering is necessary so that the MLCC-T layers will not delaminate. The next step in this process is to fire or sinter the composite MLCC-T 344 at very high temperature. This causes the ceramic grains to sinter forming a hard monolithic structure. The last step, referring to FIG. 80, is the application of the termination surfaces 336 and 338. These termination surfaces can be a thick film ink, such as palladium silver, a gold plating, or the like and applied in many processes that are known in the art. Once again, the overall MLCC-T 344, which is illustrated in FIG. 80, looks identical to a prior art MLCC 332. However, embedded within it is the novel inductor structure 346 creating the novel parallel TANK filter 146 of the present invention.

Figure 82:
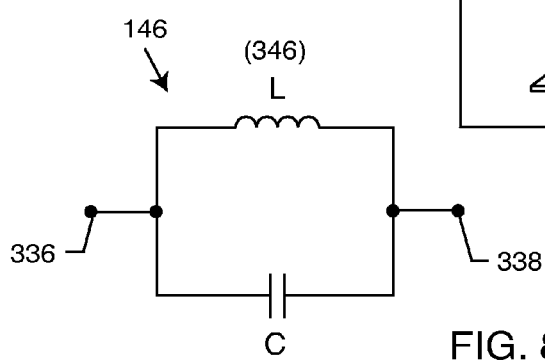
FIG. 82 is an electrical schematic diagram of the MLCC-T TANK filter of FIGS. 80 and 81.
Figure 83:
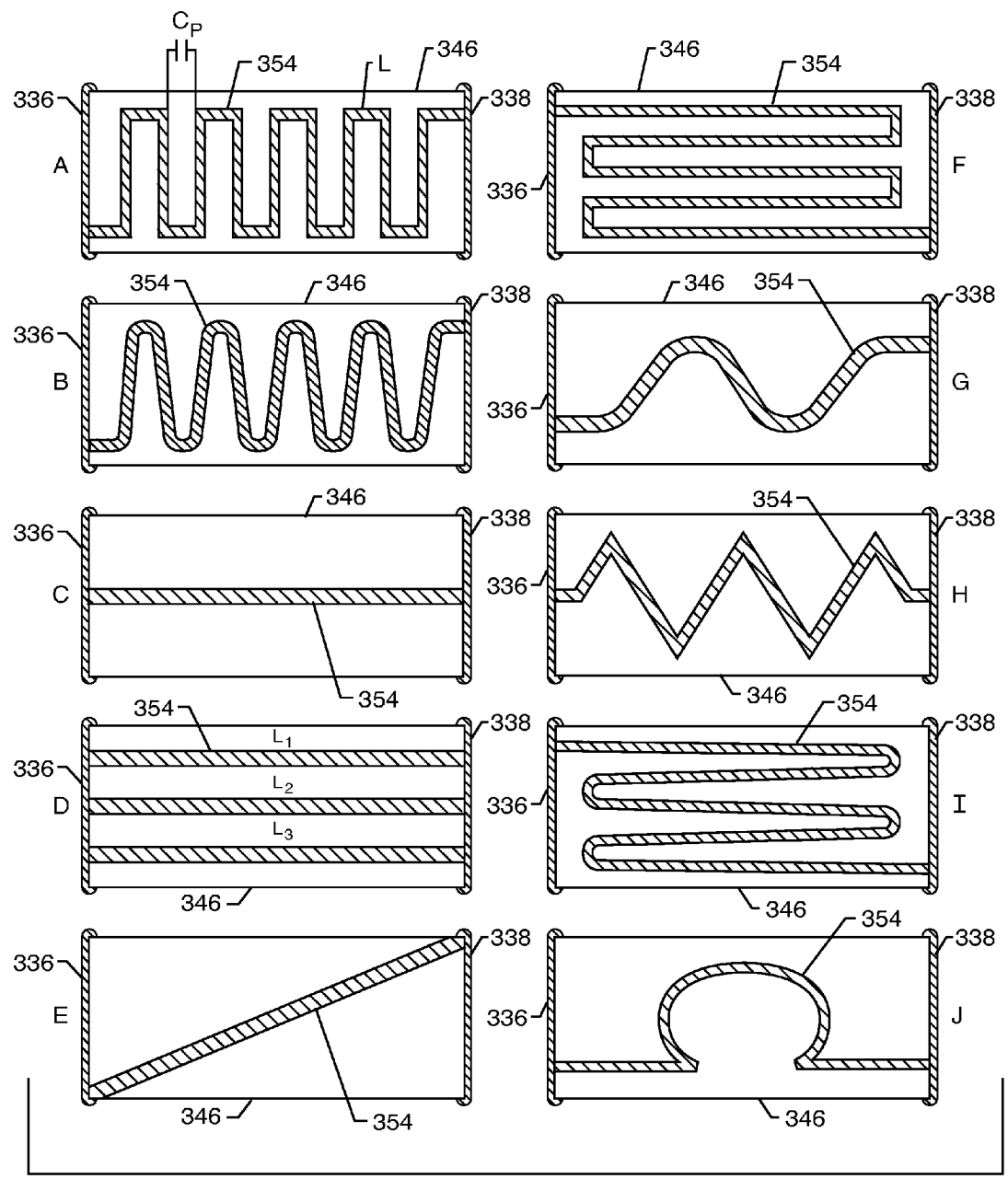
FIG. 83 illustrates various inductor meander shapes which may be embedded into the MLCC-T of FIGS. 80 and 81.

Again referring to schematic drawing FIG. 82, one can see that the inductor L has been placed in parallel with the capacitor C which is all conveniently located within the monolithic structure MLCC-T 344 shown as FIG. 80.

FIG. 83 illustrates a number of alternate inductor circuit trace layer shapes 354 which can be embedded as illustrated in FIG. 81 within the novel ceramic MLCC-T 344 of FIG. 80. It is desirable not to have these inductor layers 346 embedded between the capacitor active electrode plates 340 and 342 which forms the capacitance value C. Placing the inductor(s) 346 between the capacitor electrode plate set 340 and electrode plate set 342 would tend to interfere with the electric field which forms the desired capacitive element. This is why in the preferred embodiment, the inductor layers 346 are shown above in the stack-up of the blank interleaf sheet area 350 before one gets into the active capacitor layer.

Referring once again to FIG. 81, in a typical embodiment, one might have one to five inductor layers 346 (or many more). By putting additional inductor layers 346 in parallel, one can drop the overall DC resistance $R_L$ which is desirable in an active implantable medical device application. Referring now to capacitor electrode plate sets 340 and 342, these can vary anywhere from two to four plates all the way up to as many as hundreds of alternating parallel plates. The number of electrode plates and their overlap area, (along with the dielectric constant and dielectric thickness) determines the capacitance value for a particular resonant TANK application. Referring once again to FIG. 83, one can see examples of some of the various possible shapes for embedded meander inductor elements 346. These will typically be laid down using biocompatible materials which will be similar to the same materials used to form the metallic electrode plate sets 340 and 342. In the preferred embodiment, these would typically be of a noble metal such as pure platinum or gold which are biocompatible materials. Since these distal TIP TANK filters 146 will be placed in human tissues (for a pacemaker, literally floating in the blood stream). It is very important that all of the materials, including platinum, gold, palladium, tantalum, niobium and titanium, be biocompatible and extremely reliable. Platinum is an excellent choice for such biocompatible materials and is preferred in the novel MLCC-T 344 of the present invention in a process known as a high-fire sintering system. Platinum is the preferred embodiment because of its excellent compatibility with the ceramic layers such as Barium Titinate, Barium Strontinate, and the like. This is because of the high melting point of the platinum.

Referring once again to FIG. 83, any of these inductor 346 patterns 354 would be laid down by screen printing or equivalent deposition process methods wherein an inductor meander pattern would be laid down over the blank ceramic material and a squeegee would be passed across which would deposit the desired platinum ink pattern 354. Alternative capacitor technology, for example, stack film capacitors, would generally require a different methodology of laying down the inductor meander shapes illustrated in FIG. 83. This could include metal plating or deposition on film, flame spraying and the like. It will be obvious to those skilled in the art that a number of other possible patterns are available. Literally any pattern 354 which forms an inductor 346 and connects from one end of the capacitor to the other will do the job. In this regard, it is very important that the embedded inductor shapes 354 that are selected make an electrical contact and connection between the MLCC-T 344 end metallization areas 336 and 338. Referring once again to FIG. 83, there are technical advantages and disadvantages (in no particular order or preference) of the various inductor meander traces 354 shown. Pattern C is a straight deposited trace 354 that runs through the MLCC-T 344. This would have very low inductance, but would also have very low DC resistance. This is because of the fact that the DC resistance is determined by a number of factors. DC resistance is given by the formula $R_L = \rho L/A$ wherein ρ is the resistivity of the material, L is the length of the material and A is the cross-sectional area of the material which is determined by its deposited thickness and its width. This equation can also be expressed in an alternate form, $$R_s = \left(\frac{\rho}{t}\right)\left(\frac{l}{w}\right).$$

By assuming a standard t for all traces, this expression can be used to compare series resistances by counting the number of 'squares' required to create the desired pattern. Accordingly, one can see that the length of pattern C is short relative to many of the others, therefore, this would have desirably very low DC resistance. However, a disadvantage to the inductor shown in Pattern C is that it makes for a very inefficient inductor shape. That is, this straight trace would have very low inductance compared to some of the other shapes in FIG. 83. Pattern D comprises three parallel straight inductor paths $L_1$, $L_2$ and $L_3$. This would drop the total inductance in accordance with the parallel inductor equation shown in FIG. 84. Therefore the total inductance of the three traces 354 in parallel is much less than a single one. However, the DC resistance also desirably drops in parallel just like resistors in parallel. Accordingly, there is a trade off here between the desired inductance and the amount of DC resistance. Referring to Pattern E, one can increase the length of the deposited inductor trace 354 by going from one corner to the other forming a diagonal. This increases its length thereby increasing its inductance while at the same time also increasing its DC resistance which is undesirable. However, as previously mentioned, multiple layers can be laid down thereby decreasing the DC resistance. Patterns B and G show alternate methodologies of greatly increasing the overall length of the deposited inductor circuit trace 354 by making it curved. The advantage of the curve is that one greatly increases the length of the inductor and therefore the inductance. Another advantage of curving the meander back and forth is that mutual inductance occurs between the adjacent turns. This also tends to make the overall inductor meander more efficient. The inductance of the wire or the circuit trace is proportional to its overall length and mutual inductance. Curved traces are an efficient way of increasing the length and the mutual inductance and thereby increasing the total inductance. Patterns F and I illustrate an even more efficient way to increase the overall length and mutual inductance by a rectangular pattern by wrapping back and forth so that the distance between one termination surface 336 and the other termination surface 338 is greatly increased. Pattern A illustrates another type of inductor pattern that looks almost like a digital waveform. Pattern J is a very efficient omega pattern. Another option is shown in Pattern H wherein a saw tooth pattern could be formed. The saw tooth is not very efficient as to mutual inductance. It will be obvious to one skilled in the art that a number of patterns can be used to increase the length and thereby increase the inductance. In general, Pattern shapes A, B, F, I and J are preferred embodiments when compared to the other patterns. This takes into consideration a balance between the inductance efficiency achieved versus the amount of DC resistance.

Referring once again to FIG. 83 Pattern A, one can see that there is a parasitic capacitance $C_P$ that occurs between the adjacent meanders 354 of the novel embedded inductor 346. If the inductor trace 354 shape were in air (dielectric constant=1), this value of $C_P$ would be relatively low. However, in the composite MLCC-T 344, the inductor trace 354 is embedded within a very high dielectric constant material (such as Barium Titanate with a K of 2000 or greater). Because of this, the distributed capacitance between adjacent turns of inductor 346 will be relatively high. However, in accordance with the present invention, this would serve to add to the total amount of parallel capacitance. This is best understood by looking at the parallel TANK circuit schematic diagram illustrated in FIG. 82. The distributed capacitance that would occur in the inductor 346, would add in parallel to the desirable capacitance C in creating the parallel TANK circuit 146.

In actuality, if one is to carefully design the amount of distributed capacitance $C_P$ as illustrated in FIG. 83, one could totally eliminate the need for a separate discrete capacitor. Referring back to FIGS. 80 and 81, this means that if one were to control the distributive capacitance of the inductor 346, one could then eliminate the capacitor electrode layers 340 and 342. This would be a preferred embodiment of the present invention wherein the parallel resonant TANK filter 146 could be entirely created using the distributive capacitance of the inductor itself.

Referring back to FIG. 51 and looking at the parasitic capacitance $C_P$, one can see that the same principles can be applied to an air wound inductor (or an inductor embedded within any other dielectric material). In an air wound inductor, the distributive capacitance is not as efficient (will not be as high) as for an inductor embedded and co-fired within a high dielectric constant material. However, if there were a huge number of turns that were closely spaced, it would still be possible to use the parasitic capacitance as shown in FIG. 51 to resonate with the inductance in such a way that the entire structure becomes a resonant TANK circuit in accordance with the present invention. A major disadvantage of this approach for the present invention is that when the air wound inductor is placed into body fluid, it would be in a medium having different dielectric properties than air. This would change the distributed capacitance and thereby the resonant frequency. Worse yet, the relatively high conductivity of body fluid would cause turn to turn leakage currents to flow. One practical way to use an open solenoid inductor structure would be to place it into a hermetically sealed package. This would become very large and impractical for venous insertion and/or tissue tunneling surgical techniques. Accordingly, open solenoid inductors resonating with their own turn to turn parasitic capacitances represent a less desirable approach.

Referring to FIG. 85, one can see that any of the aforementioned inductor circuit traces 354 from FIG. 83 could also be printed or deposited right on top of a prior art MLCC capacitor 332 to form MLCC-T 344'. In this case, they do not need to be embedded and co-fired within the entire ceramic capacitor. The advantage here is that low cost MLCCs which have been produced from very high volume commercial capacitor operations could be utilized and the inductor trace 354 could be printed on as a supplemental operation.

FIG. 86 is the schematic diagram of the FIG. 85 novel MLCC-T 344'. The inductor 354 imprinted onto the capacitor 332 could be made of pure platinum or pure gold so that it would be biocompatible and suitable for direct exposure to body fluids. This is a very convenient rectilinear (flat) geometry in that it is readily adaptable to electrodes that are typically used for neurostimulators, deep brain stimulators, spinal cord stimulators and the like. The previously described coaxial parallel TANK circuits are more applicable to insertion through veins like the subclavian vein and down through the valves of the heart for convenient insertion into the right ventricle for example. Coaxial geometries are also particularly adapted where the physician must use surgical tunneling techniques to insert an electrode. For example, tunneling techniques are commonly used for neurostimulators to insert a lead wire to stimulate a particular nerve or muscle in a paralyzed patient.

Figure 87:
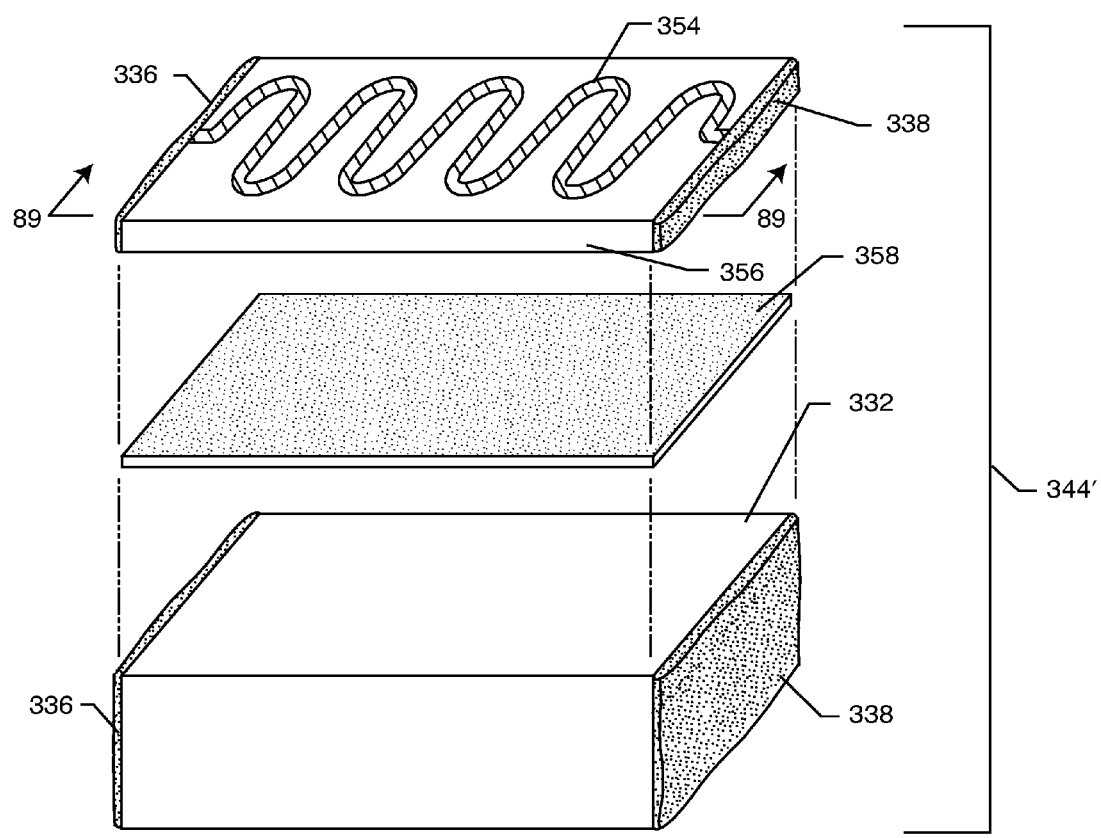
FIG. 87 is an exploded perspective view of a novel MLCC-T similar to that shown in FIG. 85, illustrating another way to deposit any of the inductor tracing shapes illustrated in FIG. 83.
Figure 88:
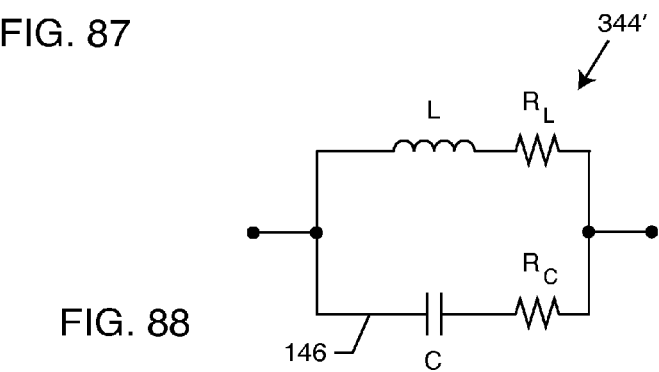
FIG. 88 is the actual (non-ideal) electrical schematic diagram (model) of the structure of FIGS. 80, 85 and 87.

FIG. 87 shows yet another way to deposit any of the inductor shapes 354 as previously described in FIG. 83 onto a separate substrate 356. For example, this substrate 356, could be of alumina ceramic or other suitable circuit board material. This could then be bonded with a thin adhesive layer 358 to a prior art MLCC capacitor 332. The composite MLCC-T structure 344", including corresponding metallization surfaces 336 and 338 on opposite ends, is illustrated in the electrical schematic diagram of FIG. 88 where it is evident that the structure forms the parallel L and C TANK circuit 146 of the present invention.

Figure 89:
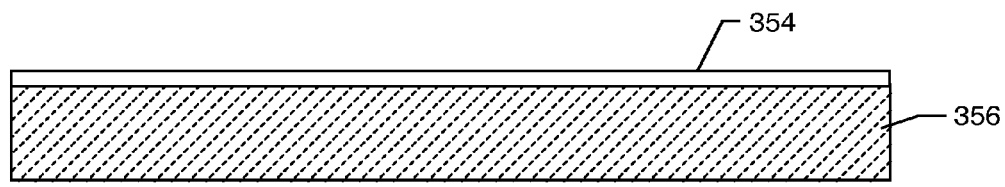
FIG. 89 is a sectional view taken along the line 89-89 of FIG. 87.
Figure 90:
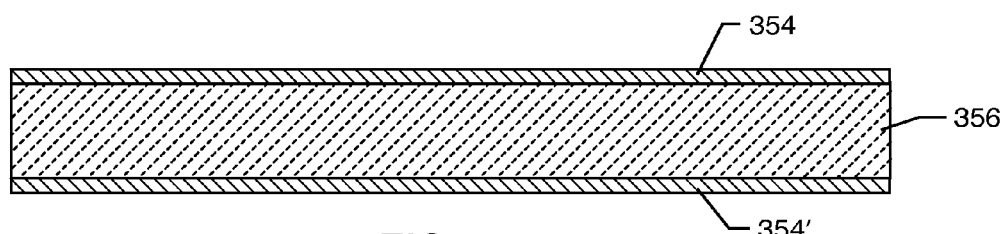
FIG. 90 is a sectional view similar to FIG. 89, illustrating an alternative configuration wherein two inductor layers are deposited on opposite sides of a substrate.
Figure 91:
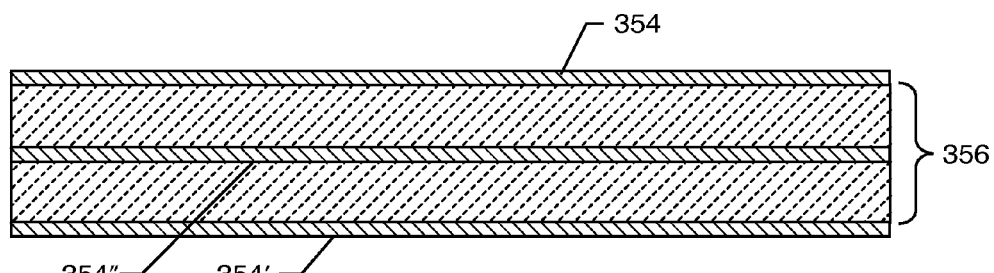
FIG. 91 is a sectional view similar to FIGS. 89 and 90, illustrating a multi-layer substrate having an embedded inductor layer along with surface inductor layers.
Figure 92:
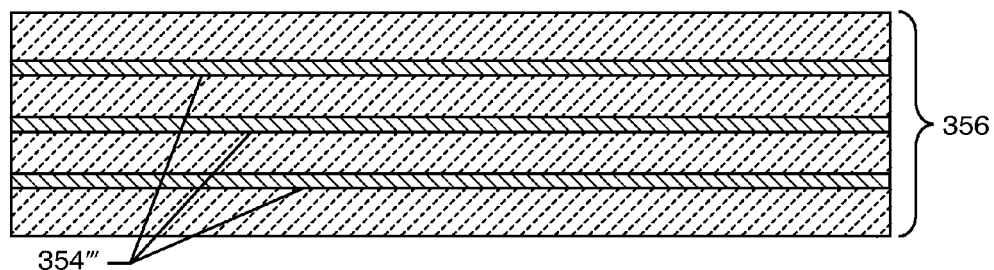
FIG. 92 is a sectional view similar to FIGS. 89-91, illustrating a completely embedded multi-layer substrate where there are no inductors on the surface.

FIG. 89 is a sectional view taken along line 89-89 of FIG. 87. FIG. 90 illustrates an alternative configuration wherein two inductor layers 354 and 354' are deposited on opposite sides of substrate 356. FIG. 91 illustrates a multilayer substrate 356 having an embedded inductor layer 354' along with surface inductor layers 354 and 354'. FIG. 92 illustrates a completely embedded multilayer substrate 356 where there are no inductors on the surface. In this case, inductors 354" are all embedded within the structure. Referring to FIGS. 89, 90, 91 and 92, all of these inductor substrate structures are designed to be co-bonded to the ceramic MLCC capacitor 338 as illustrated in FIG. 87.

Figure 93:
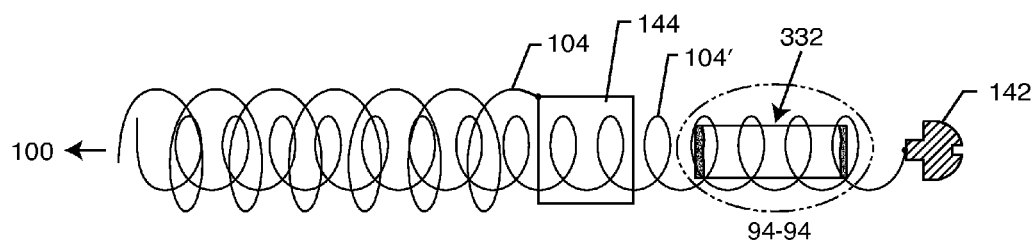
FIG. 93 is a schematic view similar to FIG. 28, illustrating a bipolar pacemaker lead wire system.
Figure 94:
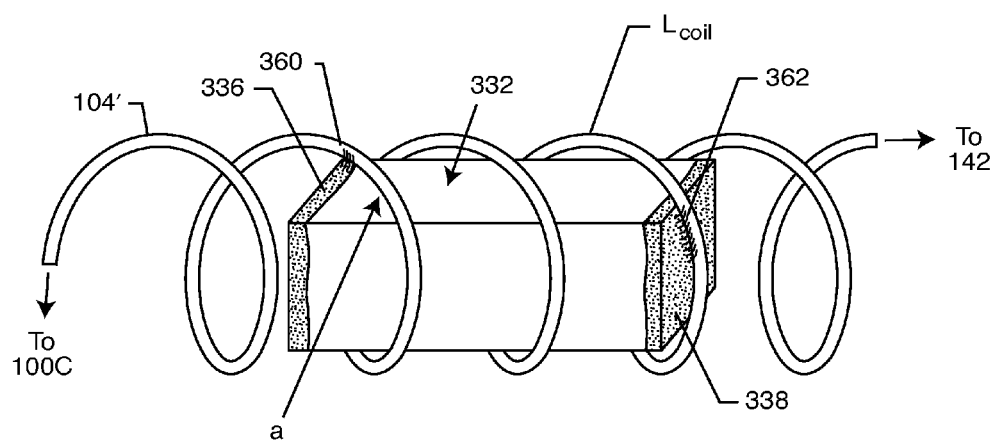
FIG. 94 is an enlarged view of the area taken generally along line 94-94 in FIG. 93.
Figure 95:
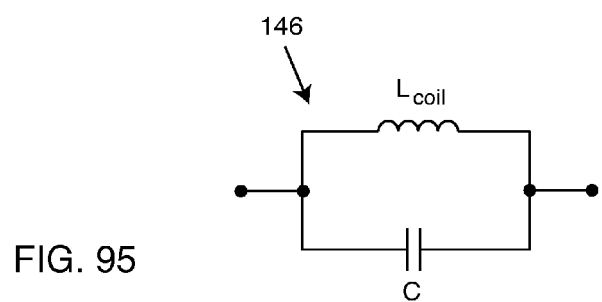
FIG. 95 is an electrical schematic representation of the coiled inductor wrapped about the prior art MLCC shown in FIGS. 93 and 94.

FIG. 93 is similar to FIG. 28 and illustrates a bipolar pacemaker lead wire system such as that shown in FIG. 10. There are two coaxial lead wires 104 and 104' that are connected to the RING electrode 144 and the cardiac TIP electrode 142 respectively. These lead wires are routed from an active implantable medical device 100 (not shown). As one can see, the lead wires 104 and 104' are coiled around each other. In most cardiac applications, the RING electrode is coaxially wound around the inner TIP electrode lead wire. Referring to TIP lead wire 104', one can see that a prior art MLCC chip capacitor 332 has been inserted such that the coils of the lead wire 104' wrap around it. This is best understood by referring to FIG. 94 which is an enlarged view generally taken of area 94-94 of FIG. 93. Such prior art MLCC chip capacitors 332 are widely available very inexpensively as they are produced in very high volumes. Electrical connections 360 and 362 connect the lead wire 104' to the capacitor metallization surfaces 336 and 338. This puts the lead wire 104' in parallel with the capacitive element. The lead wire 104', due to its coiled geometry, makes a very efficient inductor element. The combination of the coiled inductance L and the prior art MLCC yields the novel parallel resonant TANK filter circuit 146 of the present invention, as illustrated in FIG. 95. It will be obvious to those skilled in the art that all of the materials used to construct the MLCC chip capacitor 332 and its electrical attachments to the lead wire 104' should be biocompatible. This is because it will be directly exposed to either body fluids or body tissue. As previously described, it is desirable for high reliability testing and screening purposes to be able to do proper burn in and electrical measurements of the TANK capacitor element 332. As mentioned, this is very difficult to impossible to do with the inductor $L_{coil}$ connected in parallel with the capacitor 332. Referring back to FIG. 94, one can see, for example, electrical connection 360 could be left disconnected until the aforementioned capacitor high reliability screening is accomplished. Then, the small innocuous electrical connection 360 could be made. It would have to be validated during the manufacturing process that such electrical connection did not introduce any latent defects into the capacitor lot population. The way to accomplish this would be to snip $L_{coil}$ with a pair of cutters, for example, near the section marked a and then go back and do capacitor high reliability screening. This snipping disconnection would be destructive of the devices under test. This could be done during initial qualification testing on a large sample of parts. These particular parts would never be slated for commercial or human implant applications. Performing this type of testing on a capacitor element after it has been completely built will prove that the electrical connection 360 did not damage the capacitor in any way. During this follow-up high reliability screening, there should be zero failures in the capacitor lot population.

Figure 96:
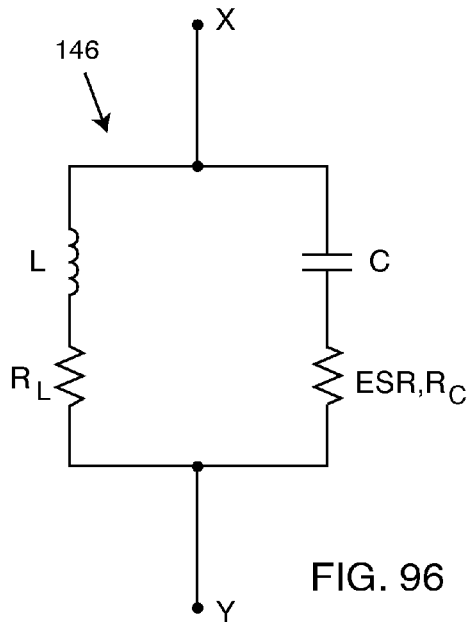
FIG. 96 is a more detailed electrical schematic illustration of the parallel TANK circuit of the present invention.

FIG. 96 is a more detailed schematic drawing of the parallel TANK circuit 146 of the present invention. One can see that there is an inductor element L and in addition, there is a resistive element $R_L$. $R_L$ represents the parasitic resistance of the circuit trace 354 or wire used to form the inductor element itself. One can also see that the capacitor element C has a resistor in series which is known as the capacitor equivalent series resistance (ESR) or $R_C$. Referring once again to FIG. 96, the resistance $R_L$ shown in series with the inductor and/or the ESR, $R_c$ shown in series with a capacitor can be either parasitic (a property of the inductor of the capacitor element itself) or they can be added resistances as separate components. For example, if it were found to be desirable to increase the value of $R_L$, one could add a small resistor chip or element in series. In the present invention, the relationship between the $R_L$, $R_C$, L and C are very important, and is best understood by understanding how the TANK filter 146 works in an actual active implantable medical device application.

Figure 97:
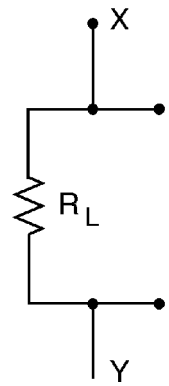
FIG. 97 is an electrical schematic showing a very low frequency (biological) model of the TANK filter circuit of FIG. 96.
Figure 98:
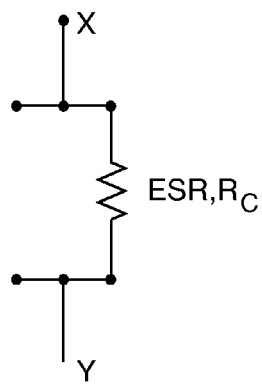
FIG. 98 is an equivalent circuit model for the TANK filter circuit of FIG. 96 at very high frequencies that are well above the resonant frequency.

Biological signals are very low in frequency. In fact, in a cardiac pacemaker application, all cardiac signals of interest occur from 10 to 1000 hertz. However, MRI pulse frequencies tend to be relatively high in frequency. For example, MRI frequencies for a 0.5 Tesla system are 21 MHz. This goes all the way up to 128 MHz for a 3 Tesla system. The novel TANK filter 146 of the present invention is designed to be placed in series with an active implantable medical device lead wire system, for example, connected between points X and Y (See FIG. 96). For example, in the case of a cardiac pacemaker, the output pulses from and sensing to the cardiac pacemaker would be connected at point X, whereas point Y could be connected to the distal TIP which is the electrode used to connect to myocardial tissue. Referring again to FIG. 96, it would be very desirable to have the overall impedance of this TANK filter circuit 146 to be very low at biological frequencies. If one considers the formulas in FIG. 15 for capacitive reactance $X_C$ and inductive reactance $X_L$, one will see that at very low frequency, the capacitor tends to look like an open circuit and the inductor tends to appear as a short circuit. At very high frequencies, such as cell phone or radar frequencies, the inductive reactance $X_L$ is very high (open circuit) and the capacitive reactance $X_C$ tends to be very low (short circuit). Therefore, at very low (biologic) frequencies, from 10 to 1000 Hz, there would be insignificant or zero current that flows through the right hand side of the FIG. 96 TANK filter circuit 146 through the capacitor element C. Accordingly, the ESR ($R_C$) of the capacitor is not important at all at biological frequencies. However, referring to the left side of the schematic shown in FIG. 96, the inductive reactance $X_L$ is quite low when the frequency is low. One can see from the $X_L$ equation that as f approaches zero the inductive reactance also approaches zero. In other words, at biological frequencies (below 1 kHz), for all practical purposes, the reactance $X_L$ of the inductor element L is zero. Therefore, at low frequency the impedance between points X and Y is entirely determined by $R_L$ which is the resistive property of the inductor. The very low frequency (biological) model of the TANK filter circuit 146 is shown in FIG. 97 which consists entirely of $R_L$. At very high frequencies (well above TANK filter circuit resonance), the inductive reactance tends to be very high or almost infinite. Therefore, at high frequencies well above TANK filter resonance, little to no current flows through the left hand side of the schematic diagram of FIG. 96. As previously discussed, at very high frequencies, the capacitive reactance $X_C$ tends to short circuit. Therefore, at high frequencies, the equivalent circuit model for the TANK filter circuit is shown in FIG. 98 which consists solely of the capacitor's equivalent series resistance (ESR), $R_C$. (Note: this assumes a high frequency coaxial feedthrough capacitor whose parasitic inductance is small enough to be ignored.)

For an AIMD lead wire application, one really doesn't care about too much high frequency attenuation. In addition to blocking and stopping the flow of RF currents introduced from MRI radio frequency signals, one is really only interested in passing low frequency biologic signals both in sensing and in delivering stimulation signals or pulses to body tissue. For example, in the case of a cardiac pacemaker, the pacing electrode which connects into the right ventricle provides low frequency pulses so that the heart can beat properly. At the same time, it is also sensing cardiac activity in the frequency range from 10 Hz to 1 kHz so that it can make rate or output threshold adjustments as appropriate. However, one does not really care whether there is a great deal of impedance in the lead wire system at high frequencies that are well above the resonant frequency of the TANK filter. In fact, a high lead wire impedance is desirable to attenuate undesirable electromagnetic interference (EMI), such as from cellular phones, etc. Accordingly, referring back to FIG. 96, when considering EMI, one does not really care how high the ESR ($R_C$) of the capacitor goes (the capacitor could also have relatively high internal inductance). In fact, it is desirable that this ESR value be relatively high. It is also desirable that the value of $R_L$ which is the resistance of the inductor be as low as possible. Keeping $R_L$ low prevents attenuation of desirable stimulation pulses (minimizing energy loss to the battery of the AIMD). Keeping $R_L$ quite low also prevents attenuating low frequency biological signals so they may be properly sensed by the AIMD. However, when considering the band pass filter characteristics and the impedance of the TANK filter at its resonant frequency, the situation is not as simple as described above. It is desirable to have some series resistance in the inductor and capacitor elements so that the bandwidth of the tank will not be too narrow at the resonant frequency. If the bandwidth is too narrow, it will literally be impossible to build the tank filter due to the practical tolerances of the components used. However, adding too much resistance to the inductor or the capacitor side of the TANK circuit will decrease the overall Q so much that the attenuation of the resonant TANK filter is reduced or even that its frequency of resonance has been shifted. This has the effect of reducing the impedance of the TANK filter at its resonant frequency and thereby undesirably reducing its attenuation to the MRI pulsed frequencies. Accordingly, a careful balance must be achieved between all of these factors to create sufficient impedance of the resonant TANK filter such that it prevents overheating of implanted lead wires and their associated electrodes.

Referring back to FIG. 24, one can see a family of curves which illustrates the resonance and the TANK characteristics of the novel TANK filter circuit 146 of the present invention. Curve trace 166 indicates the use of a very high Q capacitor and a very high Q inductor. This would mean that the resistive loss $R_L$ of the inductor and the resistive loss $R_C$ of the capacitor would both be very low. This leads to a very high Q TANK filter circuit which has a very narrow resonant dip and a correspondingly very high attenuation (or impedance Z) as shown. This is indicated by the relative close spacing of points a and b (3 dB down points) on curve 166.

It is a feature of the present invention to use a relatively high Q inductor which means that its resistive loss $R_L$ would be very low in combination with a relatively lossy low Q capacitor element C. This means that the capacitor element would have an ESR or resistive loss $R_C$ that would be relatively high. This would result in a medium Q resonant TANK circuit shown as curve 164 in FIG. 24. As previously stated, this allows biological signals to pass through the TANK filter with little to no attenuation. However, at high frequencies a great deal of attenuation would be presented both at the MRI pulsed frequencies and at even higher frequencies (such as cellular telephones). This has the desirable effect of broadening the bandwidth of the TANK filter. This is very important in that this makes it possible to attenuate the RF pulsed frequencies from multiple types of MRI systems. For example, the older style 0.5 Tesla MRI frequencies embody RF pulsed frequencies at 21 MHz. A very common MRI system that operates at 1.5 Tesla has a MRI pulsed frequency of 64 MHz. Newer MRI systems tend to operate at 3 Tesla and above and have MRI pulsed frequencies that range from 128 MHz all the way to 213 MHz (and even higher). Accordingly, by carefully controlling the inductor and the capacitor quality factors (Q), one can broaden the TANK filter resonant characteristic such that the novel parallel TANK filter circuit 146 of the present invention effectively blocks the RF pulsed frequencies from a wide variety of types of MRI systems and other emitters. Referring back to FIG. 24, one can go too far with this approach as shown in curve 162. This would be a situation where the Q of the overall TANK filter circuit is so low that it no longer offers enough attenuation at any frequency. Accordingly, a careful balance is desired between the component losses of the L and C elements and the TANK resonant bandwidth of the parallel TANK filter circuit. Modeling using P-Spice in correlation with actual prototype measurements has shown that the following set of values works well for the resonant TANK of the present invention: this includes be a capacitor value of 41.3 pf, a capacitor equivalent series resistance of 10 ohms, an inductance value of 150 nanohenries, and an inductor resistance of 1.0 ohms. This combination yields an impedance of greater than 50 ohms at the resonant frequency while keeping the bandwidth wide enough to make the device relatively easy to manufacturer and calibrate.

There is another reason that it is very important to broaden the width of the TANK filter characteristic of the present invention. This has to do with the practical limitations of component tolerances. In a very high Q TANK filter it would be very difficult to manufacture the inductor and parallel capacitor such that they resonated at the correct frequency. For example, in a 64 MHz MRI system it would be necessary to build a very high Q capacitor-inductor TANK with capacitance and inductor tolerances at less than +/−0.1%. In terms of practical component manufacturing this would be very complicated, very costly and very difficult. Laser trimming methods would be required to tune these components to the precise frequency. An added problem would occur over time. That is, most capacitor dielectrics tend to age which means they lose capacitance over time. Accordingly, even though one precisely tuned the components so that they would be resonant at the correct frequency, over the life of a typical active implantable medical device a capacitance value would drop over time which would shift the resonant frequency of the TANK. This means that the resonant frequency of the TANK could shift in such a way that it was no longer effective at the MRI RF pulsed frequency. In other words one might start with a resonant circuit precisely tuned at 64 MHz, but after five years in a human implant application this resonant frequency could shift to 50 MHz which would mean that the TANK filter would no longer be effective. This aging concept and bandwidth control are more completely described in application Ser. No. 60/767,484 entitled LOW LOSS BAND PASS FILTER FOR RF DISTANCE TELEMETRY PIN ANTENNAS OF ACTIVE IMPLANTABLE MEDICAL DEVICES, the contents of which are incorporated herein.

Figure 99:
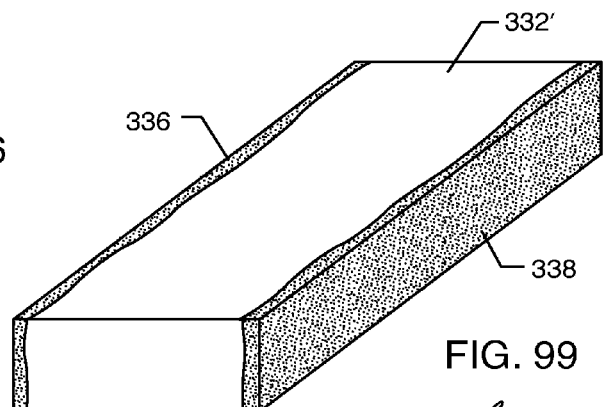
FIG. 99 is a perspective view of one geometry for a prior art MLCC capacitor wherein the length to width ratio forms a capacitor that will inherently have very low equivalent series resistance (ESR)
Figure 100:
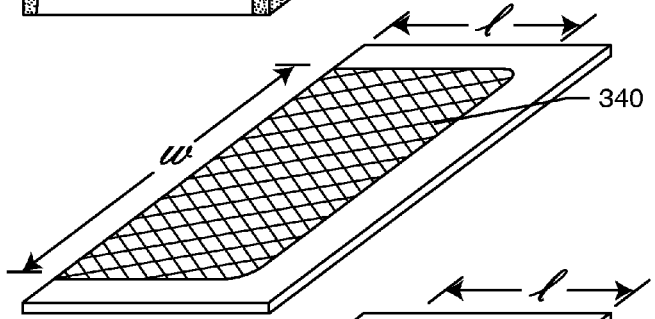
FIG. 100 is a perspective view of a first electrode plate set of the MLCC of FIG. 99.
Figure 101:
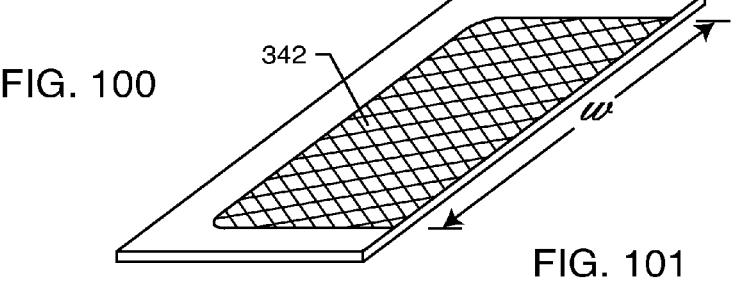
FIG. 101 is a perspective view of another electrode plate set of the MLCC of FIG. 99.

FIG. 99 illustrates one illustrative geometry (form factor) for a prior art MLCC capacitor 332 wherein the length (l) to width (w) ratio between the electrodes 340 and 342 (FIGS. 100 and 101) forms a capacitor that will inherently have very low ESR ($R_C$). The reason the ESR of the electrodes shown in FIGS. 100 and 101 is quite low is that they are very wide W compared to their length L (Ref. the basic resistance formula R=$\rho$L/A, where: $\rho$=resistivity; L=length of electrode; and, A=area of electrode (width times thickness) in that we have minimized the length and maximized the cross-sectional area by maximizing the width.

The relationship between capacitor equivalent series resistance and capacitor dissipation factor and electrode plate loss is best described in a (ESR) technical paper entitled, DISSIPATION FACTOR TESTING IS INADEQUATE FOR MEDICAL IMPLANT EMI FILTERS AND OTHER HIGH FREQUENCY MLC CAPACITOR APPLICATIONS. This paper was authored by Bob Stevenson (co-inventor) and was given at the 2003 Capacitor and Resistor Technology Symposium Mar. 31-Apr. 3, 2003 in Scottsdale, Ariz. Also cited is a technical paper entitled, A CAPACITOR'S INDUCTANCE, given at the 1999 Capacitor and Resistor Technology Symposium (CARTS—Europe), Lisbon, Portugal Oct. 19-22, 1999.

Figure 102:
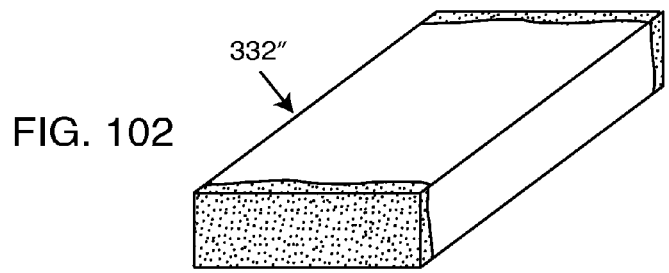
FIG. 102 is a perspective view of an alternative geometric embodiment for the prior art MLCC capacitor in comparison with that shown in FIG. 99, wherein the width to length ratios have been reversed and the ESR will be relatively increased.
Figure 103:
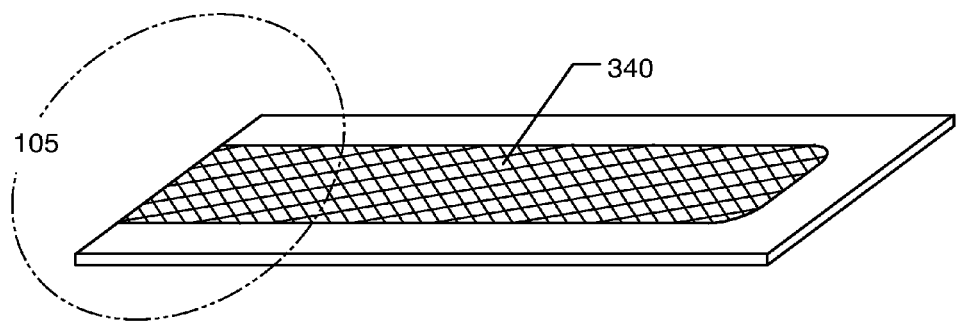
FIG. 103 is a perspective view of a first electrode plate set embedded in the MLCC capacitor of FIG. 102.
Figure 104:
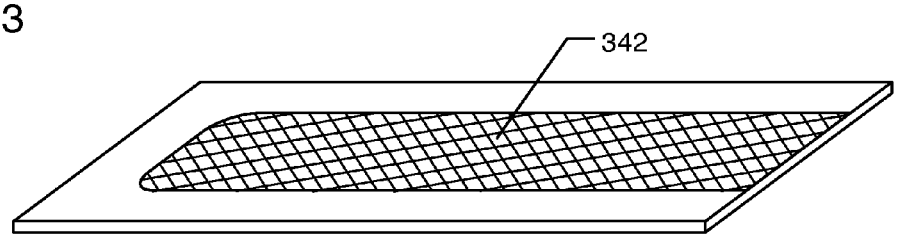
FIG. 104 is perspective view of a second electrode plate set embedded within the MLCC capacitor of FIG. 102.

FIG. 102 illustrates an alternative geometric embodiment (form factor reversed) for the prior art MLCC capacitor 332" in comparison to that shown in FIG. 99. In this case, the width (w) to length (l) ratios have been reversed. The electrodes 340 and 342 (FIGS. 103 and 104) are now quite long compared to their width. This will tend to increase their resistance ($R_C$). As previously stated, in certain designs to control the Q of the TANK, the present invention, it is actually desirable to increase the ESR of the MLCC capacitor 332". This has to do with the Q of the parallel resonant TANK filter circuit 146 and corresponding (relative) bandwidth. As previously discussed, the parallel TANK circuit is resonant at one particular frequency. This forms a notch (TANK) in the frequency attenuation characteristic. However, by increasing the capacitor ESR, which decreases the Q of the TANK filter circuit, one can widen this notch. This is important, for example, in the case of a parallel TANK filter circuit designed to reduce the heating in an MRI system. For example, in the case of a 3 Tesla MRI system which would have an RF pulse frequency of 128 MHz, one would design the parallel inductor and capacitor to be resonant at 128 MHz. The parallel TANK filter circuit 146 will look like an open circuit or infinite impedance at this one frequency only. However, it is relatively difficult to manufacture the ceramic capacitor and the parallel inductance to be precise enough to always resonate at precisely 128 MHz. In addition, MLCCs capacitors age over time. A typical MLCC capacitor will lose 2% of its capacitance for each decade of time. For example, at 1000 hours, if a ceramic capacitor had 1000 picofarads, the next decade of aging would occur at 10,000 hours whereas its capacitance value would drop by 2% (drop to 980 picofarads at the end of this 10,000 life period). This would mean that it would no longer be perfectly resonant at 128 MHz. However, by reducing the Q of the overall system, one can broaden the bandwidth so that it does not really matter. By controlling capacitor ESR, the effective bandwidth of the TANK filter 146 could be increased so that it would be resonant anywhere from, for example, 20 MHz all the way up to 213 MHz thereby accounting for tolerance variations in the capacitor and the inductor and their aging characteristics. This would also allow for attenuation of several types of MRI systems with a single L-C parallel TANK filter (MLCC-T). For example, the RF pulsed frequencies of 0.5, 1.5 and 3 Tesla MRI systems are 21, 64 and 128 MHz respectively. The MLCC-T TANK of the present invention could be designed with high enough capacitor ESR to adequately attenuate two of these MRI pulse frequencies to eliminate concerns due to lead wire or distal TIP overheating. Referring to FIG. 96, the capacitor's ESR ($R_C$) could also be supplemented (or replaced) by an additional or discrete resistor element, however, for volumetric efficiency (and cost and reliability), the preferred embodiment is to adjust the capacitor's ESR. Accordingly, it is a desirable feature in the present invention to reduce the Q of the capacitor thereby increasing the bandwidth of the parallel resonant TANK filter circuit 146. Also, the Q of the overall resonant L-C TANK filter can be controlled by increasing the series resistance of the inductor as well. However, there is a limit to this because at low frequencies, all of the desirable biological currents flow through the inductor. Therefore, one does not want to increase the resistance of the inductor too much because the desirable biological frequencies and even pacing pulses could be attenuated significantly. Therefore, increasing its resistance $L_R$ too much to affect the Q would be a highly detrimental thing to do because it would end up undesirably attenuating pacing pulses, and also undesirably degrade or attenuate biological or neurological activity that is used for sensing and adjusting the active implantable medical device. Accordingly, it is a feature of the present invention to adjust the ESR ($R_C$) of the capacitor and inductor elements in a balanced way such that the bandwidth of the parallel TANK, TANK filter is broadened at the resonant frequency in such a way that the bandwidth is wide enough and the impedance at resonance is sufficient to reduce of eliminate lead wire and distal TIP heating.

Figure 105:
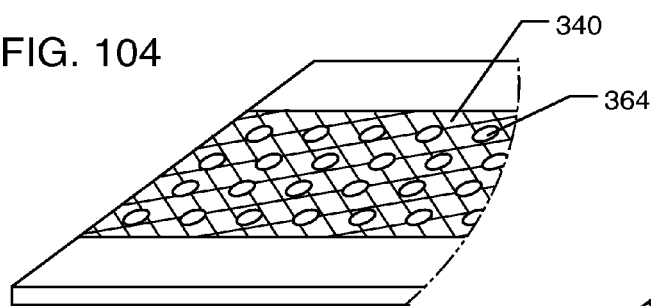
FIG. 105 is an enlarged fragmented view of the area taken along line 105 of FIG. 103, illustrating a novel method whereby one can increase the equivalent series resistance of the capacitor electrodes by including holes or apertures within the deposited electrodes.

FIG. 105 shows a novel method whereby one can further increase the equivalent series resistance ($R_C$) of the capacitor electrodes. This is done during manufacturing by depositing very thin electrodes 340 and/or putting dots in the electrode silk-screen pattern such that holes 364 appear in the deposited electrode. It will be obvious to those skilled in the art that these holes 364 can have any shape from oval to square to rectangular. By depositing very thin electrodes 340 and/or adding holes in the electrode, one can decrease the cross-sectional area of the electrode thereby increasing its equivalent series resistance. Remarkably, experiments have shown that this has little to no effect on the capacitance value itself since the electrostatic field forms a space charge across these holes.

Figure 106:
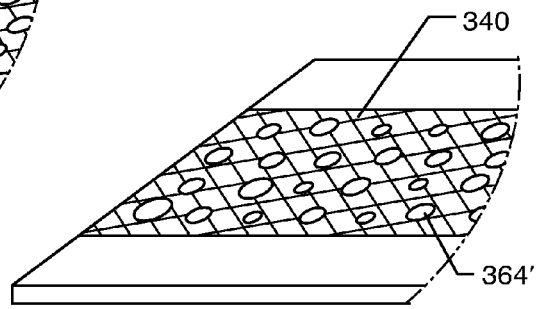
FIG. 106 is a view similar to FIG. 105 wherein the holes in the electrode plate have varying diameters.

FIG. 106 illustrates an alternative way of depositing holes 364' of various diameters which can even out the capacitor electrode's 340 electrostatic field even further, while at the same time, increasing ESR. It should be noted that the total capacitor losses include losses due to dielectric loss tangent, capacitor electrode plate losses, capacitor termination or connection losses, skin effect and the like. However, for the purposes described herein, the self-resonant frequency of modern MRI systems occurs at frequencies that are generally above 10 MHz. At frequencies above 10 MHz, the capacitor's dielectric losses (dielectric loss tangent) approaches zero. Accordingly, dielectric losses can be safely ignored in the present invention. This is more thoroughly described in U.S. Pat. No. 6,765,779. In addition, since the MLCC-T structure 344 contemplated herein is very small, skin effect can also be ignored. Skin effect usually becomes an important phenomenon at frequencies above 500 MHz. In addition, the capacitor's insulation resistance, which would be a resistor appearing in parallel across the capacitor, can also be ignored. This is because modern capacitor manufacturing technology guarantees that the value of this insulation resistance be greater than 10 megohms. Ten million ohms is so large compared to the reactance values of the other components in the circuit that the insulation resistance can be completely ignored. In addition, the capacitor's termination and contacts to those terminations are robust and highly reliable. Accordingly, the resistance of those connections is trivially small. What all of this amounts to is that the only resistance that is really critical in the present invention is the resistance of the electrode plates 340, 342 themselves. In other words, by controlling the high frequency resistance of the electrode plates, we can control the Q of the capacitor at its resonant frequency and thereby control the bandwidth of the parallel resonant TANK filter 146. Other ways of controlling the capacitor ESR or $R_C$ include using a discrete resistor element in series with the capacitor element. There are a variety of prior art resistor chips and the like that are known. One could also use electrical attachment materials to the capacitor that are relatively high in resistivity. Another approach would be to use capacitor dielectrics that have a particularly high dielectric loss tangent within the band of the MRI pulsed frequencies. High frequency dielectric loss tangent presents a resistive loss which would broaden the TANK filter characteristic (reduce its Q). In a preferred embodiment, the most efficient way to control capacitor ESR ($R_C$) is to increase the resistivity of the electrodes themselves. This results in the most efficient packaging. However, all of the aforementioned and other methods can be used. One can also make Q adjustments by adding some series resistance to the inductor. This is relatively easy to do since all inductors have some parasitic series resistance. By making an inductor trace 346 thinner, one can increase the inductor resistance. However, this can only be done slightly as one does not want to undesirably attenuate biologic signals or pacing pulses. The designer makes a careful balance between the inductor Q and the capacitor Q in order to achieve the desired (wide enough) TANK characteristic.

Figure 107:
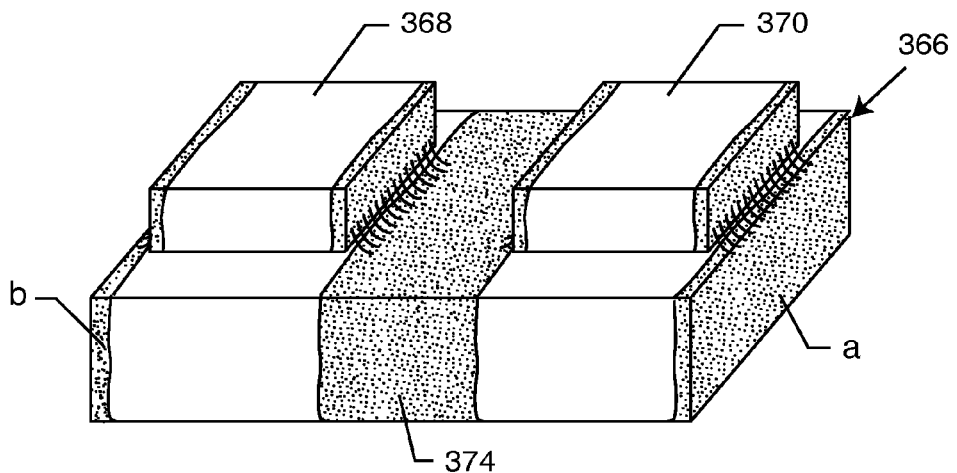
FIG. 107 is a perspective view of MLCC-T TANK filter utilizing custom or commercially available inductor chips.

FIG. 107 illustrates an MLCC-T 366 utilizing custom or commercially available inductor chips 368 and 370 to form the structure as shown. Commercial inductor chips are commonly available at very low cost. For example, Murata part no. LQP15MN2N7B02D is a 2.7 nanohenry inductor chip which has a Q of 13 and a very low DC resistance of 0.3 ohms maximum. These are available at the 100-piece quantity for only $0.16 each (sixteen cents). These are available in a wide range of inductance values and DC resistance Q values. Another is Murata part no. LQP03TLQP03T, which is a 2.7 nanofarad+/−2 nanofarads with a DC resistance of only 0.21 ohms.

A drawback to using commercial off-the-shelf inductor chips 368, 370 has to do with the fact that they typically contain ferro-magnetic materials. In an MRI system this is not preferable because any ferro-magnetic materials will produce what is known as image artifacts. This distorts the MRI image in the immediate area of the implant of distal TIP which is undesirable. In the preferred embodiments of the present invention, all inductors are perfectly composed of either air wound or circuit traced deposited inductor spirals or meanders such that no ferro-magnetic materials are utilized.

It is interesting to note that some experimenters in attempting to design filters for MRI applications have made the mistake of using the MRI RF birdcage coils only. That is, an MRI system with RF field coils without the presence of the main static field ($B_0$). One of the main expenses in installing an MRI system is related to the cost of the super conducting coils and associated cryogenics that generate the powerful static magnetic field. Accordingly, many investigators save a great deal of expense by installing what, from the outside, looks identical to an MRI system. For example, you would see the toroid shape into which the patient would normally be inserted. However, missing are all the cryogenics and the apparatus necessary to generate the main static field. This can lead one to erroneous conclusions because the static field can greatly affect the performance of electronic components particularly if they contain even trace amounts of ferrite or ferrous materials. In all of the preferred embodiments of the novel TANK filter invention herein, the inductor element and the capacitor element is constructed entirely of non-ferrous materials. Another advantage of this approach is that this will have little to no image artifact problems. Image artifact is a very important issue. It is a goal of the present invention to protect the lead wires of an implantable medical device to the extent that it would be possible to directly image (take MRI slices through) the area of the lead wires or even the distal electrode interface. For example, in a cardiac pacemaker application, this would allow for precise MRI imaging of the right ventricle which is precisely where, for example, the cardiac distal TIP would be placed. If this cardiac distal TIP created a large image artifact, then the MRI image slices that would, for example, be looking at ventricular wall motion would become useless. Accordingly, it is a very important feature of the present invention that not only does the TANK filter have to protect the lead wires and the distal TIP from overheating, but it also has almost no image artifact. Accordingly, when we refer herein to inductor chips, we are talking about specialty inductor chips that do not involve any internal ferrite material.

Figure 108:
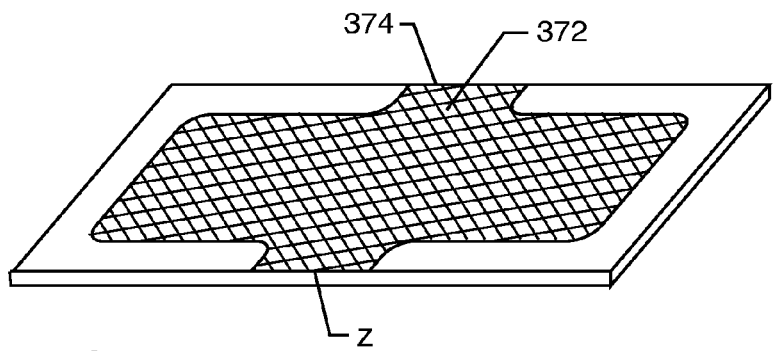
FIG. 108 is a perspective view of a first set of electrode plates embedded within the capacitor of the structure shown in FIG. 107.
Figure 109:
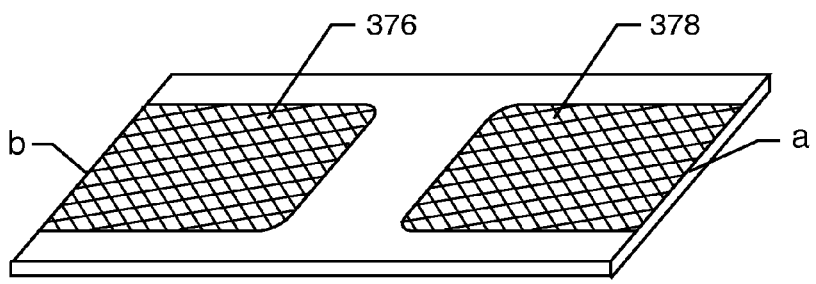
FIG. 109 is a perspective view of a second set of electrode plates embedded within the capacitor of the MLCC-T structure shown in FIG. 107.

Referring back to FIG. 87, one can see that any commercially off the shelf inductor chip 368, 370 could be substituted in place of the substrate 356. Now back to FIG. 107, one can see that two or more of these chips 368, 370 can be used in the novel configuration shown, which is better understood by referring to the electrode sets shown in FIGS. 104 and 105. The FIG. 108 electrodes 372 come out to metallization band 374. It is the overlap of the FIG. 108 electrodes 372 with the FIG. 109 electrodes 376, 378 which forms the novel series capacitor elements. This gives us two capacitor elements in series that is better understood by referring to the schematic in FIG. 110. Inductors 368 and 370 are attached mechanically and electrically as shown in FIG. 107, which forms two series parallel TANKs $F_{R1}$ and $F_{R2}$ as shown in FIG. 110. By adjusting the values of the capacitors $C_1$ and $C_2$ relative to the inductors $L_1$ (368) and $L_2$ (370), one can have the two TANKs $F_{R1}$ and $F_{R2}$ resonate at 2 different frequencies. For example, $F_{R1}$ might be resonant at 64 MHz, which is the pulsed frequency of a 1.5 Tesla MRI system. $F_{R2}$ could be designed to resonate at 128 MHz, which is the pulsed RF frequency for a 3 Tesla system. In this way, the structure shown in FIG. 107 would make the active implantable medical device lead wire system compatible with both 1.5 Tesla and 3 Tesla MRI systems. This would broaden the patient indication, which is desirable.

FIG. 111 shows yet another alternative embodiment MLCC-T 366' where a single inductor chip $L_1$ (368) could be placed across a specially formed MLCC chip 332. This is better understood by referring to the novel electrodes 372' and 376' shown in FIGS. 112 and 113. The composite structure forms a parallel TANK filter 146 of the present invention as shown in the schematic of FIG. 114.

Figure 115:
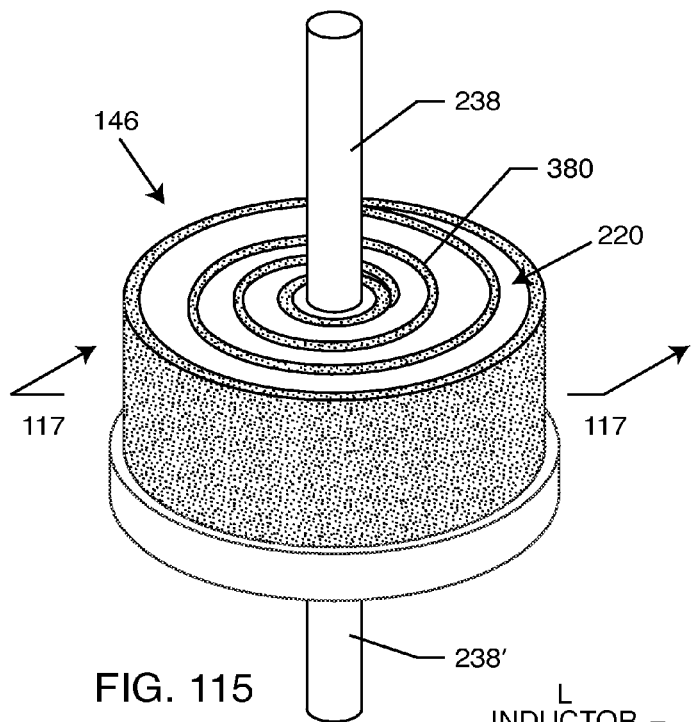
FIG. 115 is a perspective view of a prior art unipolar coaxial capacitor with a parallel inductor spiral deposited on an upper surface thereof.

FIG. 115 is a prior art unipolar coaxial capacitor 220 (feedthrough) with an inductor 380 deposited, attached, printed on, or embedded within it. The spiral inductor 380 can be placed by any of the previously discussed methods, including embedding it and co-firing it within the ceramic capacitor 220 structure, by printing it directly on top of the capacitor, or by printing it on a substrate and then co-bonding it to the capacitor. All of these techniques have been previously described. Inductor spirals are very efficient. Using modified Wheeler equations one can predict the inductance of such spirals. Because of their extreme efficiency due to the mutual inductance, the inductor spiral is the preferred embodiment of this invention.

Figure 116:
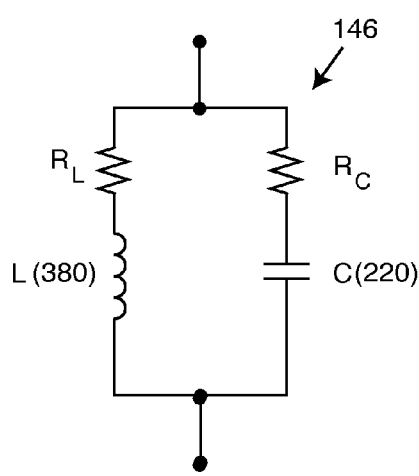
FIG. 116 is the electrical schematic diagram of the TANK filter illustrated in FIG. 115.
Figure 117:
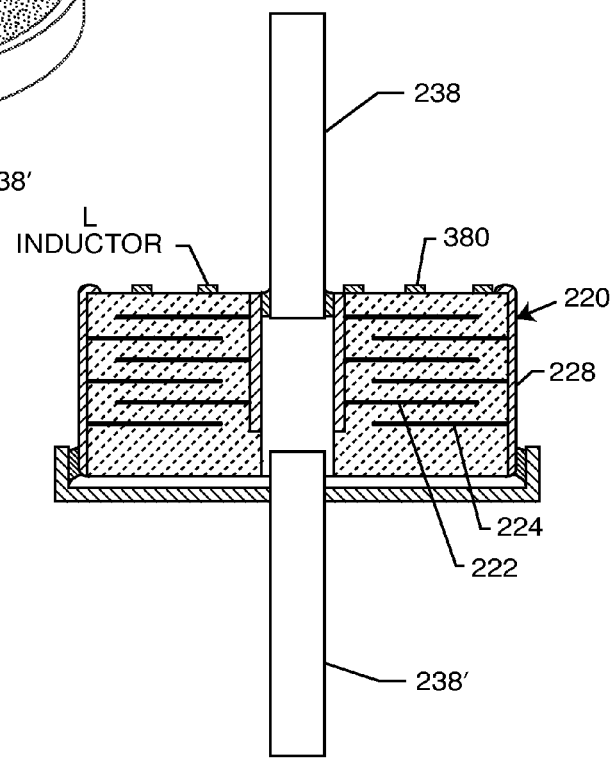
FIG. 117 is a sectional view taken generally along the line 117-117 of FIG. 115.

FIG. 116 is the schematic diagram showing the parallel inductor and capacitor of FIG. 115. FIG. 117 is a sectional view taken along line 117-117 of FIG. 115, showing how one could put this in series anywhere in the lead wire 238 system of an AIMD.

Figure 118:
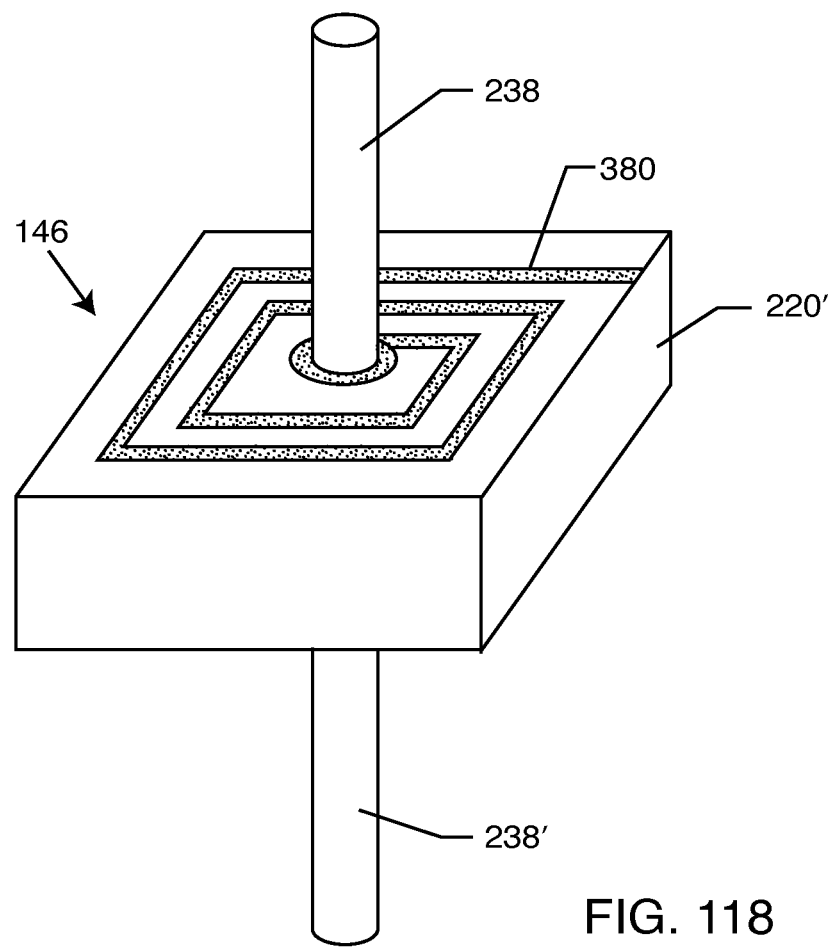
FIG. 118 is a perspective view similar to FIG. 115, wherein the feedthrough capacitor and inductor are square rather than circular.

FIG. 118 illustrate a structure that is very similar to FIG. 115 in that it is a feedthrough capacitor 220'. However, in this case, it is square. It will be obvious to those skilled in the art that this could be any feedthrough capacitor geometries including multi-hole, planar array devices.

Referring once again to prior art FIG. 2, one can see that there is typically an unfiltered RF telemetry pin 116 as shown. The RF telemetry pin is designed to pick up a very narrow band of discrete frequencies that are used to interrogate, reprogram or recover stored waveforms from the implanted device. It is not possible to use prior art low pass EMI filters (feedthrough capacitor type) on the RF telemetry pin because such filters would also undesirably eliminate the RF telemetry frequency. However, the presence of this unfiltered antenna 116 can present a very serious problem in the presence of very high power EMI fields. Once an EMI field has entered the inside of the housing 102 of the implantable medical device, it can cross couple and/or reradiate to adjacent circuits. These inappropriate EMI signals could be sensed by the cardiac pacemaker, for example, as a dangerous or inappropriate ventricular arrhythmia. Worse yet, in a pacemaker dependent patient, such cardiac signals can be interpreted as a normal heart beat which would cause the pacemaker to automatically inhibit (a life threatening situation for a pacer dependent patient). One of the most powerful RF fields that an implantable device patient will ever encounter is inside the bore of a typical MRI device. Accordingly, there is a need to protect the RF pin antenna 116. The tank filters of the present invention are ideal for this.

Referring once again to FIGS. 115 and 118, one can see two ideal examples of where tank filters could be placed immediately adjacent to the telemetry pin. This would be most easily accomplished by placing the tank filter of the present invention on the RF telemetry pin 116 on the inside of the AIMD housing. This way the tank filter would be protected from body fluids. In this case, the Q of the inductor and the capacitor used to form the tank filter should both be relatively high. This is because we want the 3 dB bandwidth to be relatively narrow. The reason for this has to do with the frequencies of interest. For example, for a 3 Tesla MRI system, the RF pulse frequency is at 128 MHz. The lowest common telemetry frequency is at 402 MHz. Therefore, it is very important that the tank filter response curve drop off very rapidly so that the desired telemetry frequency not be unduly attenuated. Another way around this is, for example, to design the tank filter to be resonant at 64 MHz and restrict the patient to only 1.5 Tesla MRIs. Yet another way to get around this is to increase the telemetry frequency. Telemetry frequencies in the 850 MHz range or even above 1 GHz, are also commonly used. It is a feature of the present invention to incorporate a novel tank filter on the RF telemetry pin antenna and at the same time, keep the RF frequency separation between the MRI pulse frequency and the telemetry frequency as wide as possible.

It should be apparent that all of the aforementioned drawings showing construction of novel TANK filters 146 could also be accomplished with various other types of capacitor materials. That is, film capacitors, metallized film capacitors, tantalum, glass, porcelain, common alumina electrolytic and the like. For example, in a film capacitor application it would be obvious to replace the ceramic dielectric with a film. It is also well known in the art to deposit metal or metallized surfaces on dielectric films. Accordingly, the aforementioned drawings showing primarily monolithic ceramic or thick film deposition technology is meant to be all encompassing to include all capacitor technologies. A specific example of this is understood by referring back to FIG. 81. The blank cover sheets 348 and 352 could simply be some sort of a dielectric film, for example, Mylar or polystyrene. The capacitor electrode set could be easily made of a flame sprayed metal deposition to form electrode layer 340 and 342 (including very thin or with holes to control $R_C$). In the same way, electrode layer 340 could be placed on another layer of film. Then a blank piece of film could be put in place of the blank interleaf 350. Additionally, metal could be deposited in another area of the film capacitor forming the inductor layers 346. A film overlay could then be placed with additional cover sheet 352. This could all be pressed and molded into a single package which is common in the art of film capacitors.

Referring back to FIGS. 23 and 24, one can see the process of selecting the appropriate values of L and C so that the TANK filter is resonant at the correct frequency. This also shows how one can adjust the Q of such components to realize the curve shapes as described in FIG. 24. As mentioned, it is highly desirable to have the TANK at or reasonably close to the resonant frequency, for example, of the MRI pulsed frequency. It is not necessary that the TANK be exactly resonant at the MRI pulsed frequency if its resonant bandwidth is sufficiently broad. In other words, even if the resonant frequency of the TANK was, for example, 55 MHz in a 64 MHz MRI system, if the TANK resonant frequency characteristic has broad enough bandwidth, it would still provide sufficient attenuation to effectively cool the distal TIP and provide patient safety.

Even after one goes through the decision making process in FIG. 23, it may still be necessary to do some fine tuning of the TANK particularly if it is constructed of very high Q components. There is a tradeoff here in that if very low loss capacitors and very low loss inductors are used then the bandwidth of the resulting TANK will be very narrow. In the art, this is known as a narrow 3 dB bandwidth. However, there is considerable manufacturing variability, for example, when manufacturing the monolithic ceramic capacitors. This manufacturing variability is also known as the tolerance. For example, for a ceramic capacitor of 50 pf, it might have +/−20% tolerance based on the capacitance value. There is also variability in manufacturing the inductor elements themselves. Accordingly, for a very high Q TANK filter, it is expected that some final tuning may be necessary so that the resonant frequency of the resulting TANK is at or near the MRI RF pulsed frequency.

Figure 119:
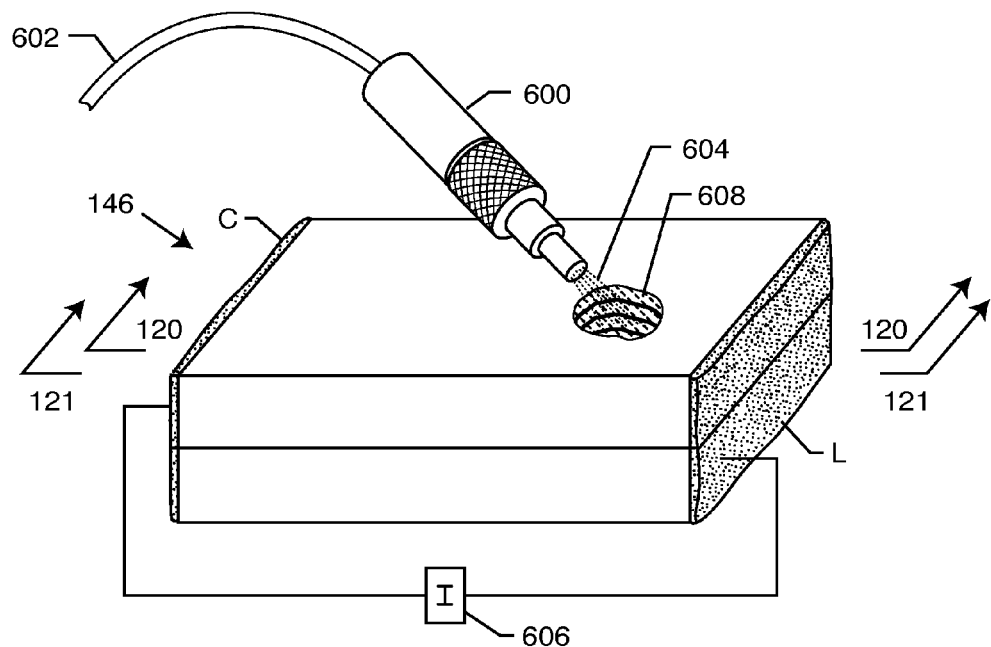

FIG. 119 illustrates a capacitor C and inductor L parallel combination, which is representative of any of the combinations discussed herein, of the present invention to form a novel L-C TANK 146. Referring to FIG. 119, one can see a nozzle 600. This nozzle 600 is attached to a special set of tubing 602 that comes from a microblaster (not shown) such as that manufactured by Comco Corporation. Microblasters direct a jet of high-pressure air containing particles 604 against any surface. Microblasters are well known in the art and are used for a variety of cleaning and trimming operations. In this case, the microblaster 600 could be filled with alumina ceramic which is a preferred cutting material. Referring once again to FIG. 119, one can see that an electronic instrument 606 has been attached to both ends of the L-C TANK filter 146. This is a scanning instrument such as a network or impedance analyzer that would be constantly measuring the resonant frequency of the TANK filter 146. The microblaster 600 can also be automated such that it is robotically dispensed and is turned on and off by the electronic instrument 606. Such adjustments are easy to accomplish through Lab View and similar programming techniques. Referring once again to FIG. 119, one can see that a hole 608 has been literally blasted away through the top cover layers of the ceramic capacitor C and into its active electrode plates 610. This hole can be enlarged or deepened as necessary to literally erode away a portion of the electrode plate layers.

The microblasting goes on until the desired resonant frequency of the TANK 146 is achieved. It should be mentioned that the exact resonant frequency of this tuning would not normally be the exact MRI pulsed resonant frequency. One might decide to tune slightly off to the side to account for the normal aging of the capacitor and/or inductor component over time. That is, as the components age, they will stay within an area of the TANK filter characteristic which provides a high degree of attenuation.

Figure 120:
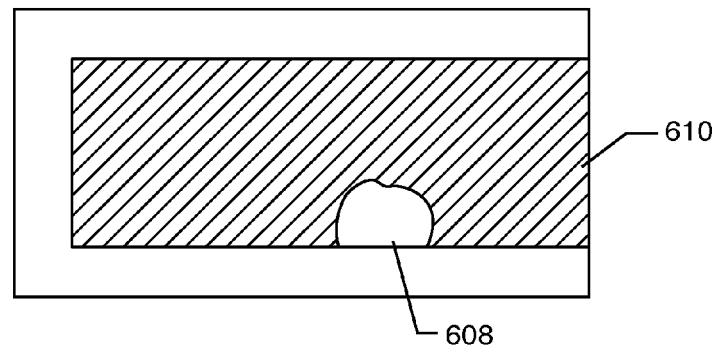
Figure 121:
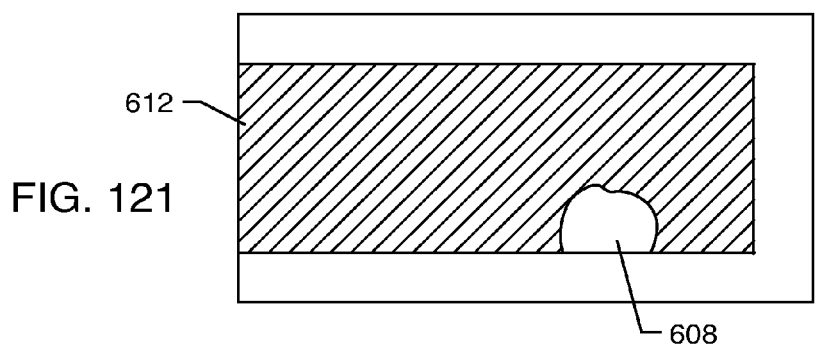

FIG. 120 shows the electrode plate layer 610 taken from FIG. 119 in section 120-120. One can see that a portion of the active electrode 610 has been eaten away. FIG. 121 is a view of the opposite electrode 612 taken generally along the plane 121-121 from FIG. 119. This automatic process reduces the electrode plate overlap area which reduces capacitance value until the precise resonant frequency that is desired of the parallel TANK 146 is achieved.

Figure 122:
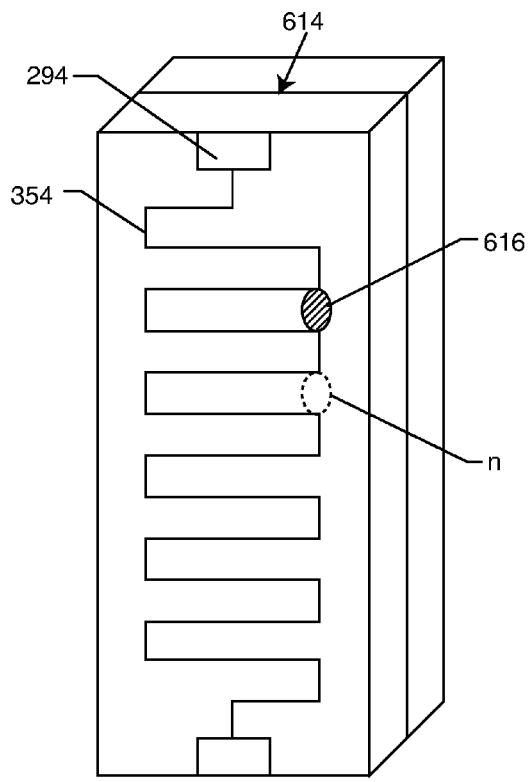
Figure 123:
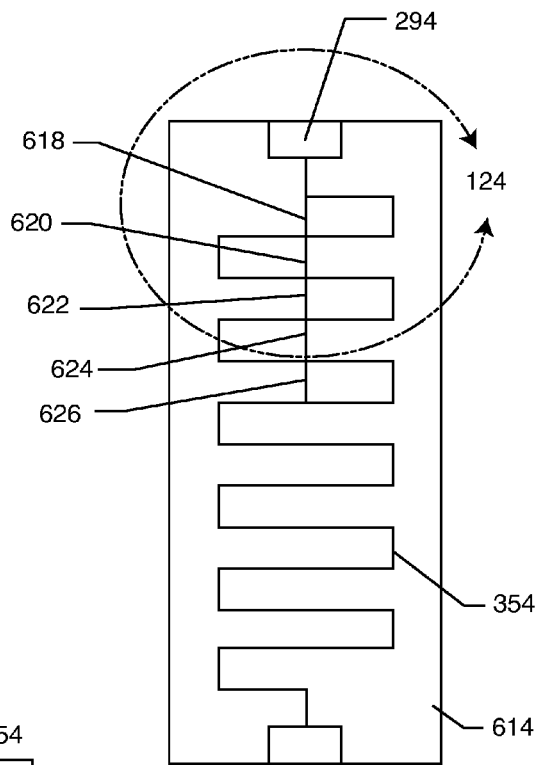
Figure 124:
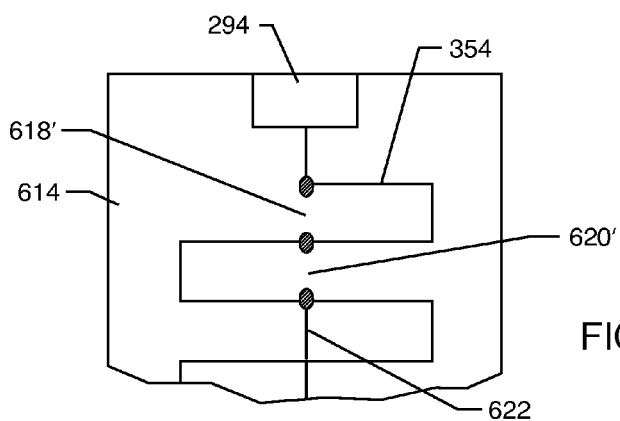

FIG. 122 illustrates a methodology of tuning a meander inductor 354 that is co-bonded to the capacitor 614 forming the TANK filter 146 of the present invention. One can apply small dots of conductor material 616 are used as required to short adjacent turns. This has the effect of reducing the amount of inductance thereby allowing one to tune the parallel L-C TANK by adjusting the inductance downward. As previously described, for FIG. 119, this would typically be done while connected to an electronic instrument 606 which would give a constant readout of the resonant frequency. An alternative methodology is illustrated in FIG. 123. In this case, the inductor pattern 354 has been deposited by various techniques, including screen printing, photolithography, electroplating and the like. However, in this case, deliberate shorting paths have been manufactured between some of the inductor turns as shown at points 618-626. It is then possible to connect the composite L-C TANK filter to the automated electronic instrument 606 used to measure the resonant frequency. Laser trimming or equivalent is then used to selectively remove the short circuits 618, 620 and so on until the desired resonant frequency is achieved. A close-up view is shown in FIG. 124 taken generally from 123 along section line 124-124. Referring again to FIG. 124, one can see areas 618' and 620' where laser trimming has occurred which opens up the previously shorted inductor turns thereby increasing the inductance of the TANK. Referring back to FIG. 119, microblasting is not the only way to make adjustments to a completed capacitor. Laser trimming is also applicable to this procedure as well as high velocity water jet cutting or mechanical abrasion or the like. After trimming is done in accordance with FIG. 119, it is typical that a dot of epoxy or a silicone or the like is used to fill the exposed hole 608. The inventors herein are familiar with these trimming techniques in the prior art for capacitors only. The inventors are not aware that such trimming techniques have ever been applied to a resonant circuit such as the TANK filter 146 of the present invention.

Figure 125:
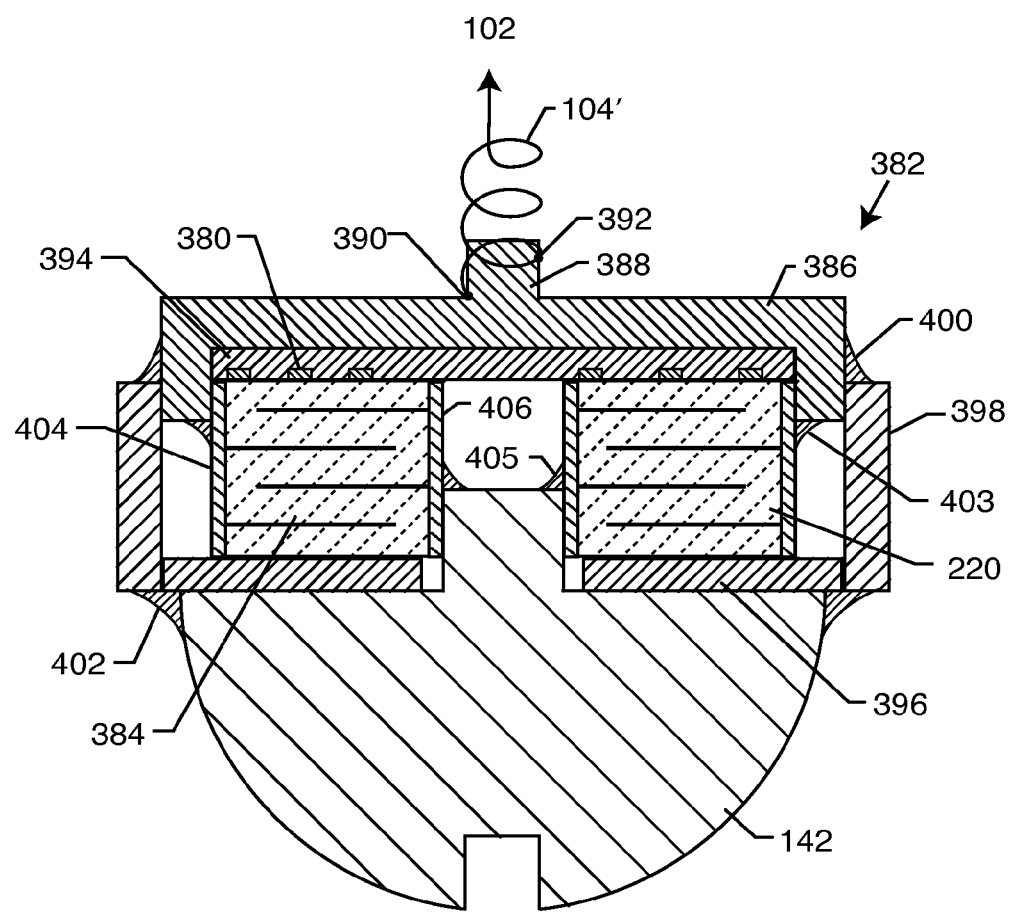

FIG. 125 shows a novel unipolar feedthrough capacitor-inductor TANK filter 382 embodying the present invention. A feedthrough capacitor TANK 384 (with a co-bonded or embedded spiral inductor) similar to that shown in FIGS. 115-117 is embedded within a hermetic housing 386. The hermetic housing 386 consists of a biocompatible end plate which has a stub 388 which allows for convenient laser weld attachment of the lead wire 104' (typically MP-35N alloy). These laser weld attachments are located at 390 and optionally 392. The lead wire 104' connects to the output of an implantable medical device 102 (See FIG. 17). The feedthrough capacitor TANK filter 384 is seated against the end plate 386 a using a non-conductive insulation layer 394. There is a similar insulation layer 396 on the other side. These insulation layers 394 and 396 serve to mechanically seat the capacitor-inductor feedthrough capacitor TANK 384 and hold it firmly in place as well as electrically isolate it. The cylinder 398 is an alumina ceramic, glass or sapphire tube or the like which is insulative and hermetic. This is gold brazed or laser welded 400 to the biocompatible end plate 386. The distal TIP 142 (tissue fixation clips not shown) is then inserted and seated into place and is then also laser welded 402 to the insulative cylinder 398. The insulative cylinder 398 has been prepared to accept braze or weld materials by a previous sputtering or equivalent selective material deposition process. There is an electrical attachment 403 between the capacitor outside diameter termination 404 and the electrically conductive end plate 386. There is also an electrical attachment 405 between the capacitor inside diameter metallization 406 and the distal TIP 142. This forms the novel TANK filter circuit 146 of the present invention by putting the capacitor (220) in parallel with its inductor L (380). The advantage of the structure illustrated in FIG. 125 is that it comprises very low cost prior art capacitor and an efficient spiral inductor. Conventional non-biocompatible materials can be used to manufacture the ceramic capacitor 220 and also to make the electrical attachments. Electrical attachments can include solders and thermal setting conductive adhesives. This is because the ceramic capacitor 220 and its corresponding electrical attachments are all hermetically sealed and isolated from body fluids. Accordingly, non-biocompatible materials such as silver and the like can also be readily used. Most commercially available monolithic ceramic capacitors are made with base metal electrodes (BME) which contain nickel. As previously mentioned, nickel is undesirable both because of image artifact and its tendency to heat in the presence of MRI fields. Other common capacitor electrodes are made from silver or palladium silver. However, silver and palladium silver, although relatively low in cost, are not biocompatible. Accordingly, the hermetic assembly of FIG. 125 allows the use of such lower cost (low sintering temperature) electrodes. As previously described, for non-hermetic capacitors, platinum electrodes are used. The tradeoff is that platinum is more expensive and the capacitor must also be fired (sintered) at a much higher temperature.

Figure 126:
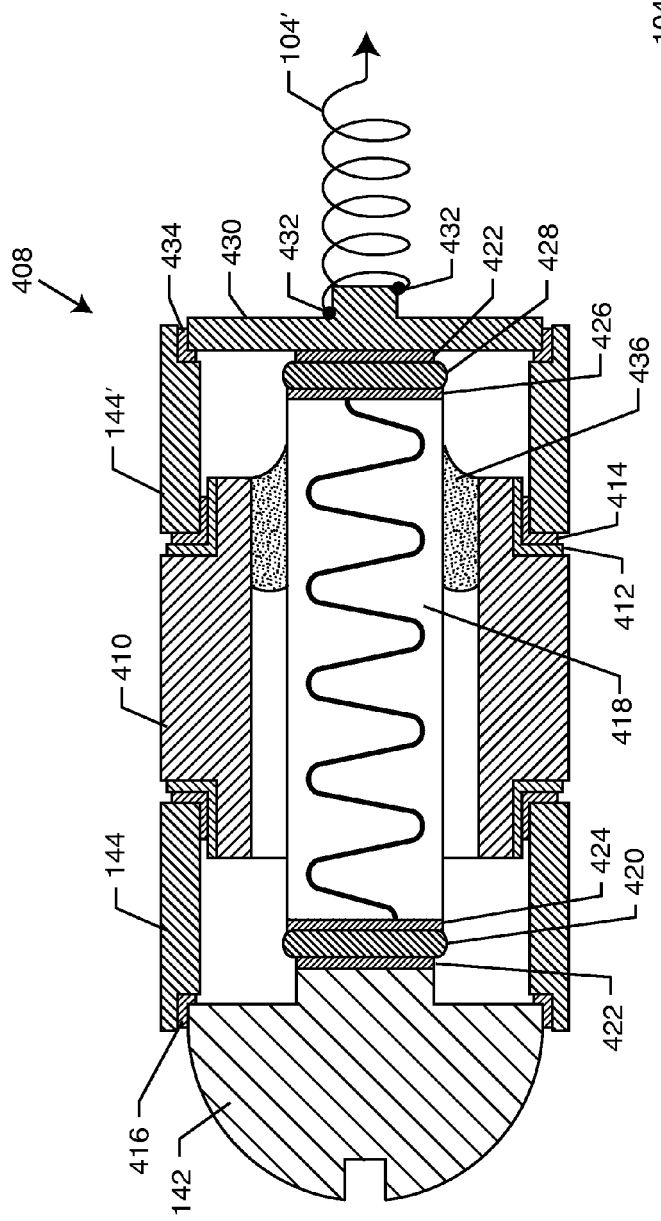
Figure 127:
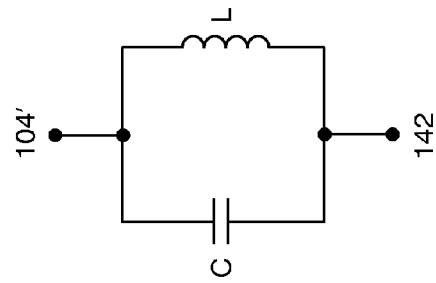

FIG. 126 illustrates an alternative embodiment for a hermetically sealed TANK filter assembly 408. In this case, there is a distal TIP 142 which is designed to intimately contact body tissue is shown on the left. An insulative cylinder 410 is preferably of either machined or pressed alumina ceramic, and includes sputtering 412 (such as a titanium-molybdenum layer) suitable for receiving a gold braze preform 414. The cylinder 410 is attached to biocompatible electrically conductive (preferably metallic) RINGS 144 and 144' as shown. Since RINGS 144 and 144' will be exposed to body fluid, they must be biocompatible and made of materials such as titanium, platinum or the like. The distal TIP 142 is laser-welded at 416 to the electrically conducting RING 144. The hermetic package shown by FIG. 126 is best suited for a rectilinear MLCC TANK 418 like those previously described in connection with FIGS. 80, 81, 85 and 87. Electrical attachment is made between the distal TIP 142 and the termination surface of the MLCC-T 418 by means of a solder or thermal setting conductive adhesive 420. A gold sputter layer 422 or equivalent makes good electrical contact between the conductive attachment material 420 and the distal TIP 142. The MLCC-T TANK end terminations are shown at 424 and 426. A thermal setting conductive adhesive, solder, braze or the like 428 is used to form an electrical connection between the TANK chip termination 426 and a sputtered layer 422 on the back side of metallic plate 430. The typically titanium or platinum end plate 430 is similar to that previously described in FIG. 125. It has attachments 432 for lead to lead wire 104'. The end plate 430 is designed to be laser-welded at 434 to the biocompatible electrically conductive housing piece or RING 144'. Material 436 is a non-conductive thermosetting polymer or adhesive. Its purpose is to provide mechanical support to the novel inductor capacitor chip 418. It can fill the entire space inside the hermetically sealed container or only a portion as illustrated. A schematic diagram for the structures of FIGS. 125 and 126 is shown in FIG. 127, wherein the novel combination of the capacitor in parallel with the inductor which forms the TANK circuit filter 146 of the present invention.

Figure 128:
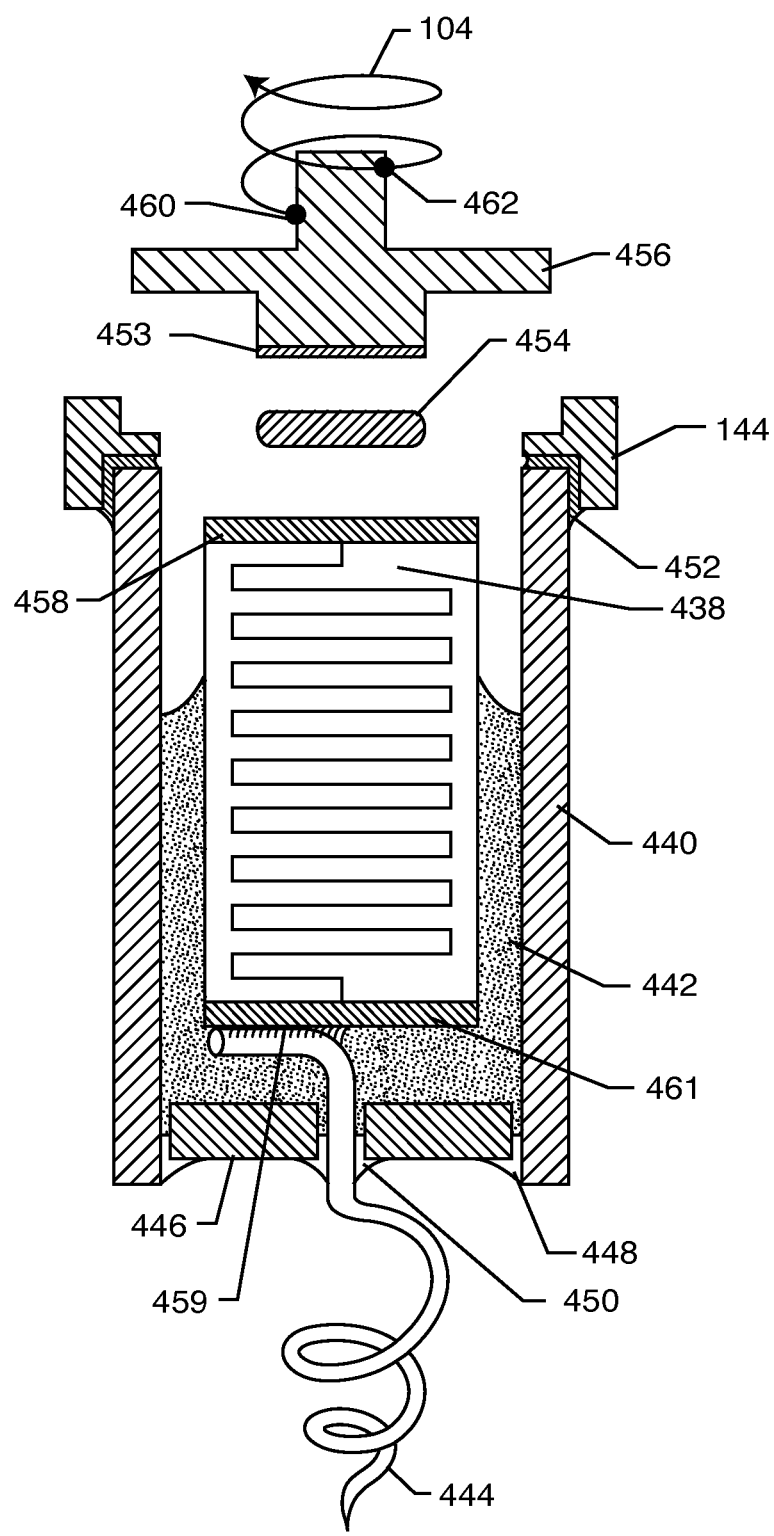

FIG. 128 illustrates an alternative hermetically sealed package that contains a novel inductor capacitor MLCC-T 438. In this case a hollow ceramic or sapphire insulative tube 440 is utilized into which the novel MLCC-T 438 is inserted. A non-conductive thermosetting polymer adhesive 442 is used to mechanically hold it in place. In this case there is a helix active fixation electrode 444 which is designed to be screwed into body tissue. This type of electrode is well known in the prior art and is used to firmly affix a distal TIP, for example, into myocardial tissue. There is a biocompatible metallic end plate 446 which has been laser welded at 448 to the insulative tube 440 and also laser welded at 450 to the helix tip lead wire 444. At the opposite biocompatible metallic end RING 144 has been pre-attached by hermetic brazing or laser welding at 452 to the insulative tube 440. Biocompatible metallic end plate 456 is typically made of titanium, platinum or the like. It will be obvious to those skilled in the art for any of the inventions herein, that other biocompatible materials, such as tantalum, niobium and the like could also be used. Referring once again to structure 456, one can see that there is a sputter area 453 in order to provide a highly conductive and oxide free surface. This sputter layer would typically be gold, platinum or the like. Instead of sputter, this could also be applied by gold brazing, plating or other techniques. A solder or thermosetting conductive adhesive preform 454 is used for the seating of end plate 456. The end plate 456 is seated against this preform 454 and is then cured such that an electrical connection is made between the end plate 456 and the end metallization surface 458 of the MLCC-T 438. The helix TIP 444 has an electrical attachment 459 to the opposite end metallization surface 461 of the MLCC-T 438. The end plate 456 is designed to be laser welded into the inside diameter (counter-bore) of the mating RING 144 forming a hermetic seal. The lead wire 104 coming from the implantable medical device is then attached by laser welding to a stub on the end plate 456 at point 460 and optionally at point 462. Additional attachment points can be added for additional mechanical strength.

FIG. 129 illustrates a distal electrode pad 464 applicable to a wide variety of neurostimulator applications. Neurostimulators include cochlear implants, deep brain stimulators, spinal cord stimulators, incontinence stimulators, general pain control stimulators, vagus nerve stimulators, Parkinson's tremor control stimulators and the like. Typical prior art stimulators often come with a variety of pads such as that shown in FIG. 129. Three neurostimulation electrodes 466, 466' and 466" are shown, however, these can vary anywhere from one, ten or even 20 or more neurostimulation electrodes. For example, in cochlear neurostimulators, there are commonly sixteen wires, which are inserted in a bundle of electrodes to make contact to the auditory nerves. Referring back to FIG. 129, one can see that there is a lead wire bundle 468 which contains three wires that are connected to an external or implanted active medical device.

FIG. 130 is a cross-sectional view taken generally along line 130-130 of FIG. 129, and illustrating one form of the novel inductor capacitor MLCC-T 470 of the present invention. One can see that there is a discoidal feedthrough capacitor 220 with an air core inductor 472 running through its center. These concepts were previously described in connection with FIGS. 45 and 47. In this case, the distal TIP electrode pad 466 has a laser weld or equivalent biocompatible electrical attachment 474 to the surrounding metallization of the capacitor 220. There is also another conductive plate 476 shown connected to the inductor 472 on the opposite side. Lead wire 478 is in turn mechanically and electrically connected to this plate 476. Lead wire 478 is then routed through the flexible neurostimulator pad 464 as shown in FIG. 129. Lead wire 478 becomes part of the wire bundle contained in 468 which would be routed to the AIMD.

FIGS. 131 and 132 describe alternative ways of accomplishing the same thing using a feedthrough capacitor structure as previously described in FIGS. 115 and 118 in the electrode pad 465. In this case, the inductor 380 has been printed onto the top of the capacitor 220 or attached to the capacitor by means of a supplemental substrate. Lead wire 478 is connected to the capacitor's internal diameter metallization 406 as shown using an intermediate contact plate 480. The electrode 466 is electrically and mechanically attached to the capacitor outside diameter metallization 404, but electrically insulated from the internal metallization 406, such as with an insulative pad or liner 481. This is shown inverted for simplicity as compared to FIG. 129.

FIG. 133 illustrates another alternative using thick film techniques to build up in layers the novel parallel inductor TANK filter for neurostimulator applications as previously shown in FIG. 129. Again, this electrode assembly 483 is shown inverted for simplicity. The distal TIP electrode 466 forms a substrate such as used for thick film deposition of various capacitor and inductor layers. The structure 483 of FIG. 133 is better understood by looking at the exploded view in FIG. 134. Starting at the bottom we have the distal TIP electrode pad 466 for neurostimulator applications. An insulative layer 482 is first imprinted on this conductive electrode 466 and then one or more inductor layers 484 are imprinted thereon. Then another insulative layer 486 is laid on top of the inductor layer 484. Onto this a capacitor inner diameter electrode 488 is printed. Then another insulative layer 490 is printed. Then an outside diameter capacitor electrode 492 is imprinted. Many alternating layers of electrodes 488 and 492 can be stacked up as desired to achieve the required capacitance value. Then an overall insulative layer 494 is laid down. As is well known in conventional thick film or tape manufacturing processes, there is usually a drying step between each one of these operations. The entire structure is then sintered at high temperature to form a rugged monolithic structure. An electrical contact 496 is then inserted using a suitable electrical connection material to make contact with both the inside diameter of the inductor 486 and the inside diameter of the inner diameter capacitor electrode plate stack 488. In turn, neurostimulator lead wire 478 is electrically connected to this contact pad insert 496. The outside diameter of the inductor makes contact with neurostimulator pad 466. The capacitor's ground electrode plates 492 also make electrical contact with the distal pad electrode 482. This has the effect of putting the capacitance in parallel with the inductance in accordance with the TANK filter of the present invention.

Table 135 illustrates various fabrication methods for manufacturing the thick film TANK circuits described in FIGS. 133 and 134.

FIG. 136 is an alternative rectilinear embodiment to build a thick film TANK filter of the present invention. This also uses similar fabrication techniques that were described in FIGS. 134 and 135. This starts with a substrate 498, onto which the various layers 504-514 are either imprinted or laid down. There are two convenient wire bond pad areas 500 and 502 suitable for connection of neurostimulator lead wires.

FIG. 137 is a schematic diagram of the neurostimulator electrodes previously described in FIG. 136, and is equally illustrative of FIGS. 130, 132, and 133.

FIG. 138 is an exploded view of the neurostimulator electrode 495 of FIG. 136, showing how the various layers of the novel distal TIP TANK circuit are laid down. As shown, one starts with the substrate layer 498. In this case, the substrate layer is insulative and could be of any suitable circuit board material such as alumina and the like. A capacitor electrode layer 504 is printed down onto the substrate 498. This is overlaid by an insulative layer 506. Then the second capacitor electrode 508 is laid down and again, and another insulative layer 510 is laid down over the top. A novel inductor shape 512 is then imprinted on the insulative layer forming a parallel TANK filter circuit 146. Shown is a meander pattern, although any of the previously described patterns can be used. On top of this is a final insulative layer 514 for both mechanical and cosmetic reasons. As previously described, as many capacitor electrode layers 504 and 508 can be laid down as required to achieve the desired capacitance value. In addition, multiple inductor layers 512 could also be laid down to achieve a desired inductance and a desired inductor resistive loss ($R_L$).

FIG. 139 illustrates the novel inductor TANK filter previously described in FIG. 136. In this case, the thick film inductor capacitor TANK has been hermetically sealed by overlaying with a suitable glass seal 516. This glass 516 can be deposited as a frit or molten and then sintered at high temperature. The glass is designed to adhere to the substrate 498 and the wire bond pads 500 and 502 such that it forms a hermetic seal over the entire TANK filter of the present invention. Material 516 can be any number of borosilicate or compression glasses or even polymer sealants such as silicone and the like.

FIG. 140 is a representation of how one could also glass hermetically seal 516 any of the novel TANK filters of the present invention. For example, reference is made to FIGS. 35, 37, 42, 44 and 58 for just a few examples of novel inductor capacitor TANK filters 146 that can be enclosed within a hermetic sealed package as illustrated in FIG. 140. It will be obvious to those skilled in the art that the hermetic seal could be of ceramic, sapphire, glass and can be sealed in a variety of ways to prevent the intrusion of body fluids into the sensitive capacitor or inductor element embedded therein. The hermetic seal structure shown in FIG. 140 is easiest done by glass. There are a number of prior art glass sealing processes that are used for capacitors and diodes and the like. In the art, many of these are known as DAP sealers.

FIG. 141 illustrates the use of a prior art feedthrough capacitor 220 with co-bonded inductor spiral substrate 518 of the present invention. The inductor spiral has been imprinted or deposited on a substrate 520 as shown. The composite structure has metallization surfaces 226 and 228 for convenient electrical attachment into a lead wire system or in combination with a distal TIP as described herein. When co-bonded together, the combination shown in FIG. 141 forms the novel parallel inductor capacitor TANK filter 146 of the present invention. Referring to FIGS. 89-92, one can see that the inductor spiral substrate 520 shown in FIG. 141 could have a number of parallel inductor layers 118.

FIG. 142 is an isometric drawing of a composite unipolar MLCC-T feedthrough 522 of the present invention. This is best understood by referring to the stack up of layers as shown in FIG. 143.

From top to bottom there are several thin ceramic cover sheets 524 as shown. Then there are one or more inductor layers 518 as shown separated by a ceramic insulator 526. Then there are a plurality of inner diameter electrodes 528 and outer diameter electrodes 530. These alternating layers can be stacked up to achieve the desired capacitance required. This is finished off by insulative ceramic cover sheets 532 as shown. These are pressed, laminated and then fired at high temperature to form the rugged monolithic structure shown in FIG. 142. Metallization bands 534 and 536 are then added for convenient electrical attachment. The cross section of the composite TANK filter 522 of FIG. 142 is shown in FIG. 144.

FIG. 145 is a cross-sectional view of a generic prior art active fixation distal TIP 628 typically used in conjunction with cardiac pacemakers. These active fixation TIPs 628 are well known in the prior art including the following patents all of which are incorporated herein by reference: U.S. Pat. Nos. 7,092,766; 6,952,613; 6,931,286; 6,876,885; 6,687,550; 6,493,591; 6,141,594; 6,055,457; 5,759,202; 5,741,321; 5,716,390; 5,545,201; 5,514,173; 5,300,108; 4,858,623; 4,799,499; and 4,858,623. In FIG. 145, one can see that there is a metallic housing 630 which contains a sharp tipped distal helix coil 632. This helix coil 632 is designed to be extended and screwed into body tissue. It is shown in its retracted position. This is to enable the physician to insert the distal TIP assembly 628 through the venous system, through the atrium, and into the ventricle so it does not snag or tear on any tissue. Once it is in the appropriate position, the physician then turns lead wire spline assembly 634 in a clockwise rotation. This is done outside the pectoral pocket with the lead wire protruding from the body. A tool is generally applied so that the physician can twist or screw the helix 632 into place. Protrusion 636 acts as a gear so that as helix 632 is turned, it is screwed forward. This makes for a very reliable fixation into myocardial tissue.

Helix 632 is generally laser welded to a protrusion 638 on the spline 634 as shown. Of course, all of the materials shown in FIG. 145 are biocompatible. Typically, the helix 632 is made of platinum iridium alloy and would be coated with various materials to improve electrical performance. Housing 630 would generally be composed of titanium or other equivalent biocompatible alloy. The spline 634 is generally a platinum iridium alloy. Attached to spline 634, usually by laser welding, is the lead wire 640 coming from the AIMD. An optional feature 642 is placed on spline 634 to create a positive stop as the physician is turning the lead wire assembly and screwing the helix 632 into body tissue. A secondary stop occurs when the gear feature 636 engages the end of the turns down near the laser weld 638.

FIG. 146 is a sectional view taken generally from section 146-146 in FIG. 145, the stop 642 has been replaced with a hermetically sealed tank filter 644 of the present invention. In general, the tank filter can be seen placed in series with the lead wire of the AIMD in FIG. 17. The tank filter of FIG. 42 could be used in this position as long as all biocompatible components were used. Referring to FIG. 65, this could also be placed in series with the lead wire system if the distal TIP feature 142 was replaced with an equivalent insulative feature so that the lead wire could be placed in series. In other words, the distal TIP would be replaced with a cap similar to 308. One could also incorporate the novel tank of FIG. 94 which incorporates the coiled lead wires encircling a novel MLCC capacitor composed of entirely biocompatible materials 332. One could also install the novel feedthrough capacitor coaxial tank of FIGS. 115 and 117 as shown in FIG. 146 as feature 644. In a preferred embodiment, one could incorporate the glass hermetically sealed encapsulated tank previously described in FIG. 140.

FIG. 147 is an adaptation of FIG. 145, including an MLCC-T 646 of the present invention. FIG. 147 shows the prior art active fixation distal TIP 628 previously described in FIG. 145. The tank filter MLCC-T 646 is shown in close proximity to the helix TIP 632. By having the distal TIP tank filter 646 in immediate proximity to the distal TIP 632, one can prevent the flow of MRI-induced RF pulsed currents into myocardial tissue. Referring once again to FIG. 147, one can see the lead wire 640 is routed from the output of the implantable medical device. Typically, this lead wire 640 would be constructed of biocompatible alloy MP-35N and laser welded at points 648 and 650 as shown. Optional stop 642 is shown and can be laser welded in place 652. This would typically be done after assembly. A novel feature of the present invention is that assembly of the entire MLCC tank filter 646 can be done with the helix 628 outside of its housing 630. This allows for easier electrical and mechanical connections (assembly), and enables high reliability screening of the tank 646, such as thermal shock, burn in, and the like. This is very important so that the MLCC tank 646 will be highly reliable in the patient application. Once all of this testing has been done, the entire assembly consisting of helix 632, MLCC-T 646, flange 654 and spline 634 can be inserted by screwing it into the assembly 628 from the right hand side of the cylinder 630. Then, novel end cap 656 is placed over the spline shaft 634 and laser welded 658 in place. It is not necessary that laser weld 658 be 360 degrees (only spot attachments are required). Subsequently, stop 642 can be laser welded in place 652 onto the shaft 634 as shown. Then the lead wire 640 consisting of MP-35N alloy can be laser welded at points 648 and 650 as shown. This completes the assembly.

FIG. 148 is a fragmented sectional view taken generally from section 148-148 from FIG. 147, illustrating the MLCC tank 646 consisting generally of the inductor assembly 660 and the feedthrough capacitor 662. The feedthrough capacitor 662 has been previously described in the drawing description of FIG. 39. Referring to FIG. 148, one can see that a protrusion 664 has been added to the spline shaft 634 so that the feedthrough capacitor 662 inside diameter 666 can be electrically connected 668 to it. This electrical connection material is shown as 668, and would generally be of the group of thermosetting conductive biocompatible polymers. There are a number of alternative materials that could be used including various biocompatible solders, brazes, welds, conductive glasses and the like. The electrical connection 668 is between the platinum spline material 664 and the inside diameter metallization 666 of the feedthrough capacitor. There is an insulative material 670 between the feedthrough capacitor 662 and the spline flange 664. The reason for this is to be sure that a short circuit does not occur between the capacitor outside diameter metallization 672 and the spline pedestal area 654. There is also an electrical connection 674 between the capacitor outside diameter metallization 672 and the inductor outside metallization 676. There is an equivalent electrical attachment 678 shown between the conductive spline protrusion 664 and the opposite of the end of the inductor metallization 676.

There is an optional insulating tube or sleeve 680 shown. This insulating sleeve 680 is to insure that neither the inductor 660, the capacitor 662, nor the distal helix 632 short (electrically contacts) against the metallic housing 630. In this preferred embodiment, after all of the high reliability testing is completed, the entire assembly consisting of the spline pedestal 654, the feedthrough capacitor 662, the co-attached inductor 660 and the first two turns of the helix 632 would all be parylene coated. Parylene is a highly biocompatible insulative material that is generally deposited by vacuum deposition chamber techniques. A coating of parylene over all surfaces provides both excellent insulation and an additional degree of immunity to body fluids. In a case where parylene coating was placed over all surfaces then optional insulating layer 680 could be eliminated.

Referring once again to FIG. 148, one can also see that the end cap 656 has been laser welded 658 in place. This is done after the entire novel tank assembly 646 including distal TIP has been high reliability tested and then threaded into place.

The construction of the novel inductor 660 will be better understood by referring to FIG. 149, which is generally taken from section 149-149 from FIG. 148. This is the exploded view of the novel inductor structure 660 that was previously shown attached to the feedthrough capacitor 662 in FIG. 148, and illustrated in FIG. 149A. One can see that the inductor 660 has been exploded into four slices as shown. Starting from the top, slice 682 generally consists of an alumina ceramic material with a via through hole 684. It also has a metallized wire bond pad surface 686 as shown. This is designed to be mated and co-fired to slice 688. As one can see, a novel inductor spiral of the present invention 690 has been imprinted onto the alumina substrate of slice 688. One should also note that the via hole 684 is aligned over the end of the inductor spiral 692 after they are mated. This allows the via hole 684 to be filled with conductive material such that an electrical connection is made between wire bond pad 686 and the central end of the inductor spiral 692. If one now follows that inductor spiral, one will see via through hole 694 as shown. Via hole 694 is carefully positioned so that it will align over the peripheral or outer end 696 of the inductor 698 shown in slice 700. This allows via hole 694 to be filled with conductive material, thereby making an electrical connection between 694 and 696. If one then follows the inductive spiral 698 on slice 700 to its end at via through hole 702, one can see that via hole 702 has been lined up to align with the end 704 of the inductor 706 from slice 708. Again, filling the via hole 702 with a suitable conductive material forms an electrical connection between 702 and 704 as shown. Referring once again to slice 708, if one follows the inductor pattern 706 around to its outside diameter, one can see that there is a full circumferential electrode exposure 710. After this completed assembly consisting of slices 682, 688, 700 and 708 has been assembled and co-fired, one can then apply the external metallization 712 around its complete outside diameter. This exterior metallization 712 makes electrical connection in slice 708 to the outside of the inductor 710.

It will be obvious to those skilled in the art that any number of inductor layers n can be used. It is also not necessary that the number of turns or even the inductor shape be the same in each one of the slices. The number of turns, the widths, pitch, and the total length of the inductors can all be varied as desired to achieve the total inductance that is required for the particular design. In addition, referring back to FIG. 149, all of the materials and all of the vias would preferably be of suitable biocompatible materials. In practice this would mean that, in a preferred embodiment, the substrates (slices 682, 688, 700 and 708) are of ultra high purity alumina ceramic and the inductor traces 690, 698 and 706 are all of pure platinum or equivalent. In addition, the via hole fills would likely be of pure gold or equivalent biocompatible material. An alternative way to fill the via holes would be to use a thermosetting conductive biocompatible polymer as previously described in FIG. 148.

Referring back to both FIGS. 148 and 149, it will be appreciated that the use of mechanically robust structures are required. That is due to the great deal of torque and sheer stresses that will be placed on the electrical components when the physician turns the spline shaft 634 and screws the helix 632 into myocardial tissue. Also, during the life of the device, as the helix 632 is attached into myocardial tissue, there are flexures, shocks and vibrations occurring during each beat of the heart. Accordingly, there is a need for both the inductor structure 660 and the feedthrough capacitor 662 to be quite mechanically robust. It is a general principle in ceramic engineering that the higher the k of the material, the lower the mechanical strength of that material. The converse is also true. The use of very low dielectric constant (low k) ceramic materials result in higher mechanical strength. The dielectric constant of alumina is approximately 6 to 7. The dielectric constant of very high k ceramic capacitor dielectrics can exceed 3000. However, these 3000 k dielectrics are mechanically very weak. It is a novel feature of the present invention that the feedthrough capacitor 662 and the inductor 660 as shown in FIG. 148 be constructed of relatively low k ceramic materials. Electronic Industries Association (EIA) has a series of standards that specify the electrical characteristics of various ceramic dielectrics. NPO, which is specified by the EIA standard and is well known in the prior art and has a k between 60 and 90, would be an ideal choice in this case. For the inductor 660 as illustrated in FIGS. 148, 149 and 149A, the use of alumina ceramic would be ideal since it is relatively low in k and is also very strong. Another suitable material for either the capacitor 662 or the inductor 660 is the use of manganese titanate (porcelain). Manganese titanate has a k between 10 and 12 and generally has NPO capacitor characteristics. This material has a very high Tensile strength, a very high yield point and it also has a very high modulus of toughness. Accordingly, manganese titanate would be an ideal candidate for the present application. In addition, there are a number of commercially available NPO dielectrics which are compatible with a ternary electrode system. A ternary electrode system consists of gold, platinum and palladium, all of which are biocompatible.

Referring once again to FIG. 149, one can see that, in the preferred embodiment, the substrate layers 682, 688, 700 and 708 are all of high purity alumina. The reason is that alumina is very low in k (less than 10) and is also very mechanically robust. In fact, alumina is commonly used in implantable medical devices for the hermetic seal where lead wires pass in and out of an implanted medical device.

In another preferred embodiment, it is desirable to completely eliminate feedthrough capacitor 662 as previously described in FIG. 148. This can be done by taking advantage of the fact that multiple inductor spirals, as shown in FIG. 149, have been added in series. This is better understood by referring to the schematic diagram in FIG. 150. One can see that the inductor spirals of slices 688, 700 and 708 are added in series where in $L_{TOTAL}=690+698+706$. Referring back to FIG. 150, there will be a distributive capacitance $C_{P1}$ between the adjacent turns of each one of these spiral inductors. This will be substantially higher than would occur in an air wound solenoid inductor. This is because air has a low dielectric constant relative to alumina or other dielectric materials. Also, compared to alumina, body fluids also have a relatively low dielectric constant. Another reason one would not want to put an air wound inductor into body fluids is the conductivity of body fluids themselves, which would tend to short adjacent inductor turns.

In FIG. 150, one can see that there is a parasitic capacitance $C_{P1}$ that actually occurs between every turn of the spiral inductors 690, 698 and 706 previously illustrated in FIG. 149. These will add up to a total parallel inductance as shown in FIG. 150 as $C_P$. One can see that in a preferred embodiment, one could adjust this total parallel capacitance $C_P$ such that it would be resonant with $L_{TOTAL}$ (690+698+706) at the RF pulsed frequency. In this way, one could completely eliminate the feedthrough capacitor 662 as a separate element. This composite MLCC-T integrated assembly 714 is shown in FIG. 151.

FIG. 151 is similar to the novel MLCC tank assembly 646 previously illustrated in FIGS. 147 and 148 wherein the tank and filter of the present invention has been incorporated inside the coaxial cylinder 630 of an active fixation distal TIP 628, for example, that of a cardiac pacemaker. In FIG. 151, the same three inductor spiral slice substrates 688, 700 and 708 are present as previously described in FIG. 149. However, wire bond pad area 716 has been electrically separated from wire bond pad area 718. Accordingly, the total series inductance consisting of 690+698+706 can be directly measured by connecting an inductance bridge between 716 and 718. Referring to substrate 708, one can see parasitic capacitance $C_P$. As previously stated, a parasitic capacitance occurs between each turn of these spiral windings. These parasitic capacitances can be controlled by controlling the width, spacing and number of the various spiral turns. Each one of the inductor substrate layers 688, 700, 708 (or n substrate layers) will all have a self resonant frequency that depends upon the total amount of capacitance and the total distributive capacitance (primary resonance). There will also be secondary resonances that occur (adjacent turn resonances).

FIG. 152 is an electrical schematic diagram of the structure 714 shown in FIG. 151A. Referring to substrate layer 688, one can see that there is a parasitic capacitance $CP_1$ that ends up in parallel with the total inductance 690. A similar thing happens for substrate layers 700 and 708. By carefully controlling the parasitic capacitance and the parallel inductance, one can create multiple resonant frequencies. For example, we could have substrate layer 688 resonate at 64 MHz, substrate 700 resonate at 128 MHz and substrate 708 resonate at close to 216 MHz. It should also be pointed out that with multiple resonances like this, it is not even important that each substrate layer resonate exactly at the MRI RF pulsed resonant frequency. All that is really important is to keep the impedance high throughout this range. This is best examined by looking at FIG. 153, which is a graph of the impedance versus frequency of the tank circuit of FIG. 150. As one can see, there are multiple resonances occurring between 64 MHz, 128 MHz, 216 MHz and even higher. This is highly desirable in that it keeps the impedance, and therefore, the attenuation to MRI-induced RF currents very high throughout the desired range.

FIG. 154 is an isometric drawing of a unique integrated tank filter 720 of the present invention. It consists of parallel inductors and parallel capacitors as further illustrated in the schematic drawing of FIG. 155. This is best understood by referring to the exploded view shown in FIG. 156. In FIG. 156, we can see that there are various substrate layers 722 through 730. Substrate layer 722 is a cover sheet with a via hole 732 and a metallization surface 734. The via hole 732 is designed to align with via hole 736 in substrate 724. Inductor 738 is formed in substrate 724 and is terminated all around the outside circumference also shown as 740. The exterior or outside diameter of the assembly 720 also has metallization shown as 742 in FIG. 154. A capacitance is formed between the overlap area of the inductor trace 738 and the capacitor ground electrode 744 shown in substrate layer 726. One can see that there is also a via hole 746 that passes through in non-conductive relation with the electrode 744 down to electrode layer 728. Filling of the via hole 732, 736 and 746 makes an electrical connection all the way from the top metallization layer 734 down to the electrode pad 748 at the center of inductor spiral 750 shown in substrate 728. A second capacitor 752 is formed between the overlap of inductor trace 750 and the capacitor electrode metallization 752 shown in substrate layer 730. As described for substrate layer 726, the capacitor electrode metallization 752 comes to the outside diameter where it makes contact with the outside diameter metallization 742. All of this has the effect of putting parasitic capacitance between the electrode traces in parallel with one another as shown in the schematic in FIG. 155. Having the two capacitors 744 and 752 in parallel is highly efficient because capacitors in parallel simply add together. However, having the two inductors 738 and 750 in parallel is not particularly efficient because the amount of inductance is thereby reduced in accordance with the parallel inductance formula.

Referring once again to FIG. 149, one can see a novel technique of placing inductors in series. Inductors in series simply add together thereby directly increasing the overall inductance. If one refers to substrate layers 688, 700 and 708 taken from FIG. 149, one can easily envision how they could replace substrate layer 730 previously shown in FIG. 156. In this way, one could greatly increase the inductance of the FIG. 156 structure 720 by using these series techniques that were previously described in FIG. 149. One skilled in the art will realize that the inductor substrate layers 688, 700 and 708 taken from FIG. 149 could be used to replace substrate layer 730 or substrate layer 726 of both as desired in order to achieve the total amount of inductance needed.

FIG. 157 illustrates a methodology of integrating both techniques of inserting capacitor ground electrode plates 726 and 730 while at the same time having series inductor elements 688, 700 and 708. The composite structure is shown at the bottom of FIG. 157 as 720', which is virtually identical to the isometric drawing of the novel tank 720 shown in FIG. 154.

FIG. 158 illustrates applying the novel tank filter 714 of FIG. 151 to a prior art active fixation distal TIP 628 previously described in FIG. 147. Referring once again to FIG. 158, one can see the attachment from the metallization 718 of novel tank MLCC-T 714 from FIG. 151 shown attached to the spline and spline pedestal 634 and 654. This is typically accomplished by a gold braze preform 756. In this case, the pedestal 654 has been counterbored to receive the end of the novel MLCC-T tank filter 714. This allows the gold braze material 756 to angle up along the sides of the MLCC-T 714, thereby adding sheer strength to the overall assembly. It will be obvious to those skilled in the art that this same counterbore could also be applied to the helix pedestal post assembly 758. This would allow gold braze material 760 to also come around the sides of the novel MLCC-T tank filter 714 to provide sheer strength in that area also. A similar gold braze preform 760 is used to attach a distal TIP helix pedestal 758 to the metallization 716 of the novel tank MLCC-T 714. Of particular advantage is that the novel MLCC-T substrate illustrated in FIG. 151 can be constructed entirely of low k, very high strength ceramics. In this case, pure alumina or porcelain would be preferred embodiments. These have the advantage of being mechanically very rugged and also very rugged to thermal shock such that it would take pure gold brazing. By use of all biocompatible materials, the assembly is greatly simplified in that it need not be hermetic. It would also be possible to replace the gold brazes 756 and 760 with equivalent laser welds. Referring once again to FIG. 158, one can see that the end cap 656 has been modified in a novel way such to make it flush with the outside diameter of the active fixation TIP assembly 630. This allows one to increase the inside diameter allowing room for the novel counterbore as previously described in pedestal 654. The metallic end cap 656 has been stepped so that it is seated for convenient fixturing and also a countersink 762 has been applied for convenient gold brazing or laser weld material 658.

FIG. 159 is an adaptation of the generic prior art active fixation distal TIP 628' previously illustrated in FIG. 145. References also made to FIGS. 147, 148 and 158. All of these previous drawings have two things in common: 1) they allow body fluid to freely penetrate to all surfaces interior to the active fixation distal TIP 628; and 2) torque experienced by the helix 632 is transmitted to any electronic component, such as the tank of the present invention and its associated electrical and mechanical connections. Referring now back to FIG. 159, the spline shaft 634 has been modified such that it has a relatively long, hollow cylindrical portion 654' which allows for the insertion of the tank filter 146 of the present invention inside of it. As will be seen, this will offer a number of important mechanical and biocompatibility advantages. The tank 146 that is shown in FIG. 159 is the tubular integrated MLCC tank 320 previously described in FIGS. 68-76. For simplicity, the internal electrode plates 324, 326 and 328 that form the capacitor and inductor elements are not shown in FIG. 159 since any of the aforementioned embodiments can be incorporated. It will also be obvious to those skilled in the art that the novel tank filters 146 that are described in FIGS. 32, 35, 37, 42, 44, 65, 80, 83, 85, 87, 115, 126, 128 and 141 can all be easily incorporated into the novel housing 654' as illustrated in FIG. 159. Referring once again to FIG. 159, one can see that the tank filter 146 of the present invention is first inserted into an insulative liquid material 762. This is then cured, which holds the tank filter 146 in place. It also performs another important function in that the metallization surfaces 764 and 766 of the tank filter 146 are prevented from shorting out against the bottom of 654'. The material 762 could also be a non-conductive washer, a thermosetting non-conductive polymer or the like. There is an electrical connection 768 that is generally made of a thermosetting conductive polymer that makes an electrical connection between the typically platinum spline 634 and cup 654' assembly and the outside diameter termination 766 of the novel tank 146 of the present invention. There is a corresponding electrical connection using similar materials 770 that connects between the inside diameter metallization 764 of the novel tank 146 of the present invention and pedestal post lead wire 772. Alternate electrical connection materials 768 and 770 could also be of the group of solders, brazes, welds and the like that are typical in the prior art. One can see by referring to FIG. 159, that there is a large advantage to the surrounding cylinder 654'. The rather sensitive electronic devices consisting of the inductor and the capacitor element are now mechanically protected by the surrounding metal material. During physician implant, where the entire assembly is twisted and the helix TIP 632 is screwed into body tissue, this means that the interior capacitor and inductor elements are completely protected and not exposed to those forces. In the ongoing application in the patient environment, there is an associated stress with every beat of the heart which tends to fatigue and cause shock and vibration loads to this entire assembly. Again, by having the sensitive capacitor and inductor elements 146 completely enclosed, they are protected from such forces. There is another advantage to the assembly shown in FIG. 159 in that it is completely hermetically sealed. The hermetic terminal assembly is first formed using prior art gold brazing or glass sealing techniques. This hermetic seal subassembly will consist of ferrule 774, alumina ceramic insulator 776 (or glass or equivalent) and the unique pedestal post one-piece assembly 758' consisting of features 772, 778 and 780. An optional spacer washer, typically consisting of alumina, 782 is used to prevent the pedestal feature 778 from shorting out to the ferrule 774. It is very important that these be kept in electrical insulative relationship. As in all prior devices, the helix 632, that is designed to be screwed into body tissue, is laser weld attached to the pedestal 778 at point 638.

Referring now back to the hermetic terminal seal assembly, one can see that the hermetic seals are formed by gold brazes 784 and 786 which makes attachment between the alumina ceramic 776 and the metal joints 772 and 774. Not shown is a typical first operation wherein the alumina ceramic 776 is first prepared by sputtering typically with a layer of titanium and then a layer of molybdenum. The first layer is the adhesion layer and the second layer provides for good wetting of the gold braze. This is all well known in prior art. The entire hermetic seal subassembly is then laser welded in a continuous 360 degree laser weld as shown in 788. This completely hermetically seals the novel tank filter of the present invention.

Referring once again to FIG. 159, one can also see that there is an end cap 656' which is flush with the outside diameter of the housing 630 of the active fixation distal TIP assembly. As described before, this will be added after the entire assembly is screwed into place as a last step. It will be obvious that FIG. 159 can also have an insulating sleeve (not shown) around the outside diameter of the complete assembly consisting of 654'. In addition, the entire assembly could be parylene coated as previously described (also not shown). Referring back to the end cap 656', one can see that it is laser welded in place 658. It is not necessary that laser weld 658 be 360 degrees. In fact, for ease of assembly it would only be spotted in a few places.

An additional advantage of having the capacitor inductor element of the tank filter 146 inside the housing 630 of the active fixation TIP 628 is that this provides a substantial degree of protection to these delicate electronic components. Doctors and other medical personnel are often notorious in the way they handle lead systems. Things can get dropped, moved or placed against them. Accordingly, having these devices inside the metal housing is highly desirable.

FIG. 160 illustrates a prior art neurostimulation electrode probe 540 or a common ablation probe or a catheter that is commonly known in the prior art. As one can see, there are a multiplicity of stimulation electrodes 542-542'''. In this particular application the end tip 544 is insulative.

FIG. 161 is the prior art probe 540, neurostimulation TIP or catheter of FIG. 160 re-drawn to include novel MLCC-T TANK filters 146 and 146' of the present invention (146'' and 146''' are not shown for simplicity). In this particular case these TANK filters are similar to those illustrated in FIG. 141 or 142. One can see that these are placed in conjunction with the stimulation electrodes 542, 542' and so on. As many as desired can be stacked as shown. This has the effect of placing the novel TANK filter of the present invention in series with each one of the stimulation rings and thereby limiting/preventing the flow of MRI induced RF currents.

A feature of the present invention that conventional low pass EMI filtering is still provided at the input to the AIMD which is very broadband in nature. However, it may still be highly desirable to control the specific MRI pulse frequencies through use of novel TANK filters placed strategically within the lead wire system. This can be at the distal TIP, along the lead wire system or at the point of lead wire ingress into the AMID housing. This is best understood by referring to FIG. 162 where the novel TANK filters 146-146''' of the present invention are shown strategically placed at the point lead wire ingress (compare with FIG. 2).

Referring now to FIG. 163 one can see a prior art broadband low pass feedthrough capacitor 120 as previously illustrated in FIG. 3. In this case, lead wire 104a has been broken into discontinuous nail head segments 550 and 552. A novel MLCC-T 344'' of the present invention is shown as taken from FIG. 87. This novel TANK filter circuit is located within location plate 554. This location plate could be an alumina ceramic, plastic or any other insulative material suitable for locating the novel inductor TANK chips MLCC-T 344''. This thin plate 554 could also be an inductor slab as described in U.S. Pat. No. 6,999,818. The electrical attachment between the lead wire segments 550 and 552 to the novel MLCC-T 344'' are made by electrical connection material 556 and 558. These electrical connection materials could be a thermal setting conductive adhesive, solder, braze or the like. The presence of the MLCC-T 344'' in series with a lead wire offers a much higher degree of protection at selected MRI pulse frequencies to the sensitive internal electronics of the AIMD. In addition, this presents a very high impedance in the lead wire system of the AIMD. Since the equivalent circuit of an AIMD lead wire consists of many series inductance, resistive, and parallel capacitance elements that are multiple loops and resonances within the overall lead wire system. Accordingly, placing the MLCC-TANK filter of the present invention only at the distal TIP may not prevent problems with overheating of a lead wire system near the AIMD. It has been shown in the literature that overheating of the lead wire immediately adjacent to an AIMD can, using a pacemaker as an example, lead to venous ablation (burning of the subclavian vein) or esophageal ablation or burning. Accordingly, having a high impedance in the lead wire system near the AIMD offers particular advantages in that lead wire currents and associated heating would be reduced or eliminated.

FIG. 164 shows an alternative method of installing MLCC-T TANK filters 146 of the present invention in series with prior art broadband feedthrough capacitor filters 120. FIG. 165 illustrates how coaxial capacitors that have been previously described in FIGS. 65 and 68-73 could all be used in combination with a prior art feedthrough capacitor 120 to achieve the desired properties previously described in connection with FIGS. 163 and 164.

FIG. 166 is a schematic diagram of the novel MLCC-T TANK filters previously described in FIGS. 163-165. One can see the MLCC-TANK filter circuit 146 of the present invention placed in series with the prior art feedthrough capacitor 120. This can be unipolar (1), bipolar, tripolar, quadpolar or many leads as desirable. In certain cardiac therapy applications there could be as many as twelve or more of these in parallel. The present invention incorporating a novel MLCC-T TANK filter is also very useful for various types of robotically or remotely controlled surgical operations. For example, in remote controlled surgery, electrocardery devices such as BOVI knives are commonly used. Anything that is placed inside the body that requires real time MRI guiding must be protected from the effects of overheating or damage to its own electronics. Accordingly, the present invention is adaptable to any of these robotically controlled surgical operations.

FIG. 167 illustrates a prior art skin electrode pad 466. This could be a surface electrode pad used for ECG/EKG cardiac monitoring. Such pads can be as many as 12 lead systems 478 or more. These skin electrodes are typically stick on the chest and other places around the body (and even on the feet). The skin electrode pads 466 shown in FIG. 167 could also be EEG (electroencephalogram) lead wires 478 that could be attached to the patient's head. FIG. 167 is made to be encompassing of any monitoring leads which could be placed anywhere on or in a patient.

FIG. 133 shows that such external lead wires 478 and electrodes 466 described in FIG. 167 are easily protected with the novel distal TIP TANK filter 146 of the present invention. Protection of these types of external lead wires is very important because often patients are sent to another location for an MRI from a hospital bedroom or other location where they had many FIG. 167 lead wires placed on them. Removal of all of these leads is a very time consuming procedure prior to MRI. Worse yet, after the MRI, the MRI technicians attempt to place these lead wires back in the correct positions, however, MRI technicians often replace them incorrectly. Even a slight difference in where you place the lead can affect subsequent data. Often the MRI technicians place the EKG leads back in an entirely different position which can lead to erroneous data. This can be very frustrating and confusing for cardiologists, for example, that do not even realize that another doctor in the hospital had sent the patient upstairs to get an MRI. Often when the patient is sent back to their hospital room, the cardiologist is puzzled by differences in cardiac readings that they cannot explain. Accordingly, this is an important application for the novel TANK filter of the present invention.

FIG. 168 is the schematic of the novel tank filter of FIG. 167.

FIG. 169 combines the principles from FIG. 8 and FIG. 17 together. Referring to FIG. 169, one can see the housing 102 of the active implantable medical device 100. Contained inside of the active implantable medical device are electronic circuit boards 790 through which a lead wire 104 egresses through a insulative hermetic feedthrough terminal 792, including a prior art feedthrough capacitor such as was previously illustrated in FIGS. 3, 4, 5, 6 and 7. Lead wire 104 is directed to the novel TANK filter 146 of the present invention which is immediately adjacent to the distal TIP 142. Referring back to FIG. 169, this forms an MRI compatible system. In this case, the value of the feedthrough capacitor must be sufficiently high so as to preclude the entry of the MRI pulsed RF signals into the interior of the AIMD housing 102 where such EMI could interfere with the proper operation of the circuit board 790. As described throughout this invention, the distal TIP TANK 146 acts to stop the flow of MRI currents near or at the distal TIP thereby preventing overheating. Said tanks can also be placed in other locations along the lead wire 104, including immediately adjacent or even inside of the feedthrough capacitor 792 as previously described in drawings 162-165. Accordingly, one can see that the distal TIP TANK 146 of the present invention acts as a system in concert with the passive feedthrough capacitor low pass filter 792 as illustrated.

Although several embodiments have been described in some detail for purposes of illustration, various modifications may be made without departing from the scope and spirit of the invention. Accordingly, the invention is not to be limited, except as by the appended claims.

What is claimed is:

1. An implantable medical therapeutic or diagnostic device, comprising:
    a) an electrode;
    b) a lead wire having a length extending from a distal portion connected to the electrode to a proximal end that is electrically connectable to an electronic circuitry of an active medical device, wherein the lead wire is at least partially coiled along its length to thereby provide a coiled wire portion forming a coil lumen; and
    c) a capacitor having a first metallization electrically connected to at least one first electrode plate interleaved with a second, opposite polarity electrode plate electrically connected to a second metallization, wherein the coiled wire portion wraps around the capacitor disposed in the coil lumen with the first capacitor metallization connected to the coiled wire portion at a first electrical connection spaced from the second capacitor metallization connected to the coiled wire portion at a second electrical connection to thereby form a tank filter having electrical inductance in parallel with capacitance;
    d) wherein the tank filter attenuates current flow over a range of selected frequencies.

2. The device of claim 1, wherein the capacitor comprises a chip capacitor.

3. The device of claim 1, wherein the tank filter has an overall circuit Q resulting in a 3 dB bandwidth on the order of MHz.

4. The device of claim 1, wherein the range of selected frequencies comprise MRI RF pulsed frequencies.

5. The device of claim 1, wherein the capacitor is comprised of biocompatible materials.

6. The device of claim 1, wherein the lead wire is connected to a cardiac TIP electrode and a second lead wire is connected to a RING electrode.

7. The device of claim 6, wherein the tank filter is formed with the first lead wire, the second lead wire, or both.

8. A medical therapeutic or diagnostic device, comprising:
    a) an electrode;
    b) a lead wire having a length extending from a distal portion connected to the electrode to electronic circuitry of an active medical device, wherein the lead wire is at least partially coiled along its length to thereby provide a coiled wire portion forming a coil lumen; and c) a chip capacitor having a first set of electrode plates conductively coupled to a first metallization surface, and a second set of electrode plates conductively coupled to a second metallization surface;

d) wherein the coiled lead wire portion wraps around the chip capacitor disposed in the coil, lumen with the first capacitor metallization connected to the coiled wire portion at a first electrical connection spaced from the second capacitor metallization connected to the coiled wire portion at a second electrical connection to thereby form a tank filter having electrical inductance in parallel with capacitance; and e) wherein the tank filter has an overall circuit Q resulting in a 3 dB bandwidth on the order of MHz such that the tank filter attenuates current flow over a range of selected frequencies.

9. The device of claim 8, wherein the range of selected frequencies comprise MRI RF pulsed frequencies.

10. The device of claim 8, wherein the capacitor is comprised of biocompatible materials.

11. The device of claim 8, wherein the lead wire is connected to a cardiac TIP electrode and a second lead wire is connected to a RING electrode.

12. The device of claim 11, wherein the tank filter is formed with the first lead wire, the second lead wire, or both.

13. An implantable medical therapeutic or diagnostic device, comprising:

a) a first lead wire connected to a cardiac TIP electrode and being connectable to electronic circuitry of an active medical device, and a second lead wire connected to a RING electrode and being connectable to the electronic circuitry, wherein at least one of the first and second lead wires is at least partially coiled along its length to thereby provide a coiled wire portion forming a coil lumen; and b) a chip capacitor comprised of biocompatible materials disposed within a coiled portion of the first or second lead wire, the capacitor having a first set of electrode plates conductively coupled to a first metallization surface, and a second set of electrode plates conductively coupled to a second metallization surface;

c) wherein the first or second lead wire is conductively coupled to the first and second metallization surfaces of the capacitor to form a tank filter having electrical inductance in parallel with capacitance; and d) wherein the tank filter has an overall circuit Q resulting in a 3 dB bandwidth on the order of MHz such that the tank filter attenuates current flow over a range of selected MRI RF pulsed frequencies.

14. The device of claim 13 wherein the first and second lead wires are connectable to a bipolar pacemaker.

* * * * *

UNITED STATES PATENT AND TRADEMARK OFFICE
CERTIFICATE OF CORRECTION

| | | |
|---|---|---|
| PATENT NO. | : 8,649,857 B2 | Page 1 of 1 |
| APPLICATION NO. | : 13/081314 | |
| DATED | : February 11, 2014 | |
| INVENTOR(S) | : Robert A. Stevenson et al. | |

It is certified that error appears in the above-identified patent and that said Letters Patent is hereby corrected as shown below:

In the Claims

Column 75, line 8, Claim 8, after the word "coil" delete the ","

Signed and Sealed this
Sixteenth Day of September, 2014

Michelle K. Lee
*Deputy Director of the United States Patent and Trademark Office*